(12) United States Patent
Otte et al.

(10) Patent No.: US 8,771,984 B2
(45) Date of Patent: Jul. 8, 2014

(54) SELECTION OF HOST CELLS EXPRESSING PROTEIN AT HIGH LEVELS

(75) Inventors: Arie P. Otte, Amersfoort (NL);
Henricus J. M. van Blokland, Wijdewormer (NL); Theodorus H. J. Kwaks, Amsterdam (NL); Richard G. A. B. Sewalt, Arnhem (NL)

(73) Assignee: ChromaGenics B.V., Leiden (NL)

( * ) Notice: Subject to any disclaimer, the term of this patent is extended or adjusted under 35 U.S.C. 154(b) by 98 days.

(21) Appl. No.: 12/807,133

(22) Filed: Aug. 26, 2010

(65) Prior Publication Data

US 2011/0014655 A1 Jan. 20, 2011

Related U.S. Application Data

(62) Division of application No. 11/269,525, filed on Nov. 7, 2005.

(60) Provisional application No. 60/626,301, filed on Nov. 8, 2004, provisional application No. 60/696,610, filed on Jul. 5, 2005.

(30) Foreign Application Priority Data

Nov. 8, 2004 (EP) ..................................... 04105593

(51) Int. Cl.
*C12N 15/00* (2006.01)
*C12N 15/09* (2006.01)
*C12N 15/63* (2006.01)
*C07K 14/00* (2006.01)

(52) U.S. Cl.
USPC ...... 435/69.1; 435/320.1; 435/455; 536/23.1; 536/23.5; 536/24.1

(58) Field of Classification Search
USPC ............ 435/69.1, 320.1, 455; 536/23.1, 23.5, 536/24.1
See application file for complete search history.

(56) References Cited

U.S. PATENT DOCUMENTS

| | | | |
|---|---|---|---|
| 4,965,196 A | 10/1990 | Levinson et al. |
| 5,021,344 A | 6/1991 | Armau et al. |
| 5,118,620 A | 6/1992 | Armau et al. |
| 5,527,701 A | 6/1996 | Yamaguchi et al. |
| 5,561,053 A | 10/1996 | Crowley |
| 5,610,053 A | 3/1997 | Chung et al. |
| 5,627,033 A | 5/1997 | Smith et al. |
| 5,648,267 A | 7/1997 | Reff |
| 5,658,763 A | 8/1997 | Dorai et al. |
| 5,733,779 A | 3/1998 | Reff |
| 5,773,695 A | 6/1998 | Thompson et al. |
| 5,888,809 A | 3/1999 | Allison |
| 5,972,605 A | 10/1999 | Villepornteau et al. |
| 5,994,128 A | 11/1999 | Fallaux et al. |
| 6,060,273 A | 5/2000 | Dirks et al. |
| 6,107,477 A | 8/2000 | Whitney et al. |
| 6,319,707 B1 | 11/2001 | Adam et al. |
| 6,395,549 B1 | 5/2002 | Tuan et al. |
| 6,413,744 B1 | 7/2002 | Morris et al. |
| 6,521,419 B1 | 2/2003 | Koduri et al. |
| 6,558,948 B1 | 5/2003 | Kochanek et al. |
| 6,586,205 B1 | 7/2003 | Glucksmann et al. |
| 6,800,457 B2 | 10/2004 | Koduri et al. |
| 6,872,524 B1 | 3/2005 | Otte |
| 7,001,772 B2 | 2/2006 | Roessler et al. |
| 7,109,029 B2 | 9/2006 | Clarke et al. |
| 7,192,741 B2 | 3/2007 | Otte et al. |
| 7,244,609 B2 | 7/2007 | Drocourt et al. |
| 7,267,965 B2 | 9/2007 | Otte et al. |
| 7,364,878 B2 | 4/2008 | Otte et al. |
| 7,442,787 B2 | 10/2008 | Antoniou et al. |
| 7,655,441 B2 | 2/2010 | Otte et al. |
| 7,659,094 B2 | 2/2010 | Otte et al. |
| 7,662,591 B2 | 2/2010 | Otte et al. |
| 7,736,868 B2 | 6/2010 | Otte et al. |
| 7,736,869 B2 | 6/2010 | Otte et al. |
| 7,736,870 B2 | 6/2010 | Otte et al. |
| 7,749,733 B2 | 7/2010 | Otte et al. |
| 7,794,977 B2 | 9/2010 | Otte et al. |

(Continued)

FOREIGN PATENT DOCUMENTS

EP 0724639 B1 1/2001
EP 1 273 666 1/2003

(Continued)

OTHER PUBLICATIONS

Kim et al, Biotechnol. Bioeng. 58:73-84, 1997.*
Alberts et al, Molecular Biology of the Cell, Third edition, Garland Publishing, New York, NY, 1983; genetic code page only.*
Birren et al, GenBank AC110588, 2002.*
Izumi, et al., Homogeneous Tetracycline-Regulatable Gene Expression in Mammalian Fibroblasts; Journal of Cellular Biochemistry 76; 1999; pp. 280-289.

(Continued)

*Primary Examiner* — Kevin Hill
(74) *Attorney, Agent, or Firm* — TraskBritt, P.C.

(57) ABSTRACT

The invention provides a DNA molecule comprising a multicistronic transcription unit coding for i) a selectable marker polypeptide functional in a eukaryotic host cell, and for ii) a polypeptide of interest, the polypeptide of interest having a translation initiation sequence separate from that of the selectable marker polypeptide, characterized in that the coding sequence for the polypeptide of interest is downstream from the coding sequence for the selectable marker in the multicistronic transcription unit, and the nucleic acid sequence coding for the selectable marker polypeptide comprises a mutation that decreases the translation efficiency of the selectable marker in a eukaryotic host cell. The invention also provides methods for obtaining host cells expressing a polypeptide of interest, the host cells comprising the DNA molecules of the invention. The invention further provides the production of polypeptides of interest, comprising culturing host cells comprising the DNA molecules according to the invention.

2 Claims, 48 Drawing Sheets

(56) References Cited

U.S. PATENT DOCUMENTS

| | | | |
|---|---|---|---|
| 7,825,232 B2 * | 11/2010 | Otte et al. | 536/23.5 |
| 8,039,230 B2 | 10/2011 | Otte et al. | |
| 2002/0155540 A1 | 10/2002 | Padidam | |
| 2003/0138908 A1 | 7/2003 | Koduri et al. | |
| 2003/0166042 A1 | 9/2003 | Glucksmann et al. | |
| 2003/0199468 A1 | 10/2003 | Otte et al. | |
| 2004/0219677 A1 | 11/2004 | Drocourt et al. | |
| 2005/0106580 A1 | 5/2005 | Enenkel et al. | |
| 2005/0106609 A1 | 5/2005 | Otte | |
| 2005/0181428 A1 | 8/2005 | Antoniou et al. | |
| 2005/0191723 A1 | 9/2005 | Otte et al. | |
| 2006/0003416 A1 | 1/2006 | Otte et al. | |
| 2006/0010506 A1 | 1/2006 | Otte et al. | |
| 2006/0141577 A1 | 6/2006 | Otte et al. | |
| 2006/0172382 A1 | 8/2006 | Otte et al. | |
| 2006/0195935 A1 | 8/2006 | Otte et al. | |
| 2006/0263882 A1 | 11/2006 | Fazio et al. | |
| 2007/0026498 A1 | 2/2007 | Otte et al. | |
| 2007/0026499 A1 | 2/2007 | Otte et al. | |
| 2007/0031933 A1 | 2/2007 | Otte et al. | |
| 2007/0031934 A1 | 2/2007 | Otte et al. | |
| 2007/0031935 A1 | 2/2007 | Otte et al. | |
| 2007/0031936 A1 | 2/2007 | Otte et al. | |
| 2007/0037256 A1 | 2/2007 | Otte et al. | |
| 2007/0128717 A1 | 6/2007 | Otte et al. | |
| 2007/0212755 A1 | 9/2007 | Otte et al. | |
| 2008/0085537 A1 | 4/2008 | Otte et al. | |
| 2008/0131930 A1 | 6/2008 | Otte et al. | |
| 2008/0206813 A1 | 8/2008 | Otte et al. | |
| 2009/0011468 A1 | 1/2009 | Otte et al. | |
| 2009/0098601 A1 | 4/2009 | Otte et al. | |
| 2010/0136616 A1 | 6/2010 | Otte et al. | |
| 2010/0190207 A1 | 7/2010 | Otte et al. | |
| 2011/0014655 A1 | 1/2011 | Otte et al. | |

FOREIGN PATENT DOCUMENTS

| | | |
|---|---|---|
| JP | 5501054 | 3/1993 |
| JP | 2004533262 | 11/2004 |
| WO | WO 91/01374 | 2/1991 |
| WO | WO 94/23046 | 10/1994 |
| WO | WO 96/04390 | 2/1996 |
| WO | WO 96/12008 | 4/1996 |
| WO | WO 97/27207 | 7/1997 |
| WO | WO 98/11207 | 3/1998 |
| WO | WO 98/39411 | 9/1998 |
| WO | WO 98/49289 | 11/1998 |
| WO | WO 00/05393 | 2/2000 |
| WO | WO 00/09749 | 2/2000 |
| WO | WO 00/17337 | 3/2000 |
| WO | WO 00/23606 | 4/2000 |
| WO | WO 01/02553 | 1/2001 |
| WO | WO 01/32901 A1 | 5/2001 |
| WO | WO 01/57188 A2 | 8/2001 |
| WO | WO 01/59117 | 8/2001 |
| WO | WO 01/59118 | 8/2001 |
| WO | WO 02/24930 A2 | 3/2002 |
| WO | WO 02/072846 | 9/2002 |
| WO | WO 02/074969 | 9/2002 |
| WO | WO 02/099070 | 12/2002 |
| WO | WO 02/099089 | 12/2002 |
| WO | WO 03/004704 | 1/2003 |
| WO | WO 03/083077 A2 | 10/2003 |
| WO | WO 03/106684 | 12/2003 |
| WO | WO 2004/027072 | 4/2004 |
| WO | WO 2004/055215 | 7/2004 |
| WO | WO 2004/056986 A2 | 7/2004 |
| WO | WO 94/23046 | 10/2004 |
| WO | WO 2005/040377 | 5/2005 |
| WO | WO 2006/005718 | 1/2006 |
| WO | WO 2006/048459 A | 5/2006 |
| WO | WO 2007/096399 | 8/2007 |
| WO | WO 2007/108675 | 9/2007 |

OTHER PUBLICATIONS

Kim, et al., Poly(A)-dependent Transcription Termination; The Journal of Biological Chemistry; vol. 278, No. 43; Oct. 24, 2003; pp. 41691-41701.

Liu, et al.; Construction of Discistronic expression vector in mammalian cell with IRES and dhfr; Bull Acad Mil Med Sci, Mar. 2000; vol. 24, No. 1; pp. 9-11.

Wells, et al., Codon optimization, gentic insulation, and an rtTA reporter improve performance of the tetracycline switch; Transgenic Research 8: 1999; pp. 371-381.

Office Action for U.S. Appl. No. 11/156,910 dated Feb. 11, 2008.
Office Action for U.S. Appl. No. 11/156,910 dated Sep. 18, 2009.
Office Action for U.S. Appl. No. 11/156,910 dated Apr. 15, 2010.
Office Action for U.S. Appl. No. 11/269,525 dated Aug. 5, 2008.
Office Action for U.S. Appl. No. 11/269,525 dated Feb. 9, 2009.
Office Action for U.S. Appl. No. 11/269,525 dated Oct. 23, 2009.
Office Action for U.S. Appl. No. 11/269,525 dated Apr. 5, 2010.
Office Action for U.S. Appl. No. 11/359,953 dated Nov. 26, 2008.
Office Action for U.S. Appl. No. 11/359,953 dated Jan. 14, 2010.
Office Action for U.S. Appl. No. 11/416,490 dated Jan. 29, 2009.
Office Action for U.S. Appl. No. 11/416,490 dated Oct. 8, 2009.
Office Action for U.S. Appl. No. 11/580,494 dated Mar. 23, 2009.
Office Action for U.S. Appl. No. 11/580,605 dated Mar. 20, 2009.
Office Action for U.S. Appl. No. 11/580,619 dated Mar. 23, 2009.
Office Action for U.S. Appl. No. 11/580,620 dated Mar. 23, 2009.
Office Action for U.S. Appl. No. 11/580,644 dated Mar. 20, 2009.
Office Action for U.S. Appl. No. 11/580,760 dated Mar. 23, 2009.
Office Action for U.S. Appl. No. 11/632,012 dated Apr. 29, 2009.
Office Action for U.S. Appl. No. 11/632,012 dated Mar. 26, 2010.
Office Action for U.S. Appl. No. 11/888,568 dated Dec. 11, 2008.
Office Action for U.S. Appl. No. 11/978,483 dated Aug. 21, 2008.
Office Action for U.S. Appl. No. 11/978,483 dated Jan. 11, 2010.
Office Action for U.S. Appl. No. 11/978,483 dated Jul. 15, 2009.
Notice of Allowance for U.S. Appl. No. 11/580,494 dated Nov. 25, 2009.
Notice of Allowance for U.S. Appl. No. 11/580,604 dated Nov. 3, 2009.
Notice of Allowance for U.S. Appl. No. 11/580,605 dated Dec. 2, 2009.
Notice of Allowance for U.S. Appl. No. 11/580,620 dated Dec. 2, 2009.
Notice of Allowance for U.S. Appl. No. 11/580,644 dated Nov. 4, 2009.
Notice of Allowance for U.S. Appl. No. 11/580,760 dated Nov. 4, 2009.
Notice of Allowance for U.S. Appl. No. 11/888,568 dated Jul. 6, 2010.

Aranda et al., Definition of Transcriptional Pause Elements in Fission Yeast, Molecular and Cellular Biology, Feb. 1999, pp. 1251-1261, vol. 19, No. 2.

Auten et al., "Effect of Scaffold Attachment Region on Transgene Expression in Retrovirus Vector-Transduced Primary T cells and Macrophages," Human Gene Therapy, May 20, 1999, pp. 1389-1399, vol. 10, No. 8.

Bell et al., Insulators and Boundaries: Versatile Regulatory Elements in the Eukaryotic Genome, Science, Jan. 19, 2001, pp. 447-450, vol. 291, No. 5503.

Bird et al., Methylation-Induced Repression-Belts, Braces and Chomatin, Cell, Nov. 24, 1999, pp. 451-454, vol. 99.

Burgess-Beusse et al., The insulation of genes from external enhancers and silencing chromatin, PNAS, Dec. 10, 2002, pp. 16433-16437, vol. 99, Suppl. 4.

Chan et al., p300-CBP proteins: HATs for transcriptional bridges and scaffolds, Journal of Cell Science, 2001, pp. 2363-2373, vol. 114.

Chung et al., A 5' Element of the Chicken Beta-Globin Domain Serves as an Insulator in Human Erythroid Cells and Protects against Position Effect in *Drosophila*, Aug. 13, 1993, Cell, pp. 505-514, vol. 74.

Database EMBL 'Online! Dec. 15, 1999. "*Homo sapiens* BAC clone RP11-572N21 from 2 complete sequence." XP002359988 retrieved from EBI accession No. EM_PRO:AC018470. database accession No. AC018470. for SEQ ID No. 17.

(56) References Cited

OTHER PUBLICATIONS

Database EMBL 'Online! Mar. 15, 1999, "*Homo sapiens* chromosome UNK clone CTA-435J10. working draft sequence, 1 unordered pieces," XP002359997 retrieved from EBI accession No. EM_PRO:AC007044, database accession No. AC007044 for SEQ ID No. 61.

Database EMBL 'Online! Mar. 19, 1998, CIT-HSP-2172C8.TF CIT-HSP *Homo sapiens* genomic clone 2172C8, genomic survey sequence, XP002359995 retrieved from EBI accession No. EM_PRO:B92131, database accession No. B92131 for SEQ ID No. 44.

Database EMBL 'Online! Dec. 23, 1999. "Human DNA sequence from clone RP11-54H19 on chromosome I Contains the 3' end of the LMNA gene for lamin A/C, the gene for a novel protein similar to semaphorins (FLJ12287). A novel gene (KIAA0446), the PMFI gene for polyamine-modulated factor 1, the BGLAP gene for bone gamma-carboxyglutamate (gla) p," XP002359989, retrieved from EBI accession No. EM_PRO:AL135927, database accession No. AL135927 for SEQ ID No. 27.

Database EMBI 'Online! Sep. 24, 2000. "*Homo sapiens* chromosome 4 clone RP11-680118. working draft sequence. 25 unordered pieces." XP002359987 retrieved from EBI accession No. EM_PRO:AC080087. database accession No. AC080087 for SEQ ID No. 9.

Database EMBL 'Online! Jan. 25, 2001, "QV2-NN0045-081200-535-c10 NN0045 *Homo sapiens* cDNA. mRNA sequence." XP002359993 retrieved from EBI accession No. EM_PRO:BF960930, database accession No. BF960930 for SEQ ID No. 43.

Database EMBL 'Online! Apr. 26, 2001, "RST28606 Athersys RAGE Library *Homo sapiens* cDNA. mRNA sequence." XP002359990 retrieved from EBI accession No. EM_PRO:BG209092. database accession No. BG209092 for SEQ ID No. 40.

Database EMBL 'Online! Dec. 15, 1999, "*Homo sapiens* BAC clone RP11-572N21 from 2, complete sequence." XP002359988 retrieved from EBI accession No. EM_PRO:AC018470, database accession No. AC018470, for SEQ ID No. 17.

Database EMBL 'Online! Oct. 28, 1998, "*Homo sapiens* neurexin III-alpha gene, partial cds." XP002359992 retrieved from EBI accession No. EM_PRO:AF099810. database accession No. AF099810 for SEQ ID No. 43.

Database EMBL 'Online! Sep. 29, 1999, "*Homo sapiens* genomic DNA, chromosome 22q11.2. Cat Eye Syndrome region, clone:N64E9." XP002359991, retrieved from EBI accession No. EM_PRO:AP000526, database accession No. AP000526 for SEQ ID No. 40.

Database EMBL 'Online! Sep. 29, 1999, *Homo sapiens* genomic DNA. chromosome 22q11.2. Cat Eye Syndrome region. clone:N14H11. XP002359994 retrieved from EBI accession No. EM_PRO:AP000525. database accession No. AP000525 for SEQ ID No. 44.

Database EMBL 'Online! Sep. 29, 1999, "*Homo sapiens* genomic DNA. chromosome 22q11.2, Cat Eye Syndrome region, clone:c91G6." XP002359996 retrieved from EBI accession No. EM_PRO:AP000528, database accession No. AP000528 for SEQ ID No. 45.

Database EMBL 'Online! Feb. 3, 2004, "Sequence 33099 from Patent W002068579," XP002359986 retrieved from EBI accession No. EM_PRO:CQ747165, database accession No. CQ747165 for SEQ ID No. 9.

Database EMBL 'Online! Aug. 4, 1999, "*Homo sapiens* chromosome 19 clone CTD-2540B15 complete sequence." XP002359985 retrieved from EBI accession No. EM_PRO:AC008738. database accession No. AC008738 for SEQ ID No. 7.

Database EMBL 'Online!, Jul. 8, 1992, *H. sapiens* HOX4B gene upstream sequence XP002348163 retrieved from EBI, Database accession No. X67079, Abstract.

De Boer et al., Portable Shine-Dalgarno regions; nucleotides between the Shine-Dalgarno sequence and the start codon affect the translation efficiency, Gene Amplification and Analysis, 1983, pp. 103-116, vol. 3.

Dummitt et al., "N-Terminal Methionine Removal and Methionine Metabolism in *Saccharomyces cerevisiae*," Journal of Cellular Biochemistry, 2003, pp. 964-974, vol. 89.

Eggermont et al., Poly(A) signals and transcriptional pause sites combine to prevent interference between RNA polymerase II promoters, The EMBO Journal, 1993, pp. 2539-2548. vol. 12, No. 6.

Emery et al., "A chromatin insulator protects retrovirus vectors from chromosomal position effects," Proceedings of the National Academy of Sciences of USA, Aug. 1, 2000, pp. 9150-9155, vol. 97, No. 16.

European Search Report for EP 04 10 5593 dated Jun. 21, 2005.

European Search Report dated Dec. 22, 2005.

Farrell et al., Conserved CTCF Insulator Elements Flank the Mouse and Human Beta-Globin Loci, Molecular and Cellular Biology, Jun. 2002, pp. 3820-3831, vol. 22. No. 11.

Genbank Accession AY237385. I (AAO89266, GI:37933202).

Glucksmann et al., Database accession No. AAH76193, Oct. 29, 2001.

Han et al., "Matrix attachment regions (MARs) enhance transformation frequency and transgene expression in poplar," Transgenic Research, 1997, pp. 415-420, vol. 6.

Hellen et al., Internal ribosome entry sites in eukaryotic mRNA molecules, Genes and Development, 2001, pp. 1593-1612, vol. 15, No. 13, Cold Spring Harbor Laboratory Press.

Johnson et al., Requirements for utilization of CREB binding protein by hypersensitive site two of the Beta-globin locus control region, Nucleic Acids Research 2002, pp. 1522-1530, vol. 30, No. 7.

Kaufman et al., Improved vectors for stable expression fo foreign genes in mammalian cells by use of the untranslated leader sequence for EMC virus, Nucleic Acids Research, Jul. 22, 1991, pp. 4485-4490, vol. 19, No. 16.

Kellum et al., A Group of scs Elements Function as Domain Boundaries in an Enhancer-Blocking Assay, Molecular and Cellular Biology, May 1992, pp. 2424-2431, vol. 12, No. 5.

Kozak, Initiation of translation in prokaryotes and eukaryotes, Gene, 1999, pp. 187-208, vol. 234.

Kozak, M., An analysis of 5'-noncoding sequences from 699 vertebrate messenger RNAs, Nucleic Acids Res.. 1987, pp. 8125-8148. vol. 15. No. 20.

Kozak. M., Context Effects and Inefficient Initiation at Non-AUG Codons in Eucaryotic Cell-Free Translation Systems. Molecular and Cellular biology, Nov. 1989. pp. 5073-5080, vol. 9, No. 11.

Kozak, M., Point Mutations Define a Sequence Flanking the AUG Initiator Codon That Modulates Translation by Eukaryotic Ribosomes, Cell. Jan. 31, 1986, pp. 283-292, vol. 44.

Kozak, M., Recognition of AUG and alternative initiator codons in augmented by G in position +4 but is not generally affected by the nucleotides in positions +5 and +6, The EMBO Journal, 1997, pp. 2482-2492, vol. 16, No. 9.

Kozak, Pushing the limits of the scanning mechanism for initiation of translation, Gene, 2002, pp. 1-34, vol. 299.

Kuhn et al., Functional Analysis of the Internal Translation Initiation Site of Foot-and-Mouth Disease Virus, Journal of Virology, Oct. 1990, pp. 4625-4631, vol. 64, No. 10.

Kwaks et al., "Indentification of anti-repressor elements that confer high stable protein in production in mammalian cells," Nature Biotechnology, May 20, 2003, pp. 553-558, vol. 21, No. 5.

Kwaks et al., Employing epigenetics to augment the expression of therapeutic proteins in mammalian cells, Trends in Biotechnology, Mar. 2006, pp. 137-142, vol. 24, No. 3.

Kwaks et al., Targeting of histonre acetyltranscerase domain to promoter enhances protein expression levels in mammalian cells, Journal of Biotechnology, 2005, pp. 35-46, vol. 115.

Lee et al., Engineering Chinese hamster ovary (CHO) cells to achieve an inverse growth-associated production of a foreign protein, β-galactosidase, Cytotechnology, 1998, pp. 73-80, vol. 28.

Lopez De Quinto et al., Parameters influencing translational efficiency in aphthovirus IRES-based bicistronic expression vectors, Gene, 1998, pp. 51-56, vol. 217.

(56) References Cited

OTHER PUBLICATIONS

Maniatis et al., Recognition Sequences of Repressor and Polymerase in the Operators of Bacteriophage Lambda, Cell, Jun. 1975, pp. 109-113, vol. 5.
Martinez-Balbas et al., The acetyltransferase activity of CBP stimulates transcription, The EMBO Journal, 1998, pp. 2886-2893, vol. 17, No. 10.
Mielke et al., "Stabilized, long-term expression of heterodimeric proteins from tricistronic mRNA," Gene, Aug. 22, 2000, pp. 1-8, vol. 254, No. 1-2.
Migliaccio et al., "Stable and unstable transgene integration sites in the human genome: extinction of the Green Fluorescent Protein transgene in K562 cells," Gene, Oct. 3, 2000, pp. 197-214, vol. 256, No. 1-2.
Otte et al., Various Expression-Augmenting DNA Elements Benefit from STAR-Select. a Novel High Stringency Selection System from Protein Expression. Biotechnol. Prog., 2007. pp. 801-807. vol. 23.
Partial European Search Report, EP 05 07 6209, dated Oct. 7, 2005.
PCT International Preliminary Report on Patentability, PCT/EP2005/055794, dated Jan. 26, 2007.
PCT International Search Report dated Apr. 24, 2007, International Application No. PCT/EP2007/053984.
PCT International Search Report, PCT/EP2007/051696, dated Mar. 5, 2008.
PCT Written Opinion, PCT/EP2007/051696 dated Mar. 5, 2008.
PCT International Preliminary Report, PCT/EP2007/053984, dated Jul. 25, 2008.
Pile et al., "GAGA Factor-dependent Transcription and Establishment of DNase Hypersensitivity Are Independent and Unrelated Events In Vivo," J. of Biological Chemistry, Jan. 14, 2000, pp. 1398-1404, vol. 275, No. 2.
Reik et al., Biotechnologies and therapeutics: Chromatin as a target, Current Opinion in Genetics & Development, 2002, pp. 233-242, vol. 12.
Razin, CpG methylation. chromatin structure and gene silencing-a three-way connection. The EMBO Journal. 1998. pp. 4905-4908, vol. 17, No. 17.
Seum et al., A GAL4-HP1 fusion protein targeted near heterochromatin promotes gene silencing, Chromosoma, 2000, pp. 453-459, vol. 109.
Sigrist et al., "Chromatin Insulator Elements Block the Silencing of a Target Gene by the *Drosophila* Polycomb Response Element (PRE) but Allow trans Interactions Between PREs on Different Chromosomes," Genetics, Sep. 1997, pp. 209-211, vol. 147, No. 1.
Van Blokland et al., A novel, high stringency selection system allows screening of few clones for high protein expression, Journal of Biotechnology, 2007, pp. 237-245, vol. 128.
Van Der Vlag et al., Transcription Repression Mediated by Polycomb Group Proteins and Other Chromatin-associated Repressors Is Selectively Blocked by Insulators, Journal of Biological Chemistry, Jan. 7, 2000, pp. 697-704, vol. 275, No. 1.
West et al., "Insulators: many functions, many mechanisms," Genes and Development, Feb. 1, 2002, pp. 271-288, vol. 16, No. 3.
Williams et al,. CpG-island fragments from the HNRPA2B1/CBX3 genomics locus reduce silencing and enhance transgene expression from the hCM V promotor/enhancer in mammalian cells, published Jun. 3, 2005. <http://www.biomedcentral.com/1472-6750/5/17>.
Yew et al., Molecular Therapy. 2002, pp. 731-738. vol. 5.
Zeocin™, Instruction Manual, Version J. Aug. 22, 2002.
Database EMBL, Jun. 19, 2002, accession No. AL773524, Human DNA sequence from clone RP11-250K24 on chromosome 9 Contains a calponin 2 (CNN2) pseudogene and a novel pseudogene.
Database EMBL, Aug. 2, 2003, accession No. AC146157, Pantroglodytes BAC clone RP43-2A11 from 7, complete sequence.
Database EMBL, May 26, 2000, accession No. AC069285, *Homo sapiens* BAC clone RP11-196D18 from 7, complete sequence.
Database EMBL, Aug. 9, 2002, accession No. AL845331, Human DNA sequence from clone RP11-407P15 on chromosome 9.
European Search Report for EP 05 07 6209 dated Dec. 22, 2005.
GenBank Accession No. AC007689.13. GI: 8573011, Jun. 25, 2000.
GenBank Accession No. AL021960, GI: 4584387, publicly available Apr. 1999, last visited Sep. 26, 2011.
GenBank Accession No. AL096766.12, GI: 5738627, Aug. 17, 1999.
GenBank Accession No. AL449105, GI: 14268199, publicly available Jun. 2001, printed as pp. 1-47.
GenBank Accession No. AL449105, GI: 46559322, publicly available Jan. 2009, printed as pp. 1-63.
Office Action for U.S. Appl. No. 11/359,953 dated Aug. 6, 2009.
Office Action for U.S. Appl. No. 11/359,953 dated Sep. 28, 2010.
PCT International Preliminary Examination Report, PCT/NL03/00850, dated Mar. 24, 2005.
PCT International Search Report for Application PCT/EP2007/052664, dated May 25, 2007.
PCT International Search Report PCT/NL02/00390. dated Jul. 29, 2003.
PCT International Search Report. PCT/NL03/00432. dated Jan. 9, 2004.
PCT International Search Report. PCT/NL03/00850. dated Jun. 9, 2004.
PCT Written Opinion of the International Searching Authority for Application PCT/EP2007/052664 dated May 25, 2007.
Chang et al., Baculovirus gp64 Gene Expression: Negative Regulation by Minicistron, Journal of Virology, Oct. 1997, pp. 7448-7460, vol. 71, No. 10/.
Frengen, et al., Modular bacterial artificial chromosome vectors for transfer of large inserts into mammalian cells, Genomics, vol. 68, No. 2, pp. 118-126, Sep. 2000.
Moser et al., An Update of pTRIDENT Multicistronic Expression Vectors: pTRIDENTs Containing novel Streptogramin-Responsive Promoters, Biotechnol. Prog., 2000, pp. 724-735, vol. 16.
Parola et al., The Peptide Product of a 5' Leader Cistron in the beta 2 Adrenergic Receptor mRNA Inhibits Receptor Synthesis, The Journal of Biol. Chem., 1994, pp. 4497-4505, vol. 269, No. 6.
Shizuya, et al., Cloning and stable maintenance of 300-kilbase-pair fragments of human DNA in *Escherichia coli* using an F-factor-based-vector. Proc Natl Acad Sci USA. vol. 89, No. 18, pp. 8794-8797, Sep. 1992.
Son et al., Excision of the First Intron from the Gonadotropin-releasing Hormone (GnRH) Transcript Serves as a Key Regulatory Step for GnR Biosynthesis, The Journal of Biological Chemistry, 2003, pp. 18037-18044, vol. 278, No. 20.
Tomita et al., Translational properties of the human papillomavirus type-6 L1-coding mRNA, Gene, Nov. 15, 1993, pp. 223-225, vol. 133, No. 2.
Youn, et al.; An Intronic Silencer of the Mouse Perforin Gene, Mol. Cells., 2001, pp. 61-68, vol. 33, No. 1.
U.S. Appl. No. 13/135,966, filed Jul. 18, 2011, Otte et al., Selection of Host Cells Expressing Protein at High Levels.
Kozak et al., The Scanning Model for Translation: An Update, The Journal of Cell Biology, Feb. 1989, pp. 229-241, vol. 108.
Sedman et al., Mechanisms of Synthesis of Virion Proteins from the Functionally Bigenic Late mRNAs of Simian Virus 40, Journal of Virology, Mar. 1988, pp. 954-961, vol. 62, No. 3.
Carroll et al., Translation of Equine Infectious Anemia Virus Bicistronic tat-rev mRNA Requires Leaky Ribosome Scanning of the tat CTG Initiation Codon, Journal of Virology, Mar. 1993, pp. 1433-1440, vol. 67, No. 3, American Society for Microbiology.
Hennecke et al., Composition and arrangement of genes define the strength of IRES-driven translation in bicistronic mRNAs, Nucleic Acids Res., 2001, pp. 3327-3334, vol. 29, No. 16, Oxford University Press.
Kozak, Downstream secondary structure facilitates recognition of initiator codons by eukaryotic ribosomes, PNAS, 1990, pp. 8301-8305, vol. 87, No. 21.
Moser et al., An Update of pTRIDENT Multicistronic Expression Vectors: pTRIDENTs Containing Novel Streptogramin-Responsive Promoters, Biotechnol. Prog., 2000, pp. 724-735, vol. 16, Zurich, Switzerland.
Rees et al., Bicistronic Vector for the Creation of Stable Mammalian Cell Lines that Predisposes All Antibiotic-Resistant Cells to Express

(56) References Cited

OTHER PUBLICATIONS

Recombinant Protein, Biotechniques, 1996, pp. 102-110, vol. 20, No. 1, Middlesex, UK.
Tang et al., A transformation system for the nonuniversal CUG$^{Ser}$ codon usage species Candida rugosa, J. Microbiol. Methods, 2003, pp. 231-238, vol. 52.

Sedman et al., "Translation Initiation at a Downstream AUG Occurs with Increased Efficiency When the Upstream AUG Is Located Very Close to the 5' Cap," Jounal of Virology, Jan. 1990, pp. 454-457, vol. 64, No. 1.

USPTO STIC Sequence search of SEQ ID No. 128 (2011, pp. 1-4).

* cited by examiner

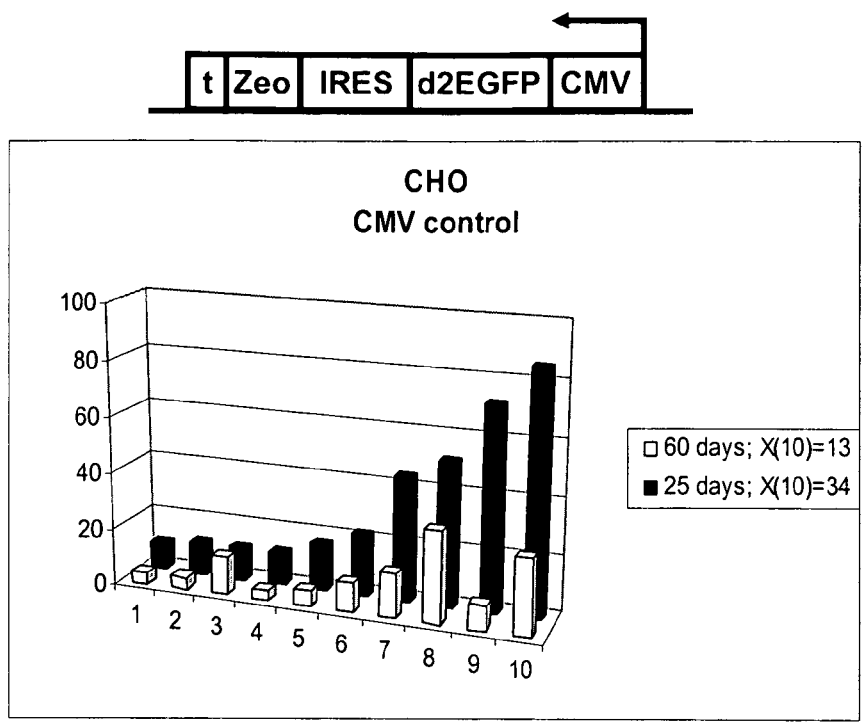
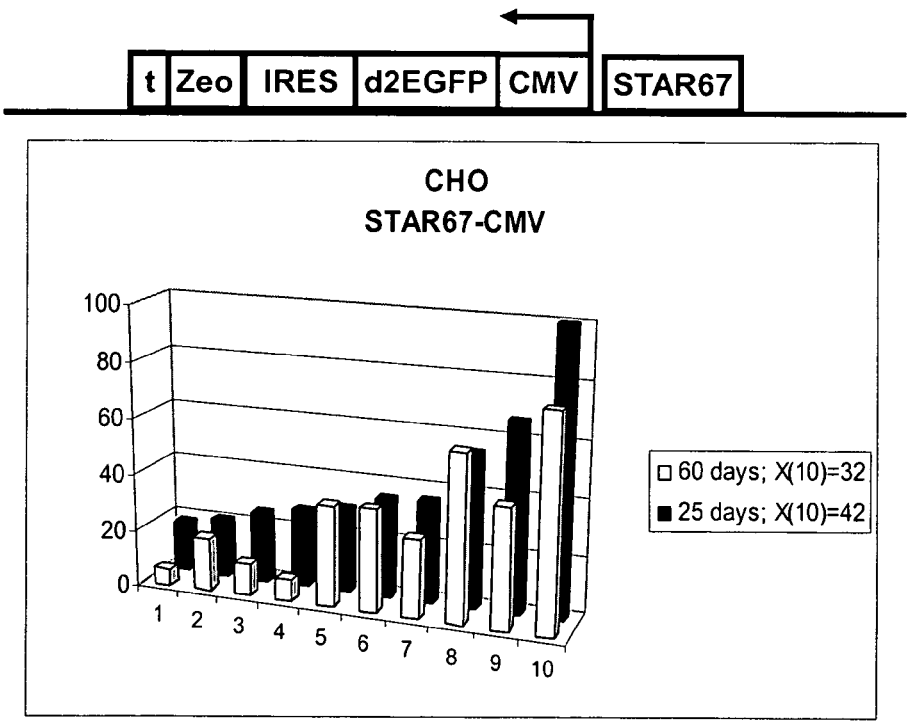
FIG. 2

A
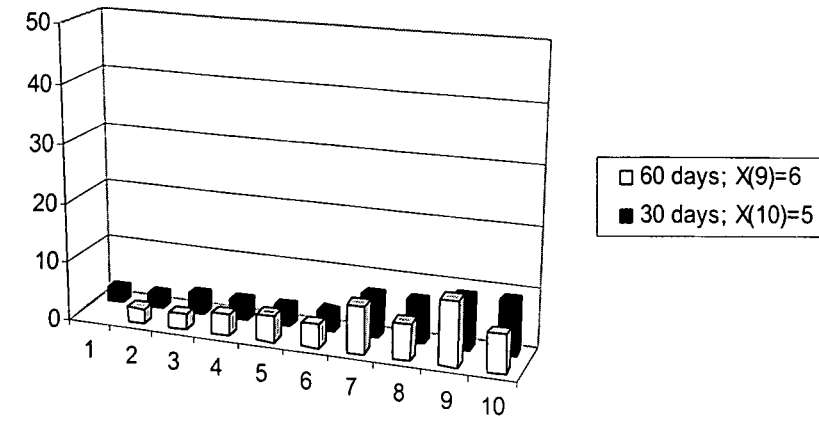
B
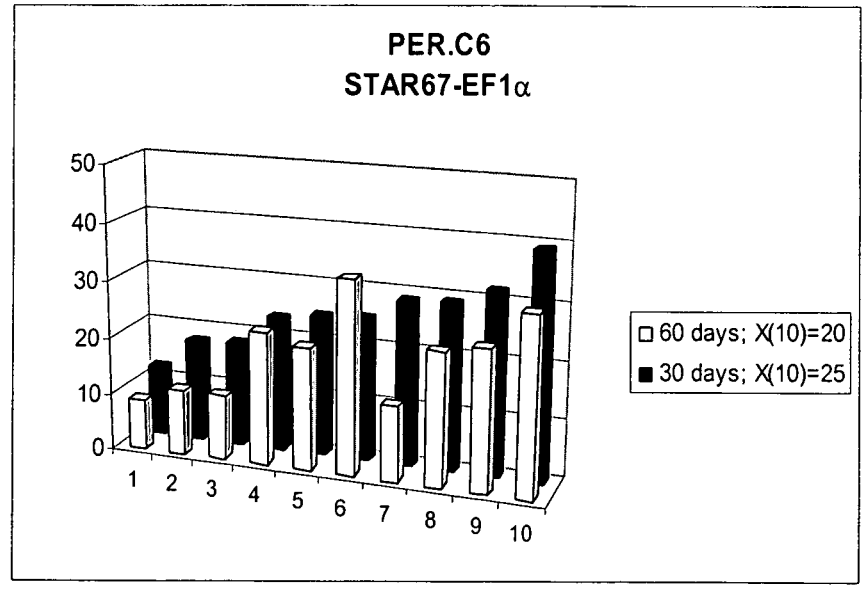
FIG. 6

A
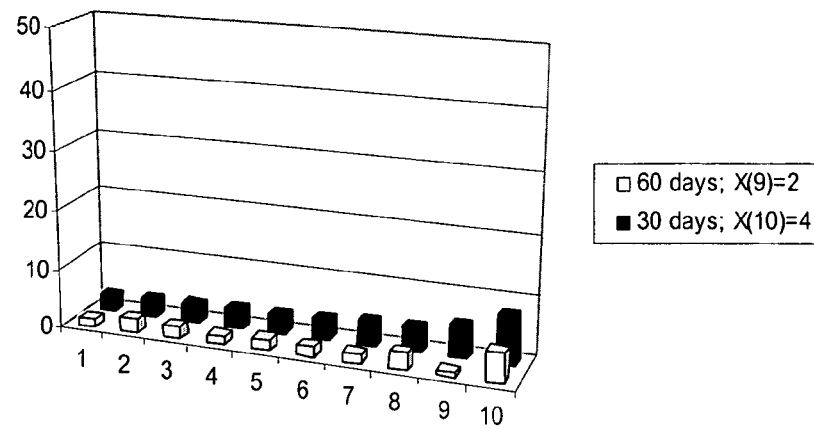
B
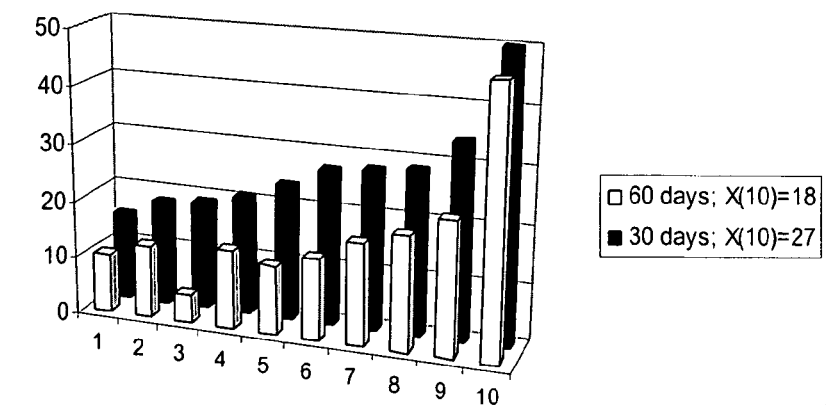
FIG. 7

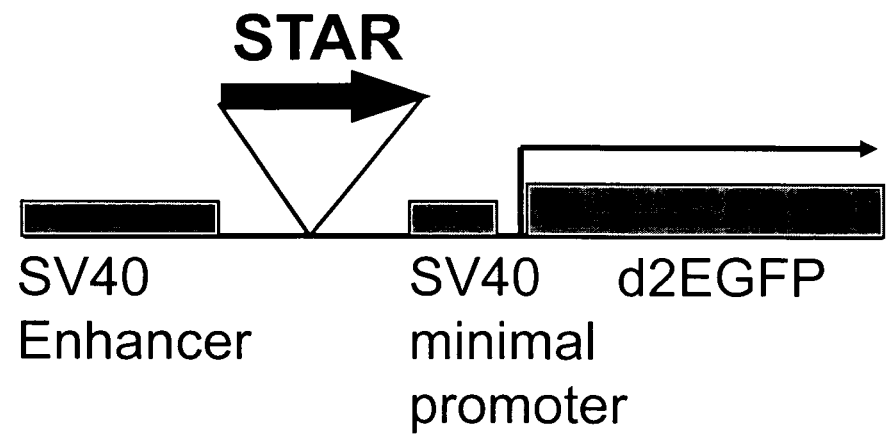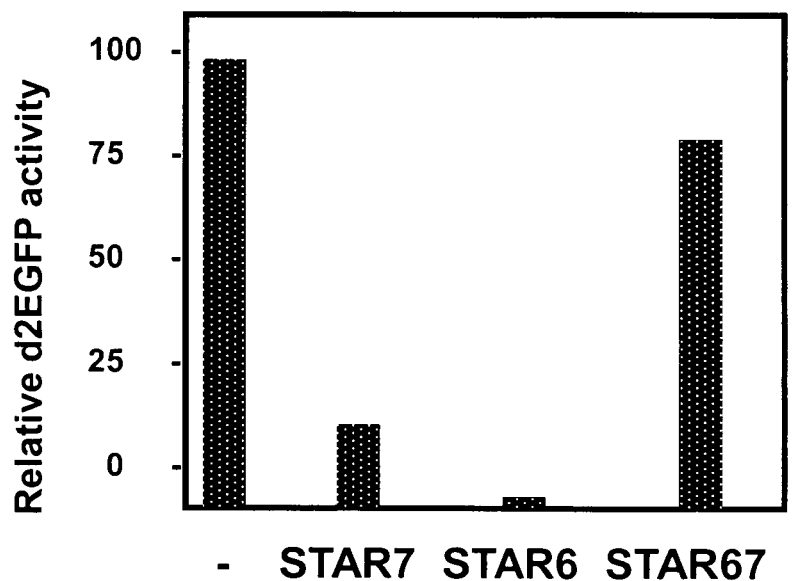
FIG. 10

A
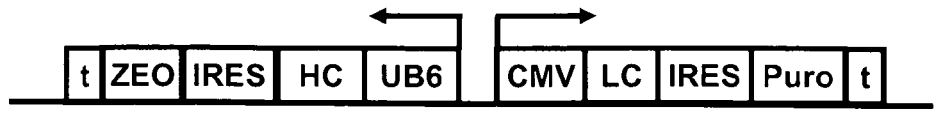
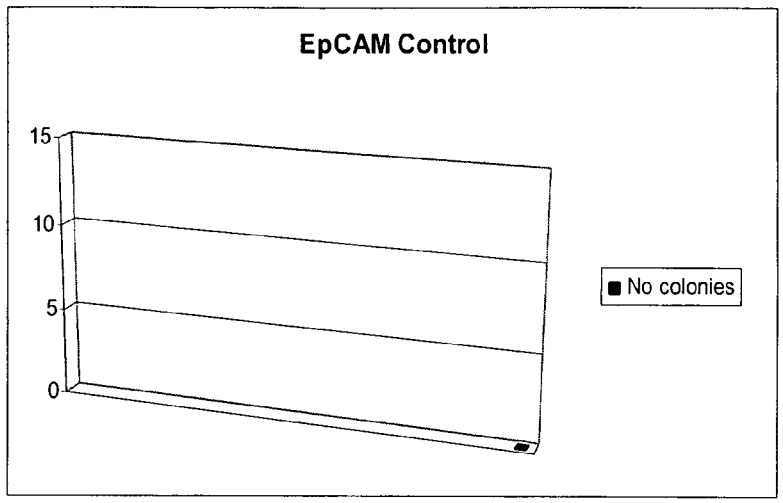
B
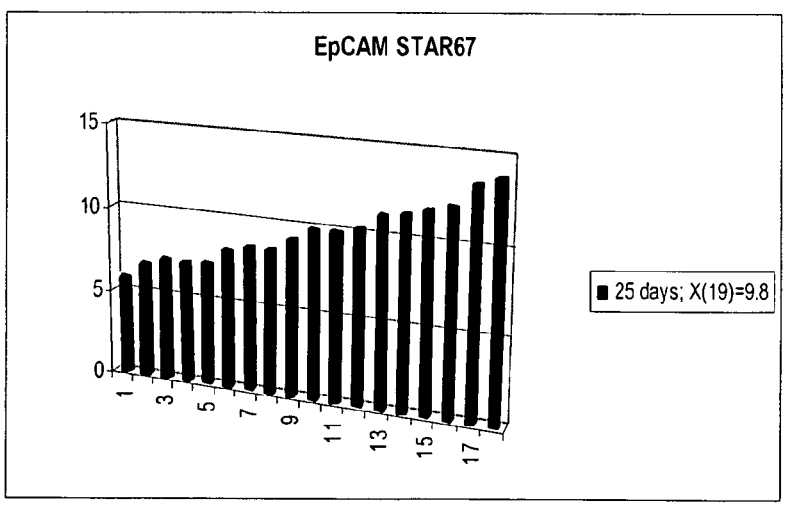
FIG. 11

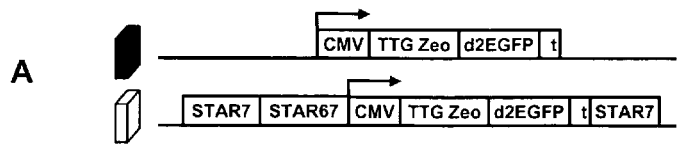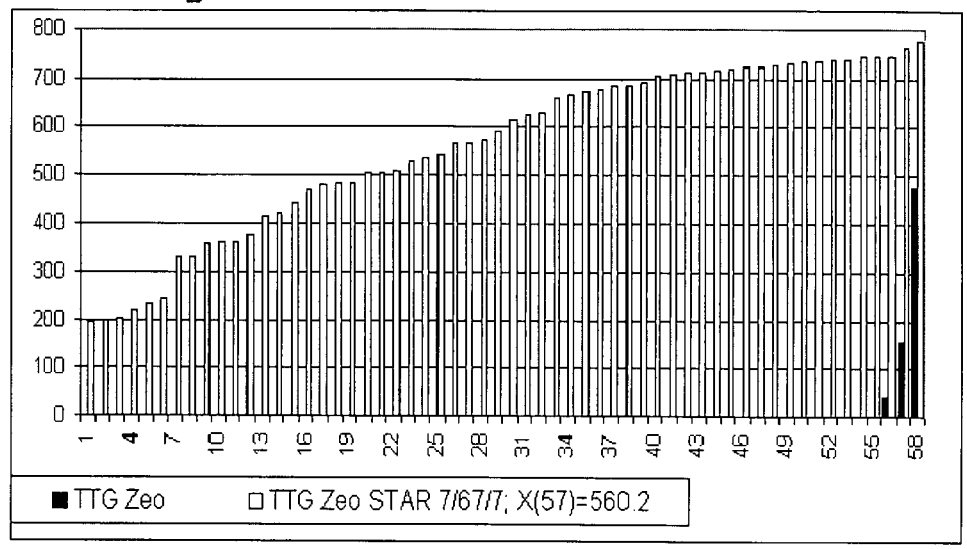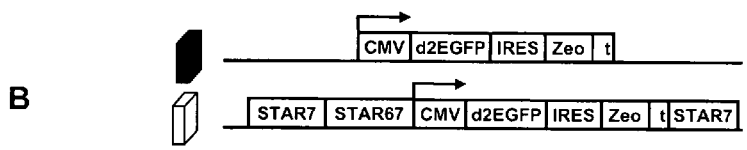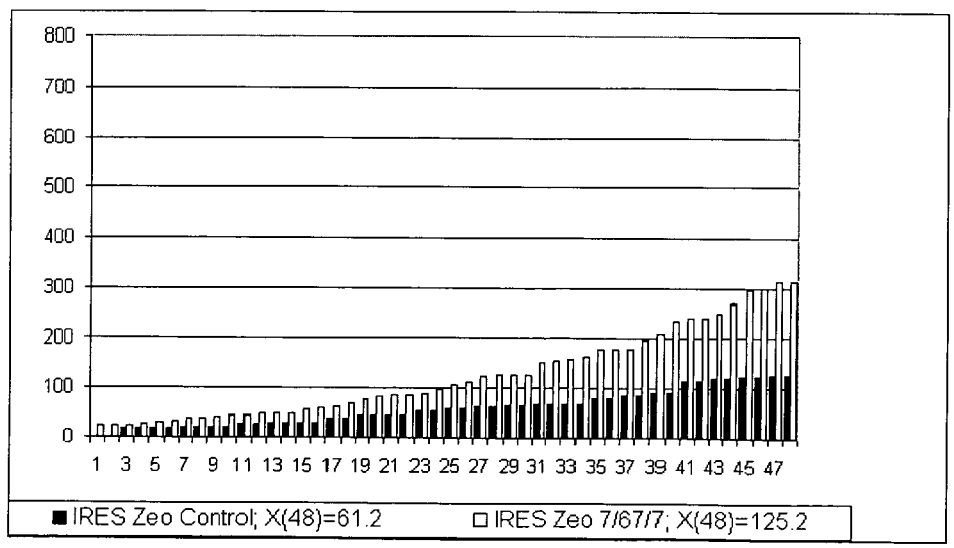
FIG. 15

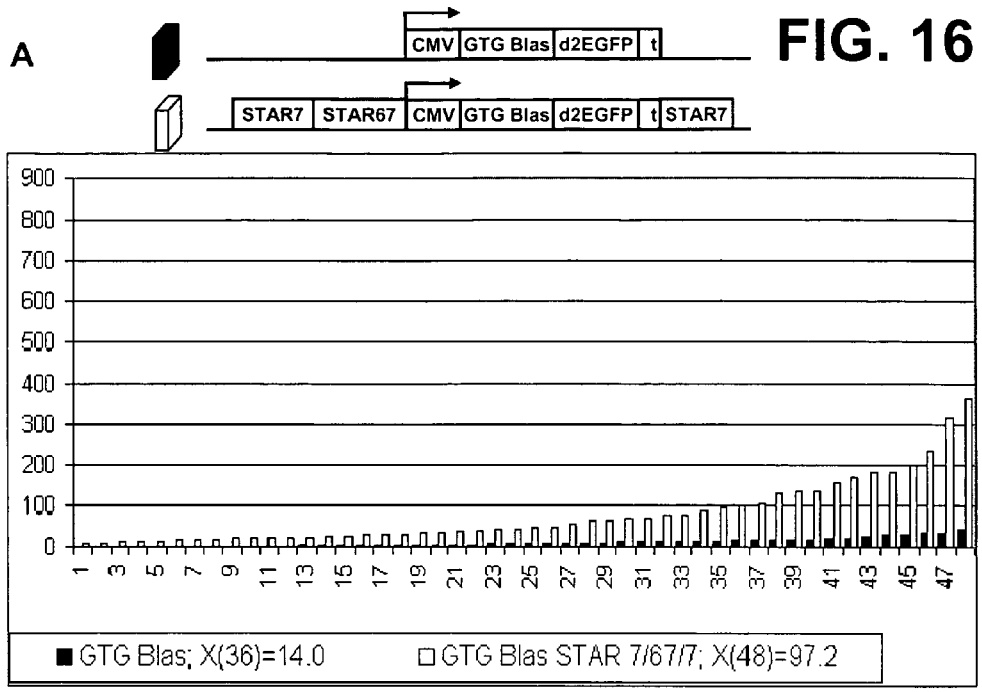
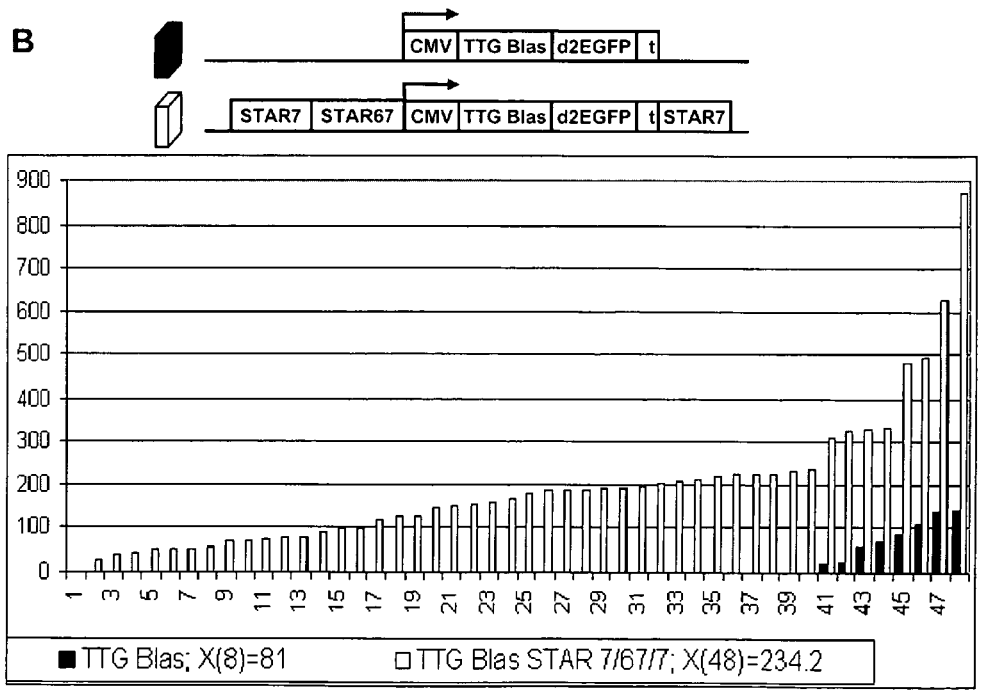
FIG. 16

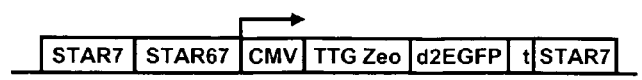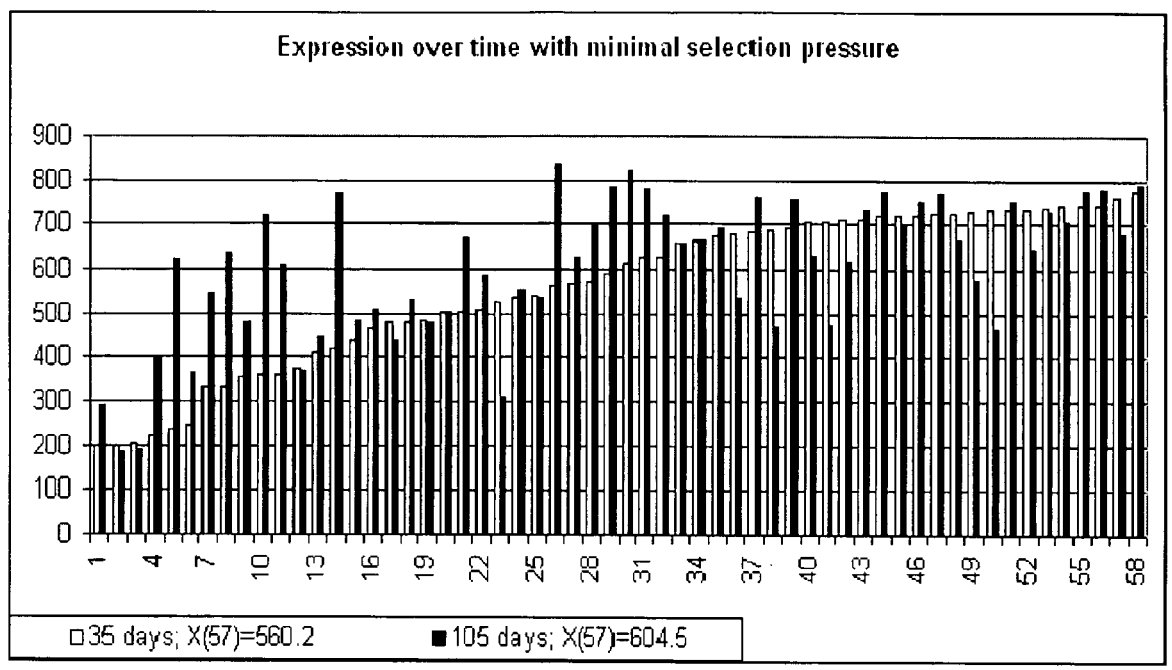
FIG. 18

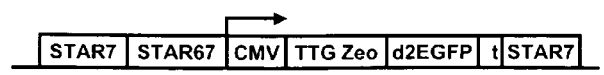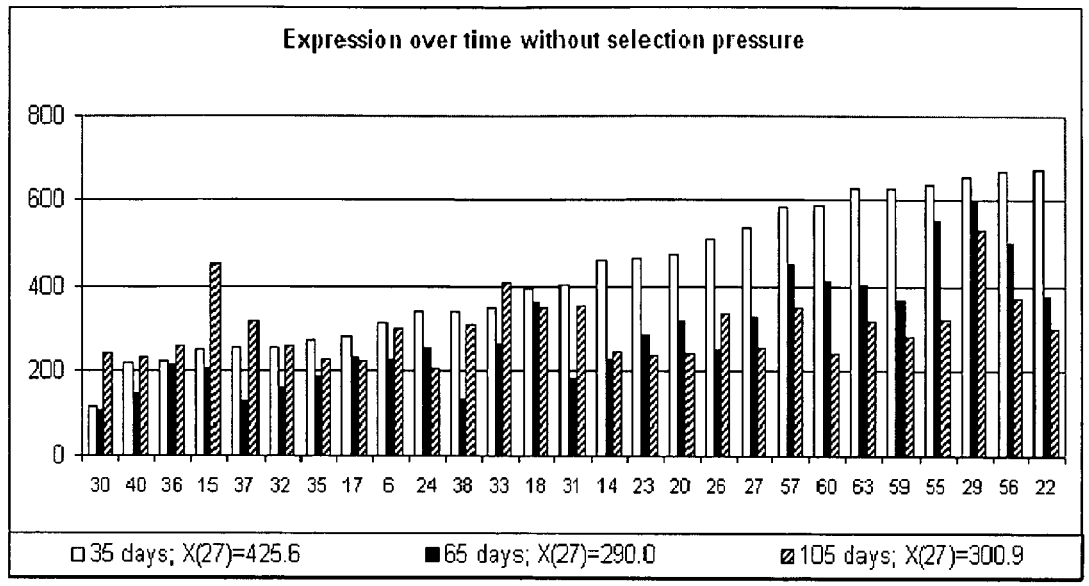
FIG. 19

ATGGCCAAGTTGACCAGTGCCGTTCCGGTGCTCACCGCGCGA
CGTCGCCGGAGCGGTCGAGTTCTGGACCGACCGGCTCGGGTTCT
CCCGGGACTTCGTGGAGGACGACTTCGCCGGTGTGGTCCGGGAC
GACGTGACCCTGTTCATCAGCGCGGTCCAGGACCAGGTGGTGCC
GGACAACACCCTGGCCTGGGTGTGGGTGCGCGGCCTGGACGAGC
TGTACGCCGAGTGGTCGGAGGTCGTGTCCACGAACTTCCGGGAC
GCCTCCGGGCCGGCCATGACCGAGATCGGCGAGCAGCCGTGGGG
GCGGGAGTTCGCCCTGCGCGACCCGGCCGGCAACTGCGTGCACT
TCGTGGCCGAGGAGCAGGACTGA

FIG. 26

ATGGCCAAGCCTTTGTCTCAAGAAGAATCCACCCTCATTGAAAGAGCAAC
GGCTACAATCAACAGCATCCCCATCTCTGAAGACTACAGCGTCGCCAGCG
CAGCTCTCTCTAGCGACGGCCGCATCTTCACTGGTGTCAATGTATATCAT
TTTACTGGGGGACCTTGTGCAGAACTCGTGGTGCTGGGCACTGCTGCTGC
TGCGGCAGCTGGCAACCTGACTTGTATCGTCGCGATCGGAAATGAGAACA
GGGGCATCTTGAGCCCCTGCGGACGGTGCCGACAGGTGCTTCTCGATCTG
CATCCTGGGATCAAAGCCATAGTGAAGGACAGTGATGGACAGCCGACGGC
AGTTGGGATTCGTGAATTGCTGCCCTCTGGTTATGTGTGGGAGGGCTAA

FIG. 27

ATGACCGAGTACAAGCCCACGGTGCGCCTCGCCACCCGCGACGACGTCCCC
AGGGCCGTACGCACCCTCGCCGCCGCGTTCGCCGACTACCCCGCCACGCGC
CACACCGTCGATCCGGACCGCCACATCGAGCGGGTCACCGAGCTGCAAGAA
CTCTTCCTCACGCGCGTCGGGCTCGACATCGGCAAGGTGTGGGTCGCGGAC
GACGGCGCCGCGGTGGCGGTCTGGACCACGCCGGAGAGCGTCGAAGCGGGG
GCGGTGTTCGCCGAGATCGGCCCGCGATGGCCGAGTTGAGCGGTTCCCGG
CTGGCCGCGCAGCAACAGATGGAAGGCCTCCTGGCGCCGCACCGGCCCAAG
GAGCCCGCGTGGTTCCTGGCCACCGTCGGCGTCTCGCCCGACCACCAGGGC
AAGGGTCTGGGCAGCGCCGTCGTGCTCCCCGGAGTGGAGGCGGCCGAGCGC
GCCGGGGTGCCCGCCTTCCTGGAGACCTCCGCGCCCCGCAACCTCCCCTTC
TACGAGCGGCTCGGCTTCACCGTCACCGCCGACGTCGAGTGCCCGAAGGAC
CGCGCGACCTGGTGCATGACCCGCAAGCCCGGTGCCTGA

FIG. 28

ATGGTTCGACCATTGAACTGCATCGTCGCCGTGTCCCAAAATATGGGGATT
GGCAAGAACGGAGACCTACCCTGGCCTCCGCTCAGGAACGAGTTCAAGTAC
TTCCAAAGAATGACCACAACCTCTTCAGTGGAAGGTAAACAGAATCTGGTG
ATTATGGGTAGGAAAACCTGGTTCTCCATTCCTGAAGAATCGACCTTTA
AAGGACAGAATTAATATAGTTCTCAGTAGAACTCAAAGAACCACCACGA
GGAGCTCATTTTCTTGCCAAAGTTTGG<u>ATGATG</u>CCTTAAGACTTATTGAA
CAACCGGAATTGGCAAGTAAAGTAGACATGGTTTGGATAGTCGGAGGCAGT
TCTGTTTACCAGGAAGCCATGAATCAACCAGGCCACCTCAGACTCTTTGTG
ACAAGGATCATGCAGGAATTTGAAAGTGACACGTTTTTCCCAGAAATTGAT
TTGGGGAAATATAAACTTCTCCCAGAATACCCAGGCGTCCTCTCTGAGGTC
CAGGAGGAAAAAGGCATCAAGTATAAGTTTGAAGTCTACGAAGAAAGAC
TAA

FIG. 29

ATGAAAAAGCCTGAACTCACCGCGACGTCTGTCGAGAAGTTTCTGATCGAA
AAGTTCGACAGCGTCTCCGACCTGATGCAGCTCTCGGAGGGCGAAGAATCT
CGTGCTTTCAGCTTCGATGTAGGAGGGCGTGGATATGTCCTGCGGGTAAAT
AGCTGCGCCGATGGTTTCTACAAAGATCGTTATGTTTATCGGCACTTTGCA
TCGGCCGCGCTCCCGATTCCGGAAGTGCTTGACATTGGGGAATTCAGCGAG
AGCCTGACCTATTGCATCTCCCGCCGTGCACAGGGTGTCACGTTGCAAGAC
CTGCCTGAAACCGAACTGCCCGCTGTTCTGCAGCCGGTCGCGGAGGCCATG
GATGCGATCGCTGCGGCCGATCTTAGCCAGACGAGCGGGTTCGGCCCATTC
GGACCGCAAGGAATCGGTCAATACACTACATGGCGTGATTTCATATGCGCG
ATTGCTGATCCCCATGTGTATCACTGGCAAACTGTGATGGACGACACCGTC
AGTGCGTCCGTCGCGCAGGCTCTCGATGAGCTGATGCTTTGGGCCGAGGAC
TGCCCCGAAGTCCGGCACCTCGTGCACGCGGATTTCGGCTCCAACAATGTC
CTGACGGACAATGGCCGCATAACAGCGGTCATTGACTGGAGCGAGGCGATG
TTCGGGGATTCCCAATACGAGGTCGCCAACATCTTCTTCTGGAGGCCGTGG
TTGGCTTGTATGGAGCAGCAGACGCGCTACTTCGAGCGGAGGCATCCGGAG
CTTGCAGGATCGCCGCGGCTCCGGGCGTATATGCTCCGCATTGGTCTTGAC
CAACTCTATCAGAGCTTGGTTGACGGCAATTTCGATGATGCAGCTTGGGCG
CAGGGTCGATGCGACGCAATCGTCCGATCCGGAGCCGGGACTGTCGGGCGT
ACACAAATCGCCCGCAGAAGCGCGGCCGTCTGGACCGATGGCTGTGTAGAA
GTACTCGCCGATAGTGGAAACCGACGCCCAGCACTCGTCCGGAGGCAAAG
GAATTCGGGAGATGGGGGAGGCTAACTGAAACACGGAAGGAGACAATACCG
GAAGGAACCCGCGCTATGACGGCAATAAAAGACAGAATAAAACGCACGGG
TGTTGGGTCGTTTGTTCATAA

FIG. 30

ATGGGATCGGCCATTGAACAAGATGGATTGCACGCAGGTTCTCCGGCCGCT
TGGGTGGAGAGGCTATTCGGCTATGACTGGGCACAACAGACAATCGGCTGC
TCTGATGCCGCCGTGTTCCGGCTGTCAGCGCAGGGGCGCCCGGTTCTTTTT
GTCAAGACCGACCTGTCCGGTGCCCTGAATGAACTGCAGGACGAGGCAGCG
CGGCTATCGTGGCTGGCCACGACGGGCGTTCCTTGCGCAGCTGTGCTCGAC
GTTGTCACTGAAGCGGGAAGGGACTGGCTGCTATTGGGCGAAGTGCCGGGG
CAGGATCTCCTGTCATCTCACCTTGCTCCTGCCGAGAAAGTATCCATCATG
GCTGATGCAATGCGGCGGCTGCATACGCTTGATCCGGCTACCTGCCCATTC
GACCACCAAGCGAAACATCGCATCGAGCGAGCACGTACTCGGATGGAAGCC
GGTCTTGTCGATCAGGATGATCTGGACGAAGAGCATCAGGGGCTCGCGCCA
GCCGAACTGTTCGCCAGGCTCAAGGCGCGATGCCCGACGGCGATGATCTC
GTCGTGACCCATGGCGATGCCTGCTTGCCGAATATATGGTGGAAATGGC
CGCTTTTCTGGATTCATCGACTGTGGCCGGCTGGGTGTGGCGGACCGCTAT
CAGGACATAGCGTTGGCTACCCGTGATATTGCTGAAGAGCTTGGCGGCGAA
TGGGCTGACCGCTTCCTCGTGCTTTACGGTATCGCCGCTCCCGATTCGCAG
CGCATCGCCTTCTATCGCCTTCTTGACGAGTTCTTCTGA

FIG. 31

ATGACCACCTCAGCAAGTTCCCACTTAAATAAAGGCATCAAGCAGGTGTAC
ATGTCCCTGCCTCAGGGTGAGAAAGTCCAGGCCATGTATATCTGGATCGAT
GGTACTGGAGAAGGACTGCGCTGCAAGACCCGGACCCTGGACAGTGAGCCC
AAGTGTGTGGAAGAGTTGCCTGAGTGGAATTTCGATGGCTCCAGTACTTTA
CAGTCTGAGGGTTCCAACAGTGACATGTATCTCGTGCCTGCTGCCATGTTT
CGGGACCCCTTCCGTAAGGACCCTAACAAGCTGGTGTTATGTGAAGTTTTC
AAGTACAATCGAAGGCCTGCAGAGACCAATTTGAGGCACACCTGTAAACGG
ATAATGACATGGTGAGCAACCAGCACCCCTGGTTTGGCATGGAGCAGGAG
TATACCCTCATGGGGACAGATGGGCACCCCTTTGGTTGGCCTTCCAACGGC
TTCCCAGGGCCCCAGGGTCCATATTACTGTGGTGTGGGAGCAGACAGAGCC
TATGGCAGGGACATCGTGGAGGCCCATTACCGGGCCTGCTTGTATGCTGGA
GTCAAGATTGCGGGACTAATGCCGAGGTCATGCCTGCCCAGTGGGAATTT
CAGATTGGACCTTGTGAAGGAATCAGCATGGGAGATCATCTCTGGGTGGCC
CGTTTCATCTTGCATCGTGTGTGAAGACTTTGGAGTGATAGCAACCTTT
GATCCTAAGCCCATTCCTGGGAACTGGATGGTGCAGGCTGCCATACCAAC
TTCAGCACCAAGGCCATGCGGGAGGAGAATGGTCTGAAGTACATCGAGGAG
GCCATTGAGAAACTAAGCAAGCGGCACCAGTACCACATCCGTGCCTATGAT
CCCAAGGGAGGCCTGGACAATGCCCGACGTCTAACTGGATTCCATGAAACC
TCCAACATCAACGACTTTTCTGGTGGTGTAGCCAATCGTAGCGCCAGCATA
CGCATTCCCCGGACTGTTGGCCAGGAGAAGAAGGGTTACTTTGAAGATCGT
CGCCCCTCTGCCAACTGCGACCCCTTTTCGGTGACAGAAGCCCTCATCCGC
ACGTGTCTTCTCATGAAACCGGCGATGAGCCCTTCCAGTACAAAAATTA

FIG. 32

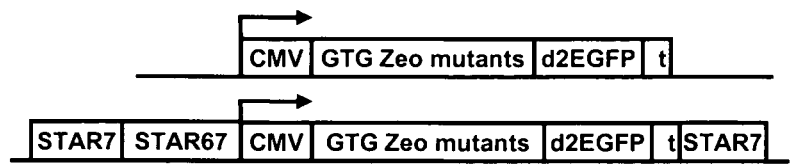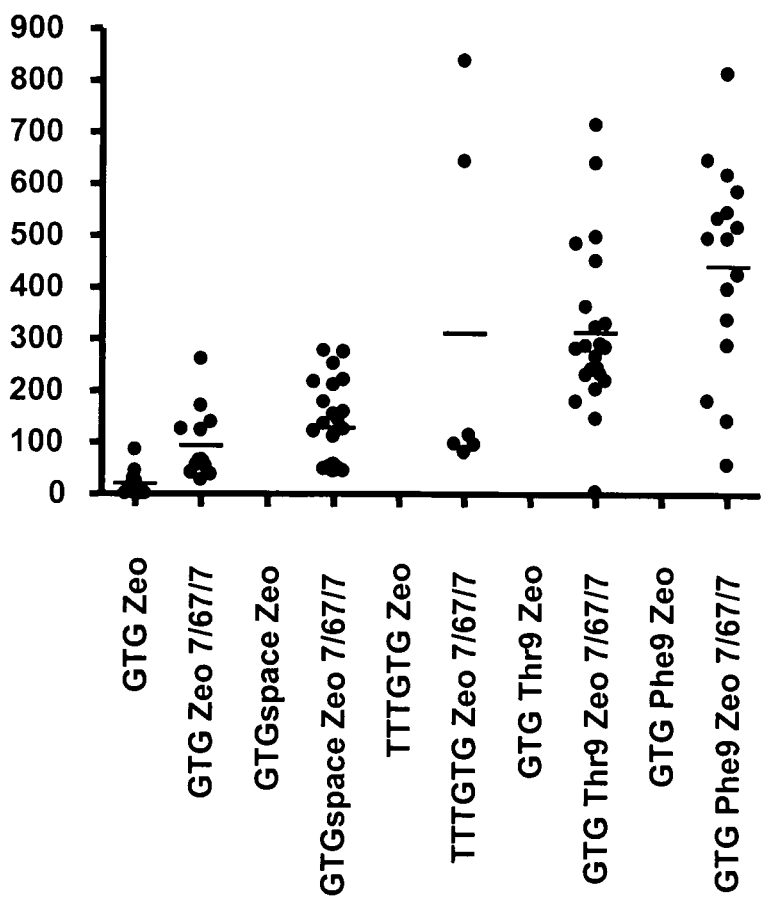
FIG. 34

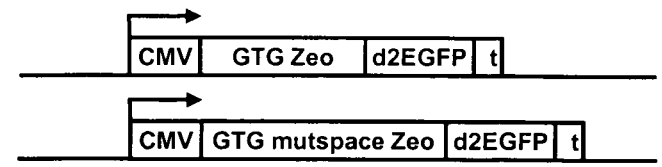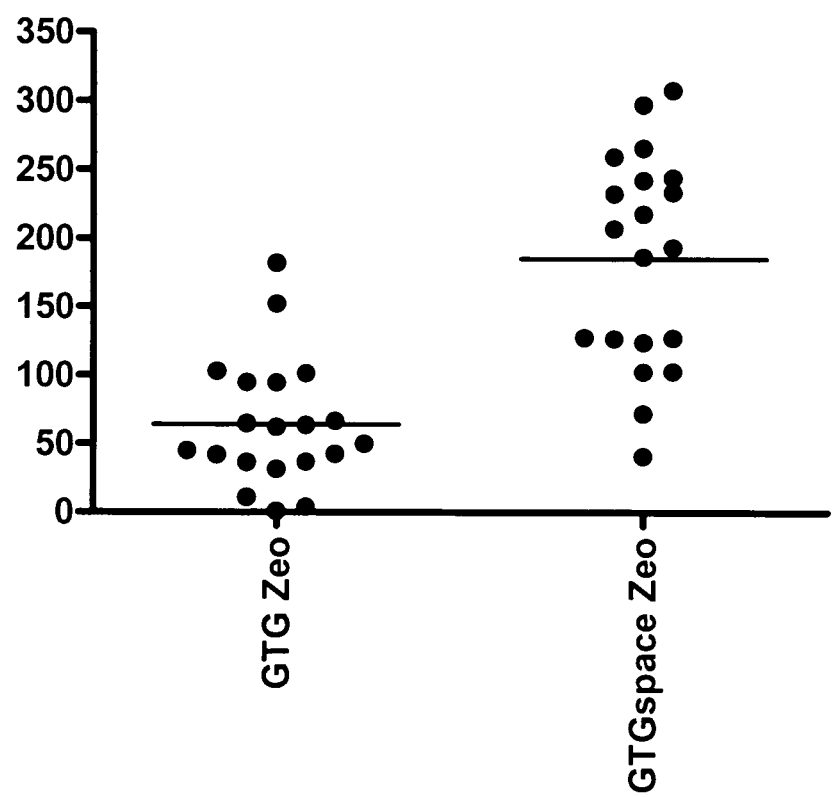
FIG. 41

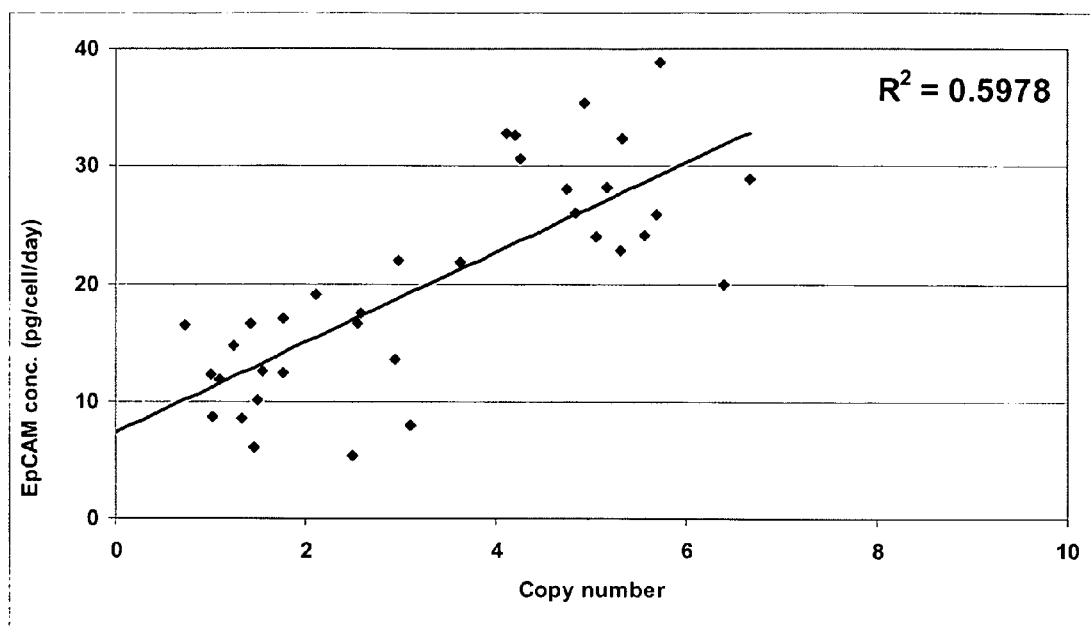
FIG. 44

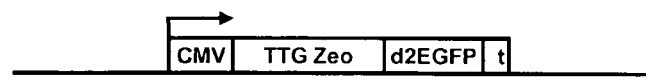
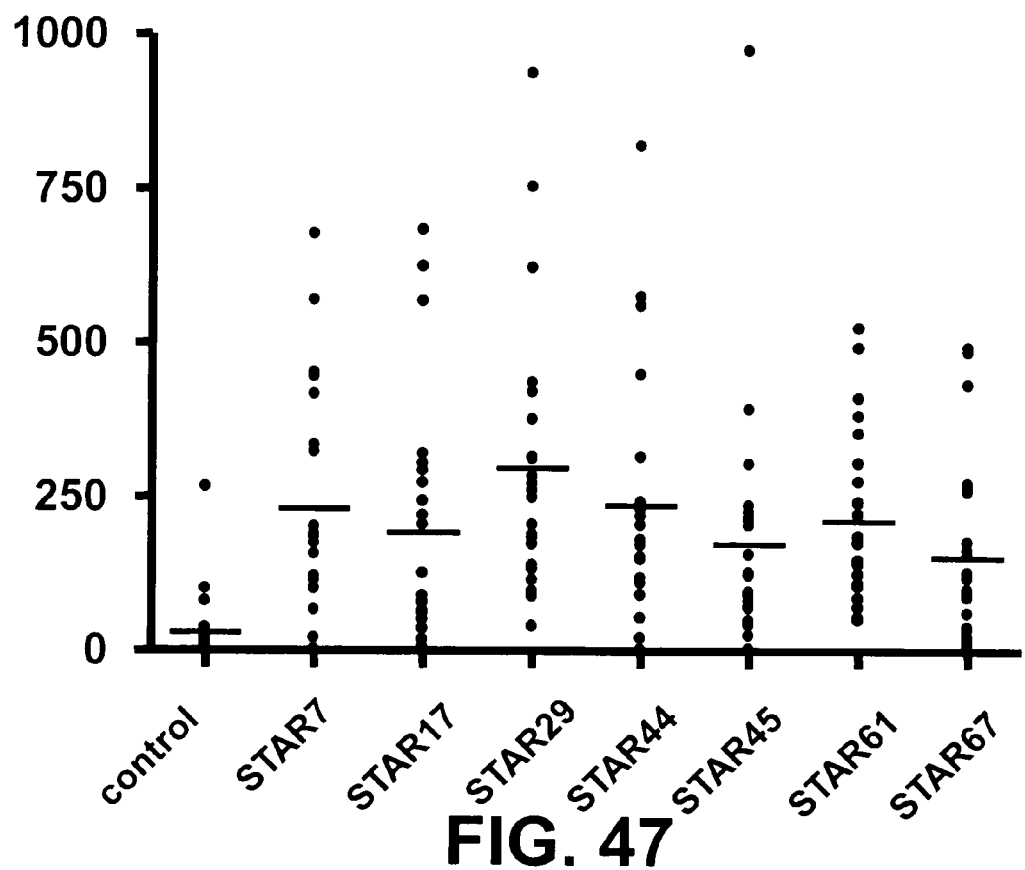
FIG. 47

US 8,771,984 B2

SELECTION OF HOST CELLS EXPRESSING PROTEIN AT HIGH LEVELS

CROSS-REFERENCE TO RELATED APPLICATIONS

This application is a divisional of U.S. patent application Ser. No. 11/269,525, filed Nov. 7, 2005, pending, which application claims the benefit, under 35 U.S.C. §119(e), to U.S. Provisional Patent Application 60/626,301, filed Nov. 8, 2004, and U.S. Provisional Patent Application 60/696,610, filed Jul. 5, 2005, the contents of the entirety of each of which are hereby incorporated by this reference. This application also claims the benefit of EP 04105593.0 filed Nov. 8, 2004.

STATEMENT ACCORDING TO 37 C.F.R. §1.52(e)(5)—SEQUENCE LISTING SUBMITTED ON COMPACT DISC

Pursuant to 37 C.F.R. §1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "0117US P01 PRO ST25 Edited.txt" which is 191 KB and created on Aug. 19, 2010.

BACKGROUND OF THE INVENTION

Field of the Invention

The invention relates to the field of molecular biology and biotechnology. More specifically the present invention relates to means and methods for improving the selection of host cells that express proteins at high levels.

Proteins can be produced in various host cells for a wide range of applications in biology and biotechnology, for instance as biopharmaceuticals. Eukaryotic and particularly mammalian host cells are preferred for this purpose for expression of many proteins, for instance when such proteins have certain posttranslational modifications such as glycosylation. Methods for such production are well established, and generally entail the expression in a host cell of a nucleic acid (also referred to as "transgene") encoding the protein of interest. In general, the transgene together with a selectable marker gene is introduced into a precursor cell, cells are selected for the expression of the selectable marker gene, and one or more clones that express the protein of interest at high levels are identified, and used for the expression of the protein of interest.

One problem associated with the expression of transgenes is that it is unpredictable, stemming from the high likelihood that the transgene will become inactive due to gene silencing (McBurney et al., 2002), and therefore many host cell clones have to be tested for high expression of the transgene.

Methods to select recombinant host cells expressing relatively high levels of desired proteins are known.

One method describes the use of selectable marker proteins with mutations in their coding sequence that diminishes, but does not destroy, the function of the marker (e.g., WO 01/32901). The rationale is that higher levels of the mutant marker expression are required when selection conditions are employed and therefore selection for high expression of the marker is achieved, therewith concomitantly selecting host cells that also express the gene of interest at high levels.

Another method makes use of a selection marker gene under control of a promoter sequence that has been mutated such that the promoter has an activity level substantially below that of its corresponding wild type (U.S. Pat. No. 5,627,033).

Another method describes the use of an impaired dominant selectable marker sequence, such as neomycin phosphotransferase with an impaired consensus Kozak sequence, to decrease the number of colonies to be screened and to increase the expression levels of a gene of interest that is co-linked to the dominant selectable marker (U.S. Pat. Nos. 5,648,267 and 5,733,779). In preferred embodiments therein, the gene of interest is placed within an (artificial) intron in the dominant selectable marker. The gene of interest and the dominant selectable marker are in different transcriptional cassettes and each contains its own eukaryotic promoter in this method (U.S. Pat. Nos. 5,648,267 and 5,733,779).

Another method uses the principle of a selectable marker gene containing an intron that does not naturally occur within the selectable gene, wherein the intron is capable of being spliced in a host cell to provide mRNA encoding a selectable protein and wherein the intron in the selectable gene reduces the level of selectable protein produced from the selectable gene in the host cell (European Patent 0724639 B1).

In yet another method, DNA constructs are used comprising a selectable gene positioned within an intron defined by a 5' splice donor site comprising an efficient splice donor sequence such that the efficiency of splicing an mRNA having the splice donor site is between about 80-99%, and a 3' splice acceptor site, and a product gene encoding a product of interest downstream of 3' splice acceptor site, the selectable gene and the product gene being controlled by the same transcriptional regulatory region (U.S. Pat. No. 5,561,053).

In certain methods, use is made of polycistronic expression vector constructs. An early report of use of this principle describes a polycistronic expression vector, containing sequences coding for both the desired protein and a selectable protein, which coding sequences are governed by the same promoter and separated by a translational stop and start signal codons (U.S. Pat. No. 4,965,196). In preferred embodiments in U.S. Pat. No. 4,965,196, the selectable marker is the amplifiable DHFR gene. In a particularly preferred embodiment of the system described in U.S. Pat. No. 4,965,196, the sequence coding for the selectable marker is downstream from that coding for the desired polypeptide, such that procedures designed to select for the cells transformed by the selectable marker will also select for particularly enhanced production of the desired protein.

In further improvements based on the concept of multicistronic expression vectors, bicistronic vectors have been described for the rapid and efficient creation of stable mammalian cell lines that express recombinant protein. These vectors contain an internal ribosome entry site (IRES) between the upstream coding sequence for the protein of interest and the downstream coding sequence of the selection marker (Rees et al., 1996). Such vectors are commercially available, for instance, the pIRES1 vectors from Clontech (CLONTECHniques, October 1996). Using such vectors for introduction into host cells, selection of sufficient expression of the downstream marker protein then automatically selects for high transcription levels of the multicistronic mRNA, and hence a strongly increased probability of high expression of the protein of interest is envisaged using such vectors.

Preferably in such methods, the IRES used is an IRES which gives a relatively low level of translation of the selection marker gene, to further improve the chances of selecting for host cells with a high expression level of the protein of interest by selecting for expression of the selection marker protein (see, e.g., international publication WO 03/106684).

The present invention aims at providing improved means and methods for selection of host cells expressing high levels of proteins of interest.

BRIEF SUMMARY OF THE INVENTION

The present invention uses a novel and unique concept for selecting host cells expressing high levels of polypeptides of interest, the concept referred to herein as "reciprocal interdependent translation." It is unique with respect to the prior art approaches in that an extra level of regulation is used to fine-tune the amount of translation products from a multicistronic transcript, whereby the level of translation of a selectable marker polypeptide is lowered, thereby increasing the level of translation of the polypeptide of interest coded on the same multicistronic transcription unit, i.e., the expression level of the polypeptide of interest is directly and more or less reciprocally dependent from the expression level of the selectable marker polypeptide (see FIG. 13 for a schematic view). In contrast, approaches using an IRES between the coding sequences for the polypeptide of interest and the selectable marker polypeptide (e.g., Rees et al., 1996), involve independent translation of both polypeptides, so that in those approaches there is no direct effect of the translation efficiency of the selectable marker polypeptide on that of the sequence coding for the polypeptide of interest.

In one aspect, the invention provides a DNA molecule comprising a multicistronic transcription unit coding for i) a selectable marker polypeptide functional in a eukaryotic host cell, and for ii) a polypeptide of interest, the polypeptide of interest having a translation initiation sequence (and start codon) separate from that of the selectable marker polypeptide, characterized in that the coding sequence for the polypeptide of interest is downstream from the coding sequence for the selectable marker in the multicistronic transcription unit, and in that the nucleic acid sequence coding for the selectable marker polypeptide comprises a mutation that decreases the translation efficiency of the selectable marker in a eukaryotic host cell. Preferably the translation initiation efficiency of the selectable marker is decreased. In a preferred embodiment, the decreased translation initiation efficiency is brought about by having a non-optimal translation start sequence of the selectable marker polypeptide.

In preferred embodiments thereof, the translation start sequence in the coding strand for the selectable marker polypeptide comprises an ATG sequence defining a start codon, the ATG sequence being in a non-optimal context for translation initiation. This results in a decreased use of this ATG as start codon, when compared to an ATG start codon in an optimal context.

In a more preferred embodiment, the translation start sequence in the coding strand for the selectable marker polypeptide comprises a start codon different from an ATG start codon, such as one of GTG, TTG, CTG, ATT, or ACG sequence, the first two thereof being the most preferred. Such non-ATG start codons preferably are flanked by sequences providing for relatively good recognition of the non-ATG sequences as start codons, such that at least some ribosomes start translation from these start codons, i.e., the translation start sequence preferably comprises the sequence ACC[non-ATG start codon]G or GCC[non-ATG start codon]G.

In preferred embodiments, the sequence encoding the selectable marker polypeptide has no ATG sequence in the coding strand following the sequence coding for the start codon of the selectable marker polypeptide up to the sequence encoding the stop codon thereof, and not in any sequences in the same strand between the stop codon and the start codon of the polypeptide of interest (which start codon preferably is defined by an ATG in the same coding strand).

In certain embodiments thereof, any ATG sequence present in frame and coding for methionine in the sequence coding for the wild-type selectable marker polypeptide has been mutated to code for valine, threonine, isoleucine or leucine.

In preferred embodiments, the selectable marker protein provides resistance against lethal and/or growth-inhibitory effects of a selection agent, such as an antibiotic.

Preferably, the coding sequence of the polypeptide of interest comprises an optimal translation start sequence.

The invention further provides expression cassettes comprising a DNA molecule according to the invention, which expression cassettes further comprise a promoter upstream of the multicistronic expression unit and being functional in a eukaryotic host cell for initiation transcription of the multicistronic expression unit, and the expression cassettes further comprising a transcription termination sequence downstream of the multicistronic expression unit.

In preferred embodiments thereof, such expression cassettes further comprise at least one chromatin control element chosen from the group consisting of a matrix or scaffold attachment region (MAR/SAR), an insulator sequence, a ubiquitous chromatin opener element (UCOE), and an anti-repressor sequence. Anti-repressor sequences are most preferred in this aspect, and in preferred embodiments, the anti-repressor sequences are chosen from the group consisting of: a) any one SEQ ID NO:1 through SEQ ID NO:66; b) fragments of any one of SEQ ID NO:1 through SEQ ID NO:66, wherein the fragments have anti-repressor activity; c) sequences that are at least 70% identical in nucleotide sequence to a) or b) wherein the sequences have anti-repressor activity; and d) the complement to any one of a) to c). In certain preferred embodiments, the anti-repressor sequences are chosen from the group consisting of: STAR67 (SEQ ID NO:66), START (SEQ ID NO:7), STAR9 (SEQ ID NO:9), STAR17 (SEQ ID NO:17), STAR27 (SEQ ID NO:27), STAR29 (SEQ ID NO:29), STAR43 (SEQ ID NO:43), STAR44 (SEQ ID NO:44), STAR45 (SEQ ID NO:45), STAR47 (SEQ ID NO:47), STAR61 (SEQ ID NO:61), and functional fragments or derivatives of these STAR sequences. In certain embodiments, the expression cassette comprises STAR67, or a functional fragment or derivative thereof, positioned upstream of the promoter driving expression of the multicistronic gene. In certain embodiments, the multicistronic gene is flanked on both sides by at least one anti-repressor sequence. In certain preferred embodiments, expression cassettes are provided according to the invention, comprising in 5' to 3' order: anti-repressor sequence A-anti-repressor sequence B-[promoter-multicistronic transcription unit according to the invention (encoding the functional selectable marker protein and downstream thereof the polypeptide of interest)-transcription termination sequence]-anti-repressor sequence C, wherein A, B and C may be the same or different.

In certain embodiments, the polypeptide of interest is a part of a multimeric protein, for example a heavy or light chain of an immunoglobulin.

The invention also provides DNA molecules comprising a sequence encoding a functional selectable marker polypeptide, characterized in that such DNA molecules comprise a mutation that decreases the translation efficiency of the functional selectable marker polypeptide in a eukaryotic host cell. Preferably, such a DNA molecule: i) has a non-optimal translation start sequence followed by an otherwise functional selectable marker coding sequence, and ii) in the coding strand of the sequence defining the selectable marker polypeptide downstream of the non-optimal start codon is devoid of ATG sequences.

The invention also provides host cells comprising DNA molecules according to the invention.

The invention further provides methods for generating host cells expressing a polypeptide of interest, the method comprising the steps of: introducing into a plurality of precursor host cells an expression cassette according to the invention, culturing the cells under conditions selecting for expression of the selectable marker polypeptide, and selecting at least one host cell producing the polypeptide of interest.

In a further aspect, the invention provides methods for producing a polypeptide of interest, the methods comprising culturing a host cell, the host cell comprising an expression cassette according to the invention, and expressing the polypeptide of interest from the expression cassette. In preferred embodiments thereof, the polypeptide of interest is further isolated from the host cells and/or from the host cell culture medium.

In further aspects, the invention provides RNA molecules having the sequence of a transcription product of a DNA molecule according to the invention.

In another aspect, the invention provides functional selectable marker polypeptides lacking methionine in their amino acid sequence, which polypeptides are obtainable by expression from certain DNA molecules according to the invention.

BRIEF DESCRIPTION OF THE SEVERAL VIEWS OF THE DRAWINGS

FIG. 2. STAR67 improves CMV driven d2EGFP expression in CHO cells. The mean of the d2EGFP signal for 10 independent stable colonies is plotted for the indicated constructs in CHO cells. A) CMV Control; B) STAR67-CMV. X(10): average d2EGFP expression levels of the ten colonies. See Example 2 for details.

FIG. 6. STAR67 improves EF1α driven d2EGFP expression in PER.C6 cells. Same as FIG. 3, but now in PER.C6 cells. A) EF1α Control; B) STAR67-EF1α.

FIG. 7. STAR67 improves UB6 driven d2EGFP expression in PER.C6 cells. Same as FIG. 4, but now in PER.C6 cells. A) UB6 Control; B) STAR67-UB6.

FIG. 10. STAR67 is not an enhancer blocker, whereas STAR 6 and 7 are. See Example 6 for details.

FIG. 11. STAR67 enhances UB6 and CMV-driven antibody expression levels in stably transfected CHO cells. See Example 7 for details. A) single DNA molecule containing anti-EpCAM heavy chain (HC) and light chain (LC), each behind a promoter, and each linked to a different selectable marker gene (simultaneous selection was used for both markers): construct without STAR elements. No colonies were found; B) same construct with STAR67 between the two promoters. The anti-EpCAM antibody concentration is presented as pg/cell/day. X(19): average production level of the 19 colonies.

FIG. 15. Results of selection system according to the invention in an up-scaled experiment (A), and comparison with selection system according to prior art using an IRES (B). d2EGFP signal for independent colonies is shown on the vertical axis. See Example 10 for details.

FIG. 16. Results of selection system with multicistronic transcription unit according to the invention, using blasticidin as a selectable marker. A. blasticidin resistance gene mutated to comprise a GTG start codon. B. blasticidin resistance gene mutated to comprise a TTG start codon. The blasticidin resistance gene has further been mutated to remove all internal ATG sequences. d2EGFP signal for independent colonies is shown on the vertical axis. See Example 11 for details.

Figure 17:
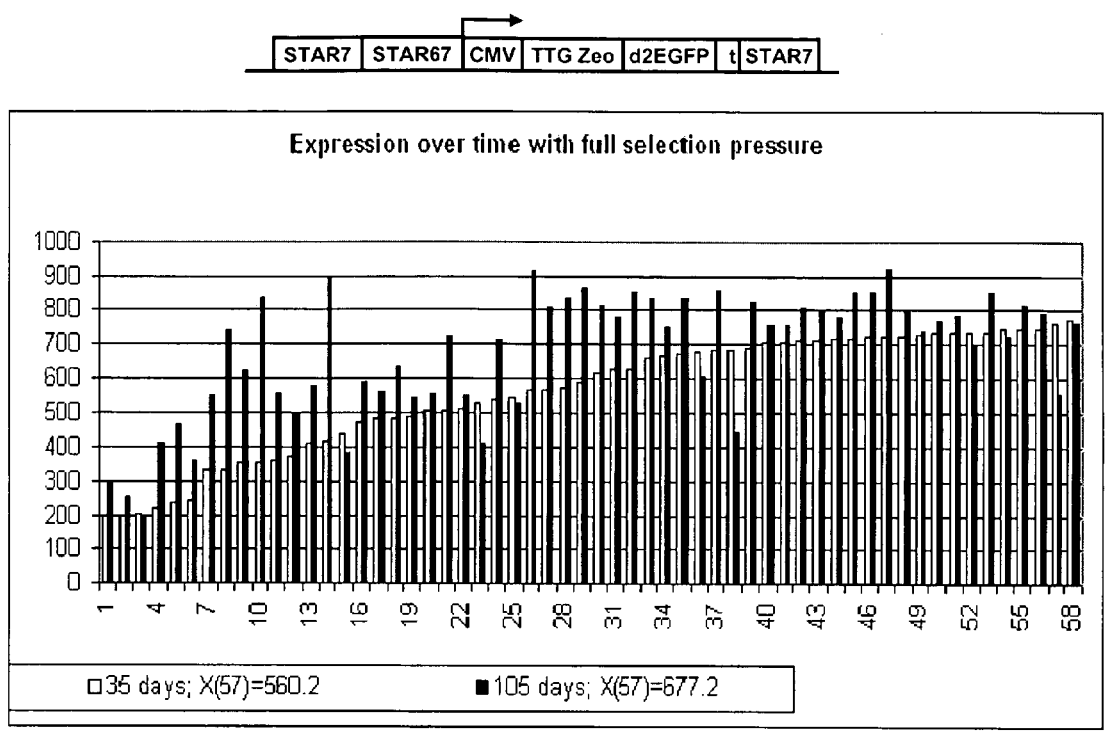

FIG. 17. Stability of expression of several clones with a multicistronic transcription unit according to the invention (including a Zeocin® antibiotic resistance gene with TTG start codon). Selection pressure (100 µg/ml Zeocin® antibiotic) was present during the complete experiment. d2EGFP signal for independent colonies is shown on the vertical axis. See Example 12 for details.

FIG. 18. As FIG. 17, but Zeocin® antibiotic concentration was lowered to 20 µg/ml after establishment of clones.

FIG. 19. As FIG. 17, but \Zeocin® antibiotic was absent from culture medium after establishment of clones.

Figure 20:
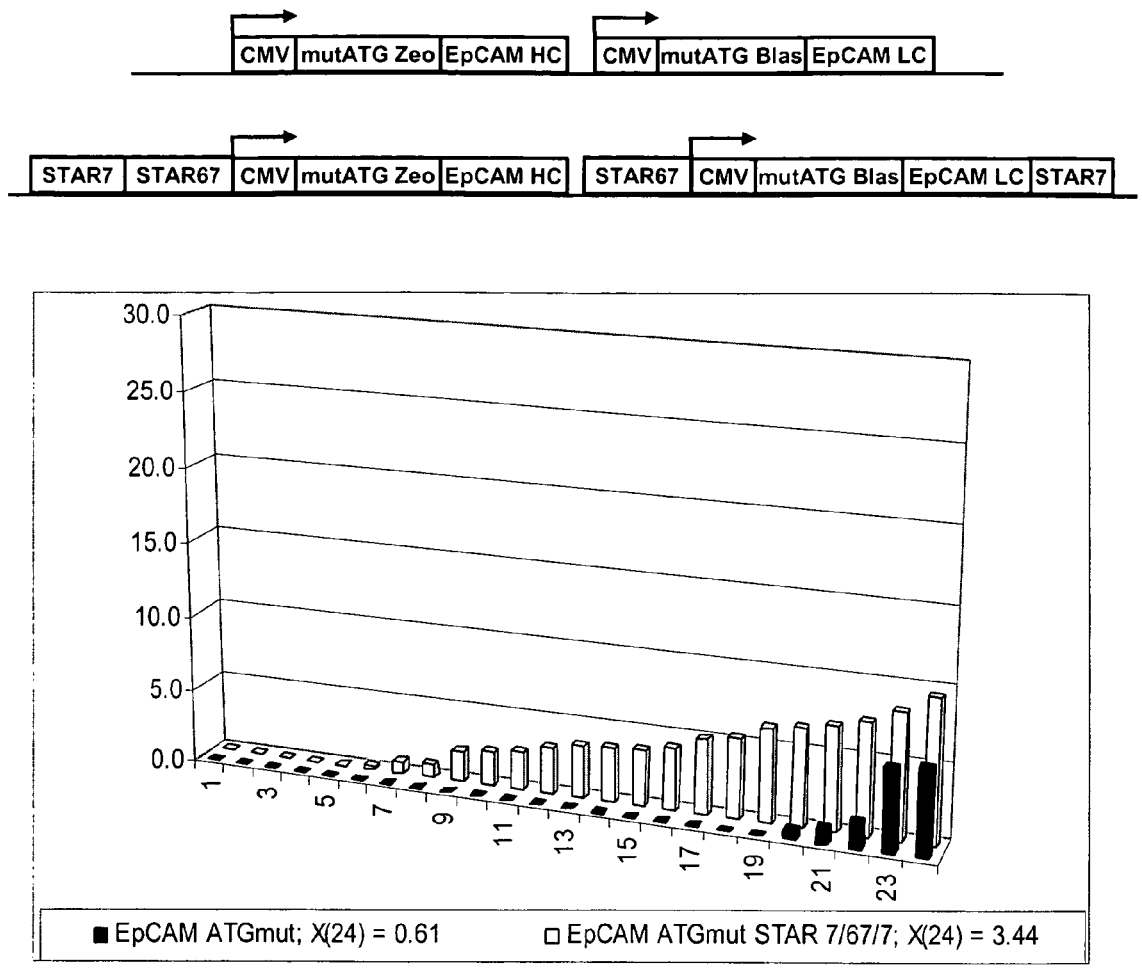

FIG. 20. Expression of an antibody (anti-EpCAM) using the selection system with the multicistronic transcription unit according to the invention. The heavy chain (HC) and light chain (LC) are the polypeptide of interest in this example. Each of these is present in a separate transcription unit, which are both on a single nucleic acid molecule in this example. The HC is preceded by the Zeocin® antibiotic resistance gene coding for a selectable marker polypeptide, while the LC is preceded by the blasticidin resistance gene coding for a selectable marker polypeptide. Both resistance genes have been mutated to comprise an ATG start codon in a non-optimal context ("mutATG" in Figure, but including a spacer sequence, and hence in the text generally referred to as "ATG-mut/space"). Each of the multicistronic transcription units is under control of a CMV promoter. Constructs with STAR sequences as indicated were compared to constructs without STAR sequences. The antibody levels obtained when these constructs were introduced into host cells are given on the vertical axis in pg/cell/day for various independent clones. See Example 13 for details.

Figure 21:
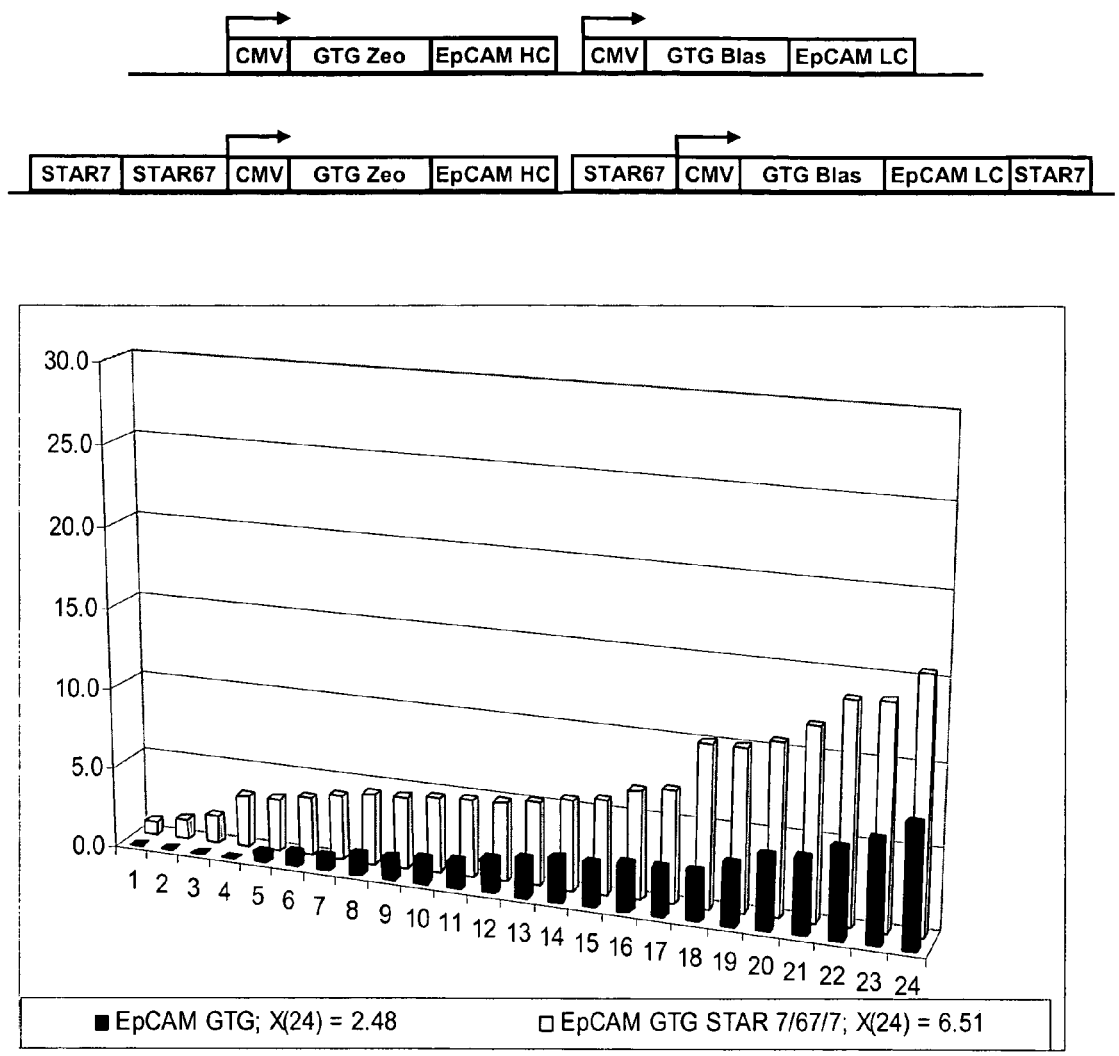

FIG. 21. As FIG. 20, but both the selection marker genes have been provided with a GTG start codon. See Example 13 for details.

Figure 22:
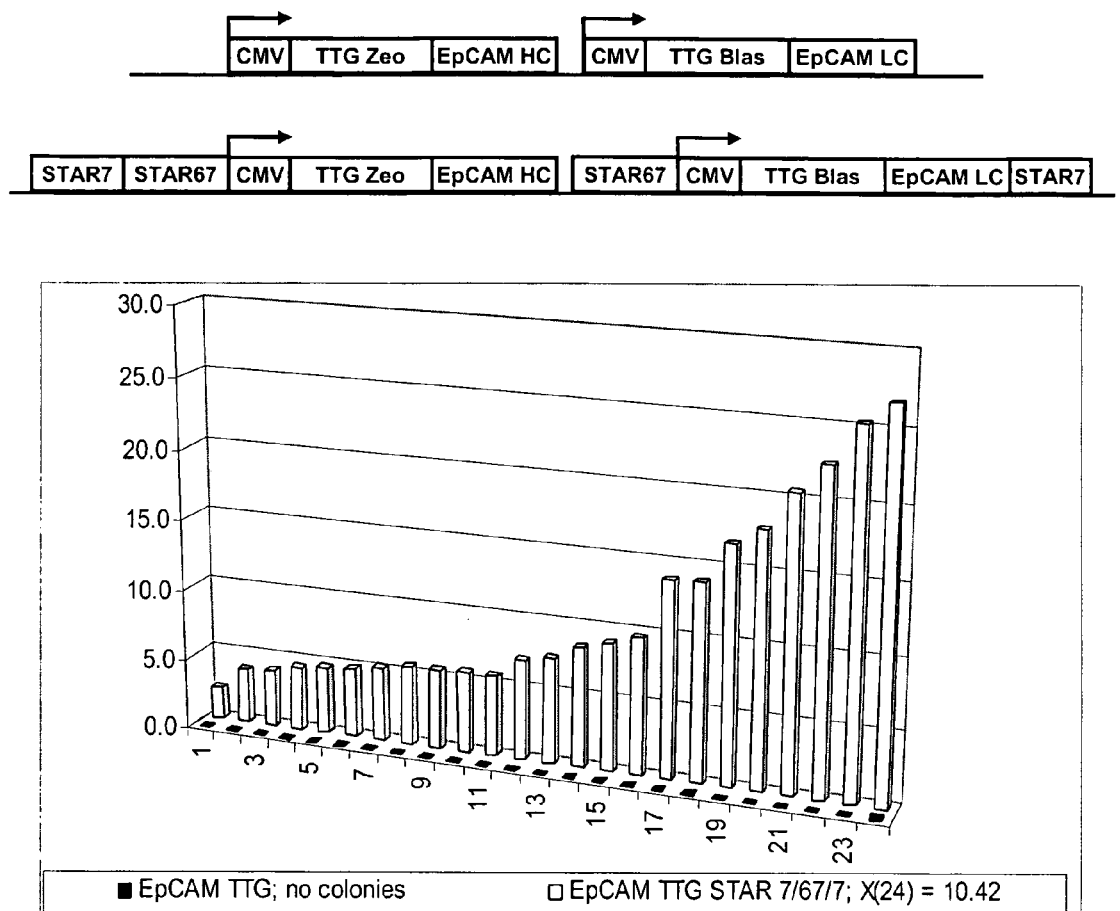

FIG. 22. As FIG. 20, but both the selection marker genes have been provided with a TTG start codon. See Example 13 for details.

Figure 23:
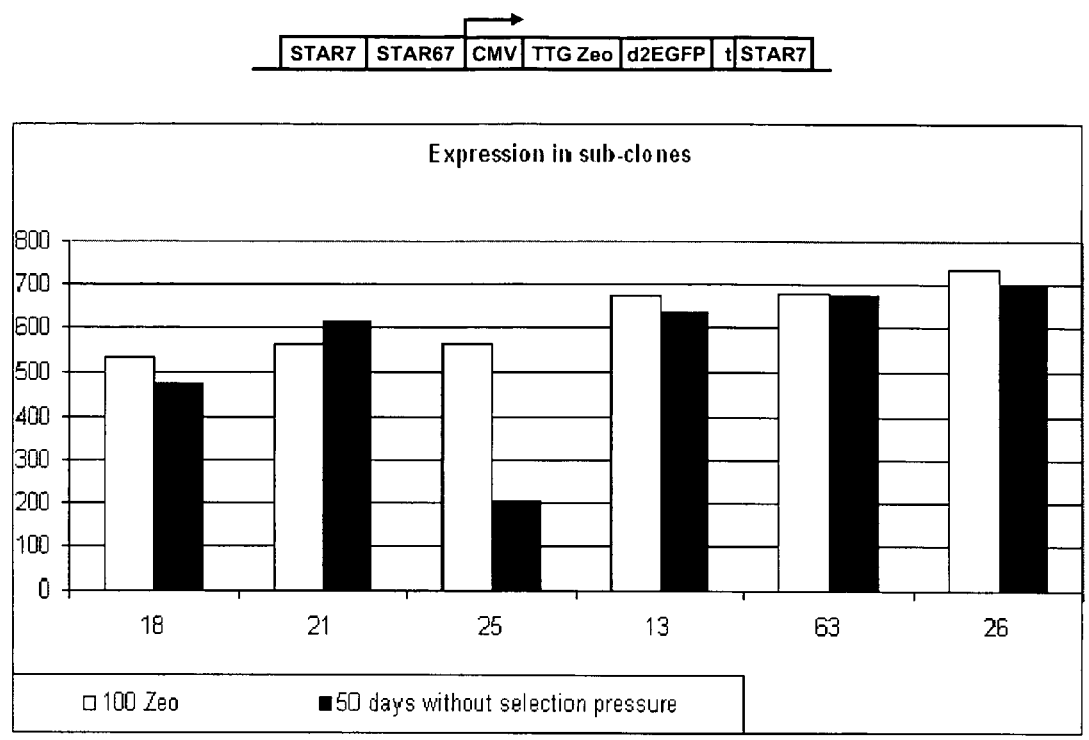

FIG. 23. Stability of expression in sub-clones in the absence of selection pressure (after establishing colonies under selection pressure, some colonies where sub-cloned in medium containing no Zeocin® antibiotic). See Example 12 for details.

Figure 24:
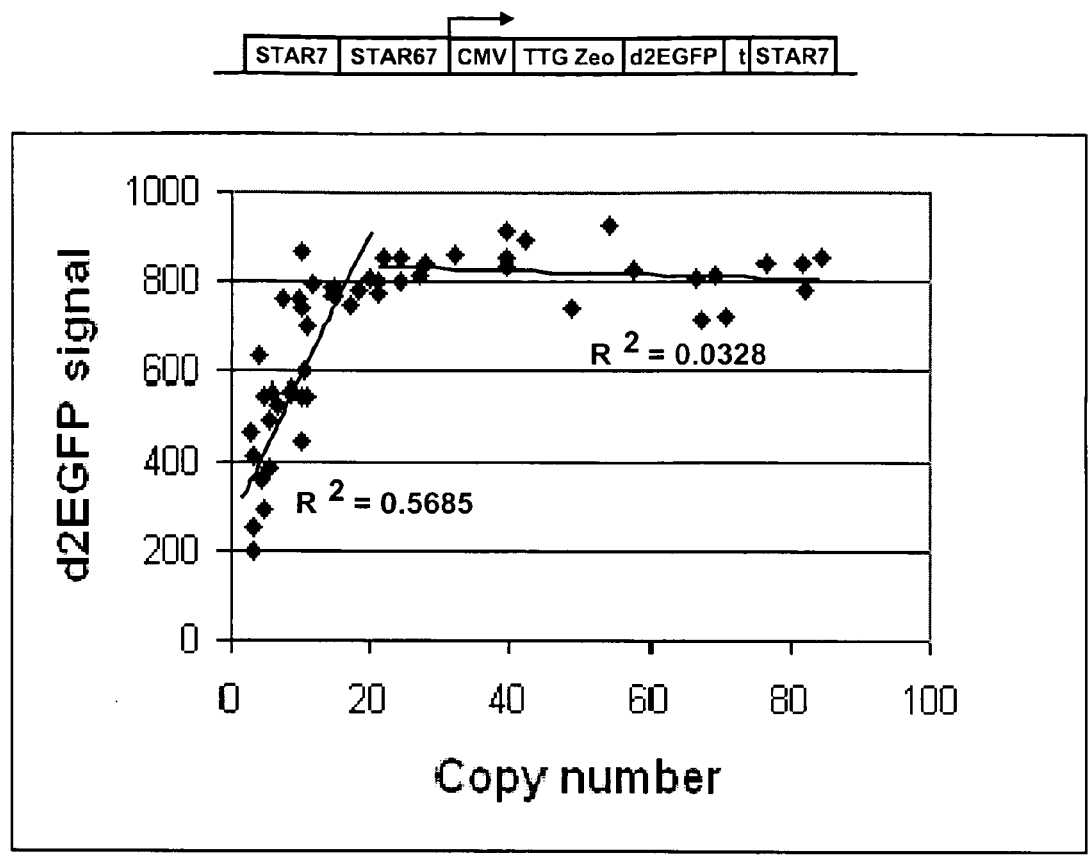

FIG. 24. Copy-number dependency of expression levels of an embodiment of the invention. See Example 12 for details.

Figure 25:
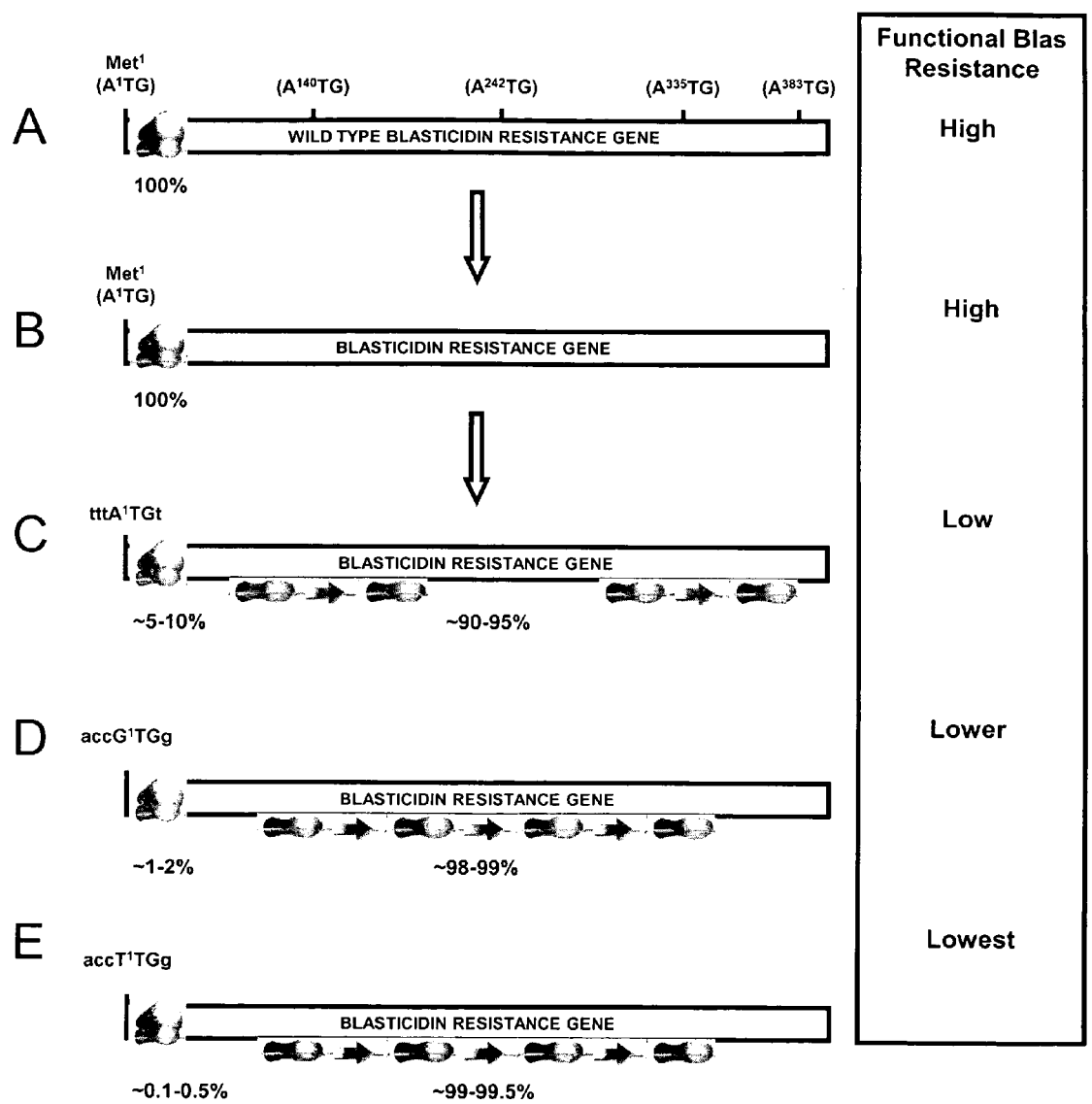

FIG. 25. As FIG. 12, but for the blasticidin resistance gene. None of the four internal ATGs in this gene are in frame coding for a methionine, and therefore the redundancy of the genetic code was used to mutate these ATGs without mutating the internal amino acid sequence of the encoded protein.

FIG. 26. Coding sequence of the wild-type Zeocin® antibiotic resistance gene (SEQ ID NO:108). Bold ATGs code for methionine. The first bold ATG is the start codon.

FIG. 27. Coding sequence of the wild-type blasticidin resistance gene (SEQ ID NO:110). Bold ATGs code for methione. The first bold ATG is the start codon. Other ATGs in the sequence are underlined: these internal ATGs do not code for methionine, because they are not in frame.

FIG. 28. Coding sequence of the wild-type puromycin resistance gene (SEQ ID NO:112). Bold ATGs code for methione. The first bold ATG is the start codon.

FIG. 29. Coding sequence of the wild-type mouse DHFR gene (SEQ ID NO:114). Bold ATGs code for methione. The first bold ATG is the start codon. Other ATGs in the sequence are underlined: these internal ATGs do not code for methionine, because they are not in frame.

FIG. 30. Coding sequence of the wild-type hygromycin resistance gene (SEQ ID NO:116). Bold ATGs code for methione. The first bold ATG is the start codon. Other ATGs in the sequence are underlined: these internal ATGs do not code for methionine, because they are not in frame.

FIG. 31. Coding sequence of the wild-type neomycin resistance gene (SEQ ID NO:118). Bold ATGs code for methione. The first bold ATG is the start codon. Other ATGs in the sequence are underlined: these internal ATGs do not code for methionine, because they are not in frame.

FIG. 32. Coding sequence of the wild-type human glutamine synthase (GS) gene (SEQ ID NO:120). Bold ATGs code for methione. The first bold ATG is the start codon. Other ATGs in the sequence are underlined: these internal ATGs do not code for methionine, because they are not in frame.

Figure 33:
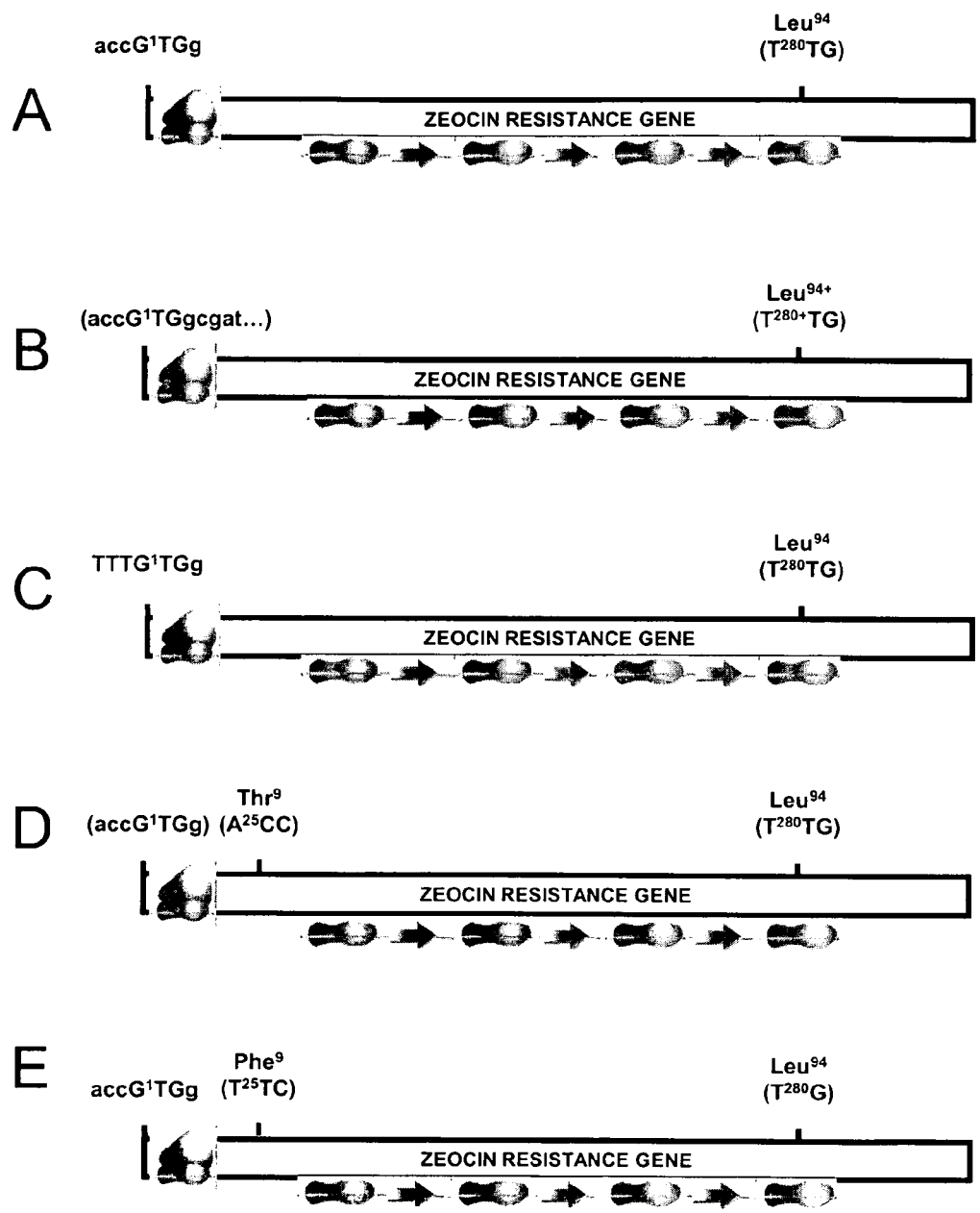

FIG. 33. Schematic representation of some further modified Zeocin® antibiotic resistance selection marker genes with a GTG start codon according to the invention, allowing for further fine-tuning of the selection stringency. See Example 14 for details.

FIG. 34. Results with expression systems containing the further modified Zeocin® antibiotic resistance selection marker genes. See Example 14 for details. Dots indicate individual data points; lines indicate the average expression levels; used constructs (see also FIG. 33) are indicated on the horizontal axis (the addition of 7/67/7 at the end of the construct name indicates the presence of STAR sequences 7 and 67 upstream of the promoter and STAR7 downstream of the transcription termination site), and schematically depicted above the graph; vertical axis indicates d2EGFP signal.

Figure 35:
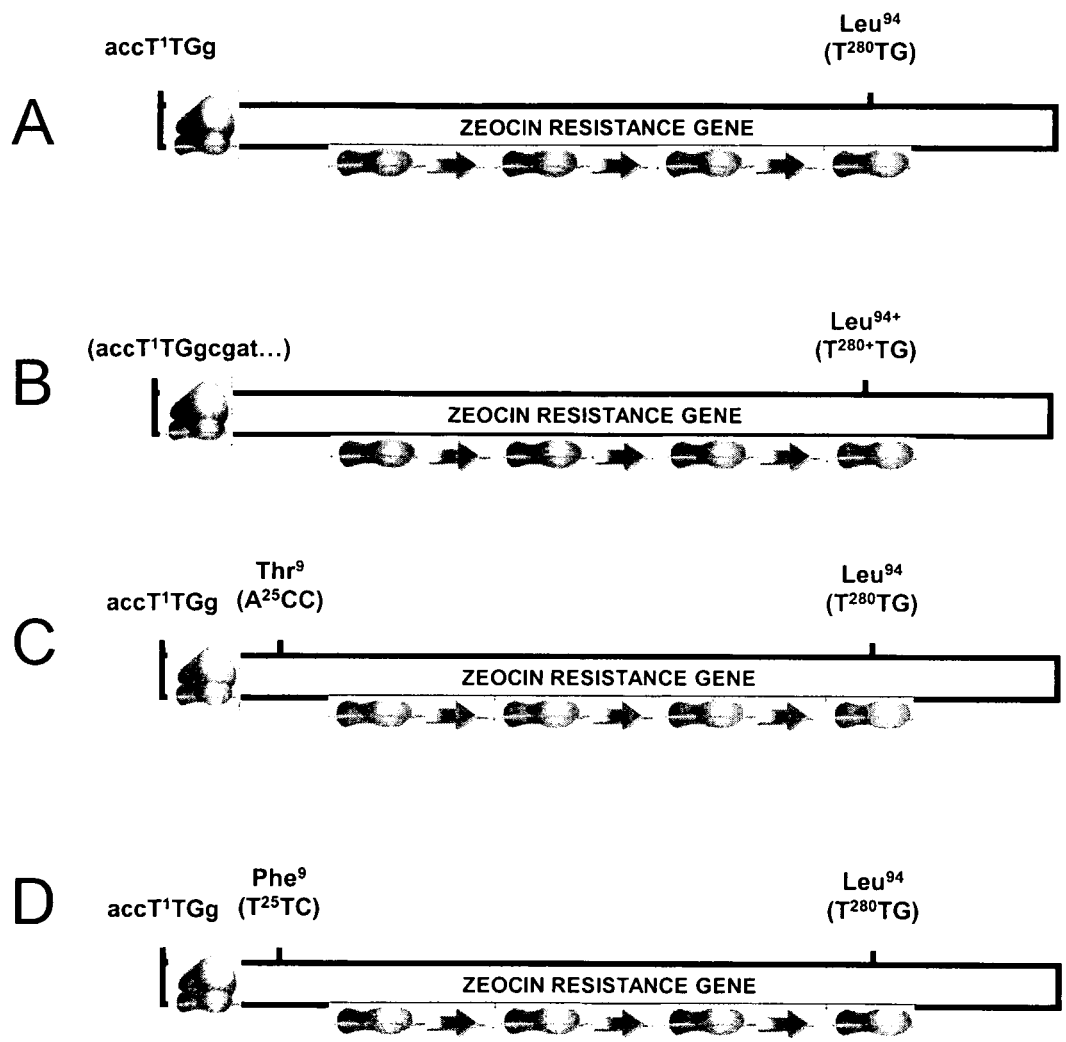

FIG. 35. Schematic representation of some further modified Zeocin® antibiotic resistance selection marker genes with a TTG start codon according to the invention, allowing for further fine-tuning of the selection stringency. See Example 15 for details.

Figure 36:
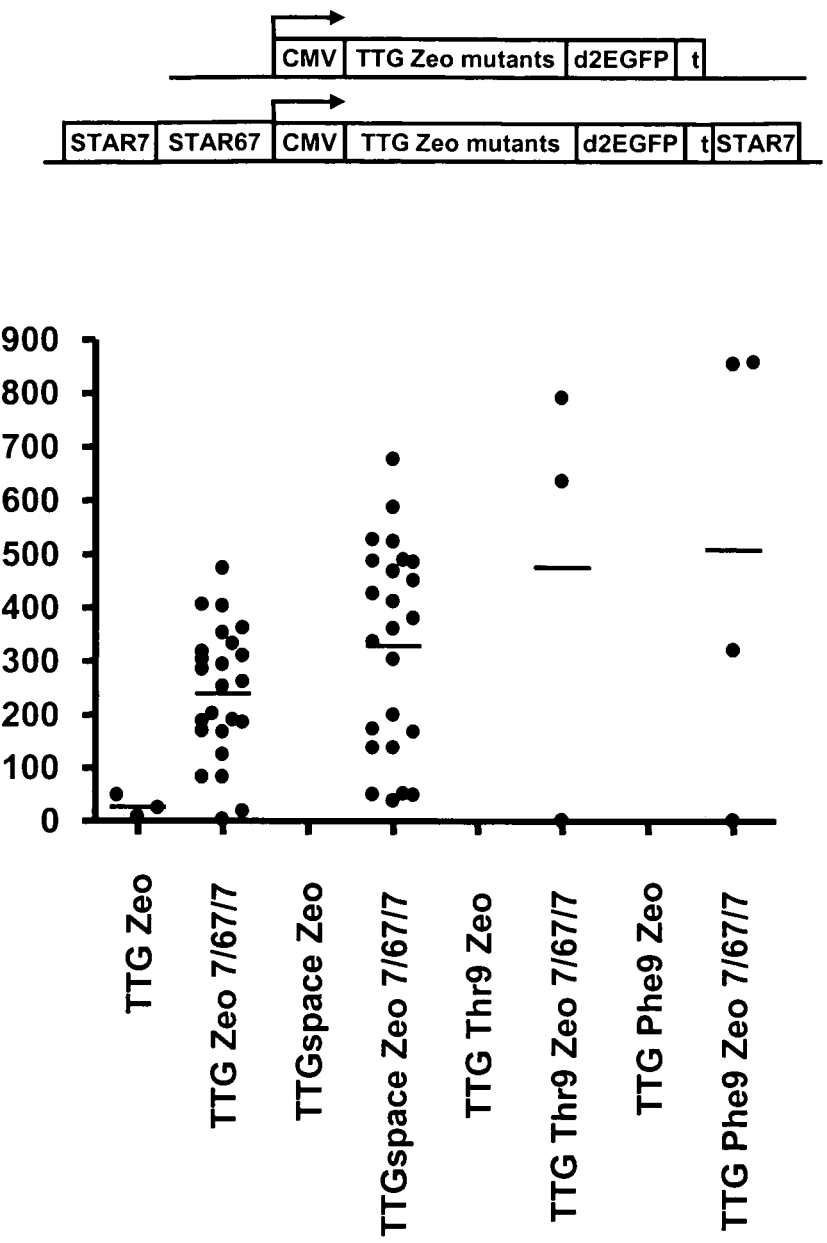

FIG. 36. Results with expression systems containing the further modified Zeocin® antibiotic resistance selection marker genes. See Example 15 for details. Dots indicate individual data points; lines indicate the average expression levels; used constructs are indicated on the horizontal axis, and schematically depicted above the graph; vertical axis indicates d2EGFP signal.

Figure 37:
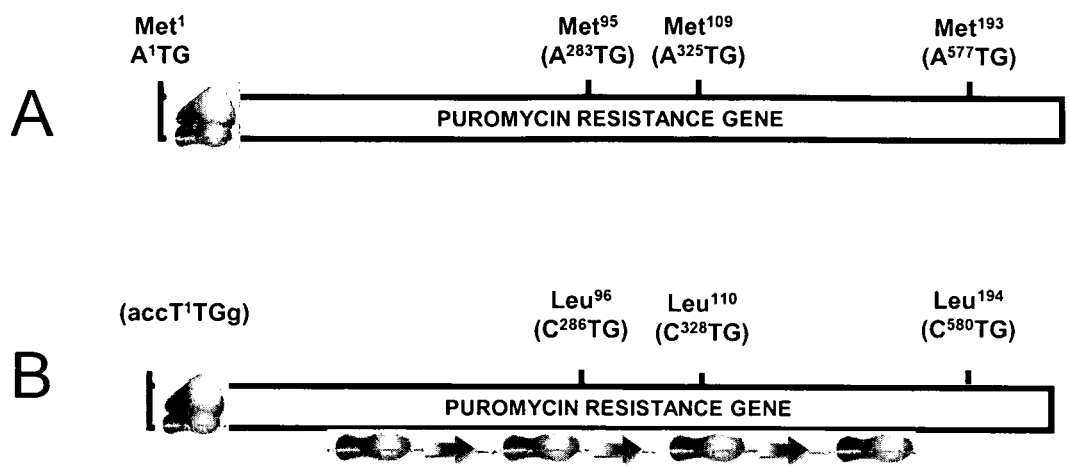

FIG. 37. As FIG. 12, but for the puromycin resistance gene. All three internal ATGs code for methione (panel A), and are replaced by CTG sequences coding for leucine (panel B). See Example 16 for details.

Figure 38:
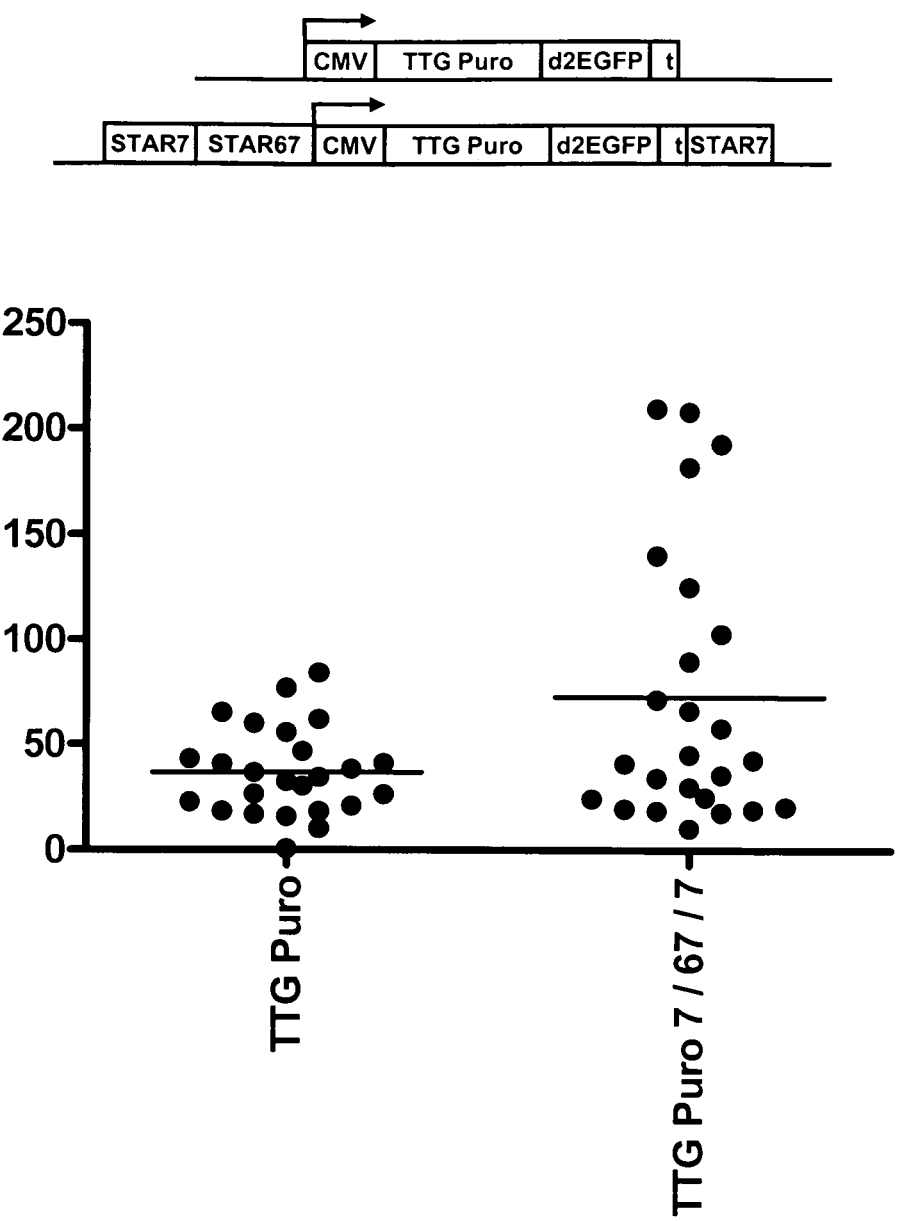

FIG. 38. Results with expression constructs containing the puromycin resistance gene with a TTG start codon and no internal ATG codons. See Example 16 for details. Dots indicate individual data points; lines indicate the average expression levels; used constructs are indicated on the horizontal axis, and schematically depicted above the graph; vertical axis indicates d2EGFP signal.

Figure 39:
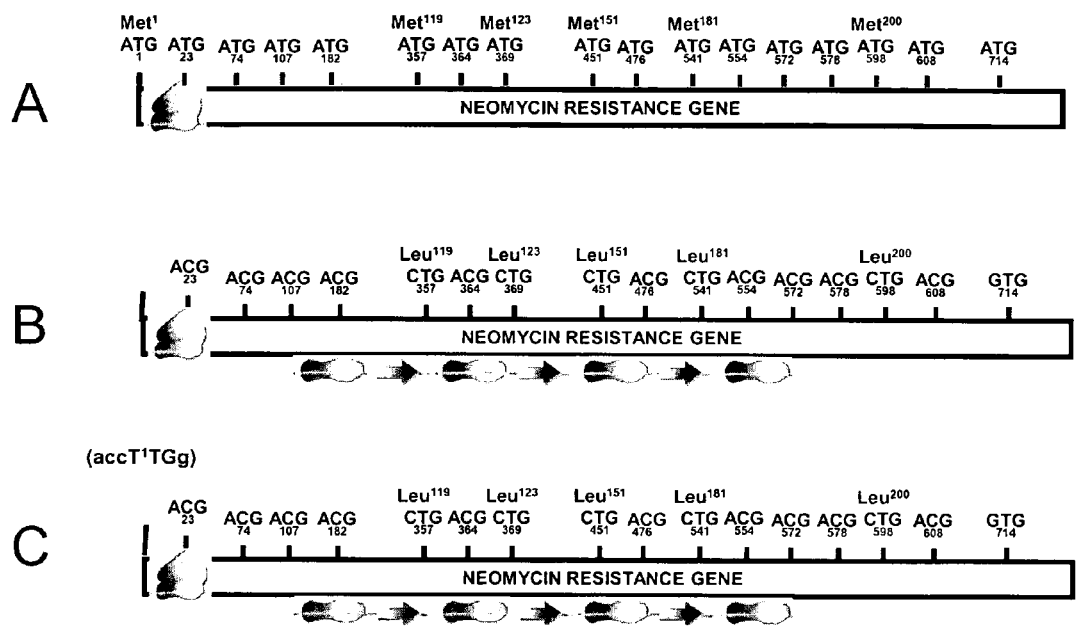

FIG. 39. As FIG. 12, but for the neomycin resistance gene. See Example 17 for details. A. wild-type neomycin resistance gene; ATG sequences are indicated, ATGs coding for methionine are indicated by Met above the ATG. B. neomycin resistance gene without ATG sequences, and with a GTG start codon. C. neomycin resistance gene without ATG sequences, and with a TTG start codon.

Figure 40:
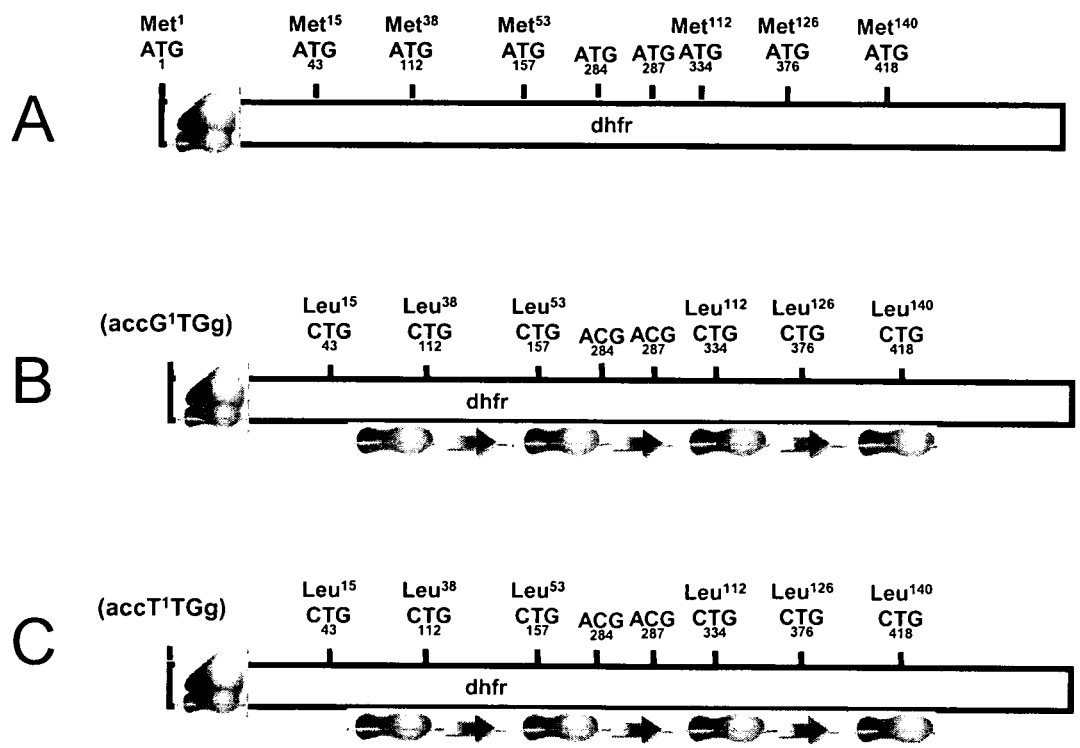

FIG. 40. As FIG. 12, but for the dhfr gene. See Example 18 for details. A. wild-type dhfr gene; ATG sequences are indicated, ATGs coding for methionine are indicated by Met above the ATG. B. dhfr gene without ATG sequences, and with a GTG start codon. C. dhfr gene without ATG sequences, and with a TTG start codon.

FIG. 41. Results with expression constructs (Zeocin® selectable marker) according to the invention in PER.C6 cells. See Example 20 for details. Dots indicate individual data points; lines indicate the average expression levels; used constructs are indicated on the horizontal axis, and schematically depicted above the graph; vertical axis indicates d2EGFP signal.

Figure 42:
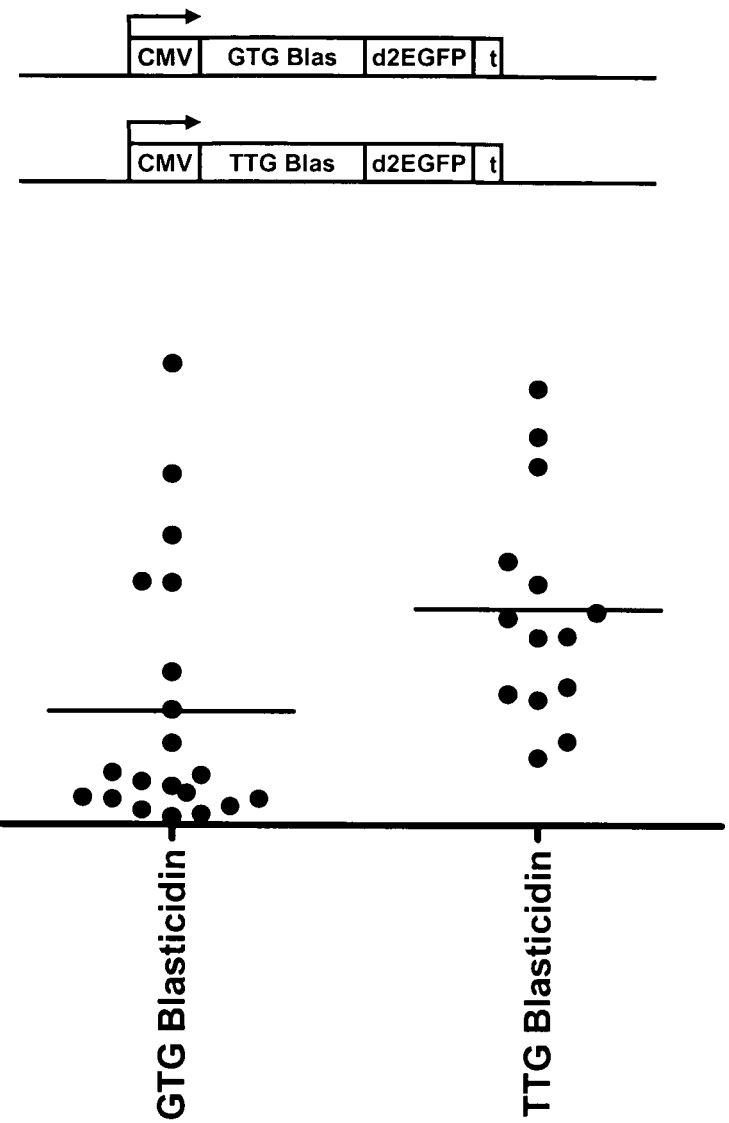

FIG. 42. Results with expression constructs (blasticidin selectable marker) according to the invention in PER.C6 cells. See Example 20 for details. Dots indicate individual data points; lines indicate the average expression levels; used constructs are indicated on the horizontal axis, and schematically depicted above the graph; vertical axis indicates d2EGFP signal.

Figure 43:
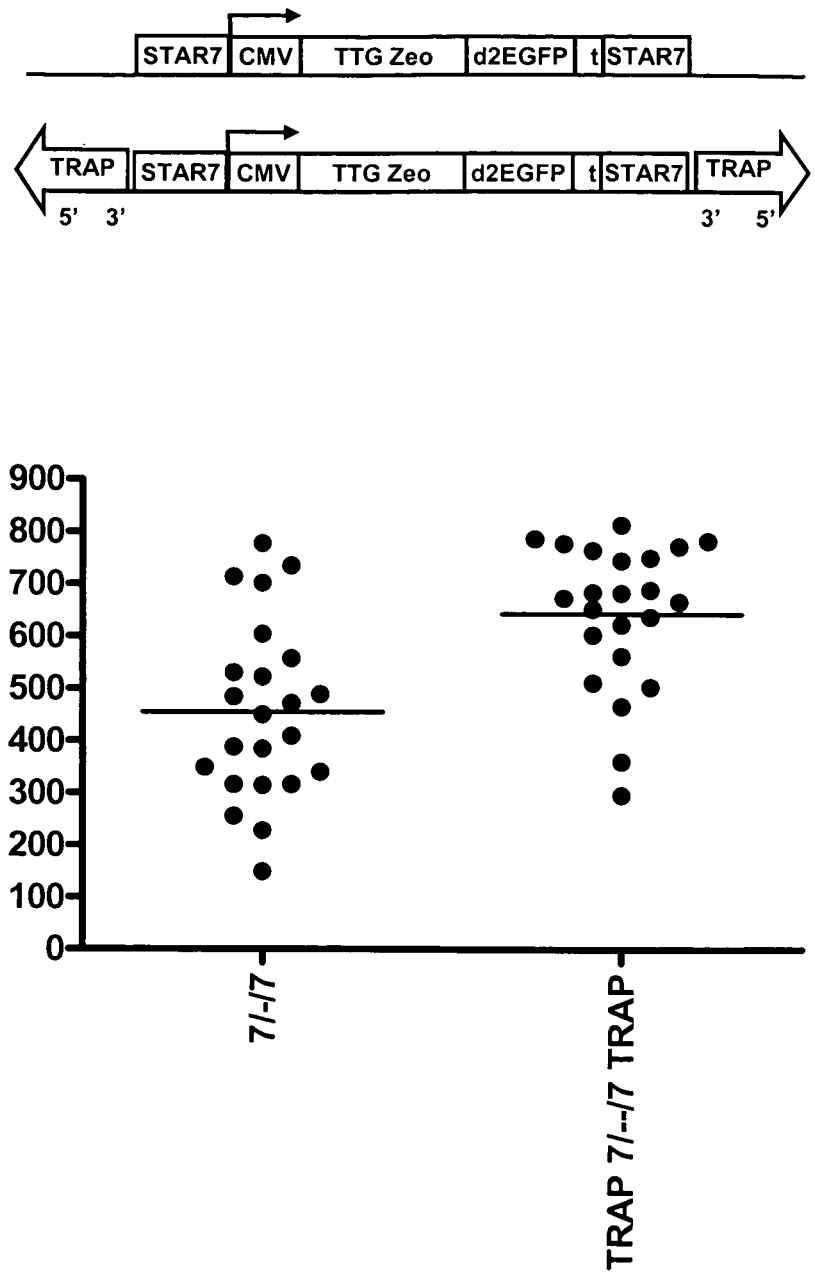

FIG. 43. Results with expression constructs according to the invention, further comprising a transcription pause (TRAP) sequence. See Example 21 for details. Dots indicate individual data points; lines indicate the average expression levels; used constructs are indicated on the horizontal axis, and schematically depicted above the graph; vertical axis indicates d2EGFP signal.

FIG. 44. Copy-number dependency of expression of an antibody using transcription units according to the invention. See Example 22 for details.

Figure 45:
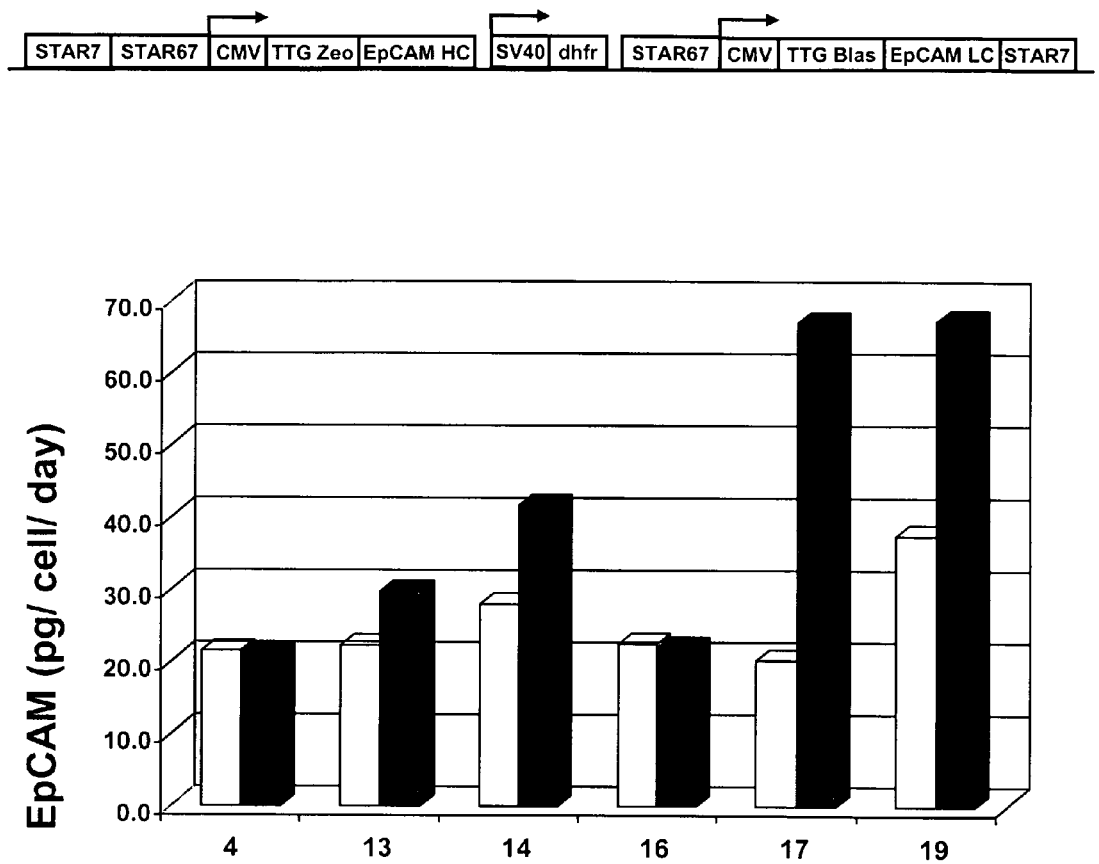

FIG. 45. Antibody expression from colonies containing expression constructs according to the invention, wherein the copy number of the expression constructs is amplified by methotrexate. See Example 23 for details. White bars: selection with Zeocin® antibiotic and blasticidin; black bars: selection with Zeocin® antibiotic, blasticidin and methotrexate (MTX). Numbers of tested colonies are depicted on the horizontal axis.

Figure 46:
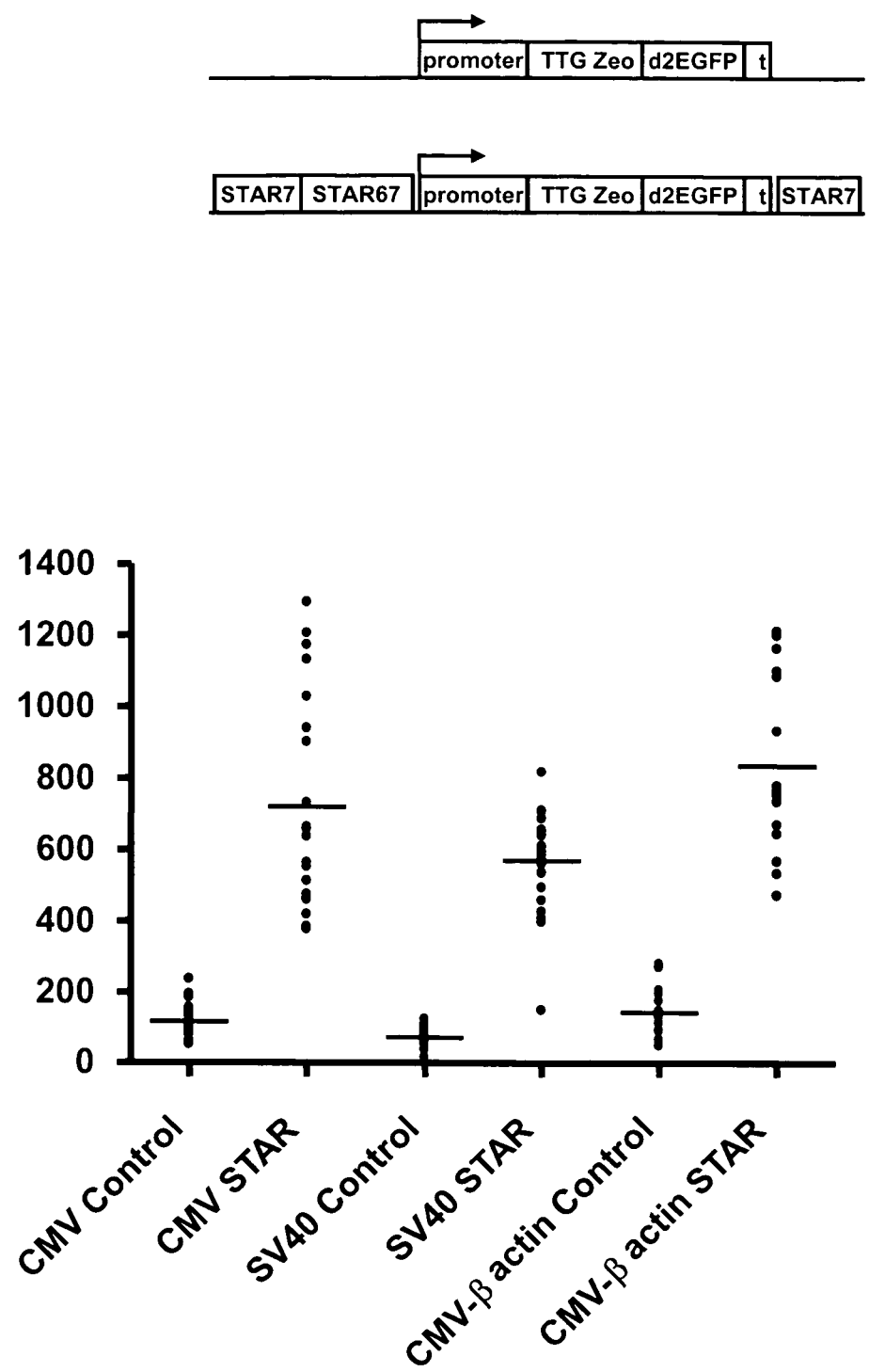

FIG. 46. Results with different promoters. See Example 24 for details. Dots indicate individual data points; lines indicate the average expression levels; used constructs are indicated on the horizontal axis, and schematically depicted above the graph; vertical axis indicates d2EGFP signal.

FIG. 47. Results with different STAR elements. See Example 25 for details. Dots indicate individual data points; lines indicate the average expression levels; used constructs are indicated on the horizontal axis, and schematically depicted above the graph; vertical axis indicates d2EGFP signal.

Figure 48:
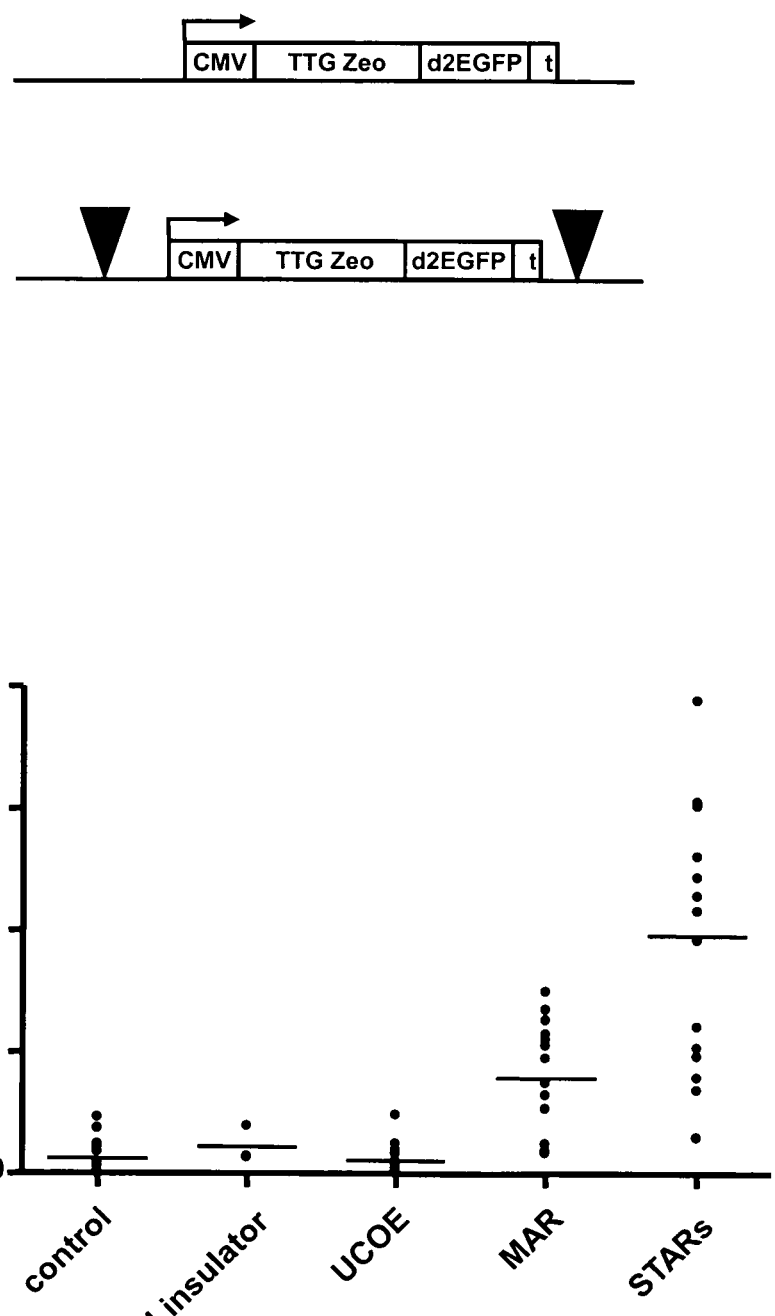

FIG. 48. Results with other chromatin control elements. See Example 26 for details. Dots indicate individual data points; lines indicate the average expression levels; used constructs are indicated on the horizontal axis, and schematically depicted above the graph (black triangles indicate different tested chromatin control elements); vertical axis indicates d2EGFP signal.

DETAILED DESCRIPTION OF THE INVENTION

In one aspect, the invention provides a DNA molecule comprising a multicistronic transcription unit coding for i) a selectable marker polypeptide functional in a eukaryotic host cell, and for ii) a polypeptide of interest, the polypeptide of interest having a translation initiation sequence separate from that of the selectable marker polypeptide, characterized in that the coding sequence for the polypeptide of interest is downstream from the coding sequence for the selectable marker in the multicistronic transcription unit, and the nucleic acid sequence coding for the selectable marker polypeptide comprises a mutation that decreases the translation efficiency of the selectable marker in a eukaryotic host cell. Such a DNA molecule can be used according to the invention for obtaining eukaryotic host cells expressing high levels of the polypeptide of interest, by selecting for the expression of the selectable marker polypeptide. Subsequently or simultaneously, one or more host cell(s) expressing the polypeptide of interest can be identified, and further used for expression of high levels of the polypeptide of interest.

The term "monocistronic gene" is defined as a gene capable of providing a RNA molecule that encodes one polypeptide. A "multicistronic transcription unit," also referred to as multicistronic gene, is defined as a gene capable of providing an RNA molecule that encodes at least two polypeptides. The term "bicistronic gene" is defined as a gene capable of providing a RNA molecule that encodes two polypeptides. A bicistronic gene is therefore encompassed within the definition of a multicistronic gene. A "polypeptide" as used herein comprises at least five amino acids linked by peptide bonds, and can for instance be a protein or a part, such as a subunit, thereof. Mostly, the terms polypeptide and protein are used interchangeably herein. A "gene" or a "transcription unit" as used in the present invention can comprise chromosomal DNA, cDNA, artificial DNA, combinations thereof, and the like. Transcription units comprising several cistrons are transcribed as a single mRNA. In contrast to approaches used in the prior art, in the multicistronic transcription units of the invention, translation of the second coding region (i.e., that for the protein of interest) present on that RNA is not dependent on the use of translation reinitiation sites or internal ribosome entry sites for translation initiation of the second coding region, but rather it is dependent on the efficiency of translation of the first coding region (i.e., that for the selectable marker protein) in a more or less reciprocal manner: the higher the translation level of the selectable marker, the lower the transcription level of the protein of interest and vice versa.

A multicistronic transcription unit according to the invention preferably is a bicistronic transcription unit coding from 5' to 3' for a selectable marker polypeptide and a polypeptide of interest. Hence, the polypeptide of interest is encoded downstream from the coding sequence for the selectable marker polypeptide.

It is also possible to include more coding sequences on the same transcription unit, downstream of the (first) polypeptide of interest, e.g., coding for a second selectable marker polypeptide or for a second polypeptide of interest. Such an extra coding sequence downstream of the coding sequence for the first polypeptide of interest then preferably is preceded by a sequence encoding a translation reinitiation site or internal ribosome entry site (IRES), such that also the second polypeptide of interest or the second selection marker polypeptide is translated, in this case independently from the earlier two coding sequences. In such an embodiment, it is for instance possible to have the coding sequences for subunits of a multimeric protein, e.g., a heavy and a light chain of an immunoglobulin, encoded as a first and second polypeptide of interest (in any order), to code for subunits of a multimeric protein within a single multicistronic expression unit. It is however preferred to use separate transcription units for the expression of different polypeptides of interest, also when these form part of a multimeric protein (see, e.g., Example 13: the heavy and light chain of an antibody each are encoded by a separate transcription unit, each of these expression units being a bicistronic expression unit according to the invention).

The DNA molecules of the invention can be present in the form of double stranded DNA, having with respect to the selectable marker polypeptide and the polypeptide of interest a coding strand and a non-coding strand, the coding strand being the strand with the same sequence as the translated RNA, except for the presence of T instead of U. Hence, an AUG start codon is coded for in the coding strand by an ATG sequence, and the strand containing this ATG sequence corresponding to the AUG start codon in the RNA is referred to as the coding strand of the DNA. It will be clear to the skilled person that start codons or translation initiation sequences are in fact present in an RNA molecule, but that these can be considered equally embodied in a DNA molecule coding for such an RNA molecule; hence, wherever the present invention refers to a start codon or translation initiation sequence, the corresponding DNA molecule having the same sequence as the RNA sequence but for the presence of a T instead of a U in the coding strand of the DNA molecule is meant to be included, and vice versa, except where explicitly specified otherwise. In other words, a start codon is for instance an AUG sequence in RNA, but the corresponding ATG sequence in the coding strand of the DNA is referred to as start codon as well in the present invention. The same is used for the reference of "in frame" coding sequences, meaning triplets (three bases) in the RNA molecule that are translated into an amino acid, but also to be interpreted as the corresponding trinucleotide sequences in the coding strand of the DNA molecule.

The selectable marker polypeptide and the polypeptide of interest encoded by the multicistronic gene each have their own translation initiation sequence, and therefore each have their own start codon (as well as stop codon), i.e., they are encoded by separate open reading frames.

The term "selection marker" or "selectable marker" is typically used to refer to a gene and/or protein whose presence can be detected directly or indirectly in a cell, for example, a polypeptide that inactivates a selection agent and protects the host cell from the agent's lethal or growth-inhibitory effects (e.g., an antibiotic resistance gene and/or protein). Another possibility is that the selection marker induces fluorescence or a color deposit (e.g., green fluorescent protein (GFP) and derivatives (e.g., d2EGFP), luciferase, lacZ, alkaline phosphatase, etc.), which can be used for selecting cells expressing the polypeptide inducing the color deposit, e.g., using a fluorescence activated cell sorter (FACS) for selecting cells that express GFP. Preferably, the selectable marker polypeptide according to the invention provides resistance against lethal and/or growth-inhibitory effects of a selection agent. The selectable marker polypeptide is encoded by the DNA of the invention. The selectable marker polypeptide according to the invention must be functional in a eukaryotic host cell, and hence capable of being selected for in eukaryotic host cells. Any selectable marker polypeptide fulfilling this criterion can in principle be used according to the present invention. Such selectable marker polypeptides are well known in the art and routinely used when eukaryotic host cell clones are to be obtained, and several examples are provided herein. In certain embodiments, a selection marker used for the invention is Zeocin® antibiotic. In other embodiments, blasticidin is used. The person skilled in the art will know that other selection markers are available and can be used, e.g., neomycin, puromycin, bleomycin, hygromycin, etc. In other embodiments, kanamycin is used. In yet other embodiments, the DHFR gene is used as a selectable marker, which can be selected for by methotrexate, especially by increasing the concentration of methotrexate cells can be selected for increased copy numbers of the DHFR gene. Similarly, the glutamine synthetase (GS) gene can be used, for which selection is possible in cells having insufficient GS (e.g., NS-0 cells) by culturing in media without glutamine, or alternatively in cells having sufficient GS (e.g., CHO cells) by adding an inhibitor of GS, methionine sulphoximine (MSX). Other selectable marker genes that could be used, and their selection agents, are for instance described in table 1 of U.S. Pat. No. 5,561,053, incorporated by reference herein; see also Kaufman, Methods in Enzymology, 185:537-566 (1990), for a review of these.

When two multicistronic transcription units are to be selected for according to the invention in a single host cell, each one preferably contains the coding sequence for a different selectable marker, to allow selection for both multicistronic transcription units. Of course, both multicistronic transcription units may be present on a single nucleic acid molecule or alternatively each one may be present on a separate nucleic acid molecule.

The term "selection" is typically defined as the process of using a selection marker/selectable marker and a selection agent to identify host cells with specific genetic properties (e.g., that the host cell contains a transgene integrated into its genome). It is clear to a person skilled in the art that numerous combinations of selection markers are possible. One antibiotic that is particularly advantageous is Zeocin®, because the Zeocin® antibiotic-resistance protein (Zeocin®-R) acts by binding the drug and rendering it harmless. Therefore, it is easy to titrate the amount of drug that kills cells with low levels of Zeocin®-R expression, while allowing the high-expressors to survive. All other antibiotic-resistance proteins in common use are enzymes, and thus act catalytically (not 1:1 with the drug). Hence, the antibiotic Zeocin® is a preferred selection marker. However, the invention also works with other selection markers.

A selectable marker polypeptide according to the invention is the protein that is encoded by the nucleic acid of the invention, which polypeptide can be detected, for instance because it provides resistance to a selection agent such as an antibiotic. Hence, when an antibiotic is used as a selection agent, the DNA encodes a polypeptide that confers resistance to the selection agent, which polypeptide is the selectable marker polypeptide. DNA sequences coding for such selectable marker polypeptides are known, and several examples of wild-type sequences of DNA encoding selectable marker proteins are provided herein (FIGS. 26-32). It will be clear that mutants or derivatives of selectable markers can also be suitably used according to the invention, and are therefore included within the scope of the term "selectable marker polypeptide," as long as the selectable marker protein is still functional.

For convenience and as generally accepted by the skilled person, in many publications as well as herein, often the gene and protein encoding the resistance to a selection agent is referred to as the "selectable agent (resistance) gene" or "selection agent (resistance) protein," respectively, although the official names may be different, e.g., the gene coding for the protein conferring resistance to neomycin (as well as to G418 and kanamycin) is often referred to as neomycin (resistance) (or neo') gene, while the official name is aminoglycoside 3'-phosphotransferase gene.

For the present invention, it is beneficial to have low levels of expression of the selectable marker polypeptide, so that stringent selection is possible. In the present invention this is brought about by using a selectable marker coding sequence with a non-optimal translation efficiency. Upon selection, only cells that have nevertheless sufficient levels of selectable marker polypeptide will be selected, meaning that such cells must have sufficient transcription of the multicistronic transcription unit and sufficient translation of the selectable marker polypeptide, which provides a selection for cells where the multicistronic transcription unit has been integrated or otherwise present in the host cells at a place where expression levels from this transcription unit are high. According to the invention the (more or less) reciprocally interdependent nature of the translation of the polypeptide of interest from that of the translation efficiency of the marker, ensures high translation levels of the polypeptide of interest. This high level of translation is superimposed on the high transcription levels selected for by the stringent selection conditions (and resulting from the use of a strong promoter in the host cells to drive transcription of the multicistronic transcription unit).

The DNA molecules according to the invention have the coding sequence for the selectable marker polypeptide upstream of the coding sequence for the polypeptide of interest, to provide for a multicistronic transcript with reciprocally interdependent translation of the polypeptide of interest and the selectable marker polypeptide. Hence, the multicistronic transcription unit comprises in the 5' to 3' direction (both in the transcribed strand of the DNA and in the resulting transcribed RNA) the coding sequence for the selectable marker polypeptide and the sequence encoding the polypeptide of interest.

According to the invention, the coding regions of the multicistronic gene are preferably translated from the cap-dependent ORF, and therefore the selectable marker polypeptide would in principle also be produced in abundance. To prevent such high translation of the selectable marker cistron, according to the invention the nucleic acid sequence coding for the selectable marker polypeptide comprises a mutation (within the open reading frame (ORF) or in the translation initiation sequences preceding the ORF, or in both) that decreases the translation efficiency of the selectable marker polypeptide in a eukaryotic host cell. The translation efficiency should be lower than that of the corresponding wild-type sequence in the same cell, i.e., the mutation should result in less polypeptide per cell per time unit, and hence less selectable marker polypeptide. This can be detected using routine methods known to the person skilled in the art. For instance in the case of antibiotic selection the mutation will result in less resistance than obtained with the sequence having no such mutation and hence normal translation efficiency, which difference can easily be detected by determining the number of surviving colonies after a normal selection period, which will be lower when a translation efficiency decreasing mutation is present. As is well known to the person skilled in the art there are a number of parameters that indicate the expression level marker polypeptide such as, the maximum concentration of selection agent to which cells are still resistant, number of surviving colonies at a given concentration, growth speed (doubling time) of the cells in the presence of selection agent, combinations of the above, and the like.

In a particularly preferred embodiment, the mutation that decreases the translation efficiency, is a mutation that decreases the translation initiation efficiency.

This can for example be established according to the invention by providing the selectable marker polypeptide coding sequence with a non-optimal translation start sequence.

For example, the translation initiation efficiency of the selectable marker gene in eukaryotic cells can be suitably decreased according to the invention by mutating the start codon and/or the nucleotides in positions −3 to −1 and +4 (where the A of the ATG start codon is nt+1), for instance in the coding strand of the corresponding DNA sequence, to provide a non-optimal translation start sequence. A translation start sequence is often referred to in the field as "Kozak sequence," and an optimal Kozak sequence is RCCATGG, the start codon underlined, R being a purine, i.e., A or G (see Kozak M, 1986, 1987, 1989, 1990, 1997, 2002). Hence, besides the start codon itself, the context thereof, in particular nucleotides −3 to −1 and +4, are relevant, and an optimal translation start sequence comprises an optimal start codon (i.e., ATG) in an optimal context (i.e., the ATG directly preceded by RCC and directly followed by G). A non-optimal translation start sequence is defined herein as any sequence that gives at least some detectable translation in a eukaryotic cell (detectable because the selection marker polypeptide is detectable), and not having the consensus sequence RCC ATGG (start codon underlined). Translation by the ribosomes starts preferably at the first start codon it encounters when scanning from the 5'-cap of the mRNA (scanning mechanism), and is most efficient when an optimal Kozak sequence is present (see Kozak M, 1986, 1987, 1989, 1990, 1997, 2002). However, in a small percentage of events, non-optimal translation initiation sequences are recognized and used by the ribosome to start translation. The present invention makes use of this principle, and allows for decreasing and even fine-tuning of the amount of translation and hence expression of the selectable marker polypeptide, which can therefore be used to increase the stringency of the selection system.

In a first embodiment of the invention, the ATG start codon of the selectable marker polypeptide (in the coding strand of the DNA, coding for the corresponding AUG start codon in the RNA transcription product) is left intact, but the positions at −3 to −1 and +4 are mutated such that they do not fulfill the optimal Kozak sequence any more, e.g., by providing the sequence TTTATGT as the translation start site (ATG start codon underlined). It will be clear that other mutations around the start codon at positions −3 to −1 and/or +4 could be used with similar results using the teaching of the present invention, as can be routinely and easily tested by the person skilled in the art. The idea of this first embodiment is that the ATG start codon is placed in a "non-optimal" context for translation initiation.

In a second and preferred embodiment, the ATG start codon itself of the selectable marker polypeptide is mutated. This will in general lead to even lower levels of translation initiation than the first embodiment. The ATG start codon in the second embodiment is mutated into another codon, which has been reported to provide some translation initiation, for instance to GTG, TTG, CTG, ATT, or ACG (collectively referred to herein as "non-optimal start codons"). In preferred embodiments, the ATG start codon is mutated into a GTG start codon. This provides still lower expression levels (lower translation) than with the ATG start codon intact but in a non-optimal context. More preferably, the ATG start codon is mutated to a TTG start codon, which provides even lower expression levels of the selectable marker polypeptide than with the GTG start codon (Kozak M, 1986, 1987, 1989, 1990, 1997, 2002; see also examples 9-13 herein).

For the second embodiment, i.e., where a non-ATG start codon is used, it is strongly preferred to provide an optimal context for such a start codon, i.e., the non-optimal start codons are preferably directly preceded by nucleotides RCC in positions −3 to −1 and directly followed by a G nucleotide (position +4). However, it has been reported that using the sequence TTT<u>GTG</u>G (start codon underlined), some initiation is observed at least in vitro, so although strongly preferred it may not be absolutely required to provide an optimal context for the non-optimal start codons.

ATG sequences within the coding sequence for a polypeptide, but excluding the ATG start codon, are referred to as "internal ATGs," and if these are in frame with the ORF and therefore code for methionine, the resulting methionine in the polypeptide is referred to as an "internal methionine." It is strongly preferred according to the invention that the coding region (following the start codon, not necessarily including the start codon) coding for the selectable marker polypeptide preferably is devoid of any ATG sequence in the coding strand of the DNA, up to (but not including) the start codon of the polypeptide of interest (obviously, the start codon of the polypeptide of interest may be, and in fact preferably is, an ATG start codon). This can be established by mutating any such ATG sequence within the coding sequence of the selectable marker polypeptide, following the start codon thereof (as is clear from the teaching above, the start codon of the selectable marker polypeptide itself may be an ATG sequence, but not necessarily so). To this purpose preferably, the degeneracy of the genetic code is used to avoid mutating amino acids in the selectable marker polypeptide wherever possible. Hence, wherever an ATG is present in the coding strand of the DNA sequence encoding the selectable marker polypeptide, which ATG is not in frame with the selectable marker polypeptide ORF, and therefore does not code for an internal methionine in the selectable marker polypeptide, the ATG can be mutated such that the resulting polypeptide has no mutations in its internal amino acid sequence. Where the ATG is an in-frame codon coding for an internal methionine, the codon can be mutated, and the resulting mutated polypeptide can be routinely checked for activity of the selectable marker polypeptide. In this way a mutation can be chosen which leads to a mutated selectable marker polypeptide that is still active as such (quantitative differences may exist, but those are less relevant, and in fact it could even be beneficial to have less active variants for the purpose of the present invention; the minimum requirement is that the selectable marker polypeptide can still be selected for in eukaryotic cells). Amino acids valine, threonine, isoleucine and leucine are structurally similar to methionine, and therefore codons that code for one of these amino acids are good starting candidates to be tested in place of methione within the coding sequence after the start codon. Of course, using the teachings of the present invention, the skilled person may test other amino acids as well in place of internal methionines, using routine molecular biology techniques for mutating the coding DNA, and routine testing for functionality of the selectable marker polypeptide. Besides routine molecular biology techniques for mutating DNA, it is at present also possible to synthesize at will (if required using subcloning steps) DNA sequences that have sufficient length for an ORF of a selectable marker polypeptide, and such synthetic DNA sequences can nowadays be ordered commercially from various companies. Hence, using the teachings of the present invention, the person skilled in the art may design appropriate sequences according to the invention encoding a selectable marker polypeptide (with a mutation decreasing translation initiation, and preferably having no internal ATGs), have this sequence synthesized, and test the DNA molecule for functionality of the encoded selectable marker by introducing the DNA molecule in eukaryotic host cells and test for expression of functional selectable marker polypeptide. The commercial availability of such sequences also makes feasible to provide without undue burden for selection marker coding sequences lacking internal ATG sequences, where the wild-type coding sequence of the selection marker polypeptide comprises several such internal ATGs.

By providing a coding sequence for a selectable marker polypeptide lacking any internal ATG sequence, the chances of inadvertent translation initiation by ribosomes that passed the (first, non-optimal) translation start sequence of the selectable marker polypeptide at a subsequent internal ATG trinucleotide is diminished, so that the ribosomes will continue to scan for the first optimal translation start sequence, i.e., that of the polypeptide of interest.

It will be clear that it is not necessarily strictly required to remove all internal ATG sequences from the coding sequence of the selectable marker, as long as the vast majority of ribosomes will not use such internal ATG sequences as a translation initiation start site, for instance because such internal ATGs usually are not in an optimal context for translation initiation. However, also in view of the fact that even an ATG sequence in a non-optimal context gives rise to significant translation initiation events (in general much higher than from a non-ATG start codon in an optimal context), it will also be clear that if several internal ATG sequences are present in the coding region of the selectable marker, each of these might subtract a fraction of ribosomes that start translation at those ATGs, preventing them from reaching the downstream translation unit encoding the polypeptide of interest, and hence result in less expression of the polypeptide of interest. This is the reason why it is preferred to have a sequence encoding the selectable marker polypeptide, which sequence is free of internal ATG sequences. Possibly, if desired, the ratio of ribosomes translating the polypeptide of interest might even be further enhanced by mutating any non-optimal potential translation initiation sites within the sequence coding for the selectable marker polypeptide.

Clearly, any sequence present in the coding strand between the stop codon of the selectable marker and the start codon of the polypeptide of interest can easily be designed such that it does not comprise ATG sequences, or other non-optimal potential translation start codons.

Clearly, it is strongly preferred according to the present invention, that the translation start sequence of the polypeptide of interest comprises an optimal translation start sequence, i.e., having the consensus sequence RCC<u>ATG</u>G (start codon underlined). This will result in a very efficient translation of the polypeptide of interest.

As a consequence of these measures, the reciprocally interdependent translation mechanism of the invention is provided: ribosomes scan from the cap of the mRNA containing the multicistronic transcription unit, and a small percentage of ribosomes will translate the first open reading frame, i.e., the selectable marker protein, because this is provided with a mutation decreasing the translation efficiency, while the great majority of the ribosomes will pass this open reading frame and start translation at the optimal translation initiation site of the polypeptide of interest, resulting in low levels of selectable marker protein and high levels of polypeptide of interest. By providing the coding sequence of the marker with different mutations leading to several levels of decreased translation efficiency, the stringency of selection is increased and reciprocally the expression levels of the polypeptide of interest go up, so that fine-tuning is possible: for instance, using a TTG start codon for the selection marker polypeptide, only very few ribosomes will translate from this start codon, resulting in very low levels of selectable marker protein, and hence a high stringency of selection, and at the same time almost all ribosomes will translate the polypeptide of interest.

It is demonstrated herein that this can be used in a very robust selection system, leading to a very large percentage of clones that express the polypeptide of interest at high levels, as desired. In addition, the expression levels obtained for the polypeptide of interest appear to be significantly higher than those obtained when an even larger number of colonies are screened using selection systems hitherto known.

In addition to a decreased translation initiation efficiency, it could be beneficial to also provide for decreased translation elongation efficiency of the selectable marker polypeptide, e.g., by mutating the coding sequence thereof so that it comprises several non-preferred codons of the host cell, in order to further decrease the translation levels of the marker polypeptide and allow still more stringent selection conditions, if desired. In certain embodiments, besides the mutation(s) that decrease the translation efficiency according to the invention, the selectable marker polypeptide further comprises a mutation that reduces the activity of the selectable marker polypeptide compared to its wild-type counterpart. This may be used to increase the stringency of selection even further. As non-limiting examples, proline at position 9 in the Zeocin® antibiotic resistance polypeptide may be mutated, e.g., to Thr or Phe, and for the neomycin resistance polypeptide, amino acid residue 182 or 261 or both may further be mutated (see, e.g., WO 01/32901).

In some embodiments of the invention, a so-called spacer sequence is placed downstream of the sequence encoding the start codon of the selectable marker polypeptide, which spacer sequence preferably is a sequence in frame with the start codon and encoding a few amino acids, and that does not contain a secondary structure (Kozak, 1990), and does not contain the sequence ATG. Such a spacer sequence can be used to further decrease the translation initiation frequency if a secondary structure is present in the RNA (Kozak, 1990) of the selectable marker polypeptide (e.g., for Zeocin® antibiotic, possibly for blasticidin), and hence increase the stringency of the selection system according to the invention.

The invention also provides a DNA molecule comprising the sequence encoding a selectable marker protein according to the invention, which DNA molecule has been provided with a mutation that decreases the translation efficiency of the functional selectable marker polypeptide in a eukaryotic host cell. In preferred embodiments hereof, the DNA molecule in the coding strand: i) has been mutated compared to the wild-type sequence encoding the selectable marker polypeptide, such that the sequence ATG is absent from the coding region following the start codon of the functional selectable marker protein up till the stop codon of the functional selectable marker protein open reading frame; and ii) has a non-optimal translation start sequence of the functional selectable marker polypeptide. Features i) and ii) can again be provided according to the description above. Such DNA molecules encompass a useful intermediate product according to the invention. These molecules can be prepared first, introduced into eukaryotic host cells and tested for functionality (for some markers this is even possible in prokaryotic host cells), if desired in a (semi-) quantitative manner, of the selectable marker polypeptide. They may then be further used to prepare a DNA molecule according to the invention, comprising the multicistronic transcription unit.

It is a preferred aspect of the invention to provide an expression cassette comprising the DNA molecule according to the invention, having the multicistronic transcription unit. Such an expression cassette is useful to express sequences of interest, for instance in host cells. An "expression cassette" as used herein is a nucleic acid sequence comprising at least a promoter functionally linked to a sequence of which expression is desired. Preferably, an expression cassette further contains transcription termination and polyadenylation sequences. Other regulatory sequences such as enhancers may also be included. Hence, the invention provides an expression cassette comprising in the following order: 5'-promoter-multicistronic transcription unit according to the invention, coding for a selectable marker polypeptide and downstream thereof a polypeptide of interest-transcription termination sequence-3'. The promoter must be capable of functioning in a eukaryotic host cell, i.e., it must be capable of driving transcription of the multicistronic transcription unit. The expression cassette may optionally further contain other elements known in the art, e.g., splice sites to comprise introns, and the like. In some embodiments, an intron is present behind the promoter and before the sequence encoding the selectable marker polypeptide.

To obtain expression of nucleic acid sequences encoding protein, it is well known to those skilled in the art that sequences capable of driving such expression, can be functionally linked to the nucleic acid sequences encoding the protein, resulting in recombinant nucleic acid molecules encoding a protein in expressible format. In the present invention, the expression cassette comprises a multicistronic transcription unit. In general, the promoter sequence is placed upstream of the sequences that should be expressed. Much used expression vectors are available in the art, e.g., the pcDNA and pEF vector series of Invitrogen, pMSCV and pTK-Hyg from BD Sciences, pCMV-Script from Stratagene, etc, which can be used to obtain suitable promoters and/or transcription terminator sequences, polyA sequences, and the like.

Where the sequence encoding the polypeptide of interest is properly inserted with reference to sequences governing the transcription and translation of the encoded polypeptide, the resulting expression cassette is useful to produce the polypeptide of interest, referred to as expression. Sequences driving expression may include promoters, enhancers and the like, and combinations thereof. These should be capable of functioning in the host cell, thereby driving expression of the nucleic acid sequences that are functionally linked to them. The person skilled in the art is aware that various promoters can be used to obtain expression of a gene in host cells. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000). Some well-known and much used promoters for expression in eukaryotic cells comprise promoters derived from viruses, such as adenovirus, e.g., the E1A promoter, promoters derived from cytomegalovirus (CMV), such as the CMV immediate early (IE) promoter (referred to herein as the CMV promoter) (obtainable for instance from pcDNA, Invitrogen), promoters derived from Simian Virus 40 (SV40) (Das et al., 1985), and the like. Suitable promoters can also be derived from eukaryotic cells, such as methallothionein (MT) promoters, elongation factor 1α (EF-1α) promoter (Gill et al., 2001), ubiquitin C or UB6 promoter (Gill et al., 2001; Schorpp et al., 1996), actin promoter, an immunoglobulin promoter, heat shock promoters, and the like. Some preferred promoters for obtaining expression in eukaryotic cells, which are suitable promoters in the present invention, are the CMV-promoter, a mammalian EF1-alpha promoter, a mammalian ubiquitin promoter such as a ubiquitin C promoter, or a SV40 promoter (e.g., obtainable from pIRES, cat. no. 631605, BD Sciences). Testing for promoter function and strength of a promoter is a matter of routine for a person skilled in the art, and in general may for instance encompass cloning a test gene such as lacZ, luciferase, GFP, etc. behind the promoter sequence, and test for expression of the test gene. Of course, promoters may be altered by deletion, addition, mutation of sequences therein, and tested for functionality, to find new, attenuated, or improved promoter sequences. According to the present invention, strong promoters that give high transcription levels in the eukaryotic cells of choice are preferred.

In certain embodiments, a DNA molecule according to the invention is part of a vector, e.g., a plasmid. Such vectors can easily be manipulated by methods well known to the person skilled in the art, and can for instance be designed for being capable of replication in prokaryotic and/or eukaryotic cells. In addition, many vectors can directly or in the form of isolated desired fragment therefrom be used for transformation of eukaryotic cells and will integrate in whole or in part into the genome of such cells, resulting in stable host cells comprising the desired nucleic acid in their genome.

Conventional expression systems are DNA molecules in the form of a recombinant plasmid or a recombinant viral genome. The plasmid or the viral genome is introduced into (eukaryotic host) cells and preferably integrated into their genomes by methods known in the art. In preferred embodiments, the present invention also uses these types of DNA molecules to deliver its improved transgene expression system. A preferred embodiment of the invention is the use of plasmid DNA for delivery of the expression system. A plasmid contains a number of components: conventional components, known in the art, are an origin of replication and a selectable marker for propagation of the plasmid in bacterial cells; a selectable marker that functions in eukaryotic cells to identify and isolate host cells that carry an integrated transgene expression system; the protein of interest, whose high-level transcription is brought about by a promoter that is functional in eukaryotic cells (e.g., the human cytomegalovirus major immediate early promoter/enhancer, pCMV (Boshart et al., 1985); and viral transcriptional terminators (e.g., the SV40 polyadenylation site (Kaufman & Sharp, 1982) for the transgene of interest and the selectable marker.

The vector used can be any vector that is suitable for cloning DNA and that can be used for transcription of a nucleic acid of interest. When host cells are used it is preferred that the vector is an integrating vector. Alternatively, the vector may be an episomally replicating vector.

It is widely appreciated that chromatin structure and other epigenetic control mechanisms may influence the expression of transgenes in eukaryotic cells (e.g., Whitelaw et al., 2001). The multicistronic expression units according to the invention form part of a selection system with a rather rigorous selection regime. This generally requires high transcription levels in the host cells of choice. To increase the chance of finding clones of host cells that survive the rigorous selection regime, and possibly to increase the stability of expression in obtained clones, it will generally be preferable to increase the predictability of transcription. Therefore, in preferred embodiments, an expression cassette according to the invention further comprises at least one chromatin control element. A "chromatin control element" as used herein is a collective term for DNA sequences that may somehow have an effect on the chromatin structure and therewith on the expression level and/or stability of expression of transgenes in their vicinity (they function "in cis," and hence are placed preferably within 5 kb, more preferably within 2 kb, still more preferably within 1 kb from the transgene) within eukaryotic cells. Such elements have sometimes been used to increase the number of clones having desired levels of transgene expression. The mechanisms by which these elements work may differ for and even within different classes of such elements, and are not completely known for all types of such elements. However, such elements have been described, and for the purpose of the present invention chromatin control elements are chosen from the group consisting of matrix or scaffold attachment regions (MARs/SARs) (e.g., Phi-Van et al., 1990; WO 02/074969, WO 2005/040377), insulators (West et al., 2002) such as the beta-globin insulator element (5' HS4 of the chicken beta-globin locus), scs, scs', and the like (e.g., Chung et al., 1993, 1997; Kellum and Schedl, 1991; WO 94/23046, WO 96/04390, WO 01/02553, WO 2004/027072), a ubiquitous chromatin opening element (UCOE) (WO 00/05393, WO 02/24930, WO 02/099089, WO 02/099070), and anti-repressor sequences (also referred to as "STAR" sequences) (Kwaks et al., 2003; WO 03/004704). Non-limiting examples of MAR/SAR sequences that could be used in the current invention are the chicken lysosyme 5' MAR (Phi-Van et al., 1990) or fragments thereof, e.g., the B, K and F regions as described in WO 02/074969); DNA sequences comprising at least one bent DNA element and at least one binding site for a DNA binding protein, preferably containing at least 10% of dinucleotide TA, and/or at least 12% of dinucleotide AT on a stretch of 100 contiguous base pairs, such as a sequence selected from the group of comprising the sequences SEQ ID NOS:1 to 27 in WO 2005/040377, fragments of any one of SEQ ID NOS:1 to 27 in WO 2005/040377 being at least 100 nucleotides in length and having MAR activity, sequences that are at least 70% identical in nucleotide sequence to any one of SEQ ID NOS:1 to 27 in WO 2005/040377 or fragments thereof and having MAR activity, wherein MAR activity is defined as being capable of binding to nuclear matrices/scaffolds in vitro and/or of altering the expression of coding sequences operably linked to a promoter; sequences chosen from any one of SEQ ID NOS:1 to 5 in WO 02/074969, fragments of any one of any one of SEQ ID NOS:1 to 5 in WO 02/074969 and having MAR activity, sequences that are at least 70% identical in nucleotide sequence to any one of SEQ ID NOS:1 to 5 in WO 02/074969 or fragments thereof and having MAR activity; sequences chosen from SEQ ID NO:1 and SEQ ID NO:2 in WO 2004/027072, functional fragments thereof and sequences being at least 70% identical thereto. A non-limiting example of insulator sequences that could be used in the present invention is a sequence that comprises SEQ ID NO:1 of WO 01/02553. Non-limiting examples of UCOEs that could be used in the present invention are sequences depicted in FIGS. 2 and 7 of WO 02/24930, functional fragments thereof and sequences being at least 70% identical thereto while still retaining activity; sequences comprising SEQ ID NO:28 of U.S. 2005/181428, functional fragments thereof and sequences being at least 70% identical thereto while still retaining activity.

Preferably, the chromatin control element is an anti-repressor sequence, preferably chosen from the group consisting of: a) any one SEQ ID NO:1 through SEQ ID NO:66; b) fragments of any one of SEQ ID NO:1 through SEQ ID NO:66, wherein the fragments have anti-repressor activity ("functional fragments"); c) sequences that are at least 70% identical in nucleotide sequence to a) or b) wherein the sequences have anti-repressor activity ("functional derivatives"); and d)

the complement to any one of a) to c). Preferably, the chromatin control element is chosen from the group consisting of STAR67 (SEQ ID NO:66), STAR7 (SEQ ID NO:7), STAR9 (SEQ ID NO:9), STAR17 (SEQ ID NO:17), STAR27 (SEQ ID NO:27), STAR29 (SEQ ID NO:29), STAR43 (SEQ ID NO:43), STAR44 (SEQ ID NO:44), STAR45 (SEQ ID NO:45), STAR47 (SEQ ID NO:47), STAR61 (SEQ ID NO:61), or a functional fragment or derivative of the STAR sequences. In a particularly preferred embodiment, the STAR sequence is STAR 67 (SEQ ID NO:66) or a functional fragment or derivative thereof. In certain preferred embodiments, STAR 67 or a functional fragment or derivative thereof is positioned upstream of a promoter driving expression of the multicistronic transcription unit. In other preferred embodiments, the expression cassettes according to the invention are flanked on both sides by at least one anti-repressor sequence.

Sequences having anti-repressor activity as used herein are sequences that are capable of at least in part counteracting the repressive effect of HP1 or HPC2 proteins when these proteins are tethered to DNA. Sequences having anti-repressor activity (sometimes also referred to as anti-repressor sequences or anti-repressor elements herein) suitable for the present invention, have been disclosed in WO 03/004704, incorporated herein by reference, and were coined "STAR" sequences therein (wherever a sequence is referred to as a STAR sequence herein, this sequence has anti-repressor activity according to the invention). As a non-limiting example, the sequences of 66 anti-repressor elements, named STAR1-65 (see WO 03/004704) and STAR67, are presented herein as SEQ ID NOS:1-65 and 66, respectively.

According to the invention, a functional fragment or derivative of a given anti-repressor element is considered equivalent to the anti-repressor element, when it still has anti-repressor activity. The presence of such anti-repressor activity can easily be checked by the person skilled in the art, for instance by the assay described below. Functional fragments or derivatives can easily be obtained by a person skilled in the art of molecular biology, by starting with a given anti-repressor sequence, and making deletions, additions, substitutions, inversions and the like (see, e.g., WO 03/004704). A functional fragment or derivative also comprises orthologs from other species, which can be found using the known anti-repressor sequences by methods known by the person skilled in the art (see, e.g., WO 03/004704). Hence, the present invention encompasses fragments of the anti-repressor sequences, wherein the fragments still have anti-repressor activity. The invention also encompasses sequences that are at least 70% identical in nucleotide sequence to the sequences having anti-repressor activity or to functional fragments thereof having anti-repressor activity, as long as these sequences that are at least 70% identical still have the anti-repressor activity according to the invention. Preferably, the sequences are at least 80% identical, more preferably at least 90% identical and still more preferably at least 95% identical to the reference native sequence or functional fragment thereof. For fragments of a given sequence, percent identity refers to that portion of the reference native sequence that is found in the fragment.

Sequences having anti-repressor activity according to the invention can be obtained by various methods, including but not limited to the cloning from the human genome or from the genome of another organism, or by for instance amplifying known anti-repressor sequences directly from such a genome by using the knowledge of the sequences, e.g., by PCR, or can in part or wholly be chemically synthesized.

Sequences having anti-repressor activity, and functional fragments or derivatives thereof, are structurally defined herein by their sequence and in addition are functionally defined as sequences having anti-repressor activity, which can be determined with the assay described below.

Any sequence having anti-repressor activity according to the present invention should at least be capable of surviving the following functional assay (see WO 03/004704, Example 1, incorporated herein by reference).

Figure 1:
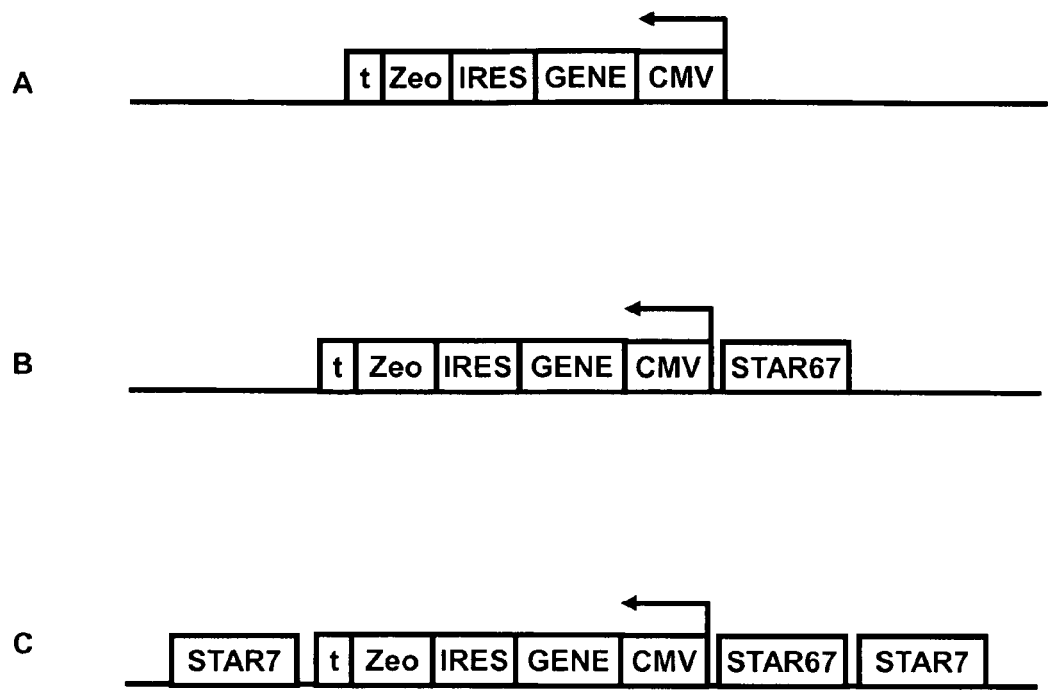
FIG. 1. Schematic diagram of transcription units without and with STAR elements. A) bicistronic gene containing (from 5' to 3') a transgene (encoding for example the d2EGFP gene), an IRES, and a selectable marker (zeo, conferring Zeocin® antibiotic resistance) under control of the CMV promoter. The expression unit has the SV40 transcriptional terminator at its 3' end (t). The name of the construct is CMV-d2EGFP-ires-Zeo (CMV Control). B) construct as in A, but now STAR 67 is cloned upstream of the CMV promoter. The name of the construct is STAR67-CMV-d2EGFP-ires-Zeo (CMV-STAR67). C) construct as in B, but upstream and downstream STAR7 elements are cloned to flank the entire construct. The name of the construct is STAR7-STAR67-CMV-d2EGFP-ires-Zeo-STAR7 (CMV-STAR67 7/7)

Human U-2 OS cells (ATCC HTB-96) are stably transfected with the pTet-Off plasmid (Clontech K1620-A) and with nucleic acid encoding a LexA-repressor fusion protein containing the LexA DNA binding domain and the coding region of either HP1 or HPC2 (*Drosophila* Polycomb group proteins that repress gene expression when tethered to DNA; the assay works with either fusion protein) under control of the Tet-Off transcriptional regulatory system (Gossen and Bujard, 1992). These cells are referred to below as the reporter cells for the anti-repressor activity assay. A reporter plasmid, which provides hygromycin resistance, contains a polylinker sequence positioned between four LexA operator sites and the SV40 promoter that controls the Zeocin® antibiotic resistance gene. The sequence to be tested for anti-repressor activity can be cloned in the polylinker. Construction of a suitable reporter plasmid, such as pSelect, is described in Example 1 and FIG. 1 of WO 00/004704. The reporter plasmid is transfected into the reporter cells, and the cells are cultured under hygromycin selection (25 μg/ml; selection for presence of the reporter plasmid) and tetracycline repression (doxycycline, 10 ng/ml; prevents expression of the LexA-repressor fusion protein). After one week of growth under these conditions, the doxycycline concentration is reduced to 0.1 ng/ml to induce the LexA-repressor gene, and after two days zeocin is added to 250 μg/ml. The cells are cultured for five weeks, until the control cultures (transfected with empty reporter plasmid, i.e., lacking a cloned anti-repressor sequence in the polylinker) are killed by the Zeocin® antibiotic (in this control plasmid, the SV40 promoter is repressed by the LexA-repressor fusion protein that is tethered to the LexA operating sites, resulting in insufficient Zeocin® antibiotic expression in such cells to survive zeocin selection). A sequence has anti-repressor activity according to the present invention if, when the sequence is cloned in the polylinker of the reporter plasmid, the reporter cells survive the 5 weeks selection under Zeocin® antibiotic. Cells from such colonies can still be propagated onto new medium containing Zeocin® antibiotic after the five weeks Zeocin® antibiotic selection, whereas cells transfected with reporter plasmids lacking anti-repressor sequences cannot be propagated onto new medium containing Zeocin® antibiotic. Any sequence not capable of conferring such growth after 5 weeks on Zeocin® antibiotic in this assay, does not qualify as a sequence having anti-repressor activity, or functional fragment or functional derivative thereof according to the present invention. As an example, other known chromatin control elements such as those tested by Van der Vlag et al. (2000), including *Drosophila* scs (Kellum and Schedl, 1991), 5'-HS4 of the chicken β-globin locus (Chung et al., 1993, 1997) or Matrix Attachment Regions (MARs) (Phi-Van et al., 1990), do not survive this assay.

In addition, it is preferred that the anti-repressor sequence or functional fragment or derivative thereof confers a higher proportion of reporter over-expressing clones when flanking a reporter gene (e.g., luciferase, GFP) which is integrated into the genome of U-2 OS or CHO cells, compared to when the reporter gene is not flanked by anti-repressor sequences, or flanked by weaker repression blocking sequences such as *Drosophila* scs. This can be verified using for instance the pSDH vector, or similar vectors, as described in Example 1 and FIG. 2 of WO 03/004704.

Anti-repressor elements can have at least one of three consequences for production of protein: (1) they increase the predictability of identifying host cell lines that express a protein at industrially acceptable levels (they impair the ability of adjacent heterochromatin to silence the transgene, so that the position of integration has a less pronounced effect on expression); (2) they result in host cell lines with increased protein yields; and/or (3) they result in host cell lines that exhibit more stable protein production during prolonged cultivation.

Any STAR sequence can be used in the expression cassettes according to the present invention, but the following STAR sequences are particularly useful: STAR67 (SEQ ID NO:66), STAR7 (SEQ ID NO:7), STAR9 (SEQ ID NO:9), STAR17 (SEQ ID NO:17), STAR27 (SEQ ID NO:27), STAR29 (SEQ ID NO:29), STAR43 (SEQ ID NO:43), STAR44 (SEQ ID NO:44), STAR45 (SEQ ID NO:45), STAR47 (SEQ ID NO:47), STAR61 (SEQ ID NO:61), or functional fragments or derivatives of these STAR sequences.

In certain embodiments the anti-repressor sequence, preferably STAR67, is placed upstream of the promoter, preferably such that less than 2 kb are present between the 3' end of the anti-repressor sequence and the start of the promoter sequence. In preferred embodiments, less than 1 kb, more preferably less than 500 nucleotides (nt), still more preferably less than about 200, 100, 50, or 30 nt are present between the 3' end of the anti-repressor sequence and the start of the promoter sequence. In certain preferred embodiments, the anti-repressor sequence is cloned directly upstream of the promoter, resulting in only about 0-20 nt between the 3' end of the anti-repressor sequence and the start of the promoter sequence.

For the production of multimeric proteins, two or more expression cassettes can be used. Preferably, both expression cassettes are multicistronic expression cassettes according to the invention, each coding for a different selectable marker protein, so that selection for both expression cassettes is possible. This embodiment has proven to give good results, e.g., for the expression of the heavy and light chain of antibodies. It will be clear that both expression cassettes may be placed on one nucleic acid molecule or both may be present on a separate nucleic acid molecule, before they are introduced into host cells. An advantage of placing them on one nucleic acid molecule is that the two expression cassettes are present in a single predetermined ratio (e.g., 1:1) when introduced into host cells. On the other hand, when present on two different nucleic acid molecules, this allows the possibility to vary the molar ratio of the two expression cassettes when introducing them into host cells, which may be an advantage if the preferred molar ratio is different from 1:1 or when it is unknown beforehand what is the preferred molar ratio, so that variation thereof and empirically finding the optimum can easily be performed by the skilled person. According to the invention, preferably at least one of the expression cassettes, but more preferably each of them, comprises a chromatin control element, more preferably an anti-repressor sequence.

In another embodiment, the different subunits or parts of a multimeric protein are present on a single expression cassette.

Instead of or in addition to the presence of a STAR sequence placed upstream of a promoter in an expression cassette, it has proven highly beneficial to provide a STAR sequence on both sides of an expression cassette, such that expression cassette comprising the transgene is flanked by two STAR sequences, which in certain embodiments are essentially identical to each other.

It is shown herein that the combination of a first anti-repressor element upstream of a promoter and flanking the expression cassette by two other anti-repressor sequences provides superior results.

As at least some anti-repressor sequences can be directional (WO 00/004704), the anti-repressor sequences flanking the expression cassette (anti-repressor A and B) may beneficially placed in opposite direction with respect to each other, such that the 3' end of each of these anti-repressor sequences is facing inwards to the expression cassette (and to each other). Hence, in preferred embodiments, the 5' side of an anti-repressor element faces the DNA/chromatin of which the influence on the transgene is to be diminished by the anti-repressor element. For an anti-repressor sequence upstream of a promoter in an expression cassette, the 3' end faces the promoter. The sequences of the anti-repressor elements in the sequence listing (SEQ ID NOS:1-66) are given in 5' to 3' direction, unless otherwise indicated.

In certain embodiments, transcription units or expression cassettes according to the invention are provided, further comprising: a) a transcription pause (TRAP) sequence upstream of the promoter that drives transcription of the multicistronic transcription unit, the TRAP being in a 5' to 3' direction; or b) a TRAP sequence downstream of the open reading frame of the polypeptide of interest and preferably downstream of the transcription termination sequence of the multicistronic transcription unit, the TRAP being in a 3' to 5' orientation; or c) both a) and b); wherein a TRAP sequence is functionally defined as a sequence which when placed into a transcription unit, results in a reduced level of transcription in the nucleic acid present on the 3' side of the TRAP when compared to the level of transcription observed in the nucleic acid on the 5' side of the TRAP. Non-limiting examples of TRAP sequences are transcription termination and/or polyadenylation signals. One non-limiting example of a TRAP sequence is given in SEQ ID NO:142. Examples of other TRAP sequences, methods to find these, and uses thereof have been described in WO 2004/055215.

DNA molecules comprising multicistronic transcription units and/or expression cassettes according to the present invention can be used for improving expression of nucleic acid, preferably in host cells. The terms "cell"/"host cell" and "cell line"/"host cell line" are respectively typically defined as a cell and homogeneous populations thereof that can be maintained in cell culture by methods known in the art, and that have the ability to express heterologous or homologous proteins.

Prokaryotic host cells can be used to propagate and/or perform genetic engineering with the DNA molecules of the invention, especially when present on plasmids capable of replicating in prokaryotic host cells such as bacteria.

A host cell according to the present invention preferably is a eukaryotic cell, more preferably a mammalian cell, such as a rodent cell or a human cell or fusion between different cells. In certain non-limiting embodiments, the host cell is a U-2 OS osteosarcoma, CHO (Chinese hamster ovary), HEK 293, HuNS-1 myeloma, WERI-Rb-1 retinoblastoma, BHK, Vero, non-secreting mouse myeloma Sp2/0-Ag 14, non-secreting mouse myeloma NS0, NCI-H295R adrenal gland carcinomal or a PER.C6® cell.

In certain embodiments of the invention, a host cell is a cell expressing at least E1A, and preferably also E1B, of an adenovirus. As non-limiting examples, such a cell can be derived from for instance human cells, for instance from a kidney (example: HEK 293 cells, see Graham et al., 1977), lung (e.g., A549, see, e.g., WO 98/39411) or retina (example: HER cells marketed under the trade mark PER.C6®, see U.S. Pat. No.

5,994,128), or from amniocytes (e.g., N52.E6, described in U.S. Pat. No. 6,558,948), and similarly from other cells. Methods for obtaining such cells are described for instance in U.S. Pat. Nos. 5,994,128 and 6,558,948. PER.C6 cells for the purpose of the present invention means cells from an upstream or downstream passage or a descendent of an upstream or downstream passage of cells as deposited under ECACC no. 96022940, i.e., having the characteristics of those cells. It has been previously shown that such cells are capable of expression of proteins at high levels (e.g., WO 00/63403, and Jones et al., 2003). In other preferred embodiments, the host cells are CHO cells, for instance CHO-K1, CHO-S, CHO-DG44, CHO-DUKXB11, and the like. In certain embodiments, the CHO cells have a dhfr⁻ phenotype.

Such eukaryotic host cells can express desired polypeptides, and are often used for that purpose. They can be obtained by introduction of a DNA molecule of the invention, preferably in the form of an expression cassette, into the cells. Preferably, the expression cassette is integrated in the genome of the host cells, which can be in different positions in various host cells, and selection will provide for a clone where the transgene is integrated in a suitable position, leading to a host cell clone with desired properties in terms of expression levels, stability, growth characteristics, and the like. Alternatively the multicistronic transcription unit may be targeted or randomly selected for integration into a chromosomal region that is transcriptionally active, e.g., behind a promoter present in the genome. Selection for cells containing the DNA of the invention can be performed by selecting for the selectable marker polypeptide, using routine methods known by the person skilled in the art. When such a multicistronic transcription unit is integrated behind a promoter in the genome, an expression cassette according to the invention can be generated in situ, i.e., within the genome of the host cells.

Preferably the host cells are from a stable clone that can be selected and propagated according to standard procedures known to the person skilled in the art. A culture of such a clone is capable of producing polypeptide of interest, if the cells comprise the multicistronic transcription unit of the invention. Cells according to the invention preferably are able to grow in suspension culture in serum-free medium.

In preferred embodiments, the DNA molecule comprising the multicistronic transcription unit of the invention, preferably in the form of an expression cassette, is integrated into the genome of the eukaryotic host cell according to the invention. This will provide for stable inheritance of the multicistronic transcription unit.

Selection for the presence of the selectable marker polypeptide, and hence for expression, can be performed during the initial obtaining of the cells, and could be lowered or stopped altogether after stable clones have been obtained. It is however also possible to apply the selection agent during later stages continuously, or only occasionally, possibly at lower levels than during initial selection of the host cells.

A polypeptide of interest according to the invention can be any protein, and may be a monomeric protein or a (part of a) multimeric protein. A multimeric protein comprises at least two polypeptide chains. Non-limiting examples of a protein of interest according to the invention are enzymes, hormones, immunoglobulin chains, therapeutic proteins like anti-cancer proteins, blood coagulation proteins such as Factor VIII, multi-functional proteins, such as erythropoietin, diagnostic proteins, or proteins or fragments thereof useful for vaccination purposes, all known to the person skilled in the art.

In certain embodiments, an expression cassette of the invention encodes an immunoglobulin heavy or light chain or an antigen binding part, derivative and/or analogue thereof. In a preferred embodiment a protein expression unit according to the invention is provided, wherein the protein of interest is an immunoglobulin heavy chain. In yet another preferred embodiment a protein expression unit according to the invention is provided, wherein the protein of interest is an immunoglobulin light chain. When these two protein expression units are present within the same (host) cell a multimeric protein and more specifically an immunoglobulin, is assembled. Hence, in certain embodiments, the protein of interest is an immunoglobulin, such as an antibody, which is a multimeric protein. Preferably, such an antibody is a human or humanized antibody. In certain embodiments thereof, it is an IgG, IgA, or IgM antibody. An immunoglobulin may be encoded by the heavy and light chains on different expression cassettes, or on a single expression cassette. Preferably, the heavy and light chain are each present on a separate expression cassette, each having its own promoter (which may be the same or different for the two expression cassettes), each comprising a multicistronic transcription unit according to the invention, the heavy and light chain being the polypeptide of interest, and preferably each coding for a different selectable marker protein, so that selection for both heavy and light chain expression cassette can be performed when the expression cassettes are introduced and/or present in a eukaryotic host cell.

The polypeptide of interest may be from any source, and in certain embodiments is a mammalian protein, an artificial protein (e.g., a fusion protein or mutated protein), and preferably is a human protein.

Obviously, the configurations of the expression cassettes of the present invention may also be used when the ultimate goal is not the production of a polypeptide of interest, but the RNA itself, for instance for producing increased quantities of RNA from an expression cassette, which may be used for purposes of regulating other genes (e.g., RNAi, antisense RNA), gene therapy, in vitro protein production, etc.

In one aspect, the invention provides a method for generating a host cell expressing a polypeptide of interest, the method comprising the steps of: a) introducing into a plurality of precursor cells an expression cassette according to the invention, and b) culturing the generated cells under conditions selecting for expression of the selectable marker polypeptide, and c) selecting at least one host cell producing the polypeptide of interest. This novel method provides a very good result in terms of the ratio of obtained clones versus clones with high expression of the desired polypeptide. Using the most stringent conditions, i.e., the weakest translation efficiency for the selectable marker polypeptide (using the weakest translation start sequence), far fewer colonies are obtained using the same concentration of selection agent than with known selection systems, and a relatively high percentage of the obtained clones produces the polypeptide of interest at high levels. In addition, the obtained levels of expression appear higher than those obtained when an even larger number of clones using the known selection systems are used.

It is an additional advantage that the selection system is swift because it does not require copy number amplification of the transgene. Hence, cells with low copy numbers of the multicistronic transcription units already provide high expression levels. High transgene copy numbers of the transgene may be prone to genetic instability and repeat-induced silencing (e.g., Kim et al., 1998; McBurney et al., 2002). Therefore, an additional advantage of the embodiments of the invention with relatively low transgene copy numbers is that lower copy numbers are anticipated to be less prone to recombination and to repeat-induced silencing, and therefore less problems in this respect are anticipated when using host cells with a limited number of copies of the transgene compared to host cells obtained using an amplification system where hundreds or even thousands of copies of the selectable marker and protein of interest coding sequences may be present in the genome of the cell. The present invention provides examples of high expression levels, using the multicistronic transcription unit selection system, while the copy number of the transgene is relatively low, i.e., less than 30 copies per cell, or even less than 20 copies per cell. Hence, the present invention allows the generation of host cells according to the invention, comprising less than 30 copies of the multicistronic transcription unit in the genome of the host cells, preferably less than 25, more preferably less than 20 copies, while at the same time providing sufficient expression levels of the polypeptide of interest for commercial purposes, e.g., more than 15, preferably more than 20 µg/cell/day of an antibody.

While clones having relatively low copy numbers of the multicistronic transcription units and high expression levels can be obtained, the selection system of the invention nevertheless can be combined with amplification methods to even further improve expression levels. This can for instance be accomplished by amplification of a co-integrated dhfr gene using methotrexate, for instance by placing dhfr on the same nucleic acid molecule as the multicistronic transcription unit of the invention, or by cotransfection when dhfr is on a separate DNA molecule.

In one aspect, the invention provides a method for producing a polypeptide of interest, the method comprising culturing a host cell, the host cell comprising a DNA molecule comprising a multicistronic expression unit or an expression cassette according to the invention, and expressing the polypeptide of interest from the coding sequence for the polypeptide of interest.

The host cell for this aspect is a eukaryotic host cell, preferably a mammalian cell, such as a CHO cell, further as described above.

Introduction of nucleic acid that is to be expressed in a cell, can be done by one of several methods, which as such are known to the person skilled in the art, also dependent on the format of the nucleic acid to be introduced. The methods include but are not limited to transfection, infection, injection, transformation, and the like. Suitable host cells that express the polypeptide of interest can be obtained by selection as described above.

In certain embodiments, selection agent is present in the culture medium at least part of the time during the culturing, either in sufficient concentrations to select for cells expressing the selectable marker polypeptide or in lower concentrations. In preferred embodiments, selection agent is no longer present in the culture medium during the production phase when the polypeptide is expressed.

Culturing a cell is done to enable it to metabolize, and/or grow and/or divide and/or produce recombinant proteins of interest. This can be accomplished by methods well known to persons skilled in the art, and includes but is not limited to providing nutrients for the cell. The methods comprise growth adhering to surfaces, growth in suspension, or combinations thereof. Culturing can be done for instance in dishes, roller bottles or in bioreactors, using batch, fed-batch, continuous systems such as perfusion systems, and the like. In order to achieve large scale (continuous) production of recombinant proteins through cell culture it is preferred in the art to have cells capable of growing in suspension, and it is preferred to have cells capable of being cultured in the absence of animal- or human-derived serum or animal- or human-derived serum components.

The conditions for growing or multiplying cells (see, e.g., *Tissue Culture*, Academic Press, Kruse and Paterson, editors (1973)) and the conditions for expression of the recombinant product are known to the person skilled in the art. In general, principles, protocols, and practical techniques for maximizing the productivity of mammalian cell cultures can be found in Mammalian Cell Biotechnology: a Practical Approach (M. Butler, ed., IRL Press, 1991).

In a preferred embodiment, the expressed protein is collected (isolated), either from the cells or from the culture medium or from both. It may then be further purified using known methods, e.g., filtration, column chromatography, etc, by methods generally known to the person skilled in the art.

The selection method according to the present invention works in the absence of chromatin control elements, but improved results are obtained when the multicistronic expression units are provided with such elements. The selection method according to the present invention works particularly well when an expression cassette according to the invention, comprising at least one anti-repressor sequence is used. Depending on the selection agent and conditions, the selection can in certain cases be made so stringent, that only very few or even no host cells survive the selection, unless anti-repressor sequences are present. Hence, the combination of the novel selection method and anti-repressor sequences provides a very attractive method to obtain only limited numbers of colonies with a greatly improved chance of high expression of the polypeptide of interest therein, while at the same time the obtained clones comprising the expression cassettes with anti-repressor sequences provide for stable expression of the polypeptide of interest, i.e., they are less prone to silencing or other mechanisms of lowering expression than conventional expression cassettes.

In certain embodiments, almost no clones are obtained when no anti-repressor sequence is present in the expression cassette according to the invention, providing for very stringent selection. The novel selection system disclosed herein therefore also provides the possibility to test parts of anti-repressor elements for functionality, by analyzing the effects of such sequences when present in expression cassettes of the invention under selection conditions. This easy screen, which provides an almost or even complete black and white difference in many cases, therefore can contribute to identifying functional parts or derivatives from anti-repressor sequences. When known anti-repressor sequences are tested, this assay can be used to characterize them further. When fragments of known anti-repressor sequences are tested, the assay will provide functional fragments of such known anti-repressor sequences.

The practice of this invention will employ, unless otherwise indicated, conventional techniques of immunology, molecular biology, microbiology, cell biology, and recombinant DNA, which are within the skill of the art. See, e.g., Sambrook, Fritsch and Maniatis, *Molecular Cloning: A Laboratory Manual*, $2^{nd}$ edition, 1989; *Current Protocols in Molecular Biology*, F. M. Ausubel, et al., eds, 1987; the series *Methods in Enzymology* (Academic Press, Inc.); *PCR2: A Practical Approach*, M. J. MacPherson, B. D. Hams, G. R. Taylor, eds, 1995; *Antibodies: A Laboratory Manual*, Harlow and Lane, eds, 1988.

The invention is further explained in the following examples. The examples do not limit the invention in any way. They merely serve to clarify the invention.

EXAMPLES

Examples 1-7 describe the testing of STAR67 and other STAR sequences in various configurations and under various circumstances. Examples 8-25 further describe the novel selection system of the invention.

Example 1

Construction of STAR67 Vectors

A novel anti-repressor (STAR) sequence was isolated using a genetic screen as described in WO 03/004704, and this novel sequence was coined STAR67. The effects of STAR67 on expression of transgenes in mammalian cell lines were tested. Here we describe the construction of the various constructs.
Materials and Methods
(Three plasmids were created (FIG. 1):
A) CMV-d2EGFP-ires-Zeo (CMV Control),
B) STAR67-CMV-d2EGFP-ires-Zeo (CMV-STAR67),
C) STAR7-STAR67-CMV-d2EGFP-ires-Zeo-STAR7 (CMV-STAR67 7/7)

The construction of construct A is described below. Plasmid pd2EGFP (Clontech 6010-1) was modified by insertion of a linker at the BsiWI site to yield pd2EGFP-link. The linker, made by annealing oligonucleotides GTACGGATAT-CAGATCTTTAATTAAG (SEQ ID NO:67) and GTACCT-TAATTAAAGATCTGATAT (SEQ ID NO:68), introduced sites for the PacI, BglII, and EcoRV restriction endonucleases. This created the multiple cloning site MCSII for insertion of STAR elements. Then primers GATCAGATCTGGCGCGC-CATTTAAATCGTCTCGCGCGTTTCGGTGATGACGG (SEQ ID NO:69) and (AGGCGGATCCGAATGTATTTA-GAAAAATAAACAAATAGGGG (SEQ ID NO:70) were used to amplify a region of 0.37 kb from pd2EGFP, which was inserted into the BglII site of pIRES (Clontech 6028-1) to yield pIRES-stuf. This introduced sites for the AscI and SwaI restriction endonucleases at MCSI, and acts as a "stuffer fragment" to avoid potential interference between STAR elements and adjacent promoters. pIRES-stuf was digested with BglII and FspI to liberate a DNA fragment composed of the stuffer fragment, the CMV promoter, the IRES element (flanked by multiple cloning sites MCS A and MCS B), and the SV40 polyadenylation signal. This fragment was ligated with the vector backbone of pd2EGFP-link produced by digestion with BamHI and StuI, to yield pIRES-link.

The open reading frame of the Zeocin® antibiotic-resistance gene was inserted into BamHI/NotI sites downstream of the pIRES as follows: the Zeocin® antibiotic-resistance ORF was amplified by PCR with primers GATCGGATCCTTC-GAAATGGCCAAGTTGACCAGTGC (SEQ ID NO:71) and AGGCGCGGCCGCAATTCTCAGTCCTGCTCCTC (SEQ ID NO:72) from plasmid pCMV/zeo (Invitrogen, cat. no. V50120), digested with BamHI and NotI, and ligated with BamHI/NotI-digested pIRES-link to yield pIRES-link-zeo. The d2EGFP reporter ORF was introduced into pIRES-link-zeo by amplification of pd2EGFP (Clontech 6010-1) with primers GATCGAATTCTCGCGAATGGTGAGCAAG-CAGATCCTGAAG (SEQ ID NO:73) and AGGCGAAT-TCACCGGTGTTTAAACTTACAC-CCACTCGTGCAGGCTGCCCAGG (SEQ ID NO:74), and insertion of the EcoRI-digested d2EGFP cassette into the EcoRI site in the pIRES-link-zeo plasmid. This created construct A, CMV-d2EGFP-IRES-Zeo (CMV Control).

STAR67 was cloned upstream of the CMV promoter, in the AscI site (about 15 nt remaining between STAR67 and the promoter). This created construct B, STAR67-CMV-d2EGFP-ires-Zeo (CMV-STAR67).

STAR67 was also tested in the context of a cassette that contains also the STAR7, cloned directionally in the 5' SalI and XbaI sites and 3' BglII and PacI sites to flank the entire cassette with STAR7. This is construct C (CMV-STAR67 7/7).

Example 2

STAR67 Enhances the Expression Level from CMV, EF1α and UB6 Promoters in Stably Transfected CHO Cells We tested whether the presence of STAR67 adjacent to the CMV, EF1α and UB6 promoters influences the expression level of these promoters in CHO cells. The constructs A and B (FIG. 1) described in Example 1 are used for this purpose, modified for the respective promoters:
1 CMV-d2EGFP-ires-Zeo (CMV Control)
2 STAR67-CMV-d2EGFP-ires-Zeo (CMV-STAR67)
3 EF1α-d2EGFP-ires-Zeo (EF1α Control)
4 STAR67-EF1α-d2EGFP-ires-Zeo (EF1α-STAR67)
5 UB6-d2EGFP-ires-Zeo (UB6 Control)
6 STAR67-UB6-d2EGFP-ires-Zeo (UB6-STAR67).
Materials and Methods The UB6 and EF1α promoters were exchanged for the CMV promoter in the plasmids described in FIG. 1. The UB6 promoter was cloned as follows. A DNA 0.37 kb stuffer from the pd2EGFP plasmid was amplified by PCR, as described in Example 1, using primers identified by SEQ ID NOS:69 and 70. The resulting DNA stuffer was cloned in the BglII site of pUB6/V5-His [Invitrogen V250-20], creating pUB6-stuf. From pUB6-stuf an AscI-SacI fragment was cloned into CMV-d2EGFP-IRES-Zeo, from which the CMV promoter was removed.

The EF1α promoter was amplified by PCR with pEF1α/V5-His [Invitrogen V920-20] as template, using primers GATCGGCGCGCCATTTAAATC-CGAAAAGTGCCACCTGACG (SEQ ID NO:79) and AGGCGGGACCCCCTCACGACACCTGAAATGGAAG (SEQ ID NO:80). The PCR fragment was cloned in the AscI and PpuMI sites of CMV-d2EGFP-IRES-Zeo, from which the CMV promoter was removed.

The Chinese Hamster Ovary cell line CHO-K1 (ATCC CCL-61) was cultured in HAMS-F12 medium+10% Fetal Calf Serum containing 2 mM glutamine, 100 U/ml penicillin, and 100 micrograms/ml streptomycin at 37° C./5% $CO_2$. Cells were transfected with the plasmids using Lipofectamine® 2000 (Invitrogen) as described by the manufacturer. Briefly, cells were seeded to culture vessels and grown overnight to 70-90% confluence. Lipofectamine® reagent was combined with plasmid DNA at a ratio of 6 microliters per microgram (e.g., for a 10 cm Petri dish, 20 micrograms DNA and 120 microliters Lipofectamine) and added to the cells. After overnight incubation the transfection mixture was replaced with fresh medium, and the transfected cells were incubated further. After overnight cultivation, cells were trypsinized and seeded into fresh culture vessels with fresh medium. After another overnight incubation Zeocin® antibiotic was added to a concentration of 50 μg/ml and the cells were cultured further. After another three days the medium was replaced by fresh medium containing Zeocin® antibiotic (100 μg/ml) and cultured further. When individual colonies became visible (approximately ten days after transfection) medium was removed and replaced with fresh medium without Zeocin® antibiotic. Individual clones were isolated and transferred to 24-well plates in medium without Zeocin® antibiotic. One day after isolation of the colonies Zeocin® antibiotic was added to the medium. Expression of the d2EGFP reporter gene was assessed approximately three weeks after transfection. d2EGFP expression levels in the colonies were measured after periods of two weeks. After the initial two weeks after transfection when the first d2EGFP measurements were performed, the colonies were cultured in medium without Zeocin® antibiotic or other antibiotics. This continued for the remainder of the experiment.

Results

FIG. 2 shows that transfection of the construct that contains STAR67 cloned upstream of the CMV promoter resulted in a number of CHO colonies that express significantly higher levels of d2EGFP protein, as compared to the "empty" control without STAR67, CMV Control. The average of the d2EGFP signal in the 10 colonies transfected with the CMV Control plasmid was 34, when measured 25 days after transfection. Sixty days after transfection the average of the d2EGFP signal in these ten colonies was reduced to 13, indicating that expression is not stable over time. In comparison, the average of the d2EGFP signal in the ten colonies transfected with the STAR67-CMV plasmid was 42 when measured after 25 days and 32 measured 60 days after transfection. Hence 60 days after transfection, a STAR67-encompassing CMV construct conveyed a factor 2.5 higher CMV promoter driven expression level of the reporter protein in stably transfected clones. Importantly, 25 days after transfection, after the first measurement, selection pressure was removed by culturing the colonies in medium without zeocin. Hence, colonies containing the STAR67 construct are more stable over time in the absence of selection pressure than colonies that do not contain a STAR67 construct.

Figure 3:
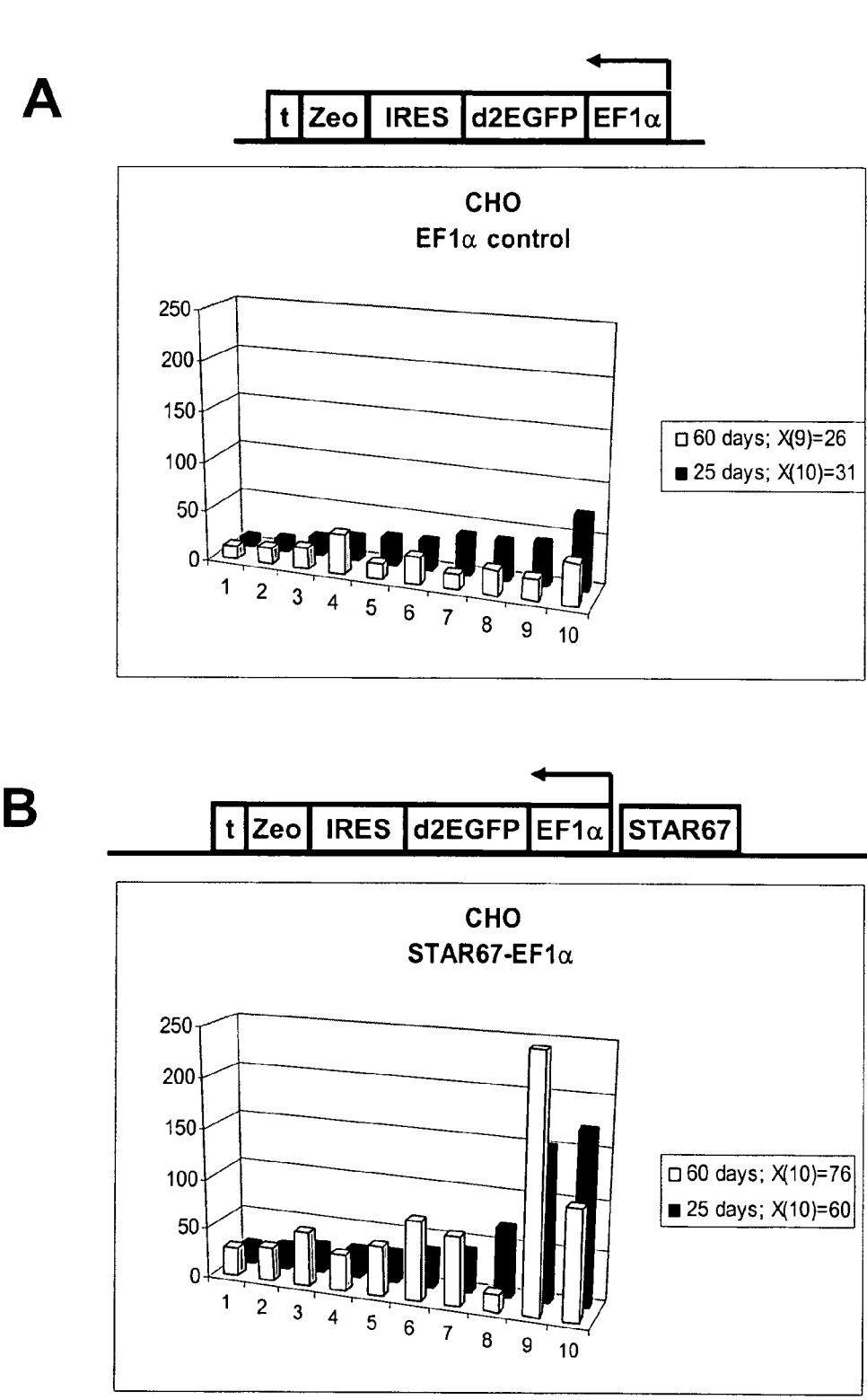
FIG. 3. STAR67 improves EF1α driven d2EGFP expression in CHO cells. Same as FIG. 2, but now with EF1a promoter. A) EF1α Control; B) STAR67-EF1α.

FIG. 3 shows that transfection of the construct that contains STAR67 cloned upstream of the EF1α-promoter resulted in a number of CHO colonies that express significantly higher levels of d2EGFP protein, as compared to the "empty" control without STAR67, EF1α Control. The average of the d2EGFP signal in the 10 colonies transfected with the EF1α Control plasmid was 31, when measured 25 days after transfection. Sixty days after transfection, the average of the d2EGFP signal in these ten colonies was 26. In comparison, the average of the d2EGFP signal in the ten colonies transfected with the EF1α-STAR67 plasmid was 60 when measured after 25 days and 76 measured 60 days after transfection. Hence, both after 25 and 60 days after transfection, a STAR67-encompassing EF1α construct conveyed a factor 2.9 higher EF1α promoter driven expression level of the reporter protein in stably transfected clones.

Figure 4:
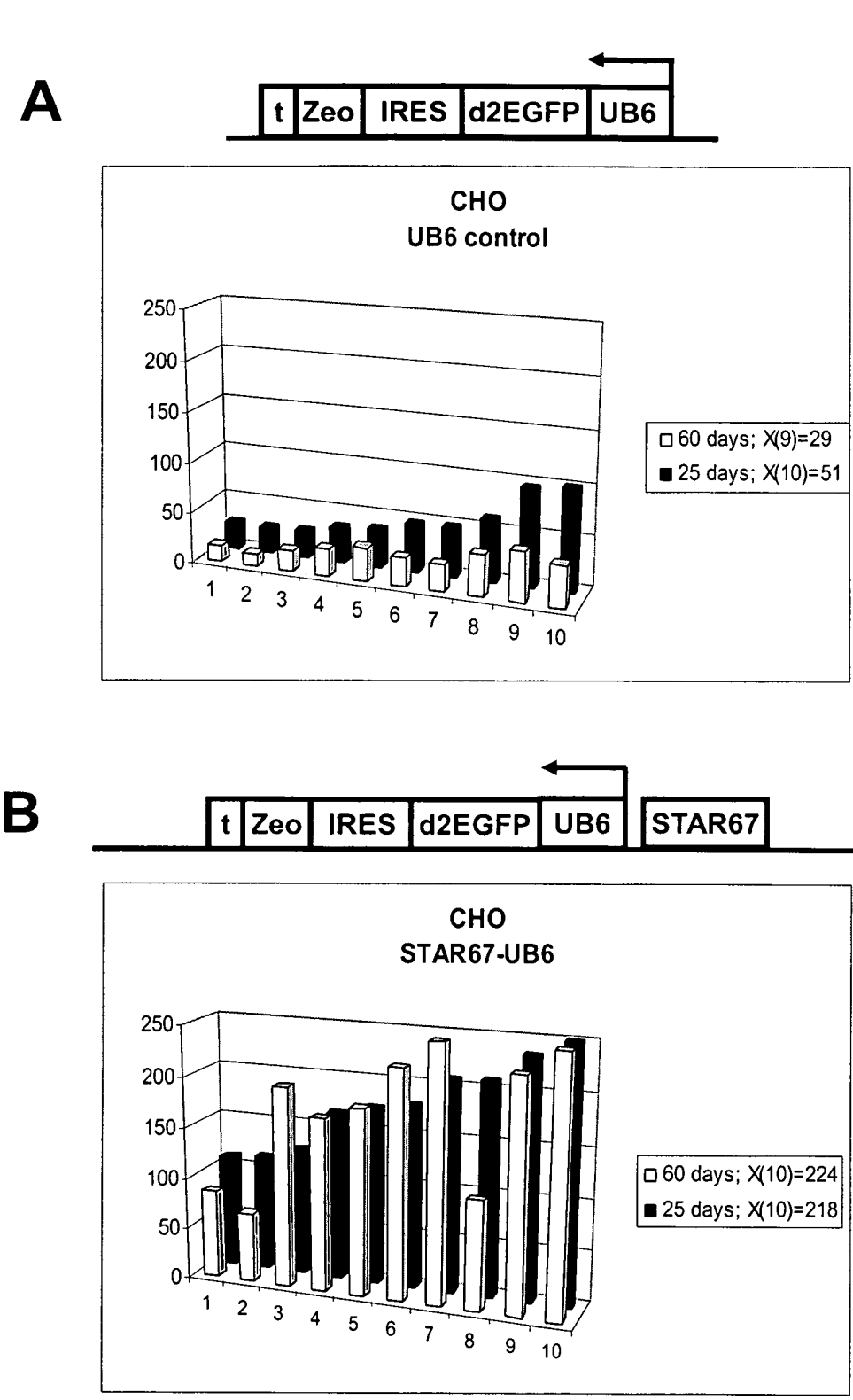
FIG. 4. STAR67 improves UB6 driven d2EGFP expression in CHO cells. Same as FIGS. 2 and 3, but now with UB6 promoter. A) UB6 Control; B) STAR67-UB6.

FIG. 4 shows that transfection of the construct that contains STAR67 cloned upstream of the UB6 promoter resulted in a number of CHO colonies that express significantly higher levels of d2EGFP protein, as compared to the "empty" control without STAR67, UB6 Control. The average of the d2EGFP signal in the ten colonies transfected with the UB6 Control plasmid was 51, when measured 25 days after transfection. 60 days after transfection the average of the d2EGFP signal in these ten colonies was 29, indicating that the expression was not stable over time. In comparison, the average of the d2EGFP signal in the ten colonies transfected with the UB6-STAR67 plasmid was 218 when measured after 25 days and 224 measured 60 days after transfection. Hence, 25 days after transfection, a STAR67-encompassing UB6 construct conveyed a factor 4.3 higher UB6 promoter driven expression level of the reporter protein in stably transfected clones. After 60 days, this factor was 7.7, due to instability of expression in the control colonies and stability in the UB6-STAR67 colonies. Importantly, 25 days after transfection, after the first measurement, selection pressure was removed by culturing the colonies in medium without Zeocin® antibiotic. Hence, colonies containing the STAR67 construct are more stable over time in the absence of selection pressure than colonies that do not contain a STAR67 construct.

In conclusion, STAR67 increases expression from three different, unrelated promoters.

Example 3

STAR67 Enhances the Expression Level from CMV, EF1α and UB6 Promoters in Stably Transfected PER.C6 Cells We tested whether the presence of STAR67 adjacent of the CMV, EF1α and UB6 promoters influences the expression level of these promoters in another cell type than CHO cells, namely human PER.C6 cells. The same constructs as in Example 1 were used.

Materials and Methods

Transfection, Culturing and Analysis of PER. C6 Cells

PER.C6® cells were cultured in DMEM medium+pyridoxine+9% Fetal Bovine Serum (Non-Heat Inactivated), 8.9 mM $MgCl_2$ 100 U/ml penicillin, and 100 micrograms/ml streptomycin at 37° C./10% $CO_2$. Cells were transfected with the plasmids using Lipofectamine 2000 (Invitrogen) as described by the manufacturer. Briefly, cells were seeded to 6-well plates and grown overnight to 70-90% confluence. Lipofectamine reagent was combined with plasmid DNA at a ratio of 15 microliters per 3 microgram (e.g., for a 10 cm Petri dish, 20 micrograms DNA and 120 microliters Lipofectamine) and added after 30 minutes incubation at 25° C. to the cells. After six hours incubation, the transfection mixture was replaced with fresh medium, and the transfected cells were incubated further. After overnight cultivation, cells were trypsinized and seeded (1:15, 1:30, 1:60, 1:120 dilutions) into fresh Petri dishes (90 mm) with fresh medium with zeocin added to a concentration of 100 µg/ml and the cells were cultured further. When colonies became visible, individual clones were isolated by scraping and transferred to 24-well plates in medium with Zeocin® antibiotic. When grown to ~70% confluence, cells were transferred to six-well plates. Stable colonies were expanded for two weeks in six-well plates before the d2EGFP signal was determined on a XL-MCL Beckman Coulter flow cytometer. The mean of the d2EGFP signal was taken as measure for the level of d2EGFP expression. Colonies were measured for a second time after two weeks. Thereafter colonies were further cultured in the absence of Zeocin® antibiotic.

Results

Figure 5:
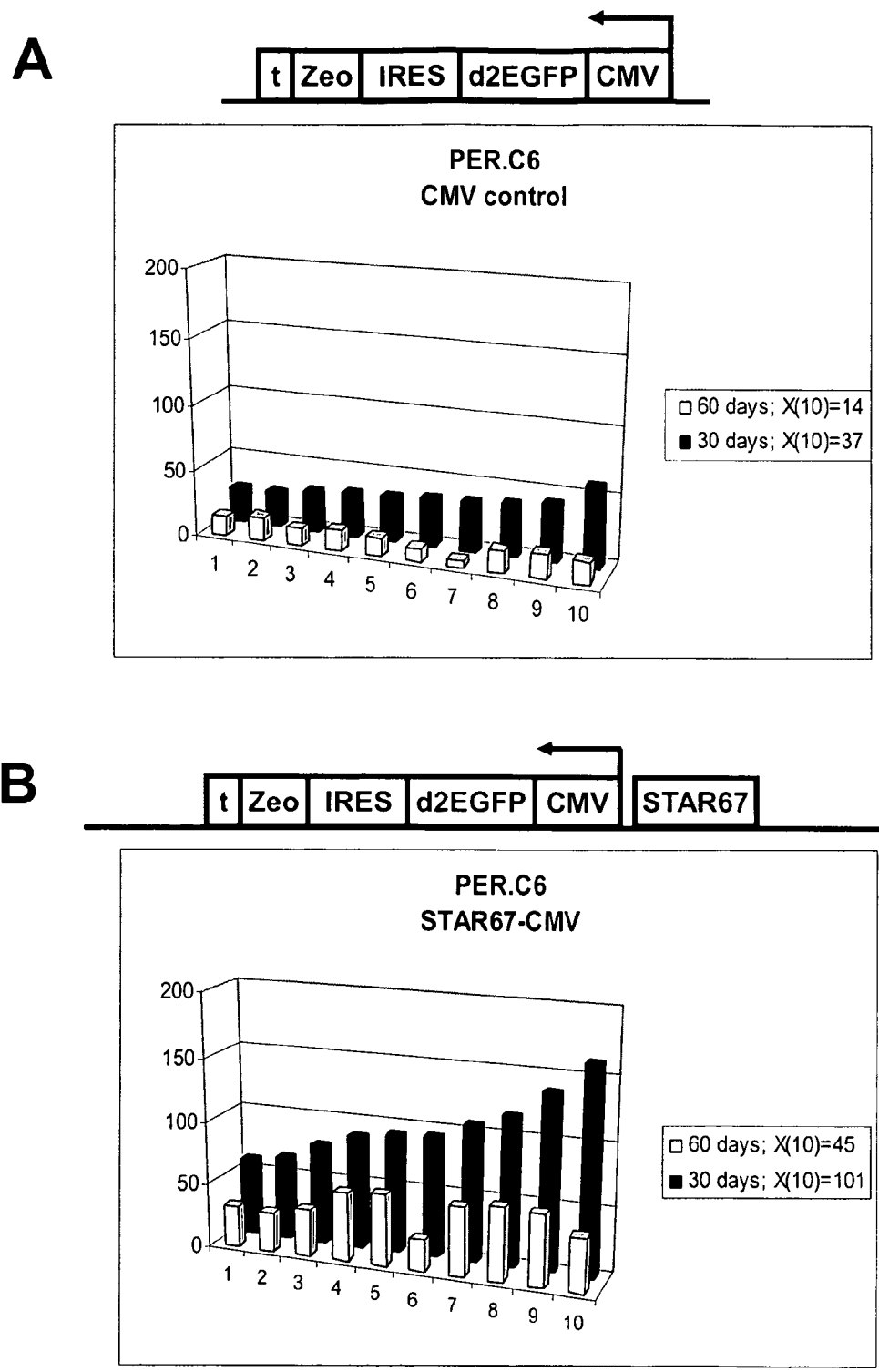
FIG. 5. STAR67 improves CMV driven d2EGFP expression in PER.C6 cells. Same as FIG. 2, but now in PER.C6 cells. A) CMV Control; B) STAR67-CMV.

FIG. 5 shows that transfection of the construct that contains STAR67 cloned upstream of the CMV promoter resulted in a number of PER.C6 colonies that express significantly higher levels of d2EGFP protein, as compared to the "empty" control without STAR67, CMV Control. The average of the d2EGFP signal in the ten colonies transfected with the CMV Control plasmid was 37, when measured 30 days after transfection. 60 days after transfection the average of the d2EGFP signal in these ten colonies was reduced to 14, indicating that expression was not stable over time. In comparison, the average of the d2EGFP signal in the 10 colonies transfected with the STAR67-CMV plasmid was 101 when measured after 30 days and 45 measured 60 days after transfection. Hence 60 days after transfection, a STAR67-encompassing CMV construct conveyed a factor 3.2 higher CMV promoter driven expression level of the reporter protein in stably transfected clones.

FIG. 6 shows that transfection of the construct that contains STAR67 cloned upstream of the EF1α-promoter resulted in a number of PER.C6 colonies that express significantly higher levels of d2EGFP protein, as compared to the "empty" control without STAR67, EF1α Control. The average of the d2EGFP signal in the ten colonies transfected with the EF1α Control plasmid was five, when measured 30 days after transfection. Sixty days after transfection the average of the d2EGFP signal in these ten colonies was six. In comparison, the average of the d2EGFP signal in the ten colonies transfected with the EF1α-STAR67 plasmid was 25 when measured after 30 days and 20 measured 60 days after transfection. Hence, both after 30 and 60 days after transfection, a STAR67-encompassing EF1α construct conveyed a factor 4 higher EF1α promoter driven expression level of the reporter protein in stably transfected clones.

FIG. 7 shows that transfection of the construct that contains STAR67 cloned upstream of the UB6 promoter resulted in a number of PER.C6 colonies that express significantly higher levels of d2EGFP protein, as compared to the "empty" control without STAR67, UB6 Control. The average of the d2EGFP signal in the ten colonies transfected with the UB6 Control plasmid was four, when measured 30 days after transfection. Sixty days after transfection the average of the d2EGFP signal in these ten colonies was two. In comparison, the average of the d2EGFP signal in the ten colonies transfected with the UB6-STAR67 plasmid was 27 when measured after 30 days and 18 measured 60 days after transfection. Hence, both after 30 and 60 days after transfection, a STAR67-encompassing UB6 construct conveyed a factor seven- to nine-fold higher UB6 promoter driven expression level of the reporter protein in stably transfected clones.

Hence placing STAR67 upstream of the promoter resulted in significantly higher protein expression levels in comparison with STAR67-less constructs, also in PER.C6 cells. Hence STAR67 functions in different, unrelated cell types.

Example 4

Novel Configuration of STAR67 Combined with Other STAR Elements to Enhance the SV40 Promoter in CHO Cells We tested whether the presence of STAR67 adjacent of the SV40 promoter influences the expression level of this promoter, either alone or in combination with another STAR element, in this example STAR7. The constructs that were used for this purpose (see FIG. 8), are:
1 SV40-d2EGFP-ires-Zeo (SV40 Control)
2 STAR67-SV40-d2EGFP-ires-Zeo (SV40-STAR67)
3 STAR7-SV40-d2EGFP-ires-Zeo-STAR7 (SV40-STAR7/7)
4 STAR7-STAR67-SV40--d2EGFP-ires-Zeo-STAR7 (SV40-STAR67 7/7)

Materials and Methods

The SV40 promoter was amplified by PCR with pIRES as template using primers TTGGTTGGGGCGCGCCGCAG-CACCATGGCCTGAAATAACCTCTGAAAGAGG (SEQ ID NO:81) and TTGGTTGGGAGCTCAAGCTTTTTG-CAAAAGCCTAGGCCTCCAAA AAAGCCTCCTC (SEQ ID NO:82). The PCR fragment was cloned in the AscI and SacI sites of CMV-d2EGFP-IRES-Zeo, from which the CMV promoter was removed.

CHO cells were transfected, colonies were isolated and propagated and analyzed as in Example 2.

Results

Figure 8:
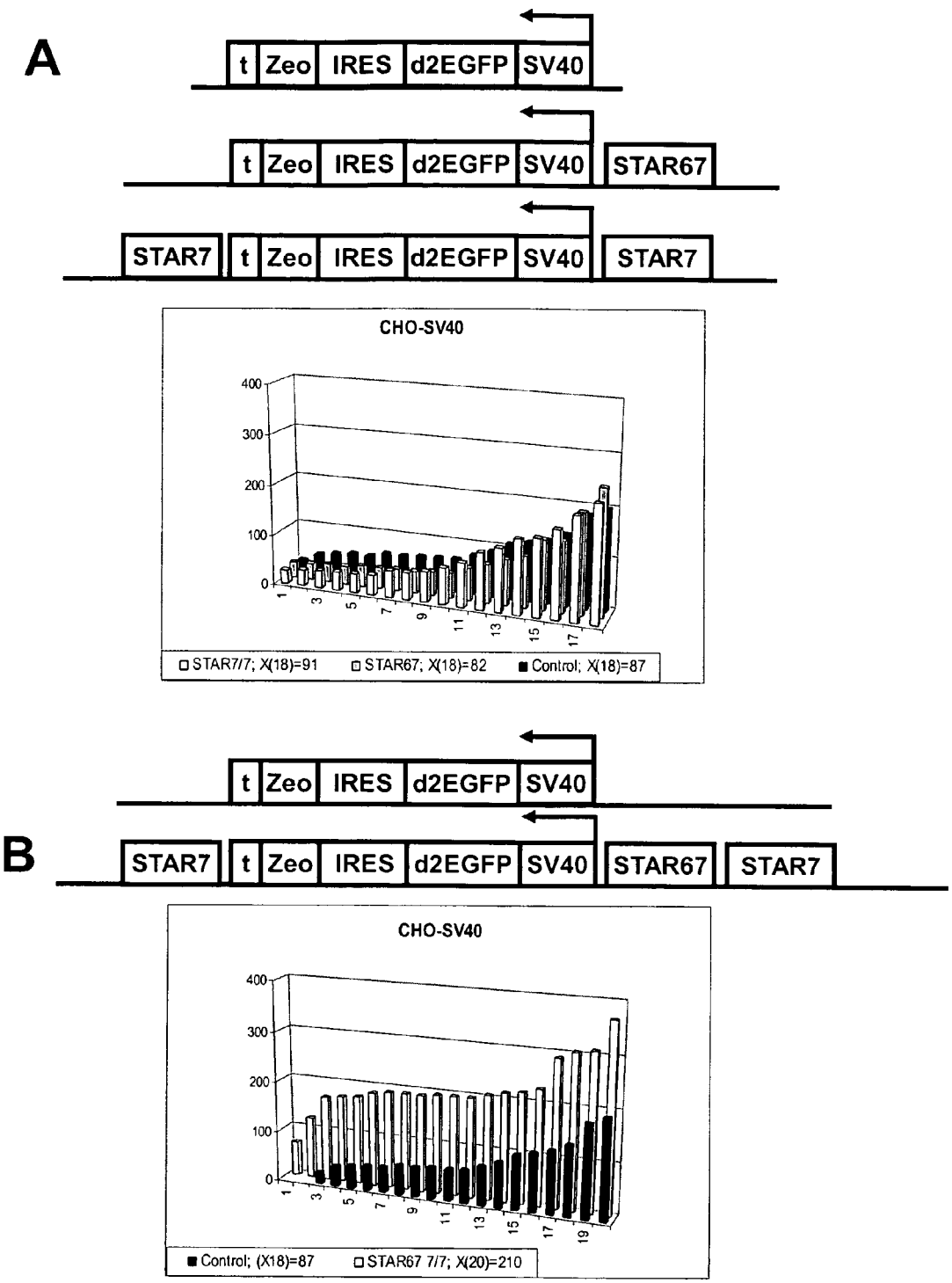
FIG. 8. STAR67 improves SV40 driven d2EGFP expression in CHO-K1 cells in combination with another STAR element. Similar as FIG. 2, but now using the SV40 promoter in CHO cells, and the indicated constructs. The mean of the d2EGFP signal is plotted for 18-20 independent stable colonies 60 days after transfection. A) SV40 Control, SV40-STAR67, SV40-STAR7/7; B) SV40 Control and SV40-STAR67 7/7. See Example 4 for details.

FIG. 8 shows that transfection of the construct that either contains STAR67 cloned upstream of the SV40 promoter (SV40-STAR67) or STAR 7 cloned to flank the entire construct (SV40-STAR 7/7) did not result in CHO colonies that express significantly higher levels of d2EGFP protein, as compared to the "empty" control without STARs (SV40 Control). The average of the d2EGFP signal in the 18 colonies transfected with the SV40 Control plasmid was 86, when measured 40 days after transfection. In comparison, the average of the d2EGFP signal in the 18 colonies transfected with the SV40-STAR67 plasmid was 82 when measured after 40 days and the average of the d2EGFP signal in the 18 colonies transfected with the SV40-STAR 7/7 plasmid was 91 when measured after 40 days. Hence, no significant effect of these STAR elements on the SV40 promoter in CHO cells was observed.

It appears that the expression levels from the SV40 promoter in these cells are already quite high, and even much higher than those observed with the CMV promoter, which was considered to be a very strong promoter. This high background expression in the absence of a STAR element using the SV40 promoter in CHO cells, may explain why no significant effect of STAR67 alone, or STAR7 flanking the transgene, was observed.

However, the average of the d2EGFP signal in the 18 colonies transfected with the SV40-STAR67 7/7 plasmid was 209 when measured after 40 days colonies, which is a factor 2.4 higher than the average of the 18 control colonies (86). Hence, when the STAR67 element is used in combination with another STAR element, this results in a number of stably transfected CHO colonies that show significantly higher d2EGFP expression levels.

Therefore in this novel configuration (5'-STAR sequence A-STAR sequence C-promoter-nucleic acid encoding a protein of interest-STAR sequence B-3', wherein in the present example STAR sequences A and B are STAR 7 and STAR sequence C is STAR67) STAR elements appear to function even better than in hitherto disclosed configurations.

We have done experiments in which the flanking STAR7 elements were replaced by flanking STAR6 elements or by flanking STAR4 elements, in combination with STAR67 upstream of the SV40 promoter (SV40-STAR67 6/6 and SV40-STAR67 4/4, respectively, using the same nomenclature as above), and observed improved expression also with these combinations. This proves that the flanking STAR7 elements can indeed be exchanged for other STAR sequences, and still the improvement of the novel configuration of the expression cassette with the STAR sequences is observed.

Example 5

A Combination of STAR67 and STAR7 Enhance UB6-Driven Antibody Expression Levels in Stably Transfected CHO Cells In Example 4, we showed that the combination of STAR67 and STAR7 enhanced the expression levels of d2EGFP protein in CHO cells. Here we tested whether the combination of STAR67 and STAR7 could be used for the production of an antibody. We chose an antibody against the EpCAM molecule (Huls et al., 1999) as test protein and used the UB6 promoter.

Materials and Methods

Plasmids

Figure 9:
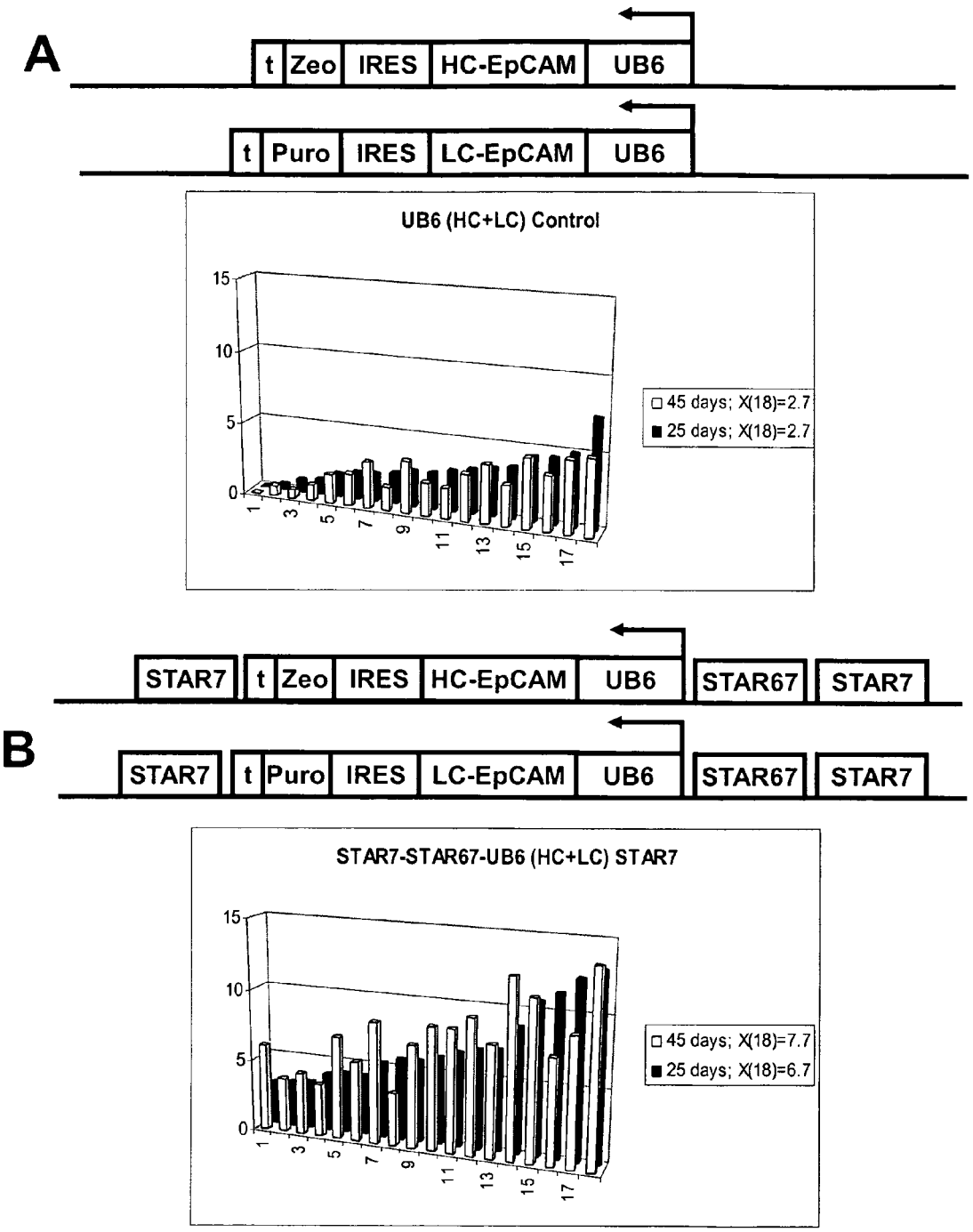
FIG. 9. STAR67 improves UB6 driven expression levels of the EpCAM antibody in CHO-K1 cells. See Example 5 for details. A) constructs without STAR elements; B) constructs with STAR67 upstream of promoter and flanking STAR7 elements. The anti-EpCAM antibody concentration is presented as pg/cell/day. X(18): average production level of the 18 colonies.

The heavy chain cDNA (HC-EpCAM) was cloned in a construct encompassing the UB6 promoter. The HC-EpCAM was coupled to the Zeocin® antibiotic resistance gene by an IRES sequence. The light chain cDNA (LC-EpCAM) was also cloned in a construct encompassing the UB6 promoter. The LC-EpCAM was coupled to the puromycin resistance gene by an IRES sequence. Together these two plasmids represent the UB6 (HC+LC) Control (FIG. 9).

To test the effects of STAR67 and STAR7, STAR67 was cloned in both HC+LC constructs, upstream of the UB6 promoters. STAR7 was cloned to flank the entire cassettes, both at the 5' and 3' end (FIG. 9). These two plasmids represent STAR7-STAR67-UB6 (HC+LC) STAR7.

Transfection and Culture of CHO Cells

The Chinese Hamster Ovary cell line CHO-K1 (ATCC CCL-61) was transfected and cultured as in Example 2, using Zeocin® antibiotic (100 µg/ml) and puromycin (2.5 µg/ml) for selection. One day after transfection, Zeocin® antibiotic was added to the culture medium. When first colonies became visible (approximately seven days after addition of Zeocin® antibiotic) the culture medium was removed and replaced with culture medium containing puromycin. After approximately seven days, colonies were isolated and transferred to 24-well plates, in culture medium containing Zeocin® antibiotic only.

Results

FIG. 9 shows that that transfection of antibody constructs that contain STAR67 cloned upstream of the UB6 promoter and two STAR7 elements cloned to flank the entire cassettes resulted in a number of CHO colonies that express significantly higher levels of EpCAM antibody (measured by ELISA using an anti-human IgG antibody) as compared to the "empty" control without STAR67 and STAR7, UB6 (HC+LC) Control. The average of the EpCAM production in the 18 colonies transfected with the UB6 (HC+LC) Control plasmid was 2.7 pg/cell/day, when measured 25 days after transfection. Selection agents Zeocin® antibiotic and puromycin were removed after 25 days. Forty-five days after transfection, the average of the EpCAM production in these 18 colonies was 2.7 pg/cell/day. In comparison, the average of the EpCAM production signal in the 18 colonies transfected with the STAR7-STAR67-UB6 (HC+LC)-STAR7 plasmid was 6.7 when measured after 25 days and 7.7 pg/cell/day, when measured 45 days after transfection. Hence, both after 30 and 45 days after transfection, a STAR67/STAR7-encompassing UB6 construct conveyed a factor 2.5 to 2.9 fold higher UB6 promoter driven EpCAM expression level in stably transfected CHO clones.

Hence placing STAR67 upstream of the promoter and two STAR7 elements to flank the cassettes resulted in significantly higher EpCAM antibody expression levels in CHO, in comparison with STAR67/STAR7-less constructs.

Example 6

STAR67 is not an Enhancer Blocker, whereas STAR6 and STAR7 are

All hitherto known STAR elements that were tested for that property, including STAR6 and STAR7, are enhancer blockers (WO 03/004704, Kwaks et al., 2003). Enhancer blocker activity is tested by placing a STAR element between a strong enhancer and a promoter. Here we tested whether also STAR67 is an enhancer blocker.

Materials and Methods

The d2EGFP gene was PCR-amplified using primers TTG-GTTGGTCATGAATGGTGAGCAAGGGC-GAGGAGCTGTTC (SEQ ID NO:75) and ATTCTCTAGAC-TACACATTGATCCTAGCAGAAGCAC (SEQ ID NO:76) and cloned into plasmid pGL3-promoter (Promega) using the NcoI and XbaI restriction sites to replace the Luciferase gene to create plasmid pGL3-promoter-GFP. A linker (created by annealing oligos CGATATCTTGGAGATCTACTAGTG-GCGCG CCTTGGGCTAGCT (SEQ ID NO:77) and GAT-CAGCTAGCCCAAGGCGCGCCACTAGTAGATCTCC AAGATATCGAGCT (SEQ ID NO:78), was cloned in the SacI and BglII sites to create multiple cloning sites. The original BglII site was destroyed upon ligation of the linker, creating a new unique BglII site within the linker DNA. The SV40-enhancer was cut from plasmid pGL3-basic (Promega) using BsaBI and BamHI and cloned into the pGL3-linker-promoter-GFP using the EcoRV and BglII sites creating plasmid pGL3-enhancer-promoter-GFP. The STAR40 element was placed upstream of the SV40 enhancer using KpnI and SacI sites to prevent action of the enhancer on upstream sequences. Finally, STAR elements 6, 7 and 67 were placed in between the SV40 enhancer and the SV40 minimal promoter using the SpeI and AscI restriction sites.

Transfection and Culture of CHO Cells

The Chinese Hamster Ovary cell line CHO-K1 (ATCC CCL-61) is transfected as in Example 2. One day after the transfection, d2EGFP levels are measured on an Epics XL flow cytometer (Beckman Coulter)

Results

FIG. 10 shows that STAR67 is not an enhancer blocker, whereas STAR6 and STAR7 act enhancer blockers in the same assay. STAR6, STAR7 and STAR67 were cloned between the SV40 enhancer and a minimal SV40-promoter upstream of the d2EGFP gene. When no STAR element was cloned between the enhancer and the promoter strong transcriptional activation occurred (arbitrarily set at 100%). When STAR6 or STAR7 was placed between the enhancer and the promoter, transcription dropped to background levels, indicating that STAR6 and STAR7 are potent enhancer blockers. In contrast, when STAR67 was cloned between the enhancer and the promoter relative transcription levels were still 80% of the control, indicating that STAR67 is not a good enhancer blocker, this in contrast with STAR6 and STAR 7, as well as other STAR elements, as previously described (WO 03/004704, Kwaks et al., 2003).

Example 7

STAR67 Enhances UB6 and CMV-driven Antibody Expression Levels in Stably Transfected CHO Cells In Example 5, we showed that the combination of STAR67 and STAR7 enhanced the expression levels of EpCAM antibody in CHO cells, in the context of two distinct plasmids, which contained the heavy and light chains. In this example we tested whether STAR67 could be used for the production of EpCAM antibody when both heavy and light chains are placed on one plasmid. We used simultaneous selection for each selectable marker.

Materials and Methods

Plasmids

The heavy chain cDNA (HC-EpCAM) is under the control of the UB6 promoter and coupled to the Zeocin resistance gene by an IRES sequence. The light chain cDNA (LC-EpCAM) is under control of the CMV promoter and coupled to the puromycin resistance gene by an IRES sequence. Basically these are the constructs used in Example 5. These two expression cassettes were placed on one plasmid, in such a manner that transcription of the two expression units had opposite directions. In the control plasmid the UB6 and CMV promoters were separated by a stuffer of 500 bp (EpCAM Control) (FIG. 10). In another plasmid STAR67 was placed between the UB6 and CMV promoter (EpCAM STAR67) (FIG. 10).

Transfection and Culture of CHO Cells

The Chinese Hamster Ovary cell line CHO-K1 (ATCC CCL-61) was transfected and cultured as in Example 2, using Zeocin® antibiotic (100 μg/ml) and puromycin (2.5 μg/ml) for selection. In Example 5, consecutive selection for both selection markers was used. In contrast, here both selection agents were present in the culture medium simultaneously. One day after transfection, Zeocin® antibiotic and puromycin were added to the culture medium. The selection medium was present until colonies were isolated (approximately 14 days after transfection). After colonies were isolated and transferred to 24-well plates, the cells were cultured in the presence of Zeocin® antibiotic and puromycin.

Results

FIG. 11 shows that that transfection of the antibody construct that contains STAR67 cloned between the UB6 and CMV promoters resulted in a number of CHO colonies that express EpCAM antibody (measured by ELISA using an anti-human IgG antibody). The average of the EpCAM production in the 19 colonies transfected with the EpCAM STAR67 plasmid was 9.8 pg/cell/day, when measured 25 days after transfection.

In contrast, surprisingly no colonies survived of the transfection with the EpCAM Control plasmid. When selection was performed with either Zeocin® antibiotic or puromycin alone, EpCAM Control colonies survived. However, when the selection pressure was increased by placing selection pressure on both the heavy and light chain, these conditions allowed only colonies to survive that have a STAR67 present in the transfected plasmid.

The results also show that incorporation of STAR67 has a beneficial effect on two promoters, the UB6 and CMV promoters, that are placed upstream and downstream of one STAR67 element. This indicates that STAR67 may operate in a bi-directional fashion.

The difference between the EpCAM control and EpCAM STAR67 plasmid is black-white in the sense that only transfection of EpCAM STAR67 results in the establishment of colonies, when the selection pressure is high. This opens an opportunity to use this plasmid configuration for identifying the region in STAR67 that is responsible for mediating this effect. Smaller, overlapping portions of STAR67 are placed between the UB6 and CMV promoters, driving the EpCAM molecule. When a portion of STAR67 is functional, colonies will survive when both Zeocin® antibiotic and puromycin are simultaneously used as selection agent. When a portion of STAR67 is not functional, no colonies will survive under identical selection conditions.

Hence placing STAR67 upstream of the promoter resulted in significantly higher EpCAM antibody expression levels in CHO, in comparison with STAR-less constructs.

Example 8

Figure 12:
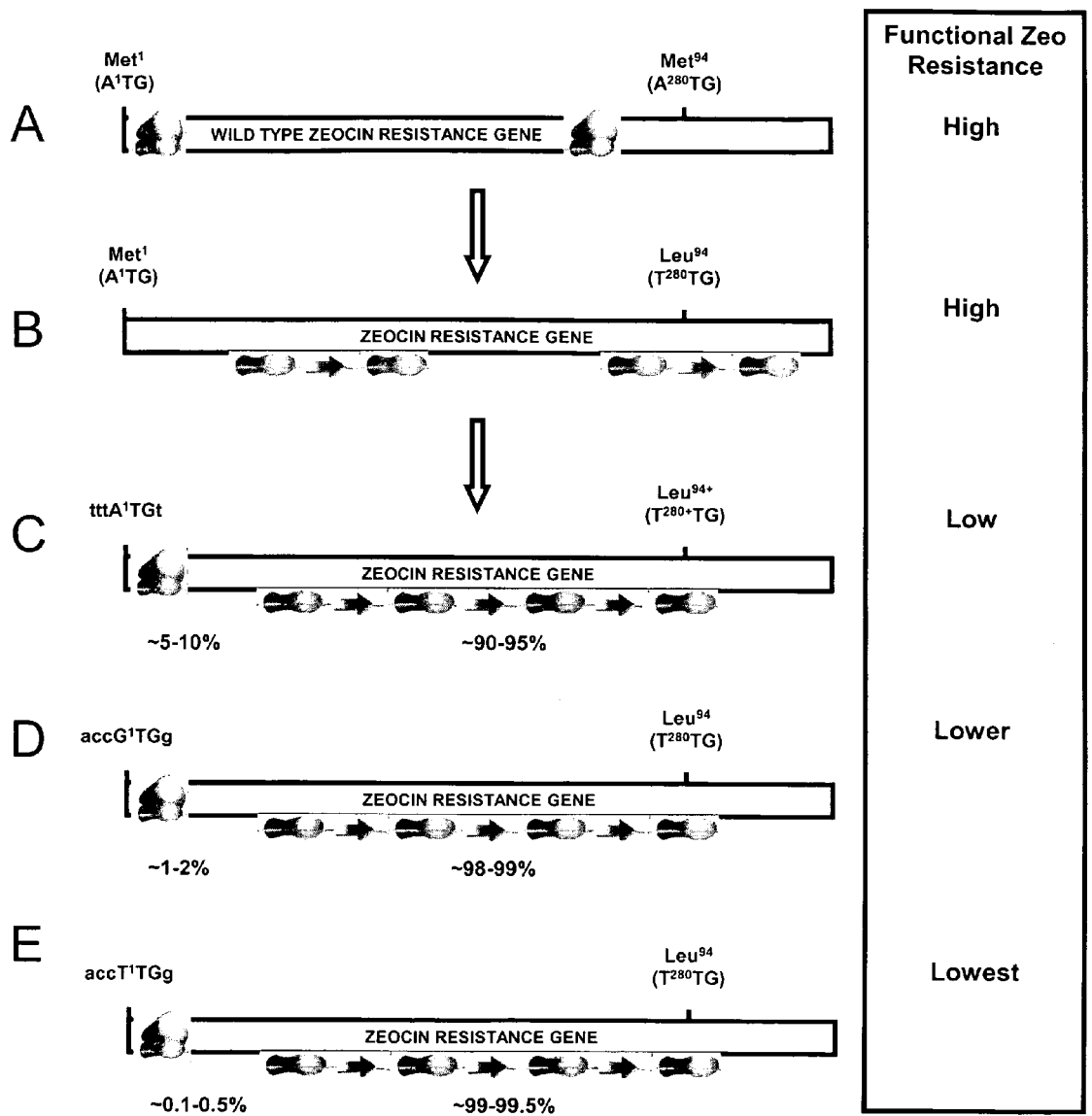
FIG. 12. Schematic representation of the use of a selection marker gene (Zeocin® antibiotic resistance gene) according to the invention. A. wild-type Zeocin® antibiotic resistance gene, having its normal translation initiation site (ATG start codon) and one internal ATG codon, which codes for methionine. B. mutant Zeocin® resistance gene, wherein the internal ATG has been mutated into a codon for leucine; this mutant is a functional Zeocin® resistance gene. C. same as B, but comprising a mutated translation initiation site, wherein the context of the ATG start codon has been mutated to decrease the translation initiation. D. same as B, but comprising a mutated start codon (GTG). E. same as B, but with a TTG start codon. The numbers under the figures C-E schematically indicate a relative amount of initiation frequency (under the start codon) and "scan-through" frequency (under the coding sequence) by the ribosomes, but only in a semi-quantitative manner, i.e., they indicate the efficiency of translation initiation compared to each other, but the qualitative numbers may differ completely: the numbers only serve to explain the invention. See Example 8 for details.
Figure 13:
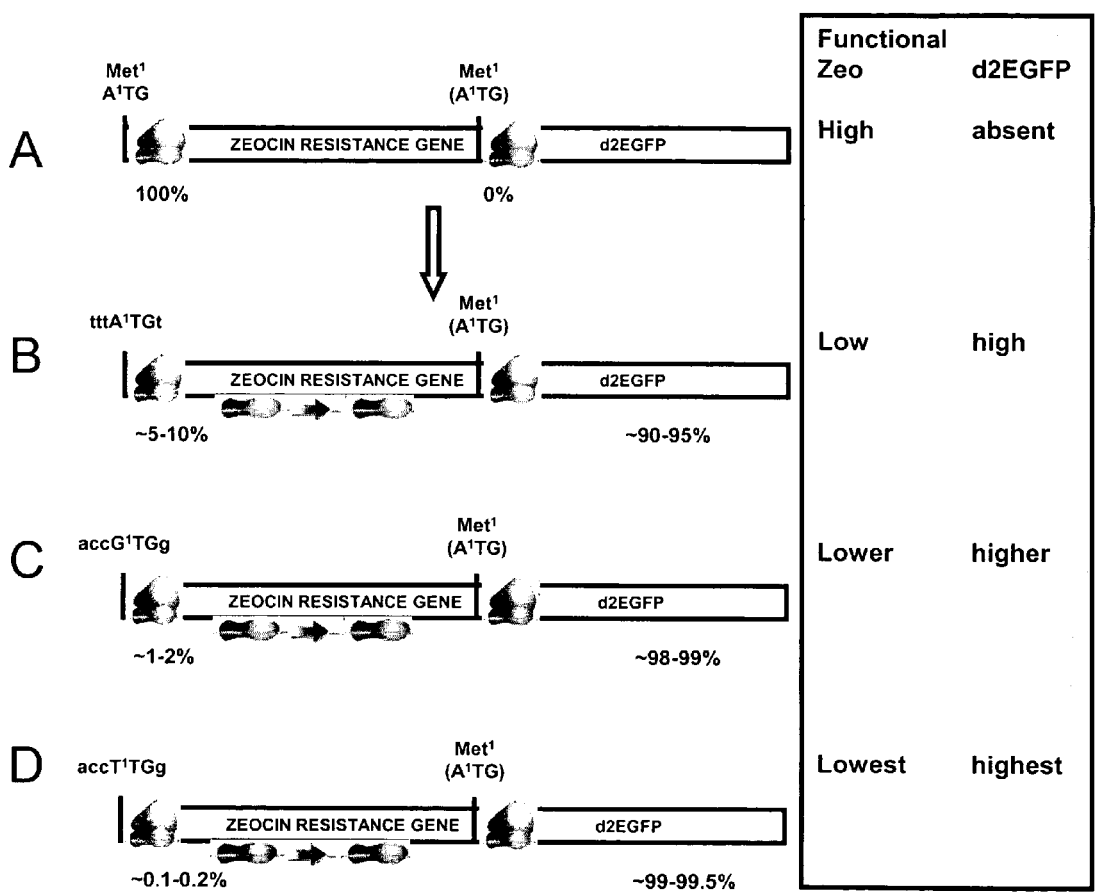
FIG. 13. Schematic representation of a multicistronic transcription unit according to the invention, with more or less reciprocal interdependent translation efficiency. Explanation as for FIG. 12, but now a dEGFP gene (here exemplifying a gene of interest) has been placed downstream of the selectable marker polypeptide coding sequence. The Zeocin® antibiotic resistance gene comprises the internal Met→Leu mutation (see FIG. 12B). See Example 9 for details.

Construction and Testing of a Zeocin Resistance Gene Product with No Internal Methionine The basic idea behind the development of a novel selection system is to place the gene encoding the resistance gene upstream of a gene of interest, and one promoter drives the expression of this bicistronic mRNA. The translation of the bicistronic mRNA is such that only in a small percentage of translation events the resistance gene will be translated into protein and that most of the time the downstream gene of interest will be translated into protein. Hence the translation efficiency of the upstream resistance gene must be severely hampered in comparison to the translation efficiency of the downstream gene of interest. To achieve this, three steps can be taken according to the invention:

1) within the resistance gene on the mRNA, the searching ribosome preferably should not meet another AUG, since any downstream AUG may serve as translation start codon, resulting in a lower translation efficiency of the second, downstream gene of interest. Hence, preferably any AUG in the resistance gene mRNA will have to be replaced. In case this AUG is a functional codon that encodes a methionine, this amino acid will have to be replaced by a different amino acid, for instance by a leucine (FIGS. 12A and B);

2) the start codon of the resistance gene must have a bad context (be part of a non-optimal translation start sequence); i.e., the ribosomes must start translation at this start codon only in a limited number of events, and hence in most events continue to search for a better, more optimal start codon (FIG. 12C-E). Three different stringencies can be distinguished: a) the normal ATG start codon, but placed in a bad context (TTT ATGT) (called ATGmut) (FIG. 12C), b) preferably when placed in an optimal context, GTG can serve as start codon (ACCGTGG) (FIG. 12D) and c) preferably when placed in an optimal context, TTG can serve as start codon (ACCTTGG) (FIG. 12E). The most stringent translation condition is the TTG codon, followed by the GTG codon (FIG. 12). The Zeo mRNA with a TTG as start codon is expected to produce the least Zeocin® antibiotic resistance protein and will hence convey the lowest functional Zeocin® antibiotic resistance to cells (FIGS. 12, 13).

3) preferably, the normal start codon (ATG) of the downstream gene of interest should have an optimal translation context (e.g., ACCATGG)(FIG. 13A-D). This warrants that, after steps 1 and 2 have been taken, in most events the start codon of the gene of interest will function as start codon of the bicistronic mRNA.

In Example 8, step 1 is performed, that is, in the Zeocin® antibiotic resistance gene one existing internal methionine is replaced by another amino acid (FIG. 12B-E). It is important that after such a change the Zeo protein still confers Zeocin® antibiotic resistance to the transfected cells. Since it is not known beforehand which amino acid will fulfill this criterion, three different amino acids have been tried: leucine, threonine and valine. The different constructs with distinct amino acids have than been tested for their ability to still confer Zeocin® antibiotic resistance to the transfected cells.

Materials and Methods

Construction of the Plasmids

The original Zeo open reading frame has the following sequence around the start codon: AAACCATGGCC (start codon in bold; SEQ ID NO:83). This is a start codon with an optimal translational context (FIG. 12A). First the optimal context of the start codon of the Zeo open reading frame was changed through amplification from plasmid pCMV-zeo [Invitrogen V50120], with primer pair ZEOforwardMUT (SEQ ID NO:84): GATCTCGCGATACAGGA*TTTATG* TGGC-CAAGTTGACCAGTGCCGTTCCG and ZEO-WTreverse (WT=Wild type; SEQ ID NO:85): AGGCGAATTCAGTC-CTGCTCCTCGGC, using pCMV-ZEO (Invitrogen; V50120) as a template. The amplified product was cut with NruI-EcoRI, and ligated into pcDNA3, resulting in pZEOAT-Gmut.

The original Zeo open reading frame contains an in frame ATG, encoding methionine at amino acid position 94 (out of 124). This internal ATG, encoding the methionine at position 94 was changed in such a way that the methionine was changed into leucine, threonine or valine respectively:

1) To replace the internal codon for methionine in the Zeo open reading frame with the codon for leucine (FIG. 12B), part of the Zeo open reading frame was amplified using primer pair ZEOforwardMUT (SEQ ID NO:84) and ZEO- LEUreverse (SEQ ID NO:86): AGGCCCCGCCCCCACG-GCTGCTCGCCGATCTCGGT<u>CAA</u> GGCCGGC. The PCR product was cut with BamHI-BglI and ligated into pZEOAT-Gmut. This resulted in pZEO(leu). To replace the internal codon for methionine in the Zeo open reading frame with the codon for threonine (not shown, but as in FIG. 12B), part of the Zeo open reading frame was amplified using primer pair ZEOforwardMUT (SEQ ID NO:84) and ZEO-THRreverse (SEQ ID NO:87): AGGCCCCGCCCCCACGGCT-GCTCGCCGATCTCGGT<u>GGT</u>GGCCGGC. The PCR product was cut with BamHI-BglI and ligated into pZEOATGmut. This resulted in pZEO(thr). To replace the internal codon for methionine in the Zeo open reading frame with the codon for valine (not shown, but as in FIG. 12B) (GTG), part of the Zeo open reading frame was amplified using primer pair ZEOforwardMUT (SEQ ID NO:84) and ZEO-VALreverse (SEQ ID NO:88): AGGCCCCGCCCCCACGGCTGCTCGC-CGATCTCGGTC<u>CAC</u>GCCGG. The PCR product was cut with BamHI-BglI and ligated into pZEOATGmut. This resulted in pZEO(val).

Transfection and Culturing of Cells

The Chinese Hamster Ovary cell line CHO-K1 (ATCC CCL-61) was cultured in HAMS-F12 medium+10% Fetal Calf Serum containing 2 mM glutamine, 100 U/ml penicillin, and 100 micrograms/ml streptomycin at 37° C./5% CO$_2$. Cells were transfected with the plasmids using Lipofectamine® 2000 (Invitrogen) as described by the manufacturer. Briefly, cells were seeded to culture vessels and grown overnight to 70-90% confluence. Lipofectamine® reagent was combined with plasmid DNA at a ratio of 6 microliters per microgram (e.g., for a 10 cm Petri dish, 20 micrograms DNA and 120 microliters Lipofectamine® reagent) and added to the cells. After overnight incubation, the transfection mixture was replaced with fresh medium, and the transfected cells were incubated further. After overnight cultivation, cells were trypsinized and seeded into fresh culture vessels with fresh medium containing Zeocin® antibiotic (100 µg/ml). When individual colonies became visible (approximately ten days after transfection), colonies were counted.

Results

Four plasmids were transfected to CHO-K1 cells, 1) pZEO (WT), 2) pZEO(leu), 3) pZEO(thr), and 4) pZEO(val). The cells were selected on 100 µg/ml Zeocin® antibiotic. Transfection of pZEO(leu) resulted in an equal number of Zeocin® antibiotic resistant colonies in comparison with the control pZEO (WT). pZEO(thr) and pZEO(val) gave less colonies, but the differences were not in the order of a magnitude. Hence it was concluded that changes of the internal methionine into leucine, threonine or valine all resulted in a Zeocin® antibiotic resistance protein that is still able to confer Zeocin® antibiotic resistance to the transfected cells. Rather arbitrarily, pZEO(leu) was chosen as starting point for creating different start codons on the Zeo open reading frame. Hence, in the examples below, the start, as well as internal methionines, are always replaced by leucine, for Zeocin® antibiotic, but also for other selectable marker genes, as will be clear from further examples.

Example 9

Creation and Testing of Zeocin®-d2EGFP Bicistronic Constructs with Differential Translation Efficiencies To create a bicistronic mRNA encompassing a mutated Zeocin® resistance mRNA with less translational efficiency, and the d2EGFP gene as downstream gene of interest, the start codon of the d2EGFP gene was first optimized (step 3 in Example 8). After that, the different versions of the Zeocin® antibiotic resistance gene were created. The differences between these versions are that they have different start codons, with distinct translational efficiency (step 2 in Example 9, FIG. 12C-E). These different Zeocin® antibiotic resistance gene versions were cloned upstream of the modified d2EGFP gene (FIG. 13).

Materials and Methods

Creation of Plasmids

The d2EGFP reporter ORF was introduced into pcDNA3. The sequence around the start codon of this d2EGFP cDNA is GAA <u>TTCATGG</u> G (start codon in bold; SEQ ID NO:89), which is not optimal. As a first step, d2EGFP was amplified from pd2EGFP (Clontech 6010-1) with primers d2EGFPforwardBamHl (SEQ ID NO:90): GATCGGATC-CTATGAGGAATTCGCC<u>ACCATGG</u> GAGCAAGGGC-GAGGAG and d2EGFPreverseNotI (SEQ ID NO:91): AAG-GAAAAAAGCGGCCGCCTACACATTGATCCTAGCAG AAG. This product contains now a start codon with an optimal translational context (<u>ACCATGG</u>). This created pd2EGFP and subsequently, the Zeo open reading frame was ligated into pd2EGFP, resulting in pZEO-d2EGFP. It is pointed out here that the optimization of the translational start sequence of the gene of interest (here: EGFP as a model gene) is not essential but preferred in order to skew the translation initiation frequency towards the gene of interest still further.

Now three classes of constructs were made:

1) ATG as a start codon in the Zeo resistance gene, but in a bad context (<u>TTTATGT</u>) (not shown, but as in FIG. 13B) and followed by spacer sequence, instead of the optimal ATG (FIG. 13A). The spacer sequence is placed downstream of the ATG sequence. In the Zeocin® antibiotic (and possibly in the blasticidin) RNA, a secondary structure is present, causing the ribosome to be temporarily delayed. Because of this, a poor start codon can in some cases be used by the ribosome, despite being a bad start codon or being in a non-optimal context for translation initiation. This causes the chance of translation to increase, and in case of the current invention therefore renders the stringency for selection lower. To decrease this effect, and hence to further decrease the translation initiation efficiency, a spacer sequence is introduced that does not contain a secondary structure (Kozak, 1990). Hence, the term "space" is introduced, and used in the plasmid and primer names to indicate the presence of such a spacer sequence. The spacer removes the "ribosome delaying sequence" from the neighborhood of the initiation codon, therewith causing the ribosome to start translating less frequently, and hence increasing the stringency of the selection according to the invention. The spacer introduces some extra amino acids in the coding sequence. This has been done in some cases for both Zeocin® antibiotic and for blasticidin, as will be apparent from the examples. The nomenclature of the plasmids and primers in general in the following is along these lines: the name of the selectable marker polypeptide is referred to by abbreviation (e.g., Zeo, Blas, etc.); the start codon is mentioned (e.g., ATG, GTG, TTG); when this start codon is placed in a non-optimal context for translation initiation, the addition "mut" is used (this is usually only done for ATG start codons, as combining a non-optimal context with a non-ATG start codon usually does not result in sufficient translation initiation to allow for selection); when a spacer sequence is used behind the start codon, the addition "space" is used (this is done usually for "ATGmut" start codons for Zeo or Blas selectable markers). The Zeo open reading frame was amplified with primer pair ZEOforward-BamHI-<u>ATG</u>mut/space (SEQ ID NO:93): GATCGGATCCT- TGG *TTTATGT* CGATCCAAAG ACTGCCAAATCTA-GATCCGAGATTTTCAGGAGCTAAGGAAGCTAAAGC CAAGTTGACCAGTGAAGTTC (wherein the sequence following the underlined sequence comprises the spacer sequence), and ZEOWTreverse (SEQ ID NO:85), the PCR product was cut with EcoRI-BamHI, and ligated into pd2EGF, cut with EcoRI-BamHI, creating pZEO-ATGmut/space-d2EGFP.

2) GTG as a start codon in the Zeo resistance gene, instead of ATG (FIG. 13C). The Zeo open reading frame was amplified with primer pair ZEOforwardBamHI-GTG (SEQ ID NO:94): GATCGGATCC*ACCGTGG* CCAAGTTGAC-CAGTGCCGTTC and ZEOWTreverse (SEQ ID NO:85), the PCR product was cut with EcoRI-BamHI, and ligated into pd2EGFP, cut with EcoRI-BamHI, creating pZEO-GTG-d2EGFP.

3) TTG as a start codon in the Zeo resistance gene, instead of ATG (FIG. 13D). The Zeo open reading frame was amplified with primer pair ZEOforwardBamHI-TTG: GATCG-GATCC*ACCTTGG* CCAAGTTGACCAGTGCCGTTC (SEQ ID NO:95) and ZEOWTreverse (SEQ ID NO:85), the PCR product was cut with EcoRI-BamHI, and ligated into pd2EGFP, cut with EcoRI-BamHI, creating pZEO-TTG-d2EGFP.

Transfection, Culturing and Analysis of CHO Cells

The Chinese Hamster Ovary cell line CHO-K1 (ATCC CCL-61) was cultured in HAMS-F12 medium+10% Fetal Calf Serum containing 2 mM glutamine, 100 U/ml penicillin, and 100 micrograms/ml streptomycin at 37° C./5% $CO_2$. Cells were transfected with the plasmids using Lipofectamine® 2000 (Invitrogen) as described by the manufacturer. Briefly, cells were seeded to culture vessels and grown overnight to 70-90% confluence. Lipofectamine® reagent was combined with plasmid DNA at a ratio of 15 microliters per 3 microgram (e.g., for a 10 cm Petri dish, 20 micrograms DNA and 120 microliters Lipofectamine® reagent) and added after 30 minutes incubation at 25° C. to the cells. After overnight incubation the transfection mixture was replaced with fresh medium, and the transfected cells were incubated further. After overnight cultivation, cells were trypsinized and seeded into fresh culture vessels with fresh medium. After another overnight incubation, Zeocin® antibiotic was added to a concentration of 50 µg/ml and the cells were cultured further. After another three days the medium was replaced by fresh medium containing Zeocin® antibiotic (100 µg/ml) and cultured further. When individual colonies became visible (approximately ten days after transfection) medium was removed and replaced with fresh medium without Zeocin® antibiotic. Individual clones were isolated and transferred to 24-well plates in medium without Zeocin® antibiotic. One day after isolation of the colonies, Zeocin® antibiotic was added to the medium. Expression of the d2EGFP reporter gene was assessed approximately three weeks after transfection. d2EGFP expression levels in the colonies were measured after periods of two weeks.

Results

Figure 14:
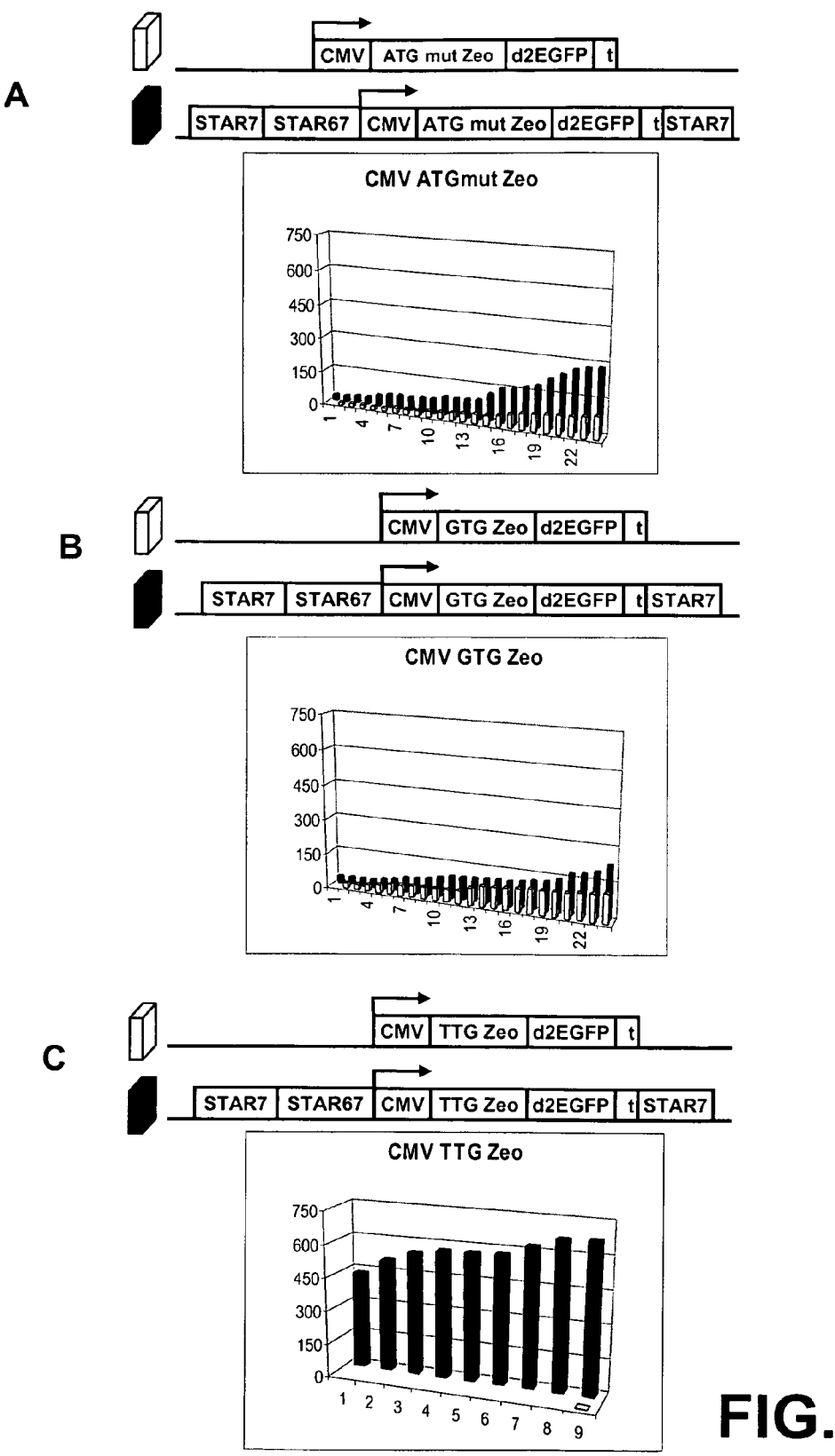
FIG. 14. Results of selection systems according to the invention, with and without STAR elements. A. Zeocin® antibiotic resistance gene with ATG start codon in bad context (referred to as "ATGmut" in the picture, but including a spacer sequence behind the ATG in the bad context, so in the text generally referred to as "ATGmut/space"). B. Zeocin® antibiotic resistance gene with GTG start codon. C. Zeocin® antibiotic resistance gene with TTG start codon. d2EGFP signal for independent colonies is shown on the vertical axis. See Example 9 for details.

CHO-K1 cells were transfected with constructs that contain the ATGmut/space Zeo (FIG. 13B), GTG Zeo (FIG. 13C) and TTG Zeo (FIG. 13D) genes as selection gene, all being cloned upstream of the d2EGFP reporter gene. These three constructs were without STAR elements (Control) or with STAR elements 7 and 67 upstream of the CMV promoter and STAR 7 downstream from the d2EGFP gene (FIG. 14). FIG. 14 shows that both the control (without STAR elements) constructs with ATGmut/space Zeo (A) and GTG Zeo (B) gave colonies that expressed d2EGFP protein. The average d2EGFP expression level of 24 ATGmut/space Zeo colonies was 46 and of GTG Zeo colonies was 75. This higher average expression level in GTG Zeo colonies may reflect the higher stringency of GTG, in comparison with ATGmut/space (Example 8). Addition of STAR elements 7 and 67 to the constructs resulted in colonies that had higher average d2EGFP expression levels. Transfection of the ATGmut/space Zeo STAR 7/67/7 construct resulted in colonies with an average d2EGFP expression level of 118, which is a factor 2.6 higher than the average in the control cells (46). Addition of STAR elements to the GTG Zeo construct resulted in an average d2EGFP expression level of 99, which is a factor 1.3 higher than the average in the control cells (75).

Importantly, no colonies were established when the TTG Zeo construct was transfected. However, the construct with TTG Zeo, flanked with STARs 7 and 67 resulted in the establishment of six colonies, with an average d2EGFP expression level of 576 (FIG. 14C). Thus the highest translation stringency, brought about by the TTG start codon (FIG. 12) yields to the highest d2EGFP expression levels, as predicted in FIG. 13. The results also indicate that the stringency of the TTG Zeo alone (without STAR elements) is at least in some experiments too high for colonies to survive. However, in later independent experiments (see below), some colonies were found with this construct without STAR elements, indicating that the stringency of the selection system with the TTG start codon in the Zeocin® antibiotic selection marker not necessarily precludes the finding of colonies when no STAR elements are present, and that the number of colonies obtained may vary between experiments.

It is concluded that the use of STAR elements in combination with the stringent selection system according to the invention allows to readily identify high producers of the gene of interest.

Example 10

Establishment of a Higher Number of TTG Zeo STAR Colonies and Comparison with an IRES-Zeo Construct The results in Example 9 indicate that the TTG Zeo has extremely stringent translation efficiency, which might be to high to convey Zeocin® antibiotic resistance to the cells. The transfection was scaled up to test whether there would be some colonies that have such high expression levels that they survive. Scaling up the experiment could also address the question whether the high average of TTG Zeo STAR 7/67/7 would become higher when more colonies were analyzed.

Materials and Methods

CHO-K1 cells were transfected with the constructs that have the TTG Zeo gene as selection marker, with and without STAR elements 7 and 67 (FIG. 15). Transfections, selection, culturing etc were as in Example 9, except that six times more cells, DNA and Lipofectamine 2000 were used. Transfections and selection were done in Petri dishes.

Results

FIG. 15A shows that transfection with the TTG Zeo STAR 7/67/7 construct resulted in the generation of many colonies with an average d2EGFP signal of 560. This is as high as in Example 9, except that now 58 colonies were analyzed. When compared to a construct with the Zeocin® antibiotic resistance gene placed behind an IRES sequence (FIG. 15B), the average d2EGFP expression level was 61, and when STAR elements 7 and 67 were added to such a construct, the average d2EGFP expression level was 125, a factor 2 above the control (FIG. 15B). The average of the TTG Zeo STAR 7/67/7 colonies was therefore a factor 9.2 higher than the STAR-less IRES-Zeo colonies and a factor 4.5 higher than the STAR7/67/7 IRES Zeo colonies.

An observation is that the form of the curve of all expressing colonies differs between the TTG Zeo STAR7/67/7 and IRES-Zeo STAR 7/67/7. In the first case (TTG Zeo) the curve levels off, whereas in the second case (IRES-Zeo) the curve has a more "exponential" shape. The plateau in the TTG Zeo curve could indicate that the cells have reached a maximum d2EGFP expression level, above which the d2EGFP expression levels become toxic and the cells die. However, it later appeared that the high values were close to the maximum value that could be detected with the settings of the detector of the FACS analyzer. In later experiments, the settings of the FACS analyzer were changed to allow for detection of higher values, and indeed in some instances higher values than obtained here were measured in later independent experiments (see below).

Due to up-scaling of the transfections three colonies with the STAR-less TTG Zeo construct could be picked. The d2EGFP expression levels of these colonies were 475, 158 and 43. The last colony died soon after the first measurement. This result indicates that the TTG Zeo construct can convey Zeocin® antibiotic resistance, resulting in colonies that also can give high expression levels in some instances. Hence, the novel selection method according to the invention can be applied with expression cassettes that do not contain chromatin control elements, although it is clearly preferred to use expression cassettes comprising at least one such element, preferably a STAR element.

The results indicate that STAR elements allow a more stringent selection system according to the invention, such as exemplified in this example, resulting in the picking of colonies that have a very high average protein expression level.

Example 11

Creation and Testing of Blasticidin-d2EGFP Bicistronic Constructs with Differential Translation Efficiencies There are four internal ATGs in the blasticidine resistance gene, none of which codes for a methionine (FIG. 25A). These ATGs have to be eliminated though (FIG. 25B), since they will serve as start codon when the ATG start codon (or the context thereof) has been modified, and this will result in peptides that do not resemble blasticidine resistance protein. More importantly, these ATGs will prevent efficient translation of the gene of interest, as represented by d2EGFP in this example for purposes of illustration. To eliminate the internal ATGs, the blasticidine resistance protein open reading frame was first amplified with four primer pairs, generating 4 blasticidine resistance protein fragments. The primer pairs were:

```
A)   BSDBamHIforward (SEQ ID NO: 96):
     GATCGGATCCACCATGGCCAAGCCTTTGTCTCAAG
     BSD150reverse (SEQ ID NO: 97):
     GTAAAATGATATACGTTGACACCAG B)   BSD150forward (SEQ ID NO: 98):
     CTGGTGTCAACGTATATCATTTTAC
     BSD250reverse (SEQ ID NO: 99):
     GCCCTGTTCTCGTTTCCGATCGCG C)   BSD250forward (SEQ ID NO: 100):
     CGCGATCGGAAACGAGAACAGGGC
```

-continued
```
     BSD350reverse (SEQ ID NO: 101):
     GCCGTCGGCTGTCCGTCACTGTCC D)   BSD350forward (SEQ ID NO: 102):
     GGACAGTGACGGACAGCCGACGGC
     BSD399reverse (SEQ ID NO: 103):
     GATCGAATTCTTAGCCCTCCCACACGTAACCAGAGGGC
```

Fragments A to D were isolated from an agarose gel and mixed together. Next, only primers BSDBamHIforward and BSD399reverse were used to create the full length blasticidine resistance protein cDNA, but with all internal ATGs replaced. The reconstituted blasticidine was then cut with EcoRI-BamHI, and cloned into pZEO-_GTG_-d2EGFP, cut with EcoRI-BamHI (which releases Zeo), resulting in pBS-Dmut-d2EGFP. The entire blasticidine resistance protein open reading frame was sequenced to verify that all ATGs were replaced.

With this mutated gene encoding blasticidine resistance protein (Blas), three classes of constructs are made (FIG. 25C-E):

1) ATG as a start codon, but in a bad context and followed by spacer sequence. The mutated blasticidine resistance protein open reading frame in pBSD-d2EGFP was amplified using primers BSDforwardBamHIAvrII-_ATGmut/space_ (SEQ ID NO:104): GATCGGATCCTAGGTTGG _TTTATGT_ CGATCC AAAGACTGCCAAATCTAGATC-CGAGATTTTCAGGAGCTAAG-GAAGCTAAAGCCAAGCCTTTGTCTCAA GAAG,
and BSD399reverseEcoRIAvrII (SEQ ID NO:105): GATCGAATTCCCTAGGTTAGCCCTCCCACACG TAACCAGAGGGC, the PCR product is cut with BamHI-EcoRI, and ligated into pZEO-_GTG_-d2EGFP, cut with EcoRI-BamHI. This results in pBSD-ATGmut/space-d2EGFP.

2) GTG as a start codon instead of ATG. The mutated blasticidine resistance protein open reading frame in pBSD-d2EGFP was amplified using primers BSDforwardBamHIAvrII-_GTG_ (SEQ ID NO:106): GATCGGATCCTAGG _ACCGTGG_ CCAAGCCTTTGTCTCAAGAAG
and BSD399reverseEcoRIAvrII (SEQ ID NO:105), the PCR product was cut with BamHI-EcoRI, and ligated into pZEO-_GTG_-d2EGFP, cut with EcoRI-BamHI. This results in pBSD-_GTG_-d2EGFP.

3) TTG as a start codon instead of ATG. The mutated blasticidine open reading frame in pBSD-d2EGFP was amplified using primers BSDforwardBamHIAvrII-_TTG_ (SEQ ID NO:107): GATCGGATCCTAGG _ACCTTGG_ CCAAGCCTTTGTCTCAAGAAG
and BSD399reverseEcoRIAvrII (SEQ ID NO:105), the PCR product was cut with BamHI-EcoRI, and ligated into pZEO-_GTG_-d2EGFP, cut with EcoRI-BamHI. This results in pBSD-_TTG_-d2EGFP.

Results

CHO-K1 cells were transfected with constructs that contain the GTG Blas (FIG. 16A) and TTG Blas (FIG. 16B) genes as selection gene, all being cloned upstream of the d2EGFP reporter gene. Selection took place in the presence of 20 µg/ml Blasticidine. The two constructs were without STAR elements (Control) or with STAR elements 7 and 67 upstream of the CMV promoter and START downstream from the d2EGFP gene (FIG. 16). FIG. 16 shows that both the control (without STAR elements) constructs with GTG Blas (A) and TTG Blas (B) gave colonies that expressed d2EGFP protein. The average d2EGFP signal of 24 GTG Blas colonies was 14.0 (FIG. 16A) and of TTG Blas colonies was 81 (FIG. 16B). This higher average expression level in TTG Blas colonies may reflect the higher stringency of TTG, in comparison with GTG (see also Example 9). However, only eight colonies survived under the more stringent TTG conditions.

Addition of STAR elements 7 and 67 to the constructs resulted in colonies that had higher average d2EGFP expression levels. Transfection of the GTG Blas STAR 7/67/7 construct resulted in colonies with an average d2EGFP expression level of 97.2 (FIG. 16A), which is a factor 6.9 higher than the average in the control cells (14.0). Addition of STAR elements to the TTG Blas construct resulted in an average d2EGFP signal of 234.2 (FIG. 16B), which is a factor 2.9 higher than the average in the control cells (81). However, note again that only eight colonies survived the harsh selection conditions of TTG Blas, whereas 48 colonies survived with TTG Blas STAR 7/67/7. When only the five highest values are compared, the average of the five highest TTG Blas was 109.1 and the average of the five highest TTG Blas STAR 7/67/7 was 561.2, which is a factor 5.1 higher.

The results indicate that STAR elements allow a more stringent selection system, resulting in the picking of colonies that have a very high average protein expression level. They also show that this selection is not restricted to the Zeocin® antibiotic resistance protein alone, but that also other selection marker polypeptides, in this case the blasticidin resistance protein, can be used.

Example 12

Stability of d2EGFP Expression in the Novel Selection System

Colonies described in Example 10 were further cultured under various conditions to assess the stability of d2EGFP expression over an extended time period.
Results
The TTG Zeo STAR 7/67/7 containing colonies in FIG. 15A were cultured for an additional 70 days in the presence of 100 μg/ml Zeocin® antibiotic. As shown in FIG. 17, the average d2EGFP signal rose from 560.2 after 35 days to 677.2 after 105 days. Except for some rare colonies, the colonies had a higher d2EGFP expression level.

When the level of Zeocin® antibiotic was lowered to 20 μg/ml Zeocin® antibiotic, there was still an increase in the average d2EGFP expression level, from 560.2 after 35 days to 604.5 after 105 days (FIG. 18).

When no selection pressure was present at all due to removal of the Zeocin® antibiotic from the culture medium, approximately 50% of the colonies became mosaic, that is, within one colony non-d2EGFP expressing cells became apparent. This resulted in lowering of d2EGFP expression levels to less than 50% of the original levels. If the signal became less than 67% (decrease of at least one-third) from the original signal, the colony was considered to be unstable in respect to d2EGFP expression. Of the 57 original colonies, 27 colonies remained stable according to this criterion; the average d2EGFP signal of these colonies after 35 days (while still under selection pressure) was 425.6, whereas the average d2EGFP signal without selection pressure after 65 days was 290.0. When measured after 105 days, the average signal in the 27 colonies was 300.9. Hence, after an initial decrease, the expression levels in the 27 colonies remained stable according to this criterion (FIG. 19).

Six of the colonies were subjected to one round of subcloning. Cells were sown in 96-well plates as such that each well contained approximately 0.3 cells. No Zeocin® antibiotic was present in the medium so that from the start the sub clones grew without selection pressure. Of each original colony, six sub clones were randomly isolated and grown in six-well plates till analysis. In FIG. 23, we compared the original values of the original clones, as already shown in FIG. 15A, with one of the sub clones. In one of the six clones (clone 25), no sub clone was present with d2EGFP signal in the range of the original clone. However, in five out of six cases at least one the sub clones had equal d2EGFP expression levels as the parent clone. These expression levels were determined after 50 days without selection pressure. We conclude that one round of sub cloning is sufficient to obtain a high number of colonies that remain stable for high expression in the absence of selection pressure. This has been confirmed in a similar experiment (not shown).

We compared the number of copies that integrated in the TTG Zeo STAR 7/67/7 colonies. DNA was isolated when colonies were 105 days old under Zeocin® antibiotic selection pressure (see FIG. 17). As shown in FIG. 24, two populations could be distinguished. In FIG. 24, the cut off was made at 20 copies and the $R^2$ value is calculated and shown. Also the $R^2$ value from data with higher than 20 copies is shown. In the range from 100 to 800 d2EGFP signal, there was a high degree of copy number dependency, as signified by a relatively high $R^2$ of 0.5685 (FIG. 24). However, in the population of colonies that fluctuate around a d2EGFP signal of 800 a high variation in copy number was observed (FIG. 24), as signified with a low $R^2$ of 0.0328. Together, the data show that in the novel selection system, in colonies that contain TTG Zeo STAR 7/67/7 constructs there is copy number dependent d2EGFP expression up to ~20 copies. Also, although copy number dependency is lost when >20 copies are present, still a substantial proportion of the colonies with high (>800) d2EGFP signal have no more than 30 copies (FIG. 24). This combination between high d2EGFP expression and a relatively low copy number (between 10 and 30) may be important for identifying colonies that remain relatively stable without selection pressure. It is an advantage to have clones with relatively low copy numbers (less than about 30, more preferably less than about 20) that give high expression levels, because such clones are believed to be less amenable to genetic instability. The present selection system allows one to generate such clones, including from CHO cells.

Example 13

Creation and Testing of Zeocin® Antibiotic-Blasticidin-EpCAM Bicistronic Constructs with Differential Translation Efficiencies To test the selection system on the production of an antibody, the anti-EpCAM antibody (see also Example 5) was taken as an example.
Results
A plasmid was created on which both the heavy chain (HC) and light chain (LC) were placed, each in a separate transcription unit (FIG. 20-22). Expression of both chains was driven by the CMV promoter. Upstream of the EpCAM heavy chain the Zeocin® antibiotic resistance gene was placed, either with the ATGmut/space (FIG. 20), GTG (FIG. 21) or TTG (FIG. 22) as start codon (see Example 9). Upstream of the EpCAM light chain, the blasticidin resistance gene was placed, either with the ATGmut/space (FIG. 20), GTG (FIG. 21) or TTG (FIG. 22) as start codon (see Example 11). Two types of constructs were made, one construct without STAR elements (Control) and one construct with a combination of STAR 7 and 67 elements. The STAR elements were placed as follows: upstream of each CMV promoter (i.e., one for the transcription unit comprising HC and one for the transcription unit comprising LC) STAR 67 was placed and the resulting construct was flanked with a 5' and 3' STAR 7 element (FIGS. 20-22). All constructs were transfected to CHO-K1 cells and selected on 100 μg/ml Zeocin® antibiotic and 20 μg/ml Blasticidin (at the same time). After selection, independent colonies were isolated and propagated under continuous selection pressure (using 100 μg/ml Zeocin® antibiotic and 20 μg/ml blasticidin). FIG. 20 shows that the STAR 7/67/7 combination had a beneficial effect on EpCAM production. The ATGmut/space Zeo and ATGmut/space Blas had no effect on the number of colonies that were formed with plasmids containing STAR elements or not. However, the average EpCAM expression levels of either 24 control versus STAR 7/67/7 colonies ranged from 0.61 pg/cell/day in the control to 3.44 pg/cell/day in the STAR7/67/7 construct (FIG. 20). This is a factor 5.6 increase. Since there were many colonies in the ATGmut/space control with 0 pg/cell/day, also the average EpCAM production in the highest five colonies was compared. In the control ATGmut/space this was 3.0 pg/cell/day, versus 7.8 pg/cell/day with the ATGmut/space STAR 7/67/7 construct, an increase of a factor 2.6.

FIG. 21 also shows that the STAR 7/67/7 combination had a beneficial effect on EpCAM production, using the GTG start codon for the markers. With the GTG Zeo and GTG Blas STAR 7/67/7 construct approximately 2 times more colonies were formed. Also, the average EpCAM expression levels of either 24 control versus STAR 7/67/7 colonies ranged from 2.44 pg/cell/day in the control to 6.51 pg/cell/day in the STAR7/67/7 construct (FIG. 21). This is a factor 2.7 increase. Also the average EpCAM production in the highest five colonies was compared. In the control GTG this was 5.7 pg/cell/day, versus 13.0 pg/cell/day with the GTG STAR 7/67/7 construct, an increase of a factor 2.3. Also note that the average EpCAM production mediated by the GTG start codon for the selection markers was significantly higher than with the ATGmut/space start codon.

FIG. 22 shows that with the TTG Zeo and TTG Blas control construct no colonies were formed, similar as in Example 9. With the STAR 7/67/7 TTG construct colonies were formed. The average EpCAM expression levels of the STAR 7/67/7 TTG colonies was 10.4 pg/celUday (FIG. 22). This is again higher than with the ATGmut/space and GTG as start codon (see FIGS. 20, 21 for comparison). The average EpCAM production in the highest five TTG STAR 7/67/7 colonies was 22.5 pg/cell/day.

The results show that the selection system can also be applied to two simultaneously produced polypeptides, in this case two polypeptides of a multimeric protein, casu quo an antibody. The EpCAM production closely follows the results obtained with d2EGFP. The TTG as start codon is more stringent than the GTG start codon, which in turn is more stringent than the ATGmut/space (FIGS. 12 and 13). Higher stringency results in a decreasing number of colonies, with no colonies in the case of the TTG control that has no STAR elements, and higher stringency of the selection marker is coupled to higher expression of the protein of interest.

Example 14

Creation and Testing of Additional GTG Zeocin®-d2EGFP Bicistronic Constructs with Differential Translation Efficiencies Different versions of the Zeocin® antibiotic resistance gene with mutated start codons were described in Example 8. Besides the described GTG codons (Example 8, FIG. 33A), additional modified start codons with distinct translational efficiency are possible. These different Zeocin® antibiotic resistance gene versions were created (FIG. 33) and cloned upstream of the modified d2EGFP gene, as in Example 9.

Materials and Methods
Creation of Plasmids

Four additional GTG constructs were made:

1) GTG as a start codon in the Zeo resistance gene (FIG. 33A), but followed by a spacer sequence (FIG. 33B). The mutspace-Zeo open reading frame was amplified with primer pair GTGspaceBamHIF (SEQ ID NO:122): GAATTCGGATCCACC GTGGCGATCCAAAGACTGCCAAATCTAG and (wherein the sequence following the underlined sequence comprises the spacer sequence), and ZEOWTreverse (SEQ ID NO:85), the PCR product was cut with EcoRI-BamHI, and ligated into pd2EGFP, cut with EcoRI-BamHI, creating pZEO-<u>GTGspace</u>-d2EGFP.

2) GTG as a start codon in the Zeo resistance gene, but in a bad context ( *TTTGTG* ) (FIG. 33C). The Zeo open reading frame was amplified with primer pair ZEOTTTGTGBamHIF (SEQ ID NO:123): GAATTCGGATCC TTTGTGGCCAAGTTGACCAGTGCCGTTCCG and ZEOWTreverse (SEQ ID NO:85), the PCR product was cut with EcoRI-BamHI, and ligated into pd2EGFP, cut with EcoRI-BamHI, creating pZEO(leu)-<u>TTTGTG</u>-d2EGFP.

3) GTG as a start codon in the Zeo resistance gene, instead of ATG (FIG. 33A), but with an additional mutation in the Zeo open reading frame at Pro9, which was replaced with threonine (Thr) (FIG. 33D). The Thr9 mutation was introduced by amplifying the Zeo open reading with primer pair ZEOForwardGTG-Thr9 (SEQ ID NO:124): AATTGGATCCACC GTGGCCAAGTTGACCAGTGCCGTT *ACC* GTGCTC and ZEOWTreverse (SEQ ID NO:85), the PCR product was cut with EcoRI-BamHI, and ligated into pd2EGFP, cut with EcoRI-BamHI, creating pZEO-<u>GTG</u>-Thr9-d2EGFP.

4) GTG as a start codon in the Zeo resistance gene, instead of ATG (FIG. 33A), but with an additional mutation in the Zeo open reading frame at Pro9, with was replaced with Phenylalanine (Phe) (FIG. 33E). The Phe9 mutation was introduced by amplifying the Zeo open reading with primer pair ZEO-Forward GTG-Phe9 (SEQ ID NO:125): AATTGGATCCACC GTGGCCAAGTTGACCAGTGCCGTT *TTC* GTGCTC and ZEOWTreverse (SEQ ID NO:85), the PCR product was cut with EcoRI-BamHI, and ligated into pd2EGFP, cut with EcoRI-BamHI, creating pZEO-<u>GTG</u>-Phe9-d2EGFP.

Transfection, Culturing and Analysis of CHO Cells

Transfection, culturing and analysis of CHO-K1 cells was performed as in Example 8.

Results

CHO-K1 cells were transfected with constructs that contain the GTG Zeo (FIG. 33A), GTGspace Zeo (FIG. 33B), TTT GTG Zeo (also called: GTGmut Zeo) (FIG. 33C), GTG Thr9 Zeo(leu) (FIG. 33D) and GTG Phe9 Zeo(leu) (FIG. 33D) genes as selection gene, all being cloned upstream of the d2EGFP reporter gene. These five constructs were without STAR elements (Control) or with STAR elements 7 and 67 upstream of the CMV promoter and STAR 7 downstream from the d2EGFP gene (FIG. 33). FIG. 34 shows that of the control constructs without STAR elements only the GTG Zeo construct without STAR elements gave colonies that expressed d2EGFP protein. In contrast, all constructs containing STAR elements gave colonies that expressed d2EGFP protein. The mean d2EGFP fluorescence signal of 11 GTG Zeo Control colonies was 20.3, of 13 GTG Zeo colonies with STARs 7/67/7 104.9, of 24 GTG space Zeo 7/67/7 colonies 201.5, of 6 TTT GTG Zeo 7/67/7 colonies 310.5, of 22 GTG Thr9 Zeo 7/67/7 colonies 423, and of 16 GTG Phe9 Zeo colonies 550.2 (FIG. 34).

The higher stringencies of the novel GTG mutations correlate with higher mean fluorescence signals (FIG. 34). The TTT GTG Zeo 7/67/7, however, gave only two high expressing colonies and a few low expressing colonies. This may indicate that this mutation is at the brink of the stringency that these cells can bear with a fixed concentration of Zeocin® antibiotic added to the culture medium.

The Thr9 and Phe9 mutations do not influence the translation efficiency of the Zeo mutants. Instead they reduce the functionality of the Zeocin® antibiotic resistance protein, by preventing an optimal interaction between the two halves of the Zeocin® antibiotic resistance protein (Dumas et al., 1994). This implies that more of the protein has to be produced to achieve resistance against the Zeocin® antibiotic in the culture medium. As a consequence, the entire cassette has to be transcribed at a higher level, eventually resulting in a higher d2EGFP expression level.

It is concluded that the use of the described translation efficiencies of the Zeocin® antibiotic resistance mRNA result in higher expression levels of the d2EGFP protein, this in combination with STAR elements.

This example further demonstrates the possibility to provide for fine-tuning of the stringency of the selection system of the invention, to achieve optimal expression levels of a protein of interest. Clearly, the person skilled in the art will be capable of combining these and other possibilities within the concepts disclosed herein (e.g., mutate the Zeocin® antibiotic at position 9 to other amino acids, or mutate it in other positions; use a GTG or other start codon in a non-optimal translation initiation context for Zeocin® antibiotic or other selection markers; or mutate other selection markers to reduce their functionality, for instance use a sequence coding for a neomycin resistance gene having a mutation at amino acid residue 182 or 261 or both, see, e.g., WO 01/32901), and the like, to provide for such fine-tuning, and by simply testing determine a suitable combination of features for the selection marker, leading to enhanced expression of the polypeptide of interest.

Example 15

Creation and Testing of Additional TTG Zeocin®-d2EGFP Bicistronic Constructs with Differential Translation Efficiencies Different versions of the Zeocin® antibiotic resistance gene with mutated start codons were described in Example 8. Besides the described TTG codons (FIG. 35A) additional modified start codons with distinct translational efficiency are possible. These different Zeocin® antibiotic resistance gene versions were created and cloned upstream of the modified d2EGFP gene (FIG. 35).
Materials and Methods
Creation of Plasmids Three additional TTG constructs were made:

1) TTG as a start codon in the Zeo resistance gene (FIG. 35A), but followed by a spacer sequence (FIG. 35B). The Zeo open reading frame (with the spacer sequence) was amplified with primer pair TTGspaceBamHIF (SEQ ID NO:126): GAATTCGGATCCACC TTGGCGATCCAAAGACTGCCAAATCTAG and ZEOWTreverse(SEQ ID NO:85), the PCR product was cut with EcoRI-BamHI, and ligated into pd2EGFP, cut with EcoRI-BamHI, creating pZEO-TTGspace-d2EGFP.

2) TTG as a start codon in the Zeo resistance gene, instead of ATG (FIG. 35A), but with an additional mutation in the Zeo open reading frame at Pro9, with was replaced with threonine (Thr) (FIG. 35C). The Thr9 mutation was introduced by amplifying the Zeo open reading with primer pair ZEOForwardTTG-Thr9 (SEQ ID NO:127): AATTGGATCCACC TTGGCCAAGTTGACCAGTGCCGTT *ACC* GTGCTC and ZEOWTreverse (SEQ ID NO:85), the PCR product was cut with EcoRI-BamHI, and ligated into pd2EGFP, cut with EcoRI-BamHI, creating pZEO-TTG-Thr9-d2EGFP.

3) TTG as a start codon in the Zeo resistance gene, instead of ATG (FIG. 35A), but with an additional mutation in the Zeo open reading frame at Pro9, with was replaced with Phenylalanine (Phe) (FIG. 35D). The Phe9 mutation was introduced by amplifying the Zeo open reading with primer pair ZEO-ForwardTTG-Phe9 (SEQ ID NO:128): AATTGGATCCACC TTGGCCAAGTTGACCAGTGCCGTT *TTC* GTGCTC and ZEOWTreverse (SEQ ID NO:85), the PCR product was cut with EcoRI-BamHI, and ligated into pd2EGFP, cut with EcoRI-BamHI, creating pZEO-TTG-Phe9-d2EGFP.
Results CHO-K1 cells were transfected with constructs that contain the TTG Zeo (FIG. 35A), TTGspace Zeo (FIG. 35B), TTG Thr9 Zeo (FIG. 35C) and TTG Phe9 Zeo (FIG. 35D) genes as selection gene, all being cloned upstream of the d2EGFP reporter gene. These four constructs were without STAR elements (Control) or with STAR elements 7 and 67 upstream of the CMV promoter and STAR 7 downstream from the d2EGFP gene (FIG. 35). FIG. 36 shows that of the control constructs without STAR elements only the TTG Zeo construct without STAR elements gave colonies that expressed d2EGFP protein. In contrast, all constructs containing STAR elements gave colonies that expressed d2EGFP protein. The mean d2EGFP fluorescence signal of three TTG Zeo Control colonies was 26.8, of 24 TTG Zeo colonies with STARs 7/67/7 426.8, of 24 TTGspace Zeo 7/67/7 colonies 595.7, of two TTG Thr9 Zeo 7/67/7 colonies 712.1, and of three TTG Phe9 Zeo colonies 677.1 (FIG. 36).

The higher stringencies of the novel TTG mutations correlate with higher mean fluorescence signals (FIG. 36). The TTG Thr9 Zeo 7/67/7 and TTG Phe9 Zeo 7/67/7 constructs, however, gave only two high expressing colonies each and a few low expressing colonies. This may indicate that these mutations are at the brink of the stringency that the cells can bear with a fixed concentration of Zeocin® antibiotic added to the culture medium.

It is concluded that the use of the described translation efficiencies of the Zeocin® antibiotic resistance mRNA result in higher expression levels of the d2EGFP protein, this in combination with STAR elements.

Example 16

Creation and Testing of Puromycin-d2EGFP Bicistronic Constructs with Differential Translation Efficiencies There are three internal ATGs in the puromycin resistance gene, each of which codes for a methionine (FIG. 28, FIG. 37A). These ATGs have to be eliminated (FIG. 37B,C), since they will serve as start codon when the ATG start codon (or the context thereof) has been modified, and this will result in peptides that do not resemble puromycin resistance protein. More importantly, these ATGs will prevent efficient translation of the gene of interest, as represented by d2EGFP in this example for purposes of illustration. The methionines were changed into leucine, like in the Zeocin® antibiotic resistance protein (Example 8). However, instead of using the TTG codon for leucine (for instance in Zeocin® antibiotic in Example 8), now the CTG codon for leucine was chosen (in humans, for leucine the CTG codon is used more often than the TTG codon). To eliminate the internal ATGs, the puromycin resistance protein open reading frame was first amplified with 4 primer pairs, generating 4 puromycin resistance protein fragments. The primer pairs were:

```
PURO BamHI F (SEQ ID NO: 129):
GATCGGATCCATGGTTACCGAGTACAAGCCCACGGT,

PURO300 R LEU (SEQ ID NO: 130):
CAGCCGGGAACCGCTCAACTCGGCCAGGCGCGGGC;
and

PURO300FLEU (SEQ ID NO: 131):
CGAGTTGAGCGGTTCCCGGCTGGCCGCGCAGCAACAGCTGGAAGGCCTC,

PURO600RLEU (SEQ ID NO: 132):
AAGCTTGAATTCAGGCACCGGGCTTGCGGGTCAGGCACCAGGTC.
```

This generates two PCR products, corresponding to the 5' and 3' part of the puromycin resistance gene. The two products were added together and amplified with PURO BamHI F (SEQ ID NO:129)-PURO600RLEU (SEQ ID NO:132). The resulting PCR product was cut with BamHI-EcoRI and ligated, creating pCMV-ATGPURO (leu). Sequencing of this clone verified that all three internal ATGs had been converted. The entire puromycin open reading frame was then amplified with PUROBamHI TTG1F (SEQ ID NO:133): GAATTCG-GATCCACCTTGGTTACCGAGTACAAGCCCACGGTG and PURO600RLEU (SEQ ID NO:132). This primer introduces an extra codon (GTT) directly after the TTG start codon, because the "G" at nucleotide +4 is introduced for an optimal context, and hence two more nucleotides are introduced to preserve the reading frame.

Results

CHO-K1 cells were transfected with the construct that contains the TTG Puro (FIG. 38) gene as selection gene, cloned upstream of the d2EGFP reporter gene. Selection was under 10 μg/ml puromycin. The construct was without STAR elements (Control) or with STAR elements 7 and 67 upstream of the CMV promoter and STAR 7 downstream from the d2EGFP gene (FIG. 38). FIG. 38 shows that the average d2EGFP fluorescence signal of 24 TTG Puro Control colonies was 37.9, of 24 TTG Puro colonies with STARs 7/67/7 75.5. Moreover, when the average of the five highest values is taken, the d2EGFP fluorescence signal of TTG Puro Control colonies was 69.5, and of TTG Puro colonies with STARs 7/67/7 186.1, an almost three-fold increase in d2EGFP fluorescence signal. This shows that the described, modified translation efficiency of the Puromycin resistance mRNA result in higher expression levels of the d2EGFP protein, this in combination with STAR elements.

This experiment demonstrates that the puromycin resistance gene can be mutated to remove the ATG sequences therefrom, while remaining functional. Moreover it is concluded that the selection method of the invention also works with yet another selection marker, puromycin.

Example 17

Creation and Testing of Neomycin Constructs with Differential Translation Efficiencies There are sixteen internal ATGs in the neomycin resistance gene, five of which code for a methionine in the neomycin open reading frame (FIG. 31, FIG. 39A). All these sixteen ATGs have to be eliminated (FIG. 39B,C), since they will serve as start codon when the ATG start codon (or the context thereof) has been modified, and this will result in peptides that do not resemble neomycin resistance protein, and this will decrease the translation from the downstream open reading frame coding for the polypeptide of interest in the transcription units of the invention. To eliminate the internal ATGs, the neomycin resistance protein open reading frame was entirely synthesized by a commercial provider (GeneArt, Germany), wherein all internal coding ATGs (for Met) where replaced by CTGs (coding for Leu), and non-coding ATGs were replaced such that a degenerated codon was used and hence no mutations in the protein sequence resulted; the synthesized sequence of the neomycin is given in SEQ ID NO:134. In order to replace the ATG start codon with GTG (FIG. 39B) or TTG FIG. 39C), the synthesized neomycin gene was amplified with primer pairs NEO-F-HindIII (SEQ ID NO:136): GATCAAGCTTTTGGATCGGCCATTGAAA-CAAGACGGATTG and NEO EcoRI 800R (SEQ ID NO:137): AAGCTTGAATTCTCAGAAGAACTCGT-CAAGAAGGCG.

Results

E. coli bacteria were used to test the functionality of the neomycin resistance protein from which all ATGs were removed. E. coli bacteria were transformed with the constructs that contain the GTG Neo (FIG. 39B) or TTG Neo (FIG. 39C) gene as selection gene. Selection took place by growing the bacteria on kanamycin. Only a functional neomycin resistance gene can give resistance against kanamycin. Transformation with either modified Neo gene resulted in the formation of E. coli colonies, from which the plasmid containing the gene could be isolated. This shows that the described, modified translation efficiencies of the Neomycin resistance mRNAs, as well as the removal of all ATGs from the Neo open reading frame result in the production of functional neomycin resistance protein.

The mutated neomycin resistance genes are incorporated in a multicistronic transcription unit of the invention, and used for selection with G418 or neomycin in eukaryotic host cells.

Example 18

Creation and Testing of dhfr Constructs with Differential Translation Efficiencies There are eight internal ATGs in the dhfr gene, six of which code for a methionine in the dhfr open reading frame (FIG. 29, FIG. 40A). All these ATGs have to be eliminated (FIGS. 40B, C), since they will serve as start codon when the ATG start codon (or the context thereof) has been modified, and this will result in peptides that do not resemble dhfr protein, and will decrease the translation from the downstream open reading frame coding for the polypeptide of interest in the transcription units of the invention. To eliminate the internal ATGs, the dhfr protein open reading frame was entirely synthesized (SEQ ID NO:138), as described above for neomycin. In order to replace the ATG start codon with GTG (FIG. 40B) or TTG (FIG. 40C), the synthesized DHFR gene was amplified with primers DHFR-F-HindIII (SEQ ID NO:140): GAT-CAAGCTTTTGTTCGACCATTGAACTGCATCGTC and DHFR-EcoRI-600-R (SEQ ID NO:141): AGCTTGAAT-TCTTAGTCTTTCTTCTCGTAGACTTC.

Results

E. coli bacteria were used to test the functionality of the dhfr protein from which all ATGs were removed. E. coli was transformed with the constructs that contain the GTG dhfr (FIG. 40B) or TTG dhfr (FIG. 40C) gene. Selection took place by growing the bacteria on trimethoprim (Sigma T7883-56). Only a functional dhfr gene can give resistance against trimethoprim. Transformation with either modified dhfr gene resulted in the formation of E. coli colonies, from which the plasmid containing the gene could be isolated. This shows that the described, modified translation efficiencies of the dhfr mRNAs, as well as the removal of all ATGs from the dhfr open reading frame result in the production of functional dhfr protein.

The mutated dhfr genes are incorporated in a multicistronic transcription unit of the invention, and used for selection with methotrexate in eukaryotic host cells.

Example 20

Testing of Zeocin®- and Blasticidin Constructs with Differential Translation Efficiencies in PER.C6® Cells Various Zeocin® and blasticidin genes with mutated start codons, all cloned upstream of the d2EGFP gene were tested in the PER.C6 cell line.
Results The GTG Zeocin® antibiotic and GTGspace Zeocin® antibiotic resistance gene modifications (see also Example 14; FIG. 41) and the GTG blasticidin and TTG blasticidin resistance gene modifications (see also Example 11; FIG. 42), all cloned upstream of the d2EGFP gene were transfected to PER.C6® cells. As shown in FIG. 41, transfection with both the GTG Zeocin® antibiotic and GTGspace Zeocin® antibiotic gene resulted in colonies that expressed d2EGFP. The average d2EGFP fluorescence signal of 20 GTG Zeo colonies was 63.8, while the average d2EGFP signal of 20 GTGspace Zeo colonies was 185, demonstrating that also in PER.C6® cells the GTGspace Zeo has a higher translation stringency than the GTG Zeo mRNA.

As shown in FIG. 42, transfection with both the GTG Blasticidin and TTG Blasticidin gene resulted in colonies that expressed d2EGFP. The average d2EGFP fluorescence signal of 20 GTG Blasticidin colonies was 71.4, while the average d2EGFP fluorescence signal of 20 TTG Blasticidin colonies was 135, demonstrating that also in PER.C6 cells the TTG Blasticidin has a higher translation stringency than the GTG Blasticidin mRNA.

This example demonstrates that the selection system of the invention can also be used in other cells than CHO cells.

Example 21

Testing of the Addition of a Transcriptional Pause Signal to a TTG Zeocin®-d2EGFP Construct A TRAnscription Pause (TRAP) sequence is thought to, at least in part, prevent formation of antisense RNA or, to at least in part, prevent transcription to enter the protein expression unit (see WO 2004/055215). A TRAP sequence is functionally defined as a sequence which when placed into a transcription unit, results in a reduced level of transcription in the nucleic acid present on the 3' side of the TRAP when compared to the level of transcription observed in the nucleic acid on the 5' side of the TRAP, and non-limiting examples of TRAP sequences are transcription termination signals. In order to function to prevent or decrease transcription to enter the transcription unit, the TRAP is to be placed upstream of a promoter driving expression of the transcription unit and the TRAP should be in a 5' to 3' direction. In order to prevent at least in part formation of antisense RNA, the TRAP should be located downstream of the open reading frame in a transcription unit and present in a 3' to 5' direction (that is, in an opposite orientation as the normal orientation of a transcriptional termination sequence that is usually present behind the open reading frame in a transcription unit). A combination of a TRAP upstream of the promoter in a 5' to 3' orientation and a TRAP downstream of the open reading frame in a 3' to 5' orientation is preferred. Adding a TRAP sequence to a STAR element improves the effects of STAR elements on transgene expression (see WO 2004/055215). Here we test the effects of the TRAP sequence in the context of the TTG Zeo resistance gene.
Results The TTG Zeocin®-d2EGFP cassette that was flanked with STAR7 elements (FIG. 43) was modified by the addition of the SPA/pause TRAP sequence (see WO 2004/055215); SEQ ID NO:142), both upstream of the 5' STAR7 (in 5' to 3' direction) and downstream of the 3' STAR7 (in 3' to 5' direction) (FIG. 43). Both STAR 7/7 and TRAP-STAR 7/7-TRAP containing vectors were transfected to CHO-K1. Stable colonies were isolated and the d2EGFP fluorescence intensities were measured. As shown in FIG. 43 the average d2EGFP fluorescence signal of 23 TTG Zeo STAR 7/7 colonies was 455.1, while the average d2EGFP fluorescence signal of 23 TTG Zeo TRAP-STAR 7/7-TRAP colonies was 642.3. The average d2EGFP fluorescence signal in highest 5 TTG Zeo STAR 7/7 colonies was 705.1, while the average d2EGFP fluorescence signal of 5 TTG Zeo TRAP-STAR 7/7-TRAP colonies was 784.7.

This result indicates that the addition of TRAPs does not enhance the d2EGFP fluorescence signal in the highest colonies, but that there is a significant raise in the number of high expressing colonies. Whereas only 5 TTG Zeo STAR 7/7 colonies had d2EGFP signal above 600, 17 TTG Zeo TRAP-STAR 7/7-TRAP colonies had a d2EGFP fluorescence signal above 600.

In the experiment 3 µg DNA of each plasmid was transfected. However, whereas the transfection efficiency was similar, the total number of colonies with the TTG Zeo STAR 7/7 plasmid was 62, while the total number of colonies with the TTG Zeo TRAP-STAR 7/7-TRAP plasmid was 116, almost a doubling.

We conclude that addition of TRAP elements to the STAR containing plasmids with modified Zeocin® antibiotic resistance gene translation codons results in a significantly higher overall number of colonies and that more colonies are present with the highest expression levels.

Example 22

Copy-Number Dependency of Expression

We analyzed the EpCAM antibody expression levels in relation to the number of integrated EpCAM DNA copies.
Results The construct that was tested was TTG-Zeo-Light Chain (LC)-TTG-Blas-Heavy Chain (HC), both expression units being under the control of the CMV promoter (see FIG. 44). This construct contained STAR 7 and 67 (see FIG. 44). Selection conditions were such that with 200 µg/ml Zeocin® antibiotic and 20 µg/ml Blasticidin in the culture medium no control colonies (no STARs) survived and only STAR 7/67/7 colonies survived.

DNA was isolated when colonies were 60 days under Zeocin® antibiotic and Blasticidin selection pressure (see FIG.

44). The $R^2$ value is calculated and shown. In the entire range from 5 to 40 pg/cell/day EpCAM there was a high degree of copy number dependency, as signified by a relatively high $R^2$ of 0.5978 (FIG. 44). The data show that in the novel selection system, in colonies that contain TTG Zeo-TTG Blas EpCAM STAR 7/67/7 constructs there is copy number dependent EpCAM expression.

Example 23

Methotrexate Induction of higher EpCAM Expression

We analyzed EpCAM antibody expression levels after incubation of clones with methotrexate (MTX). The purpose of this experiment was to determine whether amplification of a STAR-containing construct would result in higher EpCAM expression. MTX acts through inhibition of the dhfr gene product. While some CHO strains that are dhfr-deficient have been described, CHO-K1 is dhfr$^+$. Therefore relatively high concentrations of MTX in the culture medium have to be present to select for amplification by increased MTX concentrations in CHO-K1 cells.

Results

The construct that was tested was TTG-Zeo-Heavy Chain (HC)-TTG-Blas-Light Chain (LC), both expression units being under the control of the CMV promoter. Upstream of each CMV promoter STAR67 was positioned and STAR7 was used to flank the entire cassette (see also Example 13, FIG. 22 for such a construct). This construct was further modified by placing an SV40-dhfr cassette (a mouse dhfr gene under control of an SV40 promoter) between the HC and LC cassettes, upstream of the second STAR67 (FIG. 45). CHO-K1 cells were transfected. Selection was done with 100 µg/ml Zeocin® antibiotic and 10 µg/ml Blasticidin in the culture medium. No control colonies (without STAR elements) survived and only colonies with constructs containing the STAR elements survived. Colonies were isolated and propagated before measuring EpCAM expression levels. Six colonies that produced between 20 and 35 pg/cell/day were transferred to medium containing 100 nM MTX. This concentration was raised to 500 nM, 1000 nM and finally to 2000 nM with two weeks periods in between each step. After two weeks on 2000 nM MTX, EpCAM concentrations were measured. As shown in FIG. 45, four colonies showed enhanced EpCAM production. Colony 13, from 22 to 30; colony 14, from 28 to 42; colony 17, from 20 to 67 and colony 19, from 37 to 67 pg/cell/day. Colonies 4 and 16 showed no enhanced EpCAM expression. We conclude that addition of methotrexate to the culture medium of CHO-K1 colonies created with the selection system of the invention can result in enhanced protein expression. Hence, STAR elements and the selection method of the invention can be combined with and are compatible with MTX-induced enhancement of protein expression levels.

Example 24

TTG-Zeo Selection Operates in the Context of Different Promoters

We analyzed d2EGFP expression levels in the context of the TTG Zeo selection marker and different promoters. We compared the action of STAR elements in the context of the CMV enhancer/promoter, the SV40 enhancer/promoter and the CMV enhancer/β-actin promoter.

Results

In FIG. 46, we indicate the promoters we tested in the context of the TTG Zeo selection marker. The tested plasmids consisted of the indicated control constructs with three different promoters and STAR constructs which were flanked with STAR 7 and STAR 67 at the 5' end and STAR 7 at the 3' end. The constructs were transfected to CHO-K1 cell and selection was performed with 200 µg/ml Zeocin® antibiotic in the culture medium. Up to 23 independent colonies were isolated and propagated before analysis of d2EGFP expression levels. As shown in FIG. 46, incorporation of STAR elements in constructs with the CMV enhancer/promoter, the SV40 enhancer/promoter or the CMV enhancer/β-actin promoter all resulted in the formation of colonies with higher d2EGFP expression levels than with the corresponding control constructs. This shows that the selection system of the invention, in combination with STAR elements, operates well in the context of different promoters. Further analysis showed that the mean of CMV-driven d2EGFP values was significantly higher than the mean of SV40-driven d2EGFP values ($p<0.05$). In contrast, the mean of CMV-driven d2EGFP values did not significantly differ from CMV/βactin-driven d2EGFP values ($p=0.2$).

Example 25

Comparison of Different STAR Elements in the TTG-Zeo Selection System

We analyzed d2EGFP expression levels in the context of the CMV promoter-TTG Zeo selection marker and 53 different STAR elements, to obtain more insight in which STAR elements give the best results in this context.

Results

We cloned 53 STAR elements up- and downstream of the CMV promoter-TTG Zeo-d2EGFP cassette. The following STAR elements were tested in such constructs: STAR2-12, 14, 15, 17-20, 26-34, 36, 37, 39, 40, 42-49, 51, 52, 54, 55, 57-62, 64, 65, 67. The constructs were transfected to CHO-K1 cells and selection was performed with 200 µg/ml Zeocin® antibiotic in the culture medium. Up to 24 independent colonies were isolated and propagated before analysis of d2EGFP expression levels. Incorporation of STAR elements in the constructs resulted in different degrees of enhanced d2EGFP expression, as compared to the control. Incorporation of STAR elements 14, 18 and 55 in this experiment did not result in an increase of average d2EGFP expression over the control (no STAR element). Although some constructs (with STAR elements 2, 3, 10, 42, 48 and 49) in this experiment gave rise to only a few colonies, all tested STAR elements except 14, 18 and 55 resulted in average d2EGFP expression levels higher than for the control. It should be noted that some STAR elements may act in a more cell type specific manner and that it is well possible that STAR 14, 18 and 55 work better in other cell types, with other promoters, other selection markers, or in different context or configuration than in the particular set of conditions tested here. Addition of ten STAR elements, namely STAR elements 7, 9, 17, 27, 29, 43, 44, 45, 47 and 61, induced average d2EGFP expression levels higher than five times the average d2EGFP expression level of the control. We retransformed the control and seven constructs with STAR elements and repeated the experiment. The results are shown in FIG. 47. Incorporation of STAR elements in the constructs resulted in different degrees of enhanced d2EGFP expression, as compared to the control (FIG. 47). The average d2EGFP expression level in colonies transfected with the control construct was 29. The averages from d2EGFP expression levels in colonies with the seven different STAR constructs ranged between 151 (STAR 67) and 297 (STAR 29). This is a factor of five- to ten-fold higher than the average in the control colonies.

We conclude that a) the vast majority of STAR elements have a positive effect on gene expression levels, b) there is variation in the degree of positive effects induced by the different STAR elements, and c) ten out of 53 tested STAR elements induce more than five-fold average d2EGFP expression levels, as compared to the control, and that STAR elements can induce a ten-fold higher average d2EGFP expression level, as compared to the control.

Example 26

Other Chromatin Control Elements in the Context of a Selection System of the Invention DNA elements such as the HS4 hypersensitive site in the locus control region of the chicken β-globin locus (Chung et al., 1997), matrix attachment regions (MAR) (Stief et al., 1989) and a ubiquitous chromatin opening element (UCOE) (Williams et al., 2005) have been reported to have beneficial effects on gene expression when these DNA elements are incorporated in a vector. We combined these DNA elements with the selection system of the invention.
Results The 1.25 kb HS4 element was cloned into the cassette encompassing the CMV promoter, TTG Zeo and d2EGFP by a three way ligation step to obtain a construct with a tandem of 2 HS4 elements (Chung et al., 1997). This step was done both for the 5' and 3' of the cassette encompassing the CMV promoter, TTG Zeo and d2EGFP. The 2959 bp long chicken lysozyme MAR (Stief et al., 1989) was cloned 5' and 3' of the cassette encompassing the CMV promoter, TTG Zeo and d2EGFP. The 2614 bp long UCOE (Williams et al., 2005) was a NotI-KpnI fragment, excised from a human BAC clone (RP11-93D5), corresponding to nucleotide 29449 to 32063. This fragment was cloned 5' of the CMV promoter. The STAR construct contained STAR7 and STAR67 5' of the CMV promoter and STAR7 3' of the cassette. These four constructs, as well as the control construct without flanking chromatin control DNA elements, were transfected to CHO-K1 cells. Selection was performed by 200 µg/ml Zeocine® antibiotic in the culture medium. Colonies were isolated, propagated and d2EGFP expression levels were measured. As shown in FIG. 48 constructs with all DNA elements resulted in the formation of d2EGFP expressing colonies. However, incorporation of 2xHS4 elements and the UCOE did not result in the formation of colonies that displayed higher d2EGFP expression levels, in comparison with the control colonies. In contrast, incorporation of the lysozyme MAR resulted in the formation of colonies that expressed d2EGFP significantly higher. The mean expression level induced by MAR containing constructs was four-fold higher than in the control colonies. Best results were obtained, however, by incorporating STAR 7 and 67 in the construct. An almost ten-fold increase in the mean d2EGFP expression level was observed, as compared to the control colonies. We conclude that other chromatin control DNA elements such as MARs can be used in the context of the selection system of the invention. However, the best results were obtained when STAR elements were used as chromatin control elements.

REFERENCES

Boshart M., F. Weber, G. Jahn, K. Dorsch-Hasler, B. Fleckenstein, and W. Schaffner (1985). A very strong enhancer is located upstream of an immediate early gene of human cytomegalovirus. *Cell* 41:521-530.

Chung J. H., M. Whiteley and G. Felsenfeld (1993). A 5' element of the chicken beta-globin domain serves as an insulator in human erythroid cells and protects against position effect in *Drosophila*. *Cell* 74:505-514.

Chung J. H., A. C. Bell, and G. Felsenfeld (1997). Characterization of the chicken beta-globin insulator. *Proc. Natl. Acad. Sci. U.S.A.* 94:575-580.

Das G. C., S. K. Niyogi, and N. P. Salzman (1985). SV40 promoters and their regulation. *Proc. Nucleic Acid Res. Mol. Biol.* 32:217-236.

Dumas P., M. Bergdoll, C. Cagnon and J. M. Masson (1994). Crystal structure and site-directed mutagenesis of a bleomycin resistance protein and their significance for drug sequestering. *EMBO. J.* 13:2483-2492.

Gill D. R., S. E. Smyth, C. A. Goddard, I. A. Pringle, C. F. Higgins, W. H. Colledge and S. C. Hyde (2001). Increased persistence of lung gene expression using plasmids containing the ubiquitin C or elongation factor 1α promoter. *Gene Therapy* 8:1539-1546.

Gossen M. and H. Bujard (1992). Tight control of gene expression in mammalian cells by tetracycline-responsive promoters. *Proc. Natl. Acad. Sci. U.S.A.* 89:5547-5551.

Graham F. O., J. Smiley, W. Russell and R. Nairn (1977). Characteristics of a human cell line transformed by DNA from human adenovirus type 5. *J. Gen. Virol.* 36:59-72.

Huls G. A., I. A. F. M. Heijnen, M. E. Cuomo, J. C. Koningsberger, L. Wiegman, E. Boel, A.-R. van der Vuurst-de Vries, S. A. J. Loyson, W. Helfrich, G. P. van Berge Henegouwen, M. van Meijer, J. de Kruif, and T. Logtenberg (1999). A recombinant, fully human monoclonal antibody with antitumor activity constructed from phage-displayed antibody fragments. *Nat. Biotechnol.* 17:276-281.

Jones D., N. Kroos, R. Anema, B. Van Montfort, A. Vooys, S. Van Der Kraats, E. Van Der Helm, S. Smits, J. Schouten, K. Brouwer, F. Lagerwerf, P. Van Berkel, D.-J. Opstelten, T. Logtenberg, and A. Bout. (2003). High-level expression of recombinant IgG in the human cell line PER.C6. *Biotechnol. Prog.* 19:163-168.

Kaufman R. J. (2000). Overview of vector design for mammalian gene expression. *Mol. Biotechnol.* 16:151-160.

Kaufman R. J. and P. A. Sharp (1982). Construction of a modular dihydrofolate reductase cDNA gene: analysis of signals utilized for efficient expression. *Mol. Cell. Biol.* 2:1304-1319.

Kellum R. and P. Schedl (1991). A position-effect assay for boundaries of higher order chromosomal domains. *Cell* 64:941-950.

Kim S. J., N. S. Kim, C. J. Ryu, H. J. Hong, and G. M. Lee (1998). Characterization of chimeric antibody producing CHO cells in the course of dihydrofolate reductase-mediated gene amplification and their stability in the absence of selective pressure. *Biotechnol. Bioeng.* 58:73-84.

Kozak M. (1986). Point mutations define a sequence flanking the AUG initiator codon that modulates translation by eukaryotic ribosomes. *Cell* 44:283-292.

Kozak M. (1987). An analysis of 5'-noncoding sequences from 699 vertebrate messenger RNAs. *Nucleic Acids Res.* 15:8125-8148.

Kozak M. (1989). Context effects and inefficient initiation at non-AUG codons in eucaryotic cell-free translation systems. *Mol. Cell. Biol.* 9:5073-5080.

Kozak M. (1990). Downstream secondary structure facilitates recognition of initiator codons by eukaryotic ribosomes. *Proc. Natl. Acad. Sci. U.S.A.* 87:8301-8305.

Kozak M. (1997). Recognition of AUG and alternative initiator codons is augmented by G in position +4 but is not generally affected by the nucleotides in positions +5 and +6. *EMBO. J.* 16:2482-2492.

Kozak M. (2002). Pushing the limits of the scanning mechanism for initiation of translation. *Gene* 299:1-34.

Kwaks T. H., P. Barnett, W. Hemrika, T. Siersma, R. G. Sewalt, D. P. Satijn, J. F. Brons, R. van Blokland, P. Kwakman, A. L. Kruckeberg, A. Kelder, A. P. Otte (2003). Identification of anti-repressor elements that confer high and stable protein production in mammalian cells. *Nat. Biotechnol.* 21, 553-558. Erratum in: *Nat. Biotechnol.* 21, 822 (2003).

Phi-Van L., J. P. Von Kreis, W. Ostertag and W. H. Stratling (1990). The chicken lysozyme 5' matrix attachment region increases transcription from a heterologous promoter in heterologous cells and dampens position effects on the expression of transfected genes. *Mol. Cell. Biol.* 10:2302-2307.

McBurney M. W., T. Mai, X. Yang, and K. Jardine (2002). Evidence for repeat-induced gene silencing in cultured Mammalian cells: inactivation of tandem repeats of transfected genes. *Exp. Cell. Res.* 274:1-8.

Rees S., J. Coote, J. Stables, S. Goodson, S. Harris, and M. G. Lee (1996). Bicistronic vector for the creation of stable mammalian cell lines that predisposes all antibiotic-resistant cells to express recombinant protein. *Biotechniques* 20:102-104, 106, 108-110.

Schorpp M., R. Jager, K. Schellander, J. Schenkel, E. F. Wagner, H. Weiher, and P. Angel (1996). The human ubiquitin C promoter directs high ubiquitous expression of transgenes in mice. *Nucleic Acids Res.* 24:1787-8.

Stief A., D. M. Winter, W. H. Stratling, and A. E. Sippel (1989). A nuclear DNA attachment element mediates elevated and position-independent gene activity. *Nature* 341:343-345.

Van der Vlag J., J. L. den Blaauwen, R. G. Sewalt, R. van Driel, and A. P. Otte (2000). Transcriptional repression mediated by polycomb group proteins and other chromatin-associated repressors is selectively blocked by insulators. *J. Biol. Chem.* 275:697-704.

West A. G., M. Gaszner, and G. Felsenfeld (2002). Insulators: many functions, many mechanisms. *Genes Dev.* 16:271-288.

Whitelaw E., H. Sutherland, M. Kearns, H. Morgan, L. Weaving, and D. Garrick (2001). Epigenetic effects on transgene expression. *Methods Mol. Biol.* 158:351-68.

Williams S., T. Mustoe, T. Mulcahy, M. Griffiths, D. Simpson, M. Antoniou, A. Ivine, A. Mountain, and R. Crombie (2005). CpG-island fragments from the HNRPA2B1/CBX3 genomic locus reduce silencing and enhance transgene expression from the hCMV promoter/enhancer in mammalian cells. *BMC Biotechnol.* 5:17.

What is claimed is:

1. A method for utilizing a multicistronic transcription unit to produce a peptide of interest from a host cell, the method comprising:

introducing into a plurality of host cells of a eukaryotic cell line a DNA molecule comprising, in 5'-3' direction:
a promoter,
a bicistronic transcription unit comprising:
a first upstream polynucleotide with the translation start codon selected from the group consisting of GTG and TTG, wherein the first upstream polynucleotide encodes a selectable marker polypeptide with no methionine amino acids in its sequence that provides resistance against the lethal or growth-inhibitory effects of a selection marker, and a second downstream polynucleotide encoding the peptide of interest, wherein the second downstream polynucleotide has the translation initiation sequence ATG,
wherein the bicistronic transcription unit has no ATG sequence between the start codon of the first upstream polynucleotide and the start codon of the second downstream polynucleotide, and
a transcription termination sequence,
wherein the DNA molecule further comprises at least two anti-repressor (STAR) sequences flanking the bicistronic transcription unit, wherein the at least two anti-repressor (STAR) sequences flanking the bicistronic transcription unit are a STAR7 sequence (SEQ ID NO:7) and a STAR67 sequence (SEQ ID NO:66) located upstream of the promoter, and a STAR7 sequence (SEQ ID NO:7) located downstream of the transcription termination sequence;
culturing the plurality of host cells to select for expression of the selectable marker polypeptide;
selecting at least one host cell producing the peptide of interest; and
producing the peptide of interest from the host cell.

2. A recombinant expression vector comprising in a 5'-3' direction:
a promoter,
a bicistronic transcription unit comprising:
a first upstream polynucleotide with the translation start codon selected from the group consisting of GTG and TTG, wherein the first upstream polynucleotide encodes a selectable marker polypeptide with no methionine amino acids in its sequence that provides resistance against the lethal or growth-inhibitory effects of a selection marker, and a second downstream polynucleotide encoding the peptide of interest, wherein the second downstream polynucleotide has the translation initiation sequence ATG,
wherein the bicistronic transcription unit has no ATG sequence between the start codon of the first upstream polynucleotide and the start codon of the second downstream polynucleotide, and a transcription termination sequence,
wherein the recombinant expression vector further comprises at least two anti-repressor (STAR) sequences, wherein the at least two anti-repressor (STAR) sequences flanking the bicistronic transcription unit are a STAR 7 sequence (SEQ ID NO:7) and a STAR67 sequence (SEQ ID NO:66) located upstream of the promoter, and a STAR 7 sequence (SEQ ID NO:7) located downstream of the transcription termination sequence.

* * * * *

SEQUENCE LISTING

```
<160> NUMBER OF SEQ ID NOS: 142

<210> SEQ ID NO 1
<211> LENGTH: 749
<212> TYPE: DNA
<213> ORGANISM: Homo sapiens
<220> FEATURE:
<221> NAME/KEY: misc_feature
<223> OTHER INFORMATION: sequence of STAR1

<400> SEQUENCE: 1
atgcggtggg ggcgcgccag agactcgtgg gatccttggc ttggatgttt ggatctttct      60
gagttgcctg tgccgcgaaa gacaggtaca tttctgatta ggcctgtgaa gcctcctgga     120
ggaccatctc attaagacga tggtattgga gggagagtca cagaaagaac tgtggcccct     180
ccctcactgc aaaacggaag tgattttatt ttaatgggag ttggaatatg tgagggctgc     240
aggaaccagt ctccctcctt cttggttgga aaagctgggg ctggcctcag agacaggttt     300
tttggccccg ctgggctggg cagtctagtc gaccctttgt agactgtgca caccectaga     360 agagcaacta ccectataca ccaggctggc tcaagtgaaa ggggctctgg gctccagtct     420
ggaaaatctg gtgtcctggg gacctctggt cttgcttctc tcctccctg cactggctct      480 gggtgcttat ctctgcagaa gcttctcgct agcaaaccca cattcagcgc cctgtagctg     540
aacacagcac aaaaagccct agagatcaaa agcattagta tgggcagttg agcgggaggt     600
gaatatttaa cgcttttgtt catcaataac tcgttggctt tgacctgtct gaacaagtcg     660
agcaataagg tgaaatgcag gtcacagcgt ctaacaaata tgaaaatgtg tatattcacc     720
ccggtctcca gccggcgcgc caggctccc                                       749

<210> SEQ ID NO 2
<211> LENGTH: 883
<212> TYPE: DNA
<213> ORGANISM: Homo sapiens
<220> FEATURE:
```

<221> NAME/KEY: misc_feature
<223> OTHER INFORMATION: sequence of STAR2

<400> SEQUENCE: 2

| | | | | | | |
|---|---|---|---|---|---|---|
| gggtgcttcc | tgaattcttc | cctgagaagg | atggtggccg | gtaaggtccg | tgtaggtggg | 60 |
| gtgcggctcc | ccaggccccg | gcccgtggtg | gtggccgctg | cccagcggcc | cggcaccccc | 120 |
| atagtccatg | gcgcccgagg | cagcgtgggg | gaggtgagtt | agaccaaaga | gggctggccc | 180 |
| ggagttgctc | atgggctcca | catagctgcc | ccccacgaag | acggggcttc | cctgtatgtg | 240 |
| tggggtccca | tagctgccgt | tgccctgcag | gccatgagcg | tgcgggtcat | agtcggggt | 300 |
| gccccctgcg | cccgccctg | ccgccgtgta | gcgcttctgt | gggggtggcg | ggggtgcgca | 360 |
| gctgggcagg | gacgcagggt | aggaggcggg | gggcagcccg | taggtaccct | ggggggcgtt | 420 |
| ggagaagggc | gggggcgact | ggggctcata | cgggacgctg | ttgaccagcg | aatgcataga | 480 |
| gttcagatag | ccaccggctc | cggggggcac | ggggctgcga | cttggagact | ggccccccga | 540 |
| tgacgttagc | atgcccttgc | ccttctgatc | cttttttgtac | ttcatgcggc | gattctggaa | 600 |
| ccagatcttg | atctggcgct | cagtgaggtt | cagcagattg | gccatctcca | cccggcgcgg | 660 |
| ccggcacagg | tagcggttga | agtggaactc | tttctccagc | tccaccagct | gcgcgctcgt | 720 |
| gtaggccgtg | cgcgcgcgct | tggacgaagc | ctgccccggc | gggctcttgt | cgccagcgca | 780 |
| gctttcgcct | gcgaggacag | agagaggaag | agcggcgtca | ggggctgccg | cggccccgcc | 840 |
| cagcccctga | cccagcccgg | cccctccttc | caccaggccc | caa | | 883 |

<210> SEQ ID NO 3
<211> LENGTH: 2126
<212> TYPE: DNA
<213> ORGANISM: Homo sapiens
<220> FEATURE:
<221> NAME/KEY: misc_feature
<223> OTHER INFORMATION: sequence of STAR3

<400> SEQUENCE: 3

| | | | | | | |
|---|---|---|---|---|---|---|
| atctcgagta | ctgaaatagg | agtaaatctg | aagagcaaat | aagatgagcc | agaaaaccat | 60 |
| gaaaagaaca | gggactacca | gttgattcca | caaggacatt | cccaaggtga | gaaggccata | 120 |
| tacctccact | acctgaacca | attctctgta | tgcagattta | gcaaggttat | aaggtagcaa | 180 |
| aagattagac | ccaagaaaat | agagaacttc | caatccagta | aaaatcatag | caaatttatt | 240 |
| gatgataaca | attgtctcca | aaggaacaag | gcagagtcgt | gctagcagag | gaagcacgtg | 300 |
| agctgaaaac | agccaaatct | gctttgtttt | catgacacag | gagcataaag | tacacaccac | 360 |
| caactgaccct | attaaggctg | tggtaaaccg | attcatagag | agaggttcta | aatacattgg | 420 |
| tccctcacag | gcaaactgca | gttcgctccg | aacgtagtcc | ctggaaattt | gatgtccagt | 480 |
| atagaaaagc | agagcagtca | aaaaatatag | ataaagctga | accagatgtt | gcctgggcaa | 540 |
| tgttagcagc | accacactta | agatataacc | tcaggctgtg | gactccctcc | ctggggagcg | 600 |
| gtgctgccgg | cggcgggcgg | gctccgcaac | tccccggctc | tctcgcccgc | cctcccgttc | 660 |
| tcctcgggcg | gcggcggggg | ccgggactgc | gccgctcaca | gcggcggctc | ttctgcgccc | 720 |
| ggcctcggag | gcagtggcgg | tggcggccat | ggcctcctgc | gttcgccgat | gtcagcattt | 780 |
| cgaactgagg | gtcatctcct | tgggactggt | tagacagtgg | gtgcagccca | cggagggcga | 840 |
| gttgaagcag | ggtggggtgt | cacctccccc | aggaagtcca | gtgggtcagg | gaactccctc | 900 |
| ccctagccaa | gggaggccgt | gagggactgt | gcccggtgag | agactgtgcc | ctgaggaaag | 960 |
| gtgcactctg | gcccagatac | tacactttc | ccacggtctt | caaaaccgc | agaccaggag | 1020 |

```
attccctcgg gttcctacac caccaggacc ctgggtttca accacaaaac cgggccattt      1080
gggcagacac ccagctagct gcaagagttg ttttttttt tatactcctg tggcacctgg      1140
aacgccagcg agagagcacc tttcactccc ctggaaaggg ggctgaaggc agggacctt      1200 agctgcgggc tagggggttt ggggttgagt ggggagggg agaggaaaa ggcctcgtca        1260 ttggcgtcgt ctgcagccaa taaggctacg ctcctctgct gcgagtagac ccaatccttt     1320
cctagaggtg gaggggcgg gtaggtggaa gtagaggtgg cgcggtatct aggagagaga      1380
aaaagggctg gaccaatagg tgcccggaag aggcggaccc agcggtctgt tgattggtat     1440
tggcagtgga ccctccccg gggtggtgcc ggagggggg atgatgggtc gaggggtgtg       1500
tttatgtgga agcgagatga ccggcaggaa cctgccccaa tgggctgcag agtggttagt    1560
gagtgggtga cagacagacc cgtaggccaa cgggtggcct taagtgtctt tggtctcctc     1620
caatggagca gcggcgggc gggaccgcga ctcgggttta atgagactcc attgggctgt    1680
aatcagtgtc atgtcggatt catgtcaacg acaacaacag ggggacacaa aatggcggcg    1740
gcttagtcct accctggcg gcggcggcag cggtggcgga ggcgacggca ctcctccagg    1800
cggcagccgc agtttctcag gcagcggcag cgccccggc aggcgcggtg gcggtggcgc    1860
gcagccaggt ctgtcaccca ccccgcgcgt tcccagggg aggagactgg gcgggagggg    1920
ggaacagacg gggggggatt cagggcttg cgacgcccct cccacaggcc tctgcgcgag     1980
ggtcaccgcg gggccgctcg gggtcaggct gccctgagc gtgacggtag ggggcggggg     2040 aaagggagg agggacaggc cccgccctc ggcagggcct ctagggcaag ggggcgggc        2100 tcgaggagcg gagggggcg gggcgg                                           2126
```

<210> SEQ ID NO 4
<211> LENGTH: 1625
<212> TYPE: DNA
<213> ORGANISM: Homo sapiens
<220> FEATURE:
<221> NAME/KEY: misc_feature
<223> OTHER INFORMATION: sequence of STAR4

<400> SEQUENCE: 4

```
gatctgagtc atgttttaag gggaggattc ttttggctgc tgagttgaga ttaggttgag       60
ggtagtgaag gtaaaggcag tgagaccacg tagggtcat tgcagtaatc caggctggag      120
atgatggtgg ttcagttgga atagcagtgc atgtgctgta acaacctcag ctgggaagca    180
gtatatgtgg cgttatgacc tcagctggaa cagcaatgca tgtggtggtg taatgacccc    240
agctgggtag ggtgcatgtg gtgtaacgac ctcagctggg tagcagtgtg tgtgatgtaa    300
caacctcagc tgggtagcag tgtacttgat aaaatgttgg catactctag atttgttatg    360
agggtagtgc cattaaattt ctccacaaat tggttgtcac gtatgagtga aaagaggaag    420
tgatggaaga cttcagtgct tttggcctga ataaatagaa gacgtcattt ccagttaatg    480
gagacaggga agactaaagg tagggtggga ttcagtagag caggtgttca gttttgaata    540
tgatgaactc tgagagagga aaaacttttt ctacctctta gttttttgtga ctggacttaa    600 gaattaaagt gacataagac agagtaacaa gacaaaaata tgcgaggtta tttaatatt     660 ttacttgcag agggaatct tcaaagaaa aatgaagacc caagaagcc attagggtca        720 aaagctcata tgcctttta agtagaaaat gataaatttt aacaatgtga aagacaaag      780 gtgtttgagc tgagggcaat aaattgtggg acagtgatta agaaatatat ggggaaatg     840 aaatgataag ttatttagt agatttattc ttcatatcta ttttggcttc aacttccagt       900
```

```
ctctagtgat aagaatgttc ttctcttcct ggtacagaga gagcaccttt ctcatgggaa    960
attttatgac cttgctgtaa gtagaaaggg gaagatcgat ctcctgtttc ccagcatcag   1020
gatgcaaaca tttccctcca ttccagttct caaccccatg gctgggcctc atggcattcc   1080
agcatcgcta tgagtgcacc tttcctgcag gctgcctcgg gtagctggtg cactgctagg   1140
tcagtctatg tgaccaggag ctgggcctct gggcaatgcc agttggcagc ccccatccct   1200
ccactgctgg gggcctccta tccagaaggg cttggtgtgc agaacgatgg tgcaccatca   1260
tcattcccca cttgccatct ttcagggac agccagctgc tttgggcgcg gcaaaaaaca   1320
cccaactcac tcctcttcag gggcctctgg tctgatgcca ccacaggaca tccttgagtg   1380
ctgggcagtc tgaggacagg gaaggagtga tgaccacaaa acaggaatgg cagcagcagt   1440
gacaggagga agtcaaaggc ttgtgtgtcc tggccctgct gagggctggc gagggccctg   1500
ggatggcgct cagtgcctgg tcggctgcaa gaggccagcc ctctgcccat gaggggagct   1560
ggcagtgacc aagctgcact gccctggtgg tgcatttcct gccccactct ttccttctaa   1620
gatcc                                                               1625

<210> SEQ ID NO 5
<211> LENGTH: 1571
<212> TYPE: DNA
<213> ORGANISM: Homo sapiens
<220> FEATURE:
<221> NAME/KEY: misc_feature
<223> OTHER INFORMATION: sequence of STAR5

<400> SEQUENCE: 5
cacctgattt aaatgatctg tctggtgagc tcactgggtc tttactcgca tgctgggtcc     60
acagctccac tgtcctgcag ggtccgtgag tgtgggcccc ttatctattt catcatcata    120
accctgcgtg tcctcaactc ctggcacata ttgggtggcc ccatccacac acggttgttg    180
agtgaatcca tgagatgaca aaggctatga tgtagactat atcatgagcc agaaccaggc    240
tttcctacct ccagacaatc aagggccttg atttgggatt gagggagaaa ggagtagaag    300
ccaggaagga gaagagattg aggtttacca agggtgcaaa gtcctggccc ctgactgtag    360
gctgaaaact atagaaatga tagaacaatt ttgcaatgaa atgcagaaga ccctgcatca    420
actttaggtg ggacttcggg tattttatg gccacagaac atcctcccat ttacctgcat    480
ggcccagaca cagacttcaa aacagttgag gccagcaggc tccaggtaag tggtaggatt    540
ccagaatgcc ctcagagtgt tgtgggaggc agcaggcgat tttcctggac ttctgagttt    600
atgagaaccc caaaccccaa ttggcattaa cattgaggtc tcaatgtatc atggcaggaa    660
gcttccgagt ggtgaaaagg aaagtgaaca tcaaagctcg gaagacaaga gggtggagtg    720
atggcaacca agagcaagac ccttccctct cctgtgatgg ggtggctcta tgtgaagccc    780
ccaaactgga cacaggtctg gcagaatgag gaacccactg agatttagcg ccaacatcca    840
gcataaaagg gagactgaca tagaatttga gttagttaaa aataaggcac aatgcttttc    900
atgtattcct gagttttgtg gactggtgtt caatttgcag cattcttagt tgattaaatc    960
tgagatgaag aaagagtgtc caacactttc accttggaaa gctctggaaa agcaaaaggg   1020
agagacaatt agcttcatcc attaactcac ttagtcatta tgcattcatt catgtaacta   1080
ccaaacacgt actgagtgcc taacactcct gagacactga aagtttctt gggaatacaa   1140 agatgaataa aaaccacgcc aggcaggagt tggaggaagg ttctgatgc caccacgctc   1200 tacctcctgg ctggacacca ggcaatgttg gtaaccttct gcctccaatt tctgcaaata   1260
```

```
cataattaat aaacacaagg ttatcttcta aacagttctt aaaatgagtc aactttgttt    1320
aaacttgttc tttttagaga aaaatgtatt tttgaaagag ttggttagtg ctaggggaaa    1380
tgtctgggca cagctcagtc tggtgtgaga gcaggaagca gctctgtgtg tctggggtgg    1440
gtacgtatgt aggacctgtg ggagaccagg ttggggaaag gcccctcctc atcaagggct    1500
cctttgcttt ggtttgcttt ggcgtgggag gtgctgtgcc acaagggaat acgggaaata    1560
agatctctgc t                                                        1571

<210> SEQ ID NO 6
<211> LENGTH: 1173
<212> TYPE: DNA
<213> ORGANISM: Homo sapiens
<220> FEATURE:
<221> NAME/KEY: misc_feature
<223> OTHER INFORMATION: sequence of STAR6

<400> SEQUENCE: 6
tgacccacca cagacatccc ctctggcctc ctgagtggtt tcttcagcac agcttccaga      60
gccaaattaa acgttcactc tatgtctata gacaaaaagg ttttgactaa aactctgtgt     120
tttagagagg gagttaaatg ctgttaactt tttaggggtg ggcgagaggg atgacaaata     180
acaacttgtc tgaatgtttt acatttctcc ccactgcctc aagaaggttc acaacgaggt     240
catccatgat aaggagtaag acctcccagc cggactgtcc ctcggccccc agaggacact     300
ccacagagat atgctaactg acttggagac ctggctcaca ctccagagaa aagcatggag     360
cacgagcgca cagagcaggg ccaaggtccc aggacagaa tgtctaggag ggagattggg      420
gtgagggtaa tctgatgcaa ttactgtggc agctcaacat tcaagggagg gggaagaaag     480
aaacagtccc tgtcaagtaa gttgtgcagc agagatggta agctccaaaa tttgaaactt     540
tggctgctgg aaagttttag ggggcagaga taagaagaca taagagactt tgagggttta     600
ctacacacta gacgctctat gcatttattt atttattatc tcttatttat tactttgtat     660
aactcttata ataatcttat gaaaacggaa accctcatat acccatttta cagatgagaa     720
aagtgacaat tttgagagca tagctaagaa tagctagtaa gtaaaggagc tgggacctaa     780
accaaaccct atctcaccag agtacacact cttttttttt ttccagtgta attttttta     840 attttttattt tactttaagt tctgggatac atgtgcagaa ggtatggttt gttacatagg     900
tatatgtgtg ccatagtgga ttgctgcacc tatcaacccg tcatctaggt ttaagcccca     960
catgcattag ctatttgtcc tgatgctctc cctccctcc ccacaccaga caggccttgg      1020
tgtgtgatgt tcccctccct gtgtccatgt gttctcactg ttcagctccc acttatgagt     1080
gagaacgtgt ggtatttggt tttctgttcc tgtgttagtt tgctgaggat gatggcttcc    1140
agcttcatcc atgtccctgc aaaggacacg atc                                 1173

<210> SEQ ID NO 7
<211> LENGTH: 2101
<212> TYPE: DNA
<213> ORGANISM: Homo sapiens
<220> FEATURE:
<221> NAME/KEY: misc_feature
<223> OTHER INFORMATION: sequence of STAR7

<400> SEQUENCE: 7
aggtgggtgg atcacccgag gtcaggagtt caagaccagc ctggccaaca tggtaaaacc      60
tcgtctctac taaaaaatac gaaaaattag ctggttgtgg tggtgcgtgc ttgtaatccc     120
```

```
agctactcgg gaggctgagg caggagaatc acttgaatct gggaggcaga ggttgcagtg      180
agctgagata gtgccattgc actccagcct gggcaacaga cggagactct gtctccaaaa      240
aaaaaaaaaa aaatcttaga ggacaagaat ggctctctca aacttttgaa gaagaataa       300 ataaattatg cagttctaga agaagtaatg gggatatagg tgcagctcat gatgaggaag      360
acttagctta actttcataa tgcatctgtc tggcctaaga cgtggtgagc ttttttatgtc     420 tgaaaacatt ccaatataga atgataataa taatcacttc tgaccccct ttttttcct        480 ctccctagac tgtgaagcag aaaccccata tttttcttag ggaagtggct acgcactttg      540
tatttatatt aacaactacc ttatcaggaa attcatattg ttgcccttttt atggatgggg     600 aaactggaca agtgacagag caaaatccaa acacagctgg ggatttccct cttttagatg      660
atgattttaa aagaatgctg ccagagagat tcttgcagtg ttggaggaca tatatgacct      720
ttaagatatt ttccagctca gagatgctat gaatgtatcc tgagtgcatg gatggacctc      780
agttttgcag attctgtagc ttatacaatt tggtggtttt ctttagaaga aaataacaca      840
tttataaata ttaaaatagg cccaagacct tacaagggca ttcatacaaa tgagaggctc      900
tgaagtttga gtttgttcac tttctagtta attatctcct gcctgtttgt cataaatgcg      960
tttagtaggg agctgctaat gacaggttcc tccaacagag tgtggaagaa ggagatgaca     1020
gctggcttcc cctctgggac agcctcagag ctagtgggga aactatgtta gcagagtgat     1080
gcagtgacca agaaaatagc actaggagaa agctggtcca tgagcagctg gtgagaaaag     1140
gggtggtaat catgtatgcc ctttcctgtt ttattttta ttgggtttcc ttttgcctct      1200
caattccttc tgacaataca aaatgttggt tggaacatgg agcacctgga agtctggttc     1260
attttctctc agtctcttga tgttctctcg ggttcactgc ctattgttct cagttctaca     1320
cttgagcaat ctcctcaata gctaaagctt ccacaatgca gattttgtga tgacaaattc     1380
agcatcaccc agcagaactt aggttttttt ctgtcctccg tttcctgacc ttttcttct      1440 gagtgcttta tgtcacctcg tgaaccatcc tttccttagt catctaccta gcagtcctga     1500
ttcttttgac ttgtctccct acaccacaat aaatcactaa ttactatgga ttcaatccct     1560
aaaatttgca caaacttgca aatagattac ggggttgaaac ttagagattt caaacttgag    1620
aaaaaagttt aaatcaagaa aaatgacctt taccttgaga gtagaggcaa tgtcatttcc     1680
aggaataatt ataataatat tgtgtttaat atttgtatgt aacatttgaa taccttcaat     1740
gttcttattt gtgttatttt aatctcttga tgttactaac tcatttggta gggaagaaaa     1800
catgctaaaa taggcatgag tgtcttatta aatgtgacaa gtgaatagat ggcagaaggt     1860
ggattcatat tcagttttcc atcaccctgg aaatcatgcg gagatgattt ctgcttgcaa     1920
ataaaactaa cccaatgagg ggaacagctg ttcttaggtg aaaacaaaac aaacacgcca     1980
aaaaccttta ttctctttat tatgaatcaa attttcctc tcagataatt gttttattta      2040
tttattttta ttattattgt tattatgtcc agtctcactc tgtcgcctaa gctggcatga     2100
t                                                                    2101
```

<210> SEQ ID NO 8
<211> LENGTH: 1821
<212> TYPE: DNA
<213> ORGANISM: Homo sapiens
<220> FEATURE:
<221> NAME/KEY: misc_feature
<223> OTHER INFORMATION: sequence of STAR8

<400> SEQUENCE: 8

| | |
|---|---:|
| gagatcacct cgaagagagt ctaacgtccg taggaacgct ctcgggttca caaggattga | 60 |
| ccgaacccca ggatacgtcg ctctccatct gaggcttgct ccaaatggcc ctccactatt | 120 |
| ccaggcacgt gggtgtctcc cctaactctc cctgctctcc tgagcccatg ctgcctatca | 180 |
| cccatcggtg caggtccttt ctgaagagct cgggtggatt ctctccatcc cacttccttt | 240 |
| cccaagaaag aagccaccgt tccaagacac ccaatgggac attccccttc cacctccttc | 300 |
| tccaaagttg cccaggtgtt catcacaggt tagggagaga agcccccagg tttcagttac | 360 |
| aaggcatagg acgctggcat gaacacacac acacacacac acacacacac acacacacac | 420 |
| acacgactcg aagaggtagc cacaagggtc attaaacact tgacgactgt tttccaaaaa | 480 |
| cgtggatgca gttcatccac gccaaagcca agggtgcaaa gcaaacacgg aatggtggag | 540 |
| agattccaga ggctcaccaa accctctcag gaatattttc ctgaccctgg ggcagaggt | 600 |
| tggaaacatt gaggacattt cttgggacac acggagaagc tgaccgacca ggcattttcc | 660 |
| tttccactgc aaatgaccta tggcgggggc atttcacttt cccctgcaaa tcacctatgg | 720 |
| cgaggtacct ccccaagccc caccccac ttccgcgaat cggcatggct cggcctctat | 780 |
| ccgggtgtca ctccaggtag gcttctcaac gctctcggct caaagaagga caatcacagg | 840 |
| tccaagccca aagcccacac ctcttccttt tgttatacc acagaagtta gagaaaacgc | 900 |
| cacactttga dacaaattaa gagtccttta tttaagccgg cggccaaaga gatggctaac | 960 |
| gctcaaaatt ctctgggccc cgaggaaggg gcttgactaa cttctatacc ttggtttagg | 1020 |
| aaggggaggg gaactcaaat gcggtaattc tacagaagta aaaacatgca ggaatcaaaa | 1080 |
| gaagcaaatg gttatagaga gataaacagt tttaaaaggc aaatggttac aaaaggcaac | 1140 |
| ggtaccaggt gcgggctct aaatccttca tgacacttag atataggtgc tatgctggac | 1200 |
| acgaactcaa ggctttatgt tgttatctct tcgagaaaaa tcctgggaac ttcatgcact | 1260 |
| gtttgtgcca gtatcttatc agttgattgg gctcccttga aatgctgagt atctgcttac | 1320 |
| acaggtcaac tccttgcgga aggggttgg gtaaggagcc cttcgtgtct cgtaaattaa | 1380 |
| ggggtcgatt ggagtttgtc cagcattccc agctacagag agccttattt acatgagaag | 1440 |
| caaggctagt tgattaaaga gaccaacagg gaagattcaa agtagcgact tagagtaaaa | 1500 |
| acaaggttag gcatttcact ttcccagaga acgcgcaaac attcaatggg agagaggtcc | 1560 |
| cgagtcgtca aagtcccaga tgtggcgagc cccgggagg aaaaaccgtg tcttccttag | 1620 |
| gatgcccgga acaagagcta ggcttccgga gctaggcagc catctatgtc cgtgagccgg | 1680 |
| cgggagggag accgccggga ggcgaagtgg ggcgggcca tccttctttc tgctctgctg | 1740 |
| ctgccgggga gctcctggct ggcgtccaag cggcaggagg ccgccgtcct gcagggcgcc | 1800 |
| gtagagtttg cggtgcagag t | 1821 |

<210> SEQ ID NO 9
<211> LENGTH: 1929
<212> TYPE: DNA
<213> ORGANISM: Homo sapiens
<220> FEATURE:
<221> NAME/KEY: misc_feature
<223> OTHER INFORMATION: sequence of STAR9

<400> SEQUENCE: 9

| | |
|---|---:|
| cacttcctgg gagtggagca gaggctctgc gtggagcatc catgtgcagt actcttaggt | 60 |
| acggaaggga ttgggctaaa ccatggatgg gagctgggaa gggaagggac caacttcagg | 120 |
| ccccactggg acactggagc tgccaccctt tagagccctc ctaaccctac accagaggct | 180 |

```
gaggggggacc tcagacatca cacacatgct ttcccatgtt ttcagaaatc tggaaacgta    240
gaacttcagg ggtgagagtg cctagatatt gaatacaagg ctagattggg cttctgtaat    300
atcccaaagg accctccagc tttttcacca gcacctaatg cccatcagat accaaagaca    360
cagcttagga gaggttcacc ctgaagctga ggaggaggca gccggattag agttgactga    420
gcaaggatga ctgccttctc cacctgacga tttcagctgc tgcccttttc ttttcctggg    480
aatgcctgtc gccatggcct tctgtgtcca caggagagtt tgacccagat actcatggac    540
caggcaaagg tgctgttcct cccagcccag ggcccaccat gaagcatgcc tgggagcctg    600
gtaaggaccc agccactcct gggctgttga cattggcttc tcttgcccag cattgtagcc    660
acgccactgc attgtactgt gagataagtc aaggtgggct caccaggacc tgcactaaat    720
tgtgaaattc agctccaaag aactttggaa attacccatg catttaagca aaatgaatga    780
tacctgagca aacccttcca cattggcaca agttacaatc ctgtctcatc ctcttgatta    840
caaattccat ccaggcaaga gctgtatcac cctgaggtct ccccattcat gttttggtca    900
ataatattta gtttcctttt gaaaatagat ttttgtgtta ctccattatg atgggcagag    960
gccagatgct tatattctat ttaaatgact atgttttcct atctgtaact gggtttgtgt   1020
tcaggtggta aatgcttttt ttttgcagtc agaagattcc tggaaggcga ccagaaatta   1080
gctggccgct gtcagacctg aagttacttc taaagggcct ttagaaatga attctttttt   1140
atgccttctc tgaattctga aagtaggct tgacttcccc taagtgtgga gttgggagtc   1200
aactcttctg aaaagaaagt ttcagagcat tttccaaagc catggtcagc tgtgggaagg   1260
gaagacgatg gatagtacag ttgccggaaa acactgatgg aggcggatgc tccagctcag   1320
ccaaagacct ttgttctgcc caccccagaa atgcccttc ctcaatcgca gaaacgttgc    1380
cccatggctc ctgatactca gaatgcagcc tctgaccagg accatctgca tcctccagga   1440
gctcgtaaga aatgcagcat cgtgggacct gctggcacct ggtgaaccca aacctgcagg   1500
gctcctgggt gtgcttgggg cggctgcagg ggaagaggga gtcagcagcc tcctcctgac   1560
cttcccgggg gctgcttttc tgaggggcca gaatgcaccg gttgaccttg ttgcatcact   1620
ggcccatgac tggctgcttt ggtcaggtgt aaaaaggtgt ttccagaggg tctgctcctc   1680
tcactatcgg accaggtttc catggagagc tcagcctccc agcaaggata gagaacttca   1740
aatggctcaa agaactgaga ggccacacat gtgtgacctg aatagtctct gctgcaaaac   1800
aaagggtttc ttaatgtaaa acgttctctt cctcacagag gggttcccag ctgctagtgg   1860
gcatgttgca ggcatttcct gggctgcatc aggttgtcat aagccagagg atcattttg   1920 ggggctcat                                                           1929
```

<210> SEQ ID NO 10
<211> LENGTH: 1167
<212> TYPE: DNA
<213> ORGANISM: Homo sapiens
<220> FEATURE:
<221> NAME/KEY: misc_feature
<223> OTHER INFORMATION: sequence of STAR10
<220> FEATURE:
<221> NAME/KEY: misc_feature
<222> LOCATION: (452)..(452)
<223> OTHER INFORMATION: n can be a, c, g, or t
<220> FEATURE:
<221> NAME/KEY: misc_feature
<222> LOCATION: (1143)..(1143)
<223> OTHER INFORMATION: n can be a, c, g, or t

<400> SEQUENCE: 10

| | |
|---|---|
| aggtcaggag ttcaagacca gcctggccaa catggtgaaa ccctgtccct acaaaaaata | 60 |
| caaaaattag ccgggcgtgg tgggggcgc ctataatccc agctactcag gatgctgaga | 120 |
| caggagaatt gtttgaaccc gggaggtgga ggttgcagtg aactgagatc gcgccactgc | 180 |
| actccagcct ggtgacagag agagactccg tctcaacaac agacaaacaa acaaacaaac | 240 |
| aacaacaaaa atgtttactg acagctttat tgagataaaa ttcacatgcc ataaaggtca | 300 |
| ccttctacag tatacaattc agtggattta gtatgttcac aaagttgtac gttgttcacc | 360 |
| atctactcca gaacatttac atcaccccta aaagaagctc tttagcagtc acttctcatt | 420 |
| ctccccagcc cctgccaacc acgaatctac tntctgtctc tattctgaat atttcatata | 480 |
| aaggagtcct atcatatggg ccttttacgt ctaccttctt tcacttagca tcatgttttt | 540 |
| aagattcatc cacagtgtag cacgtgtcag ttaattcatt tcatcttatg ctggataat | 600 |
| gctctattgt atgcatatcc ctcactttgc ttatccattc atcaactgat tgacatttgg | 660 |
| gttatttcta cttttttgact attatgagta atgctgctat gaacattcct gtaccaatcg | 720 |
| ttacgtggac atatgctttc aattctcctg agtatgtaac tagggttgga gttgctgggt | 780 |
| catatgttaa ctcagtgttt catttttttg aagaactacc aaatggtttt ccaaagtgga | 840 |
| tgcaacactt tacattccca ccagcaagat atgaaggttc caatgtctct acattttgc | 900 |
| caacacttgt gattttcttt tatttattta tttatttatt tattttgag atggagtctc | 960 |
| actctgtcac ccaggctgga gtgcagtggc acaatttcag ctcactgcaa tctccacctc | 1020 |
| tcgggctcaa gcgatactcc tgcctcaacc tcccgagtaa ctgggattac aggcgcccac | 1080 |
| caccacacca agctaatttt ttgtattttt agtagagacg gggtttcatc atgtcggcca | 1140 |
| ggntgtactc gaactctgac ctcaagt | 1167 |

<210> SEQ ID NO 11
<211> LENGTH: 1377
<212> TYPE: DNA
<213> ORGANISM: Homo sapiens
<220> FEATURE:
<221> NAME/KEY: misc_feature
<223> OTHER INFORMATION: sequence of STAR11

<400> SEQUENCE: 11

| | |
|---|---|
| aggatcactt gagcccagga gttcaagacc agcctgggca acatagcgag aacatgtctc | 60 |
| aaaaaggaaa aaaatggggg aaaaaaccct cccagggaca gatatccaca gccagtcttg | 120 |
| ataagctcca tcattttaaa gtgcaaggcg gtgcctccca tgtggatgat tatttaatcc | 180 |
| tcttgtactt tgtttagtcc tttgtggaaa tgcccatctt ataaattaat agaattctag | 240 |
| aatctaatta aaatggttca actctacatt ttactttagg ataatatcag gaccatcaca | 300 |
| gaatgtctga gatgtggatt taccctatct gtagctcact tcttcaacca ttcttttagc | 360 |
| aaggctagtt atcttcagtg caaccccctt gctgccctct actatctcct ccctcagatg | 420 |
| gactactctg attaagcttg agctagaata agcatgttat cccgggattt catatggaat | 480 |
| attttataca tgagtgagcc attatgagtt gtttgaaaat ttattatgtt gagggagggt | 540 |
| aaccgctgta acaaccatca ccaaatctaa tcgactgaat acatttgacg tttatttctt | 600 |
| gttcacctga cagttcagtg ttacctaaat ttacatgaag acccagaggc ccacgctcct | 660 |
| tcatttggg ctccaccgac ctccaaggtt tcagggccct ctgccccgcc ttctgcaccc | 720 |
| acaggggaag agagtggagg atgcacacgc ccaggcctgg aagtgacgca tgtggcttcc | 780 |
| ccgtccacag acttcaccca cagtccattg gccttcttaa gtcatggact cctgctgagc | 840 |

| | |
|---|---|
| tgccagggtg catgggaaat ccatgtgact gtgtgccctg gaggaagggg agcgtttcgg | 900 |
| tgagcacaca ggagtctttg ccactagacg ctgatgagga ttccccacag gcgatgaagc | 960 |
| atggagactc atcttgtaac aaacagatga gttgttgaca tctcttaagt ttactttgtg | 1020 |
| tgcagttttt attcagatag gaaaggctgt taaaatctta acacctaact ggaagaaggg | 1080 |
| ttttagagaa gtgtggtttt cagtaagcca gttctttcca caatccaaga aacgaaataa | 1140 |
| atttccagca tggagcagtt ggcaggtaag gttttgttg tggtctcgcc caggcttgag | 1200 |
| tgtaaccggt gtggtcatag ctcactacat tctcaaactc ctggccttaa gtcatcctcc | 1260 |
| tgcctcagcc tcccaaaggc aagtaaggtt aagaataggg gaaaggtgaa gtttcacagc | 1320 |
| ttttctagaa ttcttttat tcaagggact ctcagatcat caaacccacc cagaatc | 1377 |

<210> SEQ ID NO 12
<211> LENGTH: 1051
<212> TYPE: DNA
<213> ORGANISM: Homo sapiens
<220> FEATURE:
<221> NAME/KEY: misc_feature
<223> OTHER INFORMATION: sequence of STAR12

<400> SEQUENCE: 12

| | |
|---|---|
| atcctgcttc tgggaagaga gtggcctccc ttgtgcaggt gactttggca ggaccagcag | 60 |
| aaacccaggt ttcctgtcag gaggaagtgc tcagcttatc tctgtgaagg gtcgtgataa | 120 |
| ggcacgagga ggcaggggct tgccaggatg ttgcctttct gtgccatatg ggacatctca | 180 |
| gcttacgttg ttaagaaata tttggcaaga agatgcacac agaatttctg taacgaatag | 240 |
| gatggagttt taagggttac tacgaaaaaa agaaaactac tggagaagag ggaagccaaa | 300 |
| caccaccaag tttgaaatcg attttattgg acgaatgtct cactttaaat ttaaatggag | 360 |
| tccaacttcc ttttctcacc cagacgtcga gaaggtggca ttcaaaatgt ttacacttgt | 420 |
| ttcatctgcc tttttgctaa gtcctggtcc cctacctcct ttccctcact tcacatttgt | 480 |
| cgtttcatcg cacacatatg ctcatctta tatttacata tatataattt ttatatatgg | 540 |
| cttgtgaaat atgccagacg agggatgaaa tagtcctgaa aacagctgga aaattatgca | 600 |
| acagtgggga gattgggcac atgtacattc tgtactgcaa agttgcacaa cagaccaagt | 660 |
| ttgttataag tgaggctggg tggtttttat tttttctcta ggacaacagc ttgcctggtg | 720 |
| gagtaggcct cctgcagaag gcatttttctt aggagcctca acttccccaa gaagaggaga | 780 |
| gggcgagact ggagttgtgc tggcagcaca gagacaaggg ggcacggcag gactgcagcc | 840 |
| tgcagagggg ctggagaagc ggaggctggc acccagtggc cagcgaggcc caggtccaag | 900 |
| tccagcgagg tcgaggtcta gagtacagca aggccaaggt ccaaggtcag tgagtctaag | 960 |
| gtccatggtc agtgaggctg agacccaggg tccaatgagg ccaaggtcca gagtccagta | 1020 |
| aggccgagat ccagggtcca gggaggtcaa g | 1051 |

<210> SEQ ID NO 13
<211> LENGTH: 1291
<212> TYPE: DNA
<213> ORGANISM: Homo sapiens
<220> FEATURE:
<221> NAME/KEY: misc_feature
<223> OTHER INFORMATION: sequence of STAR13

<400> SEQUENCE: 13

| | |
|---|---|
| agccactgag gtcctaactg cagccaaggg gccgttctgc acatgtcgct caccctctgt | 60 |
| gctctgttcc ccacagagca aacgcacatg gcaacgttgg tccgctcagc cactggttct | 120 |

```
gtggtggaac ggtggatgtc tgcactgtga catcagctga gtaagtaaca acgactgagg      180
atgccgctga cccagggctg gggaagggga ctcccagctc agacaggctt ggctgtggtt      240
tgctttggga ggagagtgaa catcacaggg aatggctcat gtcagcccca ggagggtggg      300
ctggcccctg gtcccgggc tccttctggc cctgcaggcg atagagagcc tcaacctgct      360
gccgcttctc cttggcccgg gtgatggccg tctggaagag cctgcagtag aggtgcacag      420
ccagcggaga gtcgtcattg ccgggtacag ggtaggtgat gaggcagggg ttgcagttgg      480
tgtccacgat gcccactgtg gggatgttca tcttggctgc gtctctcacg ccacgtgtg      540 gctcaaagat gttgttgagc gtgtgcagga agatgatgag gtccggcagg cggaccgtgg      600
ggccaaagag gaggcgcgcg ttggtcagca tgccgcccct gaagtagcga gtgtgggcgt      660
actcgccaca gtcacgggcc atgttctcaa tcaggtacga gaactgccgg ttgcggctta      720
taaacaagat gatgcccttg cgtaggcca tgtgggcggt gaagttcaag gccagctgga      780
ggtgcgtggc tgtctgttcc agtcgatga tgtcgtggtc caggcggctc ccaaagatgt      840
acggctccat aaacctgcca gagaccccac caaggcaagg gggatgagag ttcacggggc      900
catctccact ggctccttgc aggaacacag acgcccacca gggactcccg ggctcctctg      960
tgggggcact atgggctggg aagcacaatt gcaacgctc ccgtgtgca tggacagcag     1020 tgcagaccca tccaggccac ccctctgcat gcctcgtctc gtggcttaac ccctcctacc     1080
ctctacctct tcccgaagga atcctaatag aactgacccc atatggatgt gtggacatcc     1140
aacatgacgc caaaaggaca ttctgccccg tgcagctcac agggcagccg cctccgtcac     1200
tgtcctcttc ccgaggcttt gcggatgagg cccctctggg gttggactta gcggggtgct     1260
ctgggccaaa agcattaagg gatcagggca g                                   1291
```

<210> SEQ ID NO 14
<211> LENGTH: 711
<212> TYPE: DNA
<213> ORGANISM: Homo sapiens
<220> FEATURE:
<221> NAME/KEY: misc_feature
<223> OTHER INFORMATION: sequence of STAR14

<400> SEQUENCE: 14

```
ccctggacca gggtccgtgg tcttggtggg cactggcttc ttcttgctgg gtgttttcct       60
gtgggtctct ggcaaggcac ttttttgtggc gctgcttgtg ctgtgtgcgg gaggggcagg      120 tgctcttcc tcttggagct ggaccctctg gggcgggtcc ccgtcggcct ccttgtgtgt      180
tttctgcacc tggtacagct ggatggcctc ctcaatgccg tcgtcgctgc tggagtcgga      240
cgcctcgggc gcctgtacgg cgctcgtgac tcgctttccc ctccttgcgg tgctggcgtt      300 cctttaatc ccacttttat tctgtactgc ttctgaaggg cggtgggggt tgctggcttt      360
gtgctgccct cctctcctg cgtggtcgtg gtcgtgacct tggacctgag gcttctgggc      420
tgcacgtttg tctttgctaa ccgggggagg tctgcagaag gcgaactcct tctggacgcc      480
catcaggccc tgccggtgca ccacctttgt agccggctct tggtgggatt tcgagagtga      540
cttcgccgaa ttttcatgtg tgtctggttt cttctccact gacccatcac attttttgggt     600 ctcatgctgt cttttctcat tcagaaactg ttctatttct gccctgatgc tctgctcaaa      660
ggagtctgct ctgctcatgc tgactgggga ggcagagccc tggtccttgc t               711
```

<210> SEQ ID NO 15
<211> LENGTH: 1876

<212> TYPE: DNA
<213> ORGANISM: Homo sapiens
<220> FEATURE:
<221> NAME/KEY: misc_feature
<223> OTHER INFORMATION: sequence of STAR15

<400> SEQUENCE: 15

| | | | | | |
|---|---|---|---|---|---|
| gagtccaaga | tcaaggtgcc | agcatcttgt | gagggccttc | ttgttacgtc | actccctagc | 60 |
| gaaagggcaa | agagagggtg | agcaagagaa | aggggggctg | aactcgtcct | tgtagaagag | 120 |
| gcccattccc | gagacaatgg | cattcatcca | ttcactccac | cctcatggcc | tcaccacctc | 180 |
| tcatgaggct | ccacctccca | gccctggttt | gttggggatt | aaatttccaa | cacatgcctt | 240 |
| ttgggggaca | tgttaaaatt | atagcacccc | aaatgttaca | ctatcttttg | atgagcggta | 300 |
| gttctgattt | taagtctagc | tggcctactt | tttcttgcac | gtgggatgct | ttctgcctgt | 360 |
| tccagggcag | gcagctcttc | tctgtccctc | tgctggcccc | acctcatcct | ctgttgtcct | 420 |
| cttccctcct | tctgtgccct | ggggtcctgg | tgggggtgtg | actgtcaact | gcgttgggct | 480 |
| aacttttttc | cctgctggtg | gcccgtaatg | aaagaaagct | tcttgctccc | aagttcctta | 540 |
| aatccaagct | catagacaac | gcggtctcac | agcaggcctg | gggccagcct | cacgtgagcc | 600 |
| ccttccctgg | tgtagtcact | ggcatggggg | aatgggattt | cctgttgccc | tactgtgtgg | 660 |
| ctgaggtggg | ggttgcttcc | tggagccagg | ccttgtggaa | gggcagtgcc | cactgcagtg | 720 |
| gatgctgggc | cctgaatctg | accccagtgt | tcattggctc | tgtgagaccc | agtgagggca | 780 |
| gggagggaag | tggagctggg | gtgagaagta | gaggccctgc | agggcccacg | tgccagccac | 840 |
| caggcctcag | actaggctca | gatgacggag | agctgcacac | ctgcccaacc | caggccctgc | 900 |
| agtgcccaca | tgccagccgc | tggggcccag | acttgctcca | gagggcggag | agctttacac | 960 |
| cggcccaacc | caggccatgg | ctccaaatgc | gtgacagttt | tgctgttgct | tcttttagtc | 1020 |
| attgtcaagt | tgatgcttgt | tttgcagagg | accaaggctt | tatgaaccta | ttaccctgtg | 1080 |
| tgaagagttt | caccaggtta | tggaaatttc | tttaaaacca | taccacagtt | ttttcattat | 1140 |
| tcatgtatat | ttttaaaaat | aattactgca | ctcagtagaa | taacatgaaa | atgttgcctg | 1200 |
| ttagccctttt | tccagtttgc | cccgagaata | ctggggcac | ttgtggctgc | aatgtttatc | 1260 |
| ctgcggcagc | tttgccatga | agtatctcac | ttttattatt | attttttgcat | tgctcgagta | 1320 |
| tattgacttt | ggaaacaaaa | gacatcattc | tatttatagc | attatgtttt | tagtagtggt | 1380 |
| atttccatat | acaagataca | gtaatttttcc | gtcaatgaaa | atgtcaaatt | ctagaaaatg | 1440 |
| taacattcct | atgcgtggtg | ttaacatcgt | tctctaacag | ttgttggccg | aagattcgtt | 1500 |
| tgatgaatcc | gattttttcca | aaatagccga | ttctgatgat | tcagacgatt | ctgatgttct | 1560 |
| gtttagaaat | aattccaaga | acagttttta | cattttattt | tcacattgaa | aatcagtcag | 1620 |
| atttgcttca | gcctcaaaga | gcacgtttat | gtaaaattaa | atgagtgctg | gcagccagct | 1680 |
| gcgctttgtt | tttctaaatg | ggaaaagggt | taaatttcac | tcagctttta | aatgacagcg | 1740 |
| cacagcctgt | gtcatagagg | gttggaggag | atgactttaa | ctgcctgtgg | ttaggatccc | 1800 |
| tttcccccag | gaatgtctgg | gagcccactg | ccgggtttgc | tgtccgtctc | gtttggactc | 1860 |
| agttctgcat | gtactg | | | | | 1876 |

<210> SEQ ID NO 16
<211> LENGTH: 1282
<212> TYPE: DNA
<213> ORGANISM: Homo sapiens
<220> FEATURE:
<221> NAME/KEY: misc_feature
<223> OTHER INFORMATION: sequence of STAR16

<400> SEQUENCE: 16

| | | | | | |
|---|---|---|---|---|---|
| cgcccacctc | ggctttccaa | agtgctggga | ttacaggcat | gagtcactgc | gcccatcctg | 60 |
| attccaagtc | tttagataat | aacttaactt | tttcgaccaa | ttgccaatca | ggcaatcttt | 120 |
| gaatctgcct | atgacctagg | acatccctct | ccctacaagt | tgccccgcgt | ttccagacca | 180 |
| aaccaatgta | catcttacat | gtattgattg | aagttttaca | tctccctaaa | acatataaaa | 240 |
| ccaagctata | gtctgaccac | ctcaggcacg | tgttctcagg | acctccctgg | ggctatggca | 300 |
| tgggtcctgg | tcctcagatt | tggctcagaa | taaatctctt | caaatatttt | ccagaatttt | 360 |
| actcttttca | tcaccattac | ctatcaccca | taagtcagag | ttttccacaa | ccccttcctc | 420 |
| agattcagta | atttgctaga | atggccacca | aactcaggaa | agtattttac | ttacaattac | 480 |
| caatttatta | tgaagaactc | aaatcaggaa | tagccaaatg | aagaggcat | agggaaaggt | 540 |
| atggaggaag | gggcacaaag | cttccatgcc | ctgtgtgcac | accaccctct | cagcatcttc | 600 |
| atgtgttcac | caactcagaa | gctcttcaaa | ctttgtcatt | taggggtttt | tatggcagtt | 660 |
| ccactatgta | ggcatggttg | ataaatcact | ggtcatcggt | gatagaactc | tgtctccagc | 720 |
| tcctctctct | ctcctcccca | gaagtcctga | ggtgggctg | aaagtttcac | aaggttagtt | 780 |
| gctctgacaa | ccagccccta | tcctgaagct | attgagggt | cccccaaaag | ttaccttagt | 840 |
| atggttggaa | gaggcttatt | atgaataaca | aaagatgctc | ctatttttac | cactagggag | 900 |
| catatccaag | tcttgcggga | acaaagcatg | ttactggtag | caaattcata | caggtagata | 960 |
| gcaatctcaa | ttcttgcctt | ctcagaagaa | agaatttgac | caaggggca | taaggcagag | 1020 |
| tgagggacca | agataagttt | tagagcagga | gtgaaagttt | attaaaaagt | tttaggcagg | 1080 |
| aatgaaagaa | agtaaagtac | atttggaaga | gggccaagtg | ggcgacatga | gagagtcaaa | 1140 |
| caccatgccc | tgtttgatgt | ttggcttggg | gtcttatatg | atgacatgct | tctgagggtt | 1200 |
| gcatccttct | cccctgattc | ttcccttggg | gtgggctgtc | cgcatgcaca | atggcctgcc | 1260 |
| agcagtaggg | aggggccgca | tg | | | | 1282 |

<210> SEQ ID NO 17
<211> LENGTH: 793
<212> TYPE: DNA
<213> ORGANISM: Homo sapiens
<220> FEATURE:
<221> NAME/KEY: misc_feature
<223> OTHER INFORMATION: sequence of STAR17

<400> SEQUENCE: 17

| | | | | | |
|---|---|---|---|---|---|
| atccgagggg | aggaggagaa | gaggaaggcg | agcagggcgc | cggagcccga | ggtgtctgcg | 60 |
| agaactgttt | taaatggttg | gcttgaaaat | gtcactagtg | ctaagtggct | tttcggattg | 120 |
| tcttatttat | tactttgtca | ggtttcctta | aggagagggt | gtgttggggg | tgggggagga | 180 |
| ggtggactgg | ggaaacctct | gcgtttctcc | tcctcggctg | cacagggtga | gtaggaaacg | 240 |
| cctcgctgcc | acttaacaat | ccctctatta | gtaaatctac | gcggagactc | tatgggaagc | 300 |
| cgagaaccag | tgtcttcttc | cagggcagaa | gtcacctgtt | gggaacggcc | cccgggtccc | 360 |
| cctgctgggc | tttccggctc | ttctaggcgg | cctgatttct | cctcagccct | ccacccagcg | 420 |
| tccctcaggg | acttttcaca | cctccccacc | cccatttcca | ctacagtctc | ccagggcaca | 480 |
| gcacttcatt | gacagccaca | cgagccttct | cgttctcttc | tcctctgttc | cttctctttc | 540 |
| tcttctcctc | tgttccttct | cttctctgt | cataatttcc | ttggtgcttt | cgccacctta | 600 |

```
aacaaaaaag agaaaaaaat aaaataaaaa aaacccattc tgagccaaag tatttttaaga    660 tgaatccaag aaagcgaccc acatagccct ccccacccac ggagtgcgcc aagacgcacc    720
caggctccat cacagggccg agagcagcgc cactctggtc gtacttttgg gtcaagagat    780
cttgcaaaag agg                                                        793
```

<210> SEQ ID NO 18
<211> LENGTH: 492
<212> TYPE: DNA
<213> ORGANISM: Homo sapiens
<220> FEATURE:
<221> NAME/KEY: misc_feature
<223> OTHER INFORMATION: sequence of STAR18

<400> SEQUENCE: 18

```
atcttttgc tctctaaatg tattgatggg ttgtgttttt tttcccacct gctaataaat     60
attacattgc aacattcttc cctcaacttc aaaactgctg aactgaaaca atatgcataa    120
aagaaaatcc tttgcagaag aaaaaaagct atttctccc actgattttg aatggcactt    180
gcggatgcag ttcgcaaatc ctattgccta ttccctcatg aacattgtga atgaaacct    240 ttggacagtc tgccgcattg cgcatgagac tgcctgcgca aggcaagggg atggttccca   300
aagcacccag tggtaaatcc taacttatta ttcccttaaa attccaatgt aacaacgtgg    360
gccataaaag agtttctgaa caaaacatgt catcttgtg gaaggtgtt tttcgtaatt     420 aatgatggaa tcatgctcat ttcaaaatgg aggtccacga tttgtggcca gctgatgcct    480
gcaaattatc ct                                                        492
```

<210> SEQ ID NO 19
<211> LENGTH: 1840
<212> TYPE: DNA
<213> ORGANISM: Homo sapiens
<220> FEATURE:
<221> NAME/KEY: misc_feature
<223> OTHER INFORMATION: sequence of STAR19

<400> SEQUENCE: 19

```
tcacttcctg atattttaca ttcaaggcta gctttatgca tatgcaacct gtgcagttgc     60
acagggcttt gtgttcagaa agactagctc ttggtttaat actctgttgt tgccatcttg    120
agattcatta taatataatt tttgaatttg tgttttgaac gtgatgtcca atgggacaat    180
ggaacattca cataacagag gagacaggtc aggtggcagc ctcaattcct tgccacccctt  240 ttcacataca gcattggcaa tgccccatga gcacaaaatt tgggggaacc atgatgctaa   300
gactcaaagc acatataaac atgttacctc tgtgactaaa agaagtggag gtgctgacag    360
cccccagagg ccacagtttta tgttcaaacc aaaacttgct tagggtgcag aaagaaggca   420
atggcagggt ctaagaaaca gcccatcata tccttgttta ttcatgttac gtccctgcat    480
gaactaatca cttacactga aaatattgac agaggaggaa atggaaagat agggcaaccc    540
atagttcttt ttccttttag tctttcctta tcagtaaacc aaagatagta ttggtaaaat    600
gtgtgtgagt taattaatga gttagtttta ggcagtgttt ccactgttgg ggtaagaaca    660
aaatatatag gcttgtattg agctattaaa tgtaaattgt ggaatgtcag tgattccaag    720
tatgaattaa atatccttgt atttgcattt aaaattggca ctgaacaaca aagattaaca    780
gtaaaattaa taatgtaaaa gtttaatttt tacttagaat gacattaaat agcaaataaa    840
agcaccatga taaatcaaga gagagactgt ggaagaagg aaaacgtttt tattttagta    900
tatttaatgg gactttcttc ctgatgtttt gttttgtttt gagagagagg gatgtggggg    960
```

```
caggggaggtc tcattttgtt gcccaggctg gacttgaact cctgggctcc agctatcctg      1020
ccttagcttc ttgagtagct gggactacag gcacacacca cagtgtctga cattttctgg      1080 atttttttt  ttttttatt  tttttgtga dacaggttct ggctctgtta ctcaggttgc      1140
agtgcagtgg catgatagcg gctcactgca gcctcaacct cctcagctta agctactctc      1200
ccacttcagc ctcctgagta gccaggacta cagttgtgtg ccaccacacc tgtggctaat      1260
ttttgtagag atggggtctc tccacgttgc cgaggctggt ctccaactcc tggtctcaag      1320
cgaacctcct gacttggcct cccgaagtgc tgggattaca ggcttgagcc actgcatcca      1380
gcctgtcctc tgtgttaaac ctactccaat ttgtctttca tctctacata aacggctctt      1440
ttcaaagttc ccatagacct cactgttgct aatctaataa taaattatct gccttttctt      1500
acatggttca tcagtagcag cattagattg ggctgctcaa ttcttcttgg tatattttct      1560
tcatttggct tctggggcat cacactctct ttgagttact cattcctcat tgatagcttc      1620
ttcctagtct tctttactgg ttcttcctct tctccctgac tccttaatat tgttttctc       1680 cccaggcttt agttcttagt cctcttctgt tatctattta cacccaattc tttcagagtc      1740
tcatccagag tcatgaactt aaacctgttt ctgtgcagat aattcacatt attatatctc      1800
cagcccagac tctcccgcaa actgcagact gatcctactg                            1840

<210> SEQ ID NO 20
<211> LENGTH: 780
<212> TYPE: DNA
<213> ORGANISM: Homo sapiens
<220> FEATURE:
<221> NAME/KEY: misc_feature
<223> OTHER INFORMATION: sequence of STAR20

<400> SEQUENCE: 20
gatctcaagt tcaatatcca tgttttggca aaacattcga tgctcccaca tccttaccta        60
aagctaccag aaaggctttg ggaactgtca acagagctac agaaaagtca gtaaagacca      120
atggacccct caaacaaaaa cagccaagct tttctgccaa aaagatgact gagaagactg      180
ttaaagcaaa aaactctgtt cctgcctcag atgatggcta tccagaaata gaaaaattat      240
ttcccttcaa tcctctaggc ttcgagagtt ttgacctgcc tgaagagcac cagattgcac      300 atctccccttt gagtgaagtg cctctcatga tacttgatga ggagagagag cttgaaaagc      360
tgtttcagct gggccccccct tcacctttga agatgccctc tccaccatgg aaatccaatc      420
tgttgcagtc tcctttaagc attctgttga ccctggatgt tgaattgcca cctgtttgct      480
ctgacataga tatttaaatt tcttagtgct ttagagtttg tgtatatttc tattaataaa      540
gcattatttg tttaacagaa aaaagatat atacttaaat cctaaaataa aataaccatt      600
aaaaggaaaa acaggagtta taactaataa gggaacaaag gacataaaat gggataataa      660
tgcttaatcc aaaataaagc agaaaatgaa gaaaaatgaa atgaagaaca gataaataga      720
aaacaaatag caatatgaaa gacaaacttg accgggtgtg gtggctgatg cctgtaatcc      780

<210> SEQ ID NO 21
<211> LENGTH: 607
<212> TYPE: DNA
<213> ORGANISM: Homo sapiens
<220> FEATURE:
<221> NAME/KEY: misc_feature
<223> OTHER INFORMATION: sequence of STAR21

<400> SEQUENCE: 21
```

```
gatcaataat ttgtaatagt cagtgaatac aaaggggtat atactaaatg ctacagaaat        60
tccattcctg ggtataaatc ctagacatat ttatgcatat gtacaccaag atatatctgc       120
aagaatgttc acagcaaatc tctttgtagt agcaaaaggc caaaaggtct atcaacaaga       180
aaattaatac attgtggcac ataatggcat ccttatgcca ataaaaatgg atgaaattat       240
agttaggttc aaaaggcaag cctccagata atttatatca tataattcca tgtacaacat       300
tcaacaacaa gcaaaactaa acatatacaa atgtcaggga aaatgatgaa caaggttaga       360
aaatgattaa tataaaaata ctgcacagtg ataacattta atgagaaaaa aagaaggaag       420
ggcttaggga gggacctaca gggaactcca aagttcatgg taagtactaa atacataatc       480
aaagcactca aaatagaaaa tattttagta atgttttagc tagttaatat cttacttaaa       540
acaaggtcta ggccaggcac ggtggctcac acctgtaatc ccagcacttt gggaggctga       600
ggcgggt                                                                 607
```

<210> SEQ ID NO 22
<211> LENGTH: 1380
<212> TYPE: DNA
<213> ORGANISM: Homo sapiens
<220> FEATURE:
<221> NAME/KEY: misc_feature
<223> OTHER INFORMATION: sequence of STAR22

<400> SEQUENCE: 22

```
cccttgtgat ccacccgcct tggcctccca aagtgctggg attacaggcg tgagtcacta        60
cgcccggcca ccctccctgt atattatttc taagtatact attatgttaa aaaaagttta       120
aaaatattga tttaatgaat tcccagaaac taggatttta catgtcacgt tttcttatta       180
taaaaataaa aatcaacaat aaatatatgg taaagtaaaa aagaaaaaca aaaacaaaaa       240
gtgaaaaaaa taaacaacac tcctgtcaaa aaacaacagt tgtgataaaa cttaagtgcc       300
tgaaaattta gaaacatcct tctaaagaag ttctgaataa aataaggaat aaaataatca       360
catagttttg gtcattggtt ctgtttatgt gatggattat gtttattgat ttgtgtatgt       420
tgaacttatc tcaatagatg cagacaaggc cttgataaaa gttttttaaca cctttttcatg       480 ttgaaaactc tcaatagact aggtattgat gaaacatatc tcaaaataat agaagctatt       540
tatgataaac ccatagccaa tatcatactg agtgggcaaa agctggaagc attccctttg       600
aaaactggca caagacaagg atgccctctc tcaccactcc tattaaatgt agtattggaa       660
gttctggcca gagcaatcag gcaggagaaa gaaaaggtat taaaatagga agagaggaag       720
tcaaattgtc tctgtttgca gtaaacatga ttgtatattt agaaacccc attgtctcat       780 cctaaaaact ccttaagctg ataaacaact tcagcaaagt ctcaggatac aaaatcaatg       840
tgcaaaaatc acaagcattc ctatacaccg ataatagaca gcagagagcc aaatcatgag       900
tgaagtccca ttcacaattg cttcaaagaa aataaaatac ttaggaatac aactttcacg       960
ggacatgaag acatttttca aggacaacta aaaaccactg ctcaaggaaa tgagagagga      1020
cacaaagaaa tggaaaaaca ttccatgctc atggaagaat caatatcatg aaaatggcca      1080
tactgcccaa agtaatttat agattcaatg ctaaccccat caagccacca ttgactttct      1140
tcacagaact agaaaaaaac tatttttaaaa ctcatatgta gtcaaaaaga gtcggtatag      1200
ccaagacaat cctaagcata agaacaaaag ctggatgcat cacgctgact tcaaaccata      1260
ctacaaggct acagtaacca aaacagcatg gtactggtac caaaacagat agatagaccg      1320
atagaacaga acagaggcct cggaaataac accacacatc tacaacccctt tgatcttcaa      1380
```

<210> SEQ ID NO 23
<211> LENGTH: 1246
<212> TYPE: DNA
<213> ORGANISM: Homo sapiens
<220> FEATURE:
<221> NAME/KEY: misc_feature
<223> OTHER INFORMATION: sequence of STAR23

<400> SEQUENCE: 23

| | | | | | |
|---|---|---|---|---|---|
| atcccctcat | ccttcagggc | agctgagcag | ggcctcgagc | agctggggga | gcctcactta | 60 |
| atgctcctgg | gagggcagcc | agggagcatg | gggtctgcag | gcatggtcca | gggtcctgca | 120 |
| ggcggcacgc | accatgtgca | gccgccccca | cctgttgctc | tgcctccgcc | acctggccat | 180 |
| gggcttcagc | agccagccac | aaagtctgca | gctgctgtac | atggacaaga | agcccacaag | 240 |
| cagctagagg | accttgtgtt | ccacgtgccc | agggagcatg | gcccacagcc | caaagaccag | 300 |
| tcaggagcag | gcagggcttc | tggcaggcc | cagctctacc | tctgtcttca | cacagatggg | 360 |
| agatttctgt | tgtgattttg | agtgatgtgc | ccctttggtg | acatccaaga | tagttgctga | 420 |
| agcaccgctc | taacaatgtg | tgtgtattct | gaaaacgaga | acttctttat | tctgaaataa | 480 |
| ttgatgcaaa | ataaattagt | ttggatttga | aattctattc | atgtaggcat | gcacacaaaa | 540 |
| gtccaacatt | gcatatgaca | caaagaaaag | aaaaagcttg | cattccttaa | atacaaatat | 600 |
| ctgttaacta | tatttgcaaa | tatatttgaa | tacacttcta | ttatgttaca | tataatatta | 660 |
| tatgtatatg | tatatataat | atacatatat | atgttacata | taatatactt | ctattatgtt | 720 |
| acatataata | tttatctata | agtaaataca | taaaatataaa | gatttgagta | gctgtagaac | 780 |
| attgtcttat | gtgttatcag | ctactactac | aaaaatatct | cttccactta | tgccagtttg | 840 |
| ccatataaat | atgatcttct | cattgatggc | ccagggcaag | agtgcagtgg | gtacttattc | 900 |
| tctgtgagga | gggaggagaa | aagggaacaa | ggagaaagtc | acaaagggaa | aactctggtg | 960 |
| ttgccaaaat | gtcaagtttc | acatattccg | agacggaaaa | tgacatgtcc | cacagaagga | 1020 |
| ccctgcccag | ctaatgtgtc | acagatatct | caggaagctt | aaatgatttt | tttaaaagaa | 1080 |
| aagagatggc | attgtcactt | gtttcttgta | gctgaggctg | tgggatgatg | cagatttctg | 1140 |
| gaaggcaaag | agctcctgct | ttttccacac | cgagggactt | tcaggaatga | ggccagggtg | 1200 |
| ctgagcacta | caccaggaaa | tccctggaga | gtgttttct | tactta | | 1246 |

<210> SEQ ID NO 24
<211> LENGTH: 939
<212> TYPE: DNA
<213> ORGANISM: Homo sapiens
<220> FEATURE:
<221> NAME/KEY: misc_feature
<223> OTHER INFORMATION: sequence of STAR24

<400> SEQUENCE: 24

| | | | | | |
|---|---|---|---|---|---|
| acgaggtcac | gagttcgaga | ccagcctggc | caagatggtg | aagccctgtc | tctactaaaa | 60 |
| atacaacaag | tagccgggcg | cggtgacggg | cgcctgtaat | cccagctact | caggaggctg | 120 |
| aagcaggaga | atctctagaa | cccaggaggc | ggaggtgcag | tgagctgaga | ctgccccgct | 180 |
| gcactctagc | ctgggcaaca | cagcaagact | ctgtctcaaa | taaataaata | aataaataaa | 240 |
| taaataaata | aataaataaa | tagaaaggga | gagttggaag | tagatgaaag | agaagaaaag | 300 |
| aaatcctaga | tttcctatct | gaaggcacca | tgaagatgaa | ggccacctct | tctgggccag | 360 |
| gtcctcccgt | tgcaggtgaa | ccgagttctg | gcctccattg | gagaccaaag | gagatgactt | 420 |
| tggcctggct | cctagtgagg | aagccatgcc | tagtcctgtt | ctgtttgggc | ttgatcctgt | 480 |

```
atcacttgat tgtctctcct ggactttcca tggattccag ggatgcaact gagaagttta      540
tttttaatgc acttacttga agtaagagtt attttaaaac attttagcaa aggaaatgaa      600
ttctgacagg ttttgcactg aagacattca catgtgagga aaacaggaaa accactatgc      660
tagaaaaagc aaatgctgtt gagattgtct cacaaacaca aattgcgtgc cagcaggtag      720
gtttgagcct caggttgggc acattttacc ttaagcgcac tgttggtgga acttaaggtg      780
actgtaggac ttatatatac atacatacat ataatatata tacatattta tgtgtatata      840
cacacacaca cacacacaca cacacagggt cttgctatct tgcccagggt ggtctccaac      900
tctgggtctc aagcgatcct ctgcctcccc ttcccaaag                             939
```

<210> SEQ ID NO 25
<211> LENGTH: 1067
<212> TYPE: DNA
<213> ORGANISM: Homo sapiens
<220> FEATURE:
<221> NAME/KEY: misc_feature
<223> OTHER INFORMATION: sequence of STAR25

<400> SEQUENCE: 25

```
cagcccctct tgtgtttttc tttatttctc gtacacacac gcagttttaa gggtgatgtg       60
tgtataatta aaaggaccct tggcccatac tttcctaatt ctttagggac tgggattggg      120
tttgactgaa atatgttttg gtggggatgg acggtggac ttccattctc cctaaactgg       180
agttttggtc ggtaatcaaa actaaaagaa acctctggga gactggaaac ctgattggag      240
cactgaggaa caagggaatg aaaaggcaga ctctctgaac gtttgatgaa atggactctt      300
gtgaaaatta acagtgaata ttcactgttg cactgtacga agtctctgaa atgtaattaa      360 aagttttat tgagccccg agctttggct tgcgcgtatt tttccggtcg cggacatccc        420
accgcgcaga gcctcgcctc cccgctgccc tcagcctccg atgacttccc cgcccccgcc      480
ctgctcggtg acagacgttc tactgcttcc aatcggaggc acccttcgcg ggagcggcca      540
atcgggagct ccggcaggcg gggaggccgg gccagttaga tttggaggtt caacttcaac      600
atggccgaag caagtagcgc caatctaggc agcggctgtg aggaaaaaag gcatgagggg      660
tcgtcttcgg aatctgtgcc acccggcact accatttcga gggtgaagct cctcgacacc      720
atggtggaca ctttttcttca gaagctggtc gccgccggca ggtaaagtgg acgcagccgc      780
ggtgggagtg tttgttggca ccgaagctca atcccgcga ggtcaggacg ccgcaggct       840 ggcgcgcggt gacgtgggtc cgcgttgggg cggggcagt cggacgaggc gacccagtca      900
aatcctgagc cttaggagtc agggtattca cgcactgata acctgtagcg gaccgggata      960
gctagctact ccttcctaca ggaagccccg ttttcactaa aatttcaggt ggttgggagg     1020
aaagatagag cctttgcaaa ttagagcagg gttttttatt tttttat                   1067
```

<210> SEQ ID NO 26
<211> LENGTH: 540
<212> TYPE: DNA
<213> ORGANISM: Homo sapiens
<220> FEATURE:
<221> NAME/KEY: misc_feature
<223> OTHER INFORMATION: sequence of STAR26

<400> SEQUENCE: 26

```
ccccctgaca agcccagtg tgtgatgttc cccactctgt gtccatgcat tctcattgtt        60
caactcccat ctgtgagtga aacatgcag tgtttggttt tctgtccttg agatagtttg       120
```

| | |
|---|---|
| ctgagaatga tggttttccag cttcatccat gtccttgcaa aggaagtgaa cttatccttt | 180 |
| tttatggctt catagtattc catggcacat atgtgccaca ttttttttaat ccagtctatc | 240 |
| attgatggac atttgggttg gttccaagtc tttgctattg tgaatagcac cacaattaac | 300 |
| atatgtgtgc atgtatacat cttatatgta gcatgattta taatccttcg ggtatatacc | 360 |
| ctgtaatggg atcgctgggt caaatggtat ttctagttct agatccttga ggaatcacca | 420 |
| cactgctttc cacaatggtt gaactaattt acgctcccac cagcagtgta aaagcattcc | 480 |
| tatttctcca cgtcctctcc agtatctgtt gtttcctgac tttttaatga tcatcattct | 540 |

<210> SEQ ID NO 27
<211> LENGTH: 1520
<212> TYPE: DNA
<213> ORGANISM: Homo sapiens
<220> FEATURE:
<221> NAME/KEY: misc_feature
<223> OTHER INFORMATION: sequence of STAR27

<400> SEQUENCE: 27

| | |
|---|---|
| cttggccctc acaaagcctg tggccaggga acaattagcg agctgcttat tttgctttgt | 60 |
| atccccaatg ctgggcataa tgcctgccat tatgagtaat gccggtagaa gtatgtgttc | 120 |
| aaggaccaaa gttgataaat accaaagaat ccagagaagg gagagaacat tgagtagagg | 180 |
| atagtgacag aagagatggg aacttctgac aagagttgtg aagatgtact aggcaggggg | 240 |
| aacagcttaa ggagagtcac acaggaccga gctcttgtca agccggctgc catggaggct | 300 |
| gggtggggcc atggtagctt tcccttcctt ctcaggttca gagtgtcagc cttgaacttc | 360 |
| taattcccag aggcatttat tcaatgtttt cttctagggg catacctgcc ctgctgtgga | 420 |
| agactttctt ccctgtgggt cgccccagtc cccagatgag acggtttggg tcagggccag | 480 |
| gtgcaccgtt gggtgtgtgc ttatgtctga tgacagttag ttactcagtc attagtcatt | 540 |
| gagggaggtg tggtaaagat ggagatgctg ggtcacatcc ctagagaggt gttccagtat | 600 |
| gggcacatgg gagggctgga aggataggtt actgctagac gtagagaagc cacatccttt | 660 |
| aacaccctgg cttttcccac tgccaagatc cagaaagtcc ttgtggtttc gctgcttttct | 720 |
| ccttttttttt tttttttttt tttctgagat ggagtctggc tctgtcgccc aggctggagt | 780 |
| gcagtggcac gatttcggct cactgcaagt tccgcctcct aggttcatac cattctccca | 840 |
| cctcagcctc ccgagtagct gggactacag gcgccaccac acccagctaa ttttttgtat | 900 |
| ttttagtaga cggcgtttt caccatgtta gccaggatgg tcttgatccg cctgcctcag | 960 |
| cctcccaaag tgctgggatt acaggcgtga gccaccgcgc ccggcctgct tcttctttc | 1020 |
| atgaagcatt cagctggtga aaaagctcag ccaggctggt ctggaactct tgacctcaag | 1080 |
| tgatctgcct gcctcagcct cccaaagtgc tgagattaca ggcatgagcc agtccgaatg | 1140 |
| tggctttttt tgttttgttt tgaaacaagg tctcactgtt gcccaggctg cagtgcagtg | 1200 |
| gcatacctca gctccactgc agcctcgacc tcctgggctc aagcaatcct cccaactgag | 1260 |
| cctccccagt agctggggct acaagcgcat gccaccacgc ctggctattt ttttttttt | 1320 |
| tttttttttt gagaaggagt ttcattcttg ttgcccaggc tggagtgcaa tggcacagtc | 1380 |
| tcagctcact gcagcctccg cctcctgggt tcaagcgatt ctcctgcctc agcctcccga | 1440 |
| gtagctggga ttataggcac ctgccaccat gcctggctaa ttttttttgta tttttagtag | 1500 |
| ggatggggtt tcaccatgtt | 1520 |

<210> SEQ ID NO 28

<211> LENGTH: 961
<212> TYPE: DNA
<213> ORGANISM: Homo sapiens
<220> FEATURE:
<221> NAME/KEY: misc_feature
<223> OTHER INFORMATION: sequence of STAR28

<400> SEQUENCE: 28

| | | | | | |
|---|---|---|---|---|---|
| aggaggttat | tcctgagcaa | atggccagcc | tagtgaactg | gataaatgcc | catgtaagat | 60 |
| ctgtttaccc | tgagaagggc | atttcctaac | tctccctata | aaatgccaag | tggagcaccc | 120 |
| cagatgaaat | agctgatatg | ctttctatac | aagccatcta | ggactggctt | tatcatgacc | 180 |
| aggatattca | cccactgaat | atggctatta | cccaagttat | ggtaaatgct | gtagttaagg | 240 |
| gggtcccttc | cacatggaca | ccccaggtta | taaccagaaa | gggttcccaa | tctagactcc | 300 |
| aagagagggt | tcttagacct | catgcaagaa | agaacttggg | gcaagtacat | aaagtgaaag | 360 |
| caagtttatt | aagaaagtaa | agaaacaaaa | aaatggctac | tccataagca | aagttatttc | 420 |
| tcacttatat | gattaataag | agatggatta | ttcatgagtt | ttctgggaaa | ggggtgggca | 480 |
| attcctggaa | ctgagggttc | ctcccacttt | tagaccatat | agggtatctt | cctgatattg | 540 |
| ccatggcatt | tgtaaactgt | catggcactg | atgggagtgt | cttttagcat | tctaatgcat | 600 |
| tataattagc | atataatgag | cagtgaggat | gaccagaggt | cacttctgtt | gccatattgg | 660 |
| tttcagtggg | gtttggttgg | ctttttttttt | ttttaacca | caacctgttt | tttatttatt | 720 |
| tatttattta | tttatttatt | tatatttttt | atttttttttt | agatggagtc | ttgctctgtc | 780 |
| acccaggtta | gagtgcagtg | gcaccatctc | ggctcactgc | aagctctgcc | tccttggttc | 840 |
| acgccattct | gctgcctcag | cctcccgagt | agctgggact | acaggtgcct | gccaccatac | 900 |
| ccggctaatt | ttttctattt | ttcagtagag | acggggtttc | accgtgttag | ccaggatggt | 960 |
| c | | | | | | 961 |

<210> SEQ ID NO 29
<211> LENGTH: 2233
<212> TYPE: DNA
<213> ORGANISM: Homo sapiens
<220> FEATURE:
<221> NAME/KEY: misc_feature
<223> OTHER INFORMATION: sequence of STAR29

<400> SEQUENCE: 29

| | | | | | |
|---|---|---|---|---|---|
| agcttggaca | cttgctgatg | ccactttgga | tgttgaaggg | ccgccctctc | ccacaccgct | 60 |
| ggccactttt | aaatatgtcc | cctctgccca | gaagggcccc | agaggagggg | ctggtgaggg | 120 |
| tgacaggagt | tgactgctct | cacagcaggg | ggttccggag | ggacctttc | tccccattgg | 180 |
| gcagcataga | aggacctaga | agggcccct | ccaagcccag | ctgggcgtgc | agggccagcg | 240 |
| attcgatgcc | ttcccctgac | tcaggtggcg | ctgtcctaaa | ggtgtgtgtg | ttttctgttc | 300 |
| gccaggggt | ggcggataca | gtggagcatc | gtgcccgaag | tgtctgagcc | cgtggtaagt | 360 |
| ccctggaggg | tgcacggtct | cctccgactg | tctccatcac | gtcaggcctc | acagcctgta | 420 |
| ggcaccgctc | ggggaagcct | ctggatgagg | ccatgtggtc | atcccctgg | agtcctggcc | 480 |
| tggcctgaag | aggaggggag | gaggaggcca | gccctccct | agcccaagg | cctgcgaggc | 540 |
| tgcaagcccg | gccccacatt | ctagtccagg | cttggctgtg | caagaagcag | attgcctggc | 600 |
| cctggccagg | cttcccagct | aggatgtggt | atgcaggg | tggggacat | tgaggggctg | 660 |
| ctgtagcccc | cacaacctcc | ccaggtaggg | tggtgaacag | taggctggac | aagtggacct | 720 |
| gttcccatct | gagattcaag | agcccacctc | tcggaggttg | cagtgagccg | agatccctcc | 780 |

```
actgcactcc agcctgggca acagagcaag actctgtctc aaaaaaacag aacaacgaca    840
acaaaaaacc cacctctggc ccactgccta actttgtaaa taaagttta ttggcacata    900
gacacaccca ttcatttaca tactgctgcg gctgcttttg cattacccct gagtagacga    960
cagaccacgt ggccatggaa gccaaaaata tttactgtct ggccctttac agaagtctgc   1020
tctagaggga gaccccggcc catggggcag gaccactggg cgtgggcaga agggaggcct   1080
cggtgcctcc acgggcctag ttgggtatct cagtgcctgt ttcttgcatg gagcaccagg   1140
ggtcagggca gtacctgga ggaggcaggc tgttgcccgc ccagcactgg gacccaggag    1200
accttgagag gctcttaacg aatgggagac aagcaggacc agggctccca ttggctgggc   1260
ctcagtttcc ctgcctgtaa gtgagggagg gcagctgtga aggtgaactg tgaggcagag   1320
cctctgctca gccattgcag gggcggctct gccccactcc tgttgtgcac ccagagtgag   1380
gggcacgggg tgagatgtca ccatcagccc ataggggtgt cctcctggtg ccaggtcccc   1440
aagggatgtc ccatcccccc tggctgtgtg ggacagcag agtccctggg gctgggaggg    1500
ctccacactg ttttgtcagt ggttttctg aactgttaaa tttcagtgga aaattctctt    1560
tccccttta ctgaaggaac ctccaaagga agacctgact gtgtctgaga agttccagct    1620
ggtgctggac gtcgcccaga aagcccaggt actgccacgg gcgccggcca ggggtgtgtc   1680
tgcgccagcc atgggcacca gccagggggtg tgtctacgcc ggccagggt aggtctccgc    1740
cggcctccgc tgctgcctgg ggagggccgt gcctgacact gcaggccggg tttgtccgcg   1800
gtcagctgac ttgtagtcac cctgcccttg gatggtcgtt acagcaactc tggtggttgg   1860
ggaaggggcc tcctgattca gcctctgcgg acggtgcgcg agggtggagc tcccctccct   1920
ccccaccgcc cctggccagg gttgaacgcc cctgggaagg actcaggccc gggtctgctg   1980
ttgctgtgag cgtggccacc tctgccctag accagagctg ggccttcccc ggcctaggag   2040
cagccgggca ggaccacagg gctccgagtg acctcagggc tgcccgacct ggaggccctc   2100
ctggcgtcgc ggtgtgactg acagcccagg agcgggggct gttgtaattg ctgtttctcc   2160
ttcacacaga acctttcgg gaagatggct gacatcctgg agaagatcaa gaagtaagtc    2220
ccgccccca ccc                                                      2233

<210> SEQ ID NO 30
<211> LENGTH: 1851
<212> TYPE: DNA
<213> ORGANISM: Homo sapiens
<220> FEATURE:
<221> NAME/KEY: misc_feature
<223> OTHER INFORMATION: sequence of STAR30

<400> SEQUENCE: 30
gggtgcattt ccacccaggg gacacttggc aatggtggga gacattgctt gttgtcacaa     60
ctgggcatgg gagtgctgct gcgtctagtg ggtagaggcc agagatgctc ctaatatcct    120
acaaggcaca gaacagcccc ccacaacaga gaattatcca gcctgaaaat gtccacagtg    180
ctgaggttgg gaaaccctat tctagagcca acaggctgtg aagcttgact catggttcca    240
tcaccaatag ctgcgtgacc ttggtgagtt ccttagctgc tctgtgcctc ggattcatgg    300
taggttttcc ttgttaggtt taaatgagtg aagttataca gagggcctga agtctcatgg    360
tattttacta gagcctcatt gtgttttagt tataattaga aattgggtaa ggtaaggaca    420
cagaagaagc catctgatct gggggcttca cacttagaag tgacctcgga gcaattgtat    480
tggggtggaa agggactaac agccaggagc agagggcaca ttggaattgg ggccagaggg    540
```

```
cacagactgc cttgtccatc aggcatagca atggacagag gaaggggaat gactagttat    600
ggctgcaagg ccaagtacag gggacttatt tctcatatct atctatctat ctacctaccg    660
tctatttatc tatcatctat ctacttatttt atctatctat ttatgcatgt gtaccaaccg    720
aaagttttag taaatgcaca aactgcgata taatgaaaat ggaaattttc aaaagaagag    780
aaatcacctg ccacctgact acctttaacaa atgagtggtt ttcatctctc cttccaggcc    840
tgtcattttt acagtgcttt agtcataaaa caggtcctct attctattgt tttatgtcac    900
atgaaattgt accataagca ttttccatga tgtgactcca ctgtttcatt ttccattttt    960
ttccagaatg aagataacct cattgttttt ttcctgattg taaaaatgct ctgtgctctt   1020
tttttttttt tttaacaatg caggcagtac caaaaagtat gaagaagaat gtaatagttc   1080
ccatttccca tctcactctt taaggccagc attttggtga acatccatcc gaacaaatct   1140
ccacgcgttt atcaatttgt tgacttactc cttctttat gtaaatatga acatgattta   1200
actgccagtc catttggaac cttaaagtga aggttttta ttgttggggt ttgctatggt   1260
ctgaatatgt gtgtccccc aaaatttatg ttgaatccta acgcccaatg cgattaggag   1320
gtggggccat taggaggtga ttaagtcatg aagtcatcag ccctaatgaa tgggatttgt   1380
ggccttgaaa agggacccca gagagctgcc ttgccccttc tgccatgtaa ggacacagtg   1440
aggagctagg aaggggggcct cagcagagac caaatgtgat ggtgcctcga tattggactt   1500
cccagcctcc agaatgtgag aaatgaattt ctgttgttta taagtcaccc agtctatagt   1560
attttgttct agcagcccaa acagactaag tcagggttgt tgttttagga agtggggaat   1620
ggggccatgc atgggtgtac gccagaacaa aggaagccag caagtcctga aagatactgg   1680
aaaagggaat agtgggcacg tgcagtgtgt tagtttcctg aggctgctat aacaaagcac   1740
cacaggttgg gtggcttaaa taacagaaat tcattctccc atcattctgg ggaccagacg   1800
tctgaaatca agactcctat gccatgctcc ttctgaaggc tccaggggag g            1851
```

<210> SEQ ID NO 31
<211> LENGTH: 1701
<212> TYPE: DNA
<213> ORGANISM: Homo sapiens
<220> FEATURE:
<221> NAME/KEY: misc_feature
<223> OTHER INFORMATION: sequence of STAR31
<220> FEATURE:
<221> NAME/KEY: misc_feature
<222> LOCATION: (159)..(159)
<223> OTHER INFORMATION: n can be a, c, g, or t
<220> FEATURE:
<221> NAME/KEY: misc_feature
<222> LOCATION: (1667)..(1667)
<223> OTHER INFORMATION: n can be a, c, g, or t
<220> FEATURE:
<221> NAME/KEY: misc_feature
<222> LOCATION: (1677)..(1677)
<223> OTHER INFORMATION: n can be a, c, g, or t
<220> FEATURE:
<221> NAME/KEY: misc_feature
<222> LOCATION: (1683)..(1684)
<223> OTHER INFORMATION: n can be a, c, g, or t
<220> FEATURE:
<221> NAME/KEY: misc_feature
<222> LOCATION: (1686)..(1687)
<223> OTHER INFORMATION: n can be a, c, g, or t
<220> FEATURE:
<221> NAME/KEY: misc_feature
<222> LOCATION: (1690)..(1690)
<223> OTHER INFORMATION: n can be a, c, g, or t
<220> FEATURE:
<221> NAME/KEY: misc_feature

```
<222> LOCATION: (1693)..(1696)
<223> OTHER INFORMATION: n can be a, c, g, or t

<400> SEQUENCE: 31
cacccgcctt ggcccccccag agtgctggga ttacaagtgt aaaccaccat tcctggctag        60 atttaattt  ttaaaaaata aagagaagta ggaatagttc attttaggga gagcccctta      120
actgggacag gggcaggaca ggggtgaggc ttcccttant tcaagctcac ctcaaaccca      180
cccaggactg tgtgtcacat tctccaataa aggaaaggtt gctgccccg  cctgtgagtg      240 ctgcagtgga gggtagaggg ccgtgggcag agtgcttcat ggactgctca tcaagaaagg      300
cttcatgaca atcggcccag ctgctgtcat cccacattct acttccagct aggagaaggc      360
ggcttgccca cagtcaccca gccggcaagt gtcacccctg ggttggaccc agagctatga      420
tcctgcccag gggtccagct gagaatcagg cccacgttct aggcagaggg gctcacctac      480
tgggactcca gtagctgtag tgcatggagg catcatggct gcagcagcct ggacctggtc      540
tcacactggc tgtccctgtg ggcaggccat cctcaatgcc aggtcaggcc caagcatgta      600
tcccagacaa tgacaatggg gtggaatcct ctcttgtccc agaagccact cctcactgtt      660
ctacctgagg aaggcagggg catggtgaaa tcctgaagcc tgctgtgagg gtctccagcg      720
aacttgcaca tggtcagccc tgccttctcc tccctgaact agattgagcg agagcaagaa      780
ggacattgaa ccagcaccca aagaattttg gggaacggcc tctcatccag gtcaggctca      840
cctccttttt aaaatttaat taattaatta attaattttt ttttagagac agagtcttac      900
tgtgtggccc aggctgtagt gcagtggcac aatcatagtt cactgcagcc tcaaactccc      960
cacctcagcc tctggattag ctgagactac aggtgcacca ccaccacacc cagctaatat     1020 ttttatttt  gtagagagag ggtttcacca tcttgcccag gctggtctca aactcctggg     1080
ctcaagtgat cccgcccagg tctgaaagcc cccaggctgg cctcagactg tggggttttc     1140
catgcagcca cccgagggcg ccccccaagcc agttcatctc ggagtccagg cctggccctg     1200
ggagacagag tgaaaccagt ggttttttatg aacttaactt agagtttaaa agatttctac     1260
tcgatcactt gtcaagatgc gccctctctg gggagaaggg aacgtgactg gattccctca     1320
ctgttgtatc ttgaataaac gctgctgctt catcctgtgg gggccgtggc cctgtccctg     1380
tgtgggtggg gcctcttcca tttccctgac ttagaaacca cagtccacct agaacagggt     1440
ttgagaggct tagtcagcac tgggtagcgt tttgactcca ttctcggctt tcttcttttt     1500 cttttccagga tttttgtgca gaaatggttc ttttgttgcc gtgttagtcc tccttggaag     1560
gcagctcaga aggcccgtga aatgtcgggg gacaggaccc ccagggaggg aaccccaggc     1620
tacgcacttt agggttcgtt ctccagggag ggcgacctga ccccgnatc  cgtcggngcg     1680 cgnngnnacn aannnnttcc c                                                1701

<210> SEQ ID NO 32
<211> LENGTH: 771
<212> TYPE: DNA
<213> ORGANISM: Homo sapiens
<220> FEATURE:
<221> NAME/KEY: misc_feature
<223> OTHER INFORMATION: sequence of STAR32

<400> SEQUENCE: 32
gatcacacag cttgtatgtg ggagctagga ttggaacccc agaagtctgg ccccaggttc       60
atgctctcac ccactgcata caatggcctc tcataaatca atccagtata aaacattaga     120
atctgcttta aaaccataga attagtagcg taagtaataa atgcagagac catgcagtga     180
```

```
atggcattcc tggaaaaagc ccccagaagg aattttaaat cagctttcgt ctaatcttga      240
gcagctagtt agcaaatatg agaatacagt tgttcccaga taatgcttta tgtctgacca      300
tcttaaactg gcgctgtttt tcaaaaactt aaaaacaaaa tccatgactc ttttaattat      360
aaaagtgata catgtctact tgggaggctg aggtggtggg aggatggctt gagtttgagg      420
ctgcagtatg ctactatcat gcctataaat agccgctgca ttccagcttg gcaacatac       480 ccaggcccta tctcaaaaaa ataaaaagta atacatctac attgaagaaa attaattta       540 ttgggttttt ttgcattttt attatacaca gcacacacag cacatatgaa aaaatgggta      600
tgaactcagg cattcaactg gaagaacagt actaaatcaa tgtccatgta gtcagcgtga      660
ctgaggttgg tttgtttttt cttttttctt ctcttctctt ctcttttctt ttttttgag       720 acggagcttt gctcttttg cccaggcttg attgcaatgg cgtgatctca g                771

<210> SEQ ID NO 33
<211> LENGTH: 1368
<212> TYPE: DNA
<213> ORGANISM: Homo sapiens
<220> FEATURE:
<221> NAME/KEY: misc_feature
<223> OTHER INFORMATION: sequence of STAR33

<400> SEQUENCE: 33
gcttttatcc tccattcaca gctagcctgg cccccagagt acccaattct ccctaaaaaa       60
cggtcatgct gtatagatgt gtgtggcttg gtagtgctaa agtggccaca tacagagctc      120
tgacaccaaa cctcaggacc atgttcatgc cttctcactg agttctggct tgttcgtgac      180
acattatgac attatgatta tgatgacttg tgagagcctc agtcttctat agcactttta      240
gaatgcttta taaaaaccat ggggatgtca ttatattcta acctgttagc acttctgttc      300
gtattaccca tcacatccca acatcaattc tcatatatgc aggtacctct tgtcacgcgc      360
gtccatgtaa ggagaccaca aaacaggctt tgtttgagca acaaggtttt tatttcacct      420
gggtgcaggt gggctgagtc tgaaaagaga gtcagtgaag ggagacaggg gtgggtccac      480
tttataagat ttgggtaggt agtggaaaat tacaatcaaa gggggttgtt ctctggctgg      540
ccagggtggg ggtcacaagg tgctcagtgg gagagccttt gagccaggat gagccagaag      600
gaatttcaca aggtaatgtc atcagttaag gcagggactg gccatttca cttcttttgt       660 ggtggaatgt catcagttaa ggcaggaacc ggccattttc acttcttttg tgattcttca      720
cttgcttcag gccatctgga cgtataggtg caggtcacag tcacagggga taagatggca      780
atggcatagc ttgggctcag aggcctgaca cctctgagaa actaaagatt ataaaaatga      840
tggtcgcttc tattgcaaat ctgtgtttat tgtcaagagg cacttatttg tcaattaaga      900
acccagtggt agaatcgaat gtccgaatgt aaaacaaaat acaaaacctc tgtgtgtgtg      960
tgtgtgtgag tgtgtgtgta tgtgtgtgtg tgtgtattag agaggaaaag cctgtatttg     1020
gaggtgtgat tcttagattc taggttcttt cctgcccacc ccatatgcac ccaccccaca     1080
aaagaacaaa caacaaatcc caggacatct tagcgcaaca tttcagtttg catattttac     1140
atatttactt ttcttacata ttaaaaaact gaaaatttta tgaacacgct aagttagatt     1200
ttaaattaag tttgttttta cactgaaaat aatttaatat ttgtgaagaa tactaataca     1260 tggtatatt tcattttctt aaaattctga acccctcttc ccttatttcc ttttgacccg     1320
attggtgtat tggtcatgtg actcatggat ttgccttaag gcaggagg                 1368
```

<210> SEQ ID NO 34
<211> LENGTH: 755
<212> TYPE: DNA
<213> ORGANISM: Homo sapiens
<220> FEATURE:
<221> NAME/KEY: misc_feature
<223> OTHER INFORMATION: sequence of STAR34

<400> SEQUENCE: 34

```
actgggcacc ctcctaggca ggggaatgtg agaactgccg ctgctctggg gctgggcgcc      60
atgtcacagc aggagggagg acggtgttac accacgtggg aaggactcag ggtggtcagc     120
cacaaagctg ctggtgatga ccaggggctt gtgtcttcac tctgcagccc taacacccag     180
gctgggttcg ctaggctcca tcctgggggt gcagaccctg agagtgatgc cagtgggagc     240
ctcccgcccc tccccttcct cgaaggccca ggggtcaaac agtgtagact cagaggcctg     300
agggcacatg tttatttagc agacaaggtg gggctccatc agcggggtgg cctggggagc     360
agctgcatgg gtggcactgt ggggagggtc tcccagctcc ctcaatggtg ttcgggctgg     420
tgcggcagct ggcggcaccc tggacagagg tggatatgag ggtgatgggt ggggaaatgg     480
gaggcacccg agatggggac agcagaataa agacagcagc agtgctgggg ggcaggggga     540
tgagcaaagg caggcccaag accccccagcc cactgcaccc tggcctccca caagcccct      600
cgcagccgcc cagccacact cactgtgcac tcagccgtcg atacactggt ctgttaggga     660
gaaagtccgt cagaacaggc agctgtgtgt gtgtgtgcgt gtatgagtgt gtgtgtgtga     720
tccctgactg ccaggtcctc tgcactgccc ctggg                                755
```

<210> SEQ ID NO 35
<211> LENGTH: 1193
<212> TYPE: DNA
<213> ORGANISM: Homo sapiens
<220> FEATURE:
<221> NAME/KEY: misc_feature
<223> OTHER INFORMATION: sequence of STAR35
<220> FEATURE:
<221> NAME/KEY: misc_feature
<222> LOCATION: (312)..(312)
<223> OTHER INFORMATION: n can be a, c, g, or t
<220> FEATURE:
<221> NAME/KEY: misc_feature
<222> LOCATION: (355)..(355)
<223> OTHER INFORMATION: n can be a, c, g, or t
<220> FEATURE:
<221> NAME/KEY: misc_feature
<222> LOCATION: (361)..(361)
<223> OTHER INFORMATION: n can be a, c, g, or t
<220> FEATURE:
<221> NAME/KEY: misc_feature
<222> LOCATION: (367)..(367)
<223> OTHER INFORMATION: n can be a, c, g, or t
<220> FEATURE:
<221> NAME/KEY: misc_feature
<222> LOCATION: (370)..(370)
<223> OTHER INFORMATION: n can be a, c, g, or t
<220> FEATURE:
<221> NAME/KEY: misc_feature
<222> LOCATION: (383)..(383)
<223> OTHER INFORMATION: n can be a, c, g, or t
<220> FEATURE:
<221> NAME/KEY: misc_feature
<222> LOCATION: (390)..(390)
<223> OTHER INFORMATION: n can be a, c, g, or t
<220> FEATURE:
<221> NAME/KEY: misc_feature
<222> LOCATION: (399)..(399)
<223> OTHER INFORMATION: n can be a, c, g, or t
<220> FEATURE:
<221> NAME/KEY: misc_feature
<222> LOCATION: (413)..(413)

```
<223> OTHER INFORMATION: n can be a, c, g, or t
<220> FEATURE:
<221> NAME/KEY: misc_feature
<222> LOCATION: (417)..(417)
<223> OTHER INFORMATION: n can be a, c, g, or t
<220> FEATURE:
<221> NAME/KEY: misc_feature
<222> LOCATION: (422)..(423)
<223> OTHER INFORMATION: n can be a, c, g, or t
<220> FEATURE:
<221> NAME/KEY: misc_feature
<222> LOCATION: (445)..(445)
<223> OTHER INFORMATION: n can be a, c, g, or t
<220> FEATURE:
<221> NAME/KEY: misc_feature
<222> LOCATION: (576)..(576)
<223> OTHER INFORMATION: n can be a, c, g, or t
<220> FEATURE:
<221> NAME/KEY: misc_feature
<222> LOCATION: (578)..(578)
<223> OTHER INFORMATION: n can be a, c, g, or t
<220> FEATURE:
<221> NAME/KEY: misc_feature
<222> LOCATION: (580)..(580)
<223> OTHER INFORMATION: n can be a, c, g, or t
<220> FEATURE:
<221> NAME/KEY: misc_feature
<222> LOCATION: (589)..(589)
<223> OTHER INFORMATION: n can be a, c, g, or t
<220> FEATURE:
<221> NAME/KEY: misc_feature
<222> LOCATION: (624)..(624)
<223> OTHER INFORMATION: n can be a, c, g, or t
<220> FEATURE:
<221> NAME/KEY: misc_feature
<222> LOCATION: (681)..(681)
<223> OTHER INFORMATION: n can be a, c, g, or t
<220> FEATURE:
<221> NAME/KEY: misc_feature
<222> LOCATION: (702)..(702)
<223> OTHER INFORMATION: n can be a, c, g, or t
<220> FEATURE:
<221> NAME/KEY: misc_feature
<222> LOCATION: (756)..(756)
<223> OTHER INFORMATION: n can be a, c, g, or t
<220> FEATURE:
<221> NAME/KEY: misc_feature
<222> LOCATION: (761)..(761)
<223> OTHER INFORMATION: n can be a, c, g, or t
<220> FEATURE:
<221> NAME/KEY: misc_feature
<222> LOCATION: (828)..(828)
<223> OTHER INFORMATION: n can be a, c, g, or t
<220> FEATURE:
<221> NAME/KEY: misc_feature
<222> LOCATION: (845)..(845)
<223> OTHER INFORMATION: n can be a, c, g, or t
<220> FEATURE:
<221> NAME/KEY: misc_feature
<222> LOCATION: (868)..(868)
<223> OTHER INFORMATION: n can be a, c, g, or t
<220> FEATURE:
<221> NAME/KEY: misc_feature
<222> LOCATION: (880)..(881)
<223> OTHER INFORMATION: n can be a, c, g, or t
<220> FEATURE:
<221> NAME/KEY: misc_feature
<222> LOCATION: (923)..(923)
<223> OTHER INFORMATION: n can be a, c, g, or t
<220> FEATURE:
<221> NAME/KEY: misc_feature
<222> LOCATION: (925)..(925)
<223> OTHER INFORMATION: n can be a, c, g, or t
<220> FEATURE:
<221> NAME/KEY: misc_feature
<222> LOCATION: (1019)..(1019)
<223> OTHER INFORMATION: n can be a, c, g, or t
<220> FEATURE:
<221> NAME/KEY: misc_feature
```

```
<222> LOCATION: (1021)..(1021)
<223> OTHER INFORMATION: n can be a, c, g, or t
<220> FEATURE:
<221> NAME/KEY: misc_feature
<222> LOCATION: (1055)..(1055)
<223> OTHER INFORMATION: n can be a, c, g, or t
<220> FEATURE:
<221> NAME/KEY: misc_feature
<222> LOCATION: (1062)..(1063)
<223> OTHER INFORMATION: n can be a, c, g, or t
<220> FEATURE:
<221> NAME/KEY: misc_feature
<222> LOCATION: (1074)..(1074)
<223> OTHER INFORMATION: n can be a, c, g, or t
<220> FEATURE:
<221> NAME/KEY: misc_feature
<222> LOCATION: (1089)..(1089)
<223> OTHER INFORMATION: n can be a, c, g, or t
<220> FEATURE:
<221> NAME/KEY: misc_feature
<222> LOCATION: (1100)..(1101)
<223> OTHER INFORMATION: n can be a, c, g, or t
<220> FEATURE:
<221> NAME/KEY: misc_feature
<222> LOCATION: (1106)..(1107)
<223> OTHER INFORMATION: n can be a, c, g, or t
<220> FEATURE:
<221> NAME/KEY: misc_feature
<222> LOCATION: (1117)..(1117)
<223> OTHER INFORMATION: n can be a, c, g, or t
<220> FEATURE:
<221> NAME/KEY: misc_feature
<222> LOCATION: (1138)..(1138)
<223> OTHER INFORMATION: n can be a, c, g, or t
<220> FEATURE:
<221> NAME/KEY: misc_feature
<222> LOCATION: (1140)..(1140)
<223> OTHER INFORMATION: n can be a, c, g, or t
<220> FEATURE:
<221> NAME/KEY: misc_feature
<222> LOCATION: (1145)..(1146)
<223> OTHER INFORMATION: n can be a, c, g, or t
<220> FEATURE:
<221> NAME/KEY: misc_feature
<222> LOCATION: (1158)..(1159)
<223> OTHER INFORMATION: n can be a, c, g, or t
<220> FEATURE:
<221> NAME/KEY: misc_feature
<222> LOCATION: (1180)..(1180)
<223> OTHER INFORMATION: n can be a, c, g, or t
<220> FEATURE:
<221> NAME/KEY: misc_feature
<222> LOCATION: (1187)..(1188)
<223> OTHER INFORMATION: n can be a, c, g, or t
<220> FEATURE:
<221> NAME/KEY: misc_feature
<222> LOCATION: (1191)..(1191)
<223> OTHER INFORMATION: n can be a, c, g, or t

<400> SEQUENCE: 35
cgacttggtg atgcgggctc ttttttggtt ccatatgaac tttaaagtag tcttttccaa      60
ttctgtgaag aaagtcattg gtaggttgat ggggatggca ttgaatctgt aaattacctt     120
gggcagtatg gccattttca caatgttgat tcttcctatc catgatgatg gaatgttctt     180
ccattagttt gtatcctctt ttatttcctt gagcagtggt ttgtagttct ccttgaagag     240
gtccttcaca tcccttgtaa gttggattcc taggtatttt attctctttg aagcaaattg     300
tgaatgggag tncactcacg atttggctct ctgtttgtct gctgggtgta taanaatgt      360 ngtgatnttn gtacattgat ttngtatccn tgagacttng ctgaatttgc ttnatcngct     420 tnnggaacc ttttgggctg aaacnatggg attttctaaa tatacaatca tgtcgtctgc      480
aaacagggaa caatttgact tcctcttttc ctaattgaat acactttatc tccttctcct     540
```

| | |
|---|---|
| gcctaattgc cctgggcaaa acttccaaca ctatgntngn aataggagnt ggtgagagag | 600 |
| ggcatccctg ttcttgttgc cagnttttca aagggaatgc ttccagtttt ggcccattca | 660 |
| gtatgatatg ggctgtgggt ngtgtcataa atagctctta tnattttgaa atgtgtccca | 720 |
| tcaataccta atttattgaa agttttagc atgaangcat ngttgaattt ggtcaaaggc | 780 |
| tttttctgca tctatggaaa taatcatgtg gttttgtct ttggctcntg tttatatgct | 840 |
| ggatnacatt tattgatttg tgtatatnga acccagcctn ncatcccagg atgaagccc | 900 |
| acttgatcca agcttggcgc gcngnctagc tcgaggcagg caaaagtatg caaagcatgc | 960 |
| atctcaatta gtcagcaccc atagtccgcc cctacctccg cccatccgcc cctaactcng | 1020 |
| nccgttcgcc cattctcgcc catggctgac taatnttttt annatccaag cggngccgcc | 1080 |
| ctgcttganc attcagagtn nagagnnttg gaggccnagc cttgcaaaac tccggacngn | 1140 |
| ttctnnggat tgacccccnnt taaatatttg gtttttgtn ttttcanngg nga | 1193 |

<210> SEQ ID NO 36
<211> LENGTH: 1712
<212> TYPE: DNA
<213> ORGANISM: Homo sapiens
<220> FEATURE:
<221> NAME/KEY: misc_feature
<223> OTHER INFORMATION: sequence of STAR36

<400> SEQUENCE: 36

| | |
|---|---|
| gatcccatcc ttagcctcat cgatacctcc tgctcacctg tcagtgcctc tggagtgtgt | 60 |
| gtctagccca ggcccatccc ctggaactca ggggactcag gactagtggg catgtacact | 120 |
| tggcctcagg ggactcagga ttagtgagcc ccacatgtac acttggcctc agtggactca | 180 |
| ggactagtga gccccacatg tacacttggc ctcaggggac tcaggattag tgagccccca | 240 |
| catgtacact tggcctcagg ggactcagga ttagtgagcc ccacatgtac acttggcctc | 300 |
| agggactca ggactagtga gccccacatg tacacttggc ctcaggggac tcagaactag | 360 |
| tgagccccac atgtacactt ggcttcaggg gactcaggat tagtgagccc cacatgtaca | 420 |
| cttggacacg tgaaccacat cgatgtgctg cagagctcag ccctctgcag atgaaatgtg | 480 |
| gtcatggcat tccttcacag tggcacccct cgttccctcc ccacctcatc tcccattctt | 540 |
| gtctgtcttc agcacctgcc atgtccagcc ggcagattcc accgcagcat cttctgcagc | 600 |
| accccgacc acacacctcc ccagcgcctg cttggcccctc cagcccagct cccgccttc | 660 |
| ttccttgggg aagctccctg gacagacacc ccctcctccc agccatggct ttttcctgct | 720 |
| ctgccccacg cgggacccctg ccctggatgt gctacaatag acacatcaga tacagtcctt | 780 |
| cctcagcagc cggcagaccc agggtggact gctcggggcc tgcctgtgag gtcacacagg | 840 |
| tgtcgttaac ttgccatctc agcaactagt gaatatgggc agatgctacc ttccttccgg | 900 |
| ttccctggtg agaggtactg gtggatgtcc tgtgttgccg gccaccttttt gtccctggat | 960 |
| gccatttatt tttttccaca aatatttccc aggtctcttc tgtgtgcaag gtattagggc | 1020 |
| tgcagcgggg gccaggccac agatctctgt cctgagaaga cttggattct agtgcaggag | 1080 |
| actgaagtgt atcacaccaa tcagtgtaaa ttgttaactg ccacaaggag aaaggccagg | 1140 |
| aaggagtggg gcatggtggt gttctagtgt tacaagaaga agccagggag ggcttcctgg | 1200 |
| atgaagtggc atctgacctg ggatctggag gaggagaaaa atgtcccaaa agagcagaga | 1260 |
| gcccacccta ggctctgcac caggaggcaa cttgctgggc ttatggaatt cagagggcaa | 1320 |
| gtgataagca gaaagtcctt gggggccaca attaggattt ctgtcttcta aagggcctct | 1380 |

-continued

| | |
|---|---|
| gccctctgct gtgtgacctt gggcaagtta cttcacctct agtgctttgg ttgcctcatc | 1440 |
| tgtaaagtgg tgaggataat gctatcacac tggttgagaa ttgaagtaat tattgctgca | 1500 |
| aagggcttat aagggtgtct aatactagta ctagtaggta cttcatgtgt cttgacaatt | 1560 |
| ttaatcatta ttattttgtc atcaccgtca ctcttccagg ggactaatgt ccctgctgtt | 1620 |
| ctgtccaaat taaacattgt ttatccctgt gggcatctgg cgaggtggct aggaaagcct | 1680 |
| ggagctgttt cctgttgacg tgccagacta gt | 1712 |

```
<210> SEQ ID NO 37
<211> LENGTH: 1321
<212> TYPE: DNA
<213> ORGANISM: Homo sapiens
<220> FEATURE:
<221> NAME/KEY: misc_feature
<223> OTHER INFORMATION: sequence of STAR37

<400> SEQUENCE: 37
```

| | |
|---|---|
| aggatcacat ttaaggaagt gtgtggggtc cctggatgac accagcaccc agtgcggctc | 60 |
| tgtctggcaa ccgctcccaa ggtggcagga gtgggtgtcc cctgtgtgtc agtgggcagc | 120 |
| tcctgctgag cctacagctc actggggagc ctgacagcgg ggccatgtgc ctgacactcc | 180 |
| tctctgcttg tggacctggc aaggcaggga gcagaaaaca gagccacttg aaggctttct | 240 |
| gtctgcgtct gtgtgcagtg tggatttagt tgtgcttttt tcttgctggg agagcacagc | 300 |
| caccatttac aagcagtgtc accctcatgg gtggcgagga cagaacagga gcctctgctc | 360 |
| tctgtaccta tctgggcccg gtgggctccc ttgtcctggc ttccatctct gtctcagcga | 420 |
| ccattcagcc ctgcgcagga acacatgttg cttagaaaag ccaaattcag cccttgtctc | 480 |
| tgcctcctct ggtctcatga tgtgcatctg ttaccttgaa actggaaacc agtctatcaa | 540 |
| tgtctgtgcc aattttttat tccctcccca acctccttcc ccatacgact ttttatttat | 600 |
| gtaggatgtg tgctgtctaa tgatgggatg accacatttt tccatgttct aaaagtgctc | 660 |
| ctctcccgca gggtcccagg gctggtggtt gctttgggtc tacagctacg tcttacccgc | 720 |
| ctcctgcctc aacagcctgt gtggtggcaa agccggtgtg gggctgggga acgcagcgtt | 780 |
| ctccaggagg gggacccggc tctccttctg cagtgcaggc gaaggcctag atgccagtgt | 840 |
| gacctcccac aaggcgtggc ttccagactc cccggctgga agtgatgctt ttttgcctcc | 900 |
| ggccctgggt ttgaagcagc ctggctttct cttggtaagt ggctggtgtc ttagcagctg | 960 |
| caatctgagc tcagccacct acacaccacc gtggccgaca ctttcattaa aaagtttcct | 1020 |
| gagacgactt gcgtgcatgt tgacttcatg atcagcgccg ctgggaagaa ccctgagcc | 1080 |
| ggtggggtgg ggctggaagc agcaggtgca gtgatgggc tgggtgccca ggaggcctca | 1140 |
| gtgctcaatc aggccaaggt ggccaagccc aggctgcagg gaaggccggc ctgggggttg | 1200 |
| tgggtgagca caggcaggca ccagctgggc agtgttagga tgctggagca gcatccgtaa | 1260 |
| ccccactgag tggggtagtc tggttgggc agggaccgct gttgctttgg cagagagaga | 1320 |
| t | 1321 |

```
<210> SEQ ID NO 38
<211> LENGTH: 1445
<212> TYPE: DNA
<213> ORGANISM: Homo sapiens
<220> FEATURE:
<221> NAME/KEY: misc_feature
<223> OTHER INFORMATION: sequence of STAR38
<220> FEATURE:
<221> NAME/KEY: misc_feature
```

```
<222> LOCATION: (348)..(348)
<223> OTHER INFORMATION: n can be a, c, g, or t
<220> FEATURE:
<221> NAME/KEY: misc_feature
<222> LOCATION: (888)..(888)
<223> OTHER INFORMATION: n can be a, c, g, or t
<220> FEATURE:
<221> NAME/KEY: misc_feature
<222> LOCATION: (896)..(896)
<223> OTHER INFORMATION: n can be a, c, g, or t
<220> FEATURE:
<221> NAME/KEY: misc_feature
<222> LOCATION: (949)..(949)
<223> OTHER INFORMATION: n can be a, c, g, or t

<400> SEQUENCE: 38
gatctatggg agtagcttcc ttagtgagct ttcccttcaa atactttgca accaggtaga      60
gaattttgga gtgaaggttt tgttcttcgt ttcttcacaa tatggatatg catcttcttt     120
tgaaaatgtt aaagtaaatt acctctcttt tcagatactg tcttcatgcg aacttggtat     180
cctgtttcca tcccagcctt ctataaccca gtaacatctt ttttgaaacc agtgggtgag     240
aaagacacct ggtcaggaac gcggaccaca ggacaactca ggctcaccca cggcatcaga     300
ctaaaggcaa acaaggactc tgtataaagt accggtggca tgtgtatnag tggagatgca     360
gcctgtgctc tgcagacagg gagtcacaca gacacttttc tataatttct taagtgcttt     420
gaatgttcaa gtagaaagtc taacattaaa tttgattgaa caattgtata ttcatggaat     480
attttggaac ggaataccaa aaaatggcaa tagtggttct ttctggatgg aagacaaact     540
tttcttgttt aaaataaatt ttattttata tatttgaggt tgaccacatg accttaagga     600
tacatataga cagtaaactg gttactacag tgaagcaaat taacatatct accatcgtac     660
atagttacat ttttttgtgt gacaggaaca gctaaaatct acgtatttaa caaaaatcct     720
aaagacaata cattttt att aactatagcc ctcatgatgt acattagatc gtgtggttgt     780
ttcttccgtc cccgccacgc cttcctcctg ggatggggat tcattcccta gcaggtgtcg     840
gagaactggc gcccttgcag ggtaggtgcc ccggagcctg aggcgggnac tttaanatca     900
gacgcttggg ggccggctgg gaaaaactgg cggaaaatat tataactgna ctctcaatgc     960
cagctgttgt agaagctcct gggacaagcc gtggaagtcc cctcaggagg cttccgcgat    1020
gtcctaggtg gctgctccgc ccgccacggt catttccatt gactcacacg cgccgcctgg    1080
aggaggaggc tgcgctggac acgccggtgg cgcctttgcc tggggagcg cagcctggag     1140
ctctggcggc agcgctggga gcggggcctc ggaggctggg cctggggacc caaggttggg    1200
cggggcgcag gaggtgggct cagggttctc cagagaatcc ccatgagctg acccgcaggg    1260
cggccgggcc agtaggcacc gggcccccgc ggtgacctgc ggacccgaag ctggagcagc    1320
cactgcaaat gctgcgctga ccccaaatgc tgtgtccttt aaatgtttta attaagaata    1380
attaataggt ccgggtgtgg aggctcaagc cttaatcccc agcacctggc gaggccgagg    1440
aggga                                                                1445

<210> SEQ ID NO 39
<211> LENGTH: 2331
<212> TYPE: DNA
<213> ORGANISM: Homo sapiens
<220> FEATURE:
<221> NAME/KEY: misc_feature
<223> OTHER INFORMATION: sequence of STAR39

<400> SEQUENCE: 39
gtgaaataga tcactaaagc tgattcctct tgtctaaatg aaactttcta cccctttgatg     60
```

```
gacagctatg ctttccccat cctctcccgt cccccagccc ttggtaacca tcatcctact    120
ctctacttgt aggagttcaa cttgtttaga ttttgtgagt gagaacatgt ggtatttgcc    180
tttagagtcc tctaggttta tccatattgt gttaaatgac aggattccct gccttttaa    240 ggctgaatag tatttcattg taatatatat acatacacac acacatatac acacacatat    300
atatacatat atacatatat gtacatagat acatatatat gtacatatat acacacacat    360
atacacacat atatacacat atatacatat acatatatac acatatatgt acatatatat    420 aactttttt catttatcca ttcacttaat acatatgatg gagggcttta tatatgccag    480
gctctgtgat gaatgctgga aattcaatag tgagaaagac tcagtctctg cctccaaaga    540
gcatcatggg ctaggtgctg caacgaggaa ttgccaactg ttgtcatgag agcacagaga    600
agggactcaa ccagccttga agaatcaggg gaggcttcta agctaatggt gtgtgcctgg    660
ggatcacatt gtttcaagca gcagtaacag gatgtgctca ggtccagatg tgagagagag    720
agagagcata tgtcttcaag aaactaacag tagctcccta tagctgaagc aggagtacaa    780
aatagtgagt ttaagtgatg aggcaagaga tatgaagaag cttgaccatg cagctacacc    840
gggcagcatg ccctctgaga catctcatgg aagccgaaaa tgggagtgcc ttgataccaa    900
gccagagaaa ttataatact aagtagatag actgagcagc actcctcctg ggaagaatga    960
gacaagccct gaatttggag gtaagttgtg gattggtgat tagaggagag gtaacaggca   1020
ccaaagcaag aaatagtatt gatgcaaagc tgaggttaat tggatgacaa aatgaagagc   1080
ataaggggct cagacacaga ctgagcagaa aacgagtagc atctgaacct agattgagtt   1140
actaatggat gagaaagagt tcttaaagtt gatgaccacg ggatccatat ataagaatgt   1200
ccaatctccc caaattgatc cacgagttca gtgcaatgcc aatcaaaatc ccactaacaa   1260
gtttatttta aaatgtaaat gaaaatacaa aattttttaaa aagcaaagca atattgaaaa   1320
cccaggaaaa attaggagga cttacacaac ctgatctcaa aacttaccat tatcaagaca   1380
gagtgttatt gacacaagga gagacaaata gataaacgga atgtggtagt ctggagatgc   1440
acccacatgt atgtggtcaa ttgatttttg gccaaggcac caagtcaatt caaaggagca   1500
aggaaagtag tacagaaaca accaaatatt gttttggaaa ataatgacaa agggcttata   1560
accagaatat aagcatataa atataattct ttcaaatcaa taataagaag gcaaatatct   1620
aataaaaatg agcaaagact tgaaaagtca cttaaaaagg cttattaatt agaaatatgc   1680
aaatgttatt agtcttcagt ggaatttaca ttaaaccaca agggatacta ttatatctta   1740
tgcccactag aataaccaaa ggaaaaaaga cagacaaaac aaaatgctgg tgaggatgtg   1800
aagcaactgg aactctcata cattattggt ggtaatgtaa aatttataca accattatga   1860
ataaaggttt ggcagtttct tacaaagttg aatgcacttc tccacgatga ctaggctttt   1920
cactcatagg cgtctggctc cctagaactg aaaacatatg ttcacaagaa gacttgcaaa   1980
tatatattct cccacgtcag gagatatttg ctatgcattt aactgacata agattagtgc   2040
tagagtttat aatgaggttc ttcaaatcta aagaaaatg caaagcatat aatagtaagg   2100
ggtgcaggcc aggcgcagtg gctcactctg taatcccagc actttgggag gccgaggtgg   2160
gcggatcaca aggtcaggag ttcgagacca acctggccaa catagtgaaa ccctgtctct   2220
actaaaaata caaaaactag ccaggtgcgg tgtcatgcac ctgtagtccc agctactcgg   2280
gaggccgagg caggagaatc acttgaacct gggaggtgga ggttgcagtg a            2331

<210> SEQ ID NO 40
```

<211> LENGTH: 1071
<212> TYPE: DNA
<213> ORGANISM: Homo sapiens
<220> FEATURE:
<221> NAME/KEY: misc_feature
<223> OTHER INFORMATION: sequence of STAR40

<400> SEQUENCE: 40

| | | | | | |
|---|---|---|---|---|---|
| gctgtgattc | aaactgtcag | cgagataagg | cagcagatca | agaaagcact | ccgggctcca | 60 |
| gaaggagcct | tccaggccag | ctttgagcat | aagctgctga | tgagcagtga | gtgtcttgag | 120 |
| tagtgttcag | ggcagcatgt | taccattcat | gcttgacttc | tagccagtgt | gacgagaggc | 180 |
| tggagtcagg | tctctagaga | gttgagcagc | tccagcctta | gatctcccag | tcttatgcgg | 240 |
| tgtgcccatt | cgctttgtgt | ctgcagtccc | ctggccacac | ccagtaacag | ttctgggatc | 300 |
| tatgggagta | gcttccttag | tgagcttttcc | cttcaaatac | tttgcaacca | ggtagagaat | 360 |
| tttggagtga | aggttttgtt | cttcgtttct | tcacaatatg | gatatgcatc | ttcttttgaa | 420 |
| aatgttaaag | taaattacct | ctcttttcag | atactgtctt | catgcgaact | tggtatcctg | 480 |
| tttccatccc | agccttctat | aacccagtaa | catctttttt | gaaaccagtg | ggtgagaaag | 540 |
| acacctggtc | aggaacgcgg | accacaggac | aactcaggct | cacccacggc | atcagactaa | 600 |
| aggcaaacaa | ggactctgta | taaagtaccg | gtggcatgtg | tattagtgga | gatgcagcct | 660 |
| gtgctctgca | gacagggagt | cacacagaca | cttttctata | atttcttaag | tgctttgaat | 720 |
| gttcaagtag | aaagtctaac | attaaatttg | attgaacaat | tgtatattca | tggaatattt | 780 |
| tggaacggaa | taccaaaaaa | tggcaatagt | ggttctttct | ggatggaaga | caaacttttc | 840 |
| ttgtttaaaa | taaattttat | tttatatatt | tgaggttgac | cacatgacct | taaggataca | 900 |
| tatagacagt | aaactggtta | ctacagtgaa | gcaaattaac | atatctacca | tcgtacatag | 960 |
| ttacattttt | ttgtgtgaca | ggaacagcta | aaatctacgt | atttaacaaa | aatcctaaag | 1020 |
| acaatacatt | tttattaact | atagccctca | tgatgtacat | tagatctcta | a | 1071 |

<210> SEQ ID NO 41
<211> LENGTH: 1135
<212> TYPE: DNA
<213> ORGANISM: Homo sapiens
<220> FEATURE:
<221> NAME/KEY: misc_feature
<223> OTHER INFORMATION: sequence of STAR41

<400> SEQUENCE: 41

| | | | | | |
|---|---|---|---|---|---|
| cgtgtgcagt | ccacggagag | tgtgttctcc | tcatcctcgt | tccggtggtt | gtggcgggaa | 60 |
| acgtggcgct | gcaggacacc | aacatcagtc | acgtatttca | ttctggaaaa | aaaagtagca | 120 |
| caagcctcgg | ctggttccct | ccagctctta | ccaggcagcc | taagcctagg | ctccattccc | 180 |
| gctcaaggcc | ttcctcaggg | gcctgctcac | cacaggagct | gttcccatgc | agggactaag | 240 |
| gacatgcagc | ctgcatagaa | accaagcacc | caggaaaaca | tgattggatg | gagcgggggg | 300 |
| gtgtggtctc | tagccttgtc | cacctccggt | cctcatgggt | ctcacacctc | ctgagaatgg | 360 |
| gcaccgcaga | ggccacagcc | catacagcca | agatgacaga | ctccgtaagt | gacagggatc | 420 |
| cacagcagag | tgggtgaaat | gttccctata | aactttacaa | aattaatgag | ggcaggggga | 480 |
| ggggagaaat | gaaaatgaac | ccagctcgca | gcacatcagc | atcagtcact | aggtcggcgt | 540 |
| gctctctgac | tgcttcctcg | tagctgcttg | gtgtctcatt | gcctcagaag | catgtagacc | 600 |
| ctgtcacaag | attgtagttc | ccctaactgc | tccgtagatc | acaacttgaa | ccttaggaaa | 660 |
| tgctgttttc | cctttgagat | attcctttgg | gtcctgtata | ctgatggagc | tactgactga | 720 |

```
gctgctccga aggacoccac gaggagctga ctaaaccaag agtgcagttt gtacaccctg    780
atgattacat ccccottgcc ccaccaatca actctcccaa ttttccagcc cctcaccctc    840
cagtcccctt aaaagcccca gcccaggccg ggcacagtgg ctcatgcctg taatcccagc    900
actttgggag gccaaggtgg gcagatcacc tgagggcagg aatttgagac cagcctgacc    960
aacatgaaga acoccgtct ctattacaaa tacaaaatta gccgggcgtg ttgctgcata   1020
ctggtaatcc cagctacttg ggaggtgag gcaggagaat cacttgaatc tgggaggcgg   1080
aggttgcgat gagccgagac agcgccattg cactgcagcc tgggcaacaa gagca        1135
```

```
<210> SEQ ID NO 42
<211> LENGTH: 735
<212> TYPE: DNA
<213> ORGANISM: Homo sapiens
<220> FEATURE:
<221> NAME/KEY: misc_feature
<223> OTHER INFORMATION: sequence of STAR42

<400> SEQUENCE: 42
aagggtgaga tcactaggga gggaggaagg agctataaaa gaaagaggtc actcatcaca     60
tcttacacac ttttaaaac cttggttttt taatgtccgt gttcctcatt agcagtaagc    120
cctgtggaag caggagtctt tctcattgac caccatgaca agaccctatt tatgaaacat    180
aatagacaca caaatgttta tcggatattt attgaaatat aggattttt ccctcacac     240 ctcatgacca cattctggta cattgtatga atgaatatac cataatttta cctatggctg    300
tatatttagg tcttttcgtg caggctataa aaatatgtat gggccggtca cagtgactta    360
cgcccgtagt cccagaactt tgggaggccg aggcgggtgg atcacctgag gtcgggagtt    420
caaaaccagc ctgaccaaca tggagaaacc ccgtctctgc taaaaataca aaattaact    480 ggacacggtg gcgtatgcct gtaatcccag ctactcggga agctgaggca ggagaactgc    540
ttgaacccag gaggcggagg ttgtggtgag tcgagattgc gccattgcac tccagcctgg    600
gcaacaagag cgaaattcca tctcaaaaaa agaaaaaag tatgactgta tttagagtag    660
tatgtggatt tgaaaaatta ataagtgttg ccaacttacc ttagggttta taccatttat    720
gagggtgtcg gtttc                                                    735
```

```
<210> SEQ ID NO 43
<211> LENGTH: 1227
<212> TYPE: DNA
<213> ORGANISM: Homo sapiens
<220> FEATURE:
<221> NAME/KEY: misc_feature
<223> OTHER INFORMATION: sequence of STAR43

<400> SEQUENCE: 43
caaatagatc tacacaaaac aagataatgt ctgcccattt ttccaaagat aatgtggtga     60
agtgggtaga gagaaatgca tccattctcc ccacccaacc tctgctaaat tgtccatgtc    120
acagtactga gaccagggg cttattccca gcgggcagaa tgtgcaccaa gcacctcttg    180
tctcaatttg cagtctaggc cctgctattt gatggtgtga aggcttgcac ctggcatgga    240
aggtccgttt tgtacttctt gctttagcag ttcaaagagc agggagagct gcgagggcct    300
ctgcagcttc agatggatgt ggtcagcttg ttggaggcgc cttctgtggt ccattatctc    360 cagccccct gcggtgttgc tgtttgcttg gcttgtctgg ctctccatgc cttgttggct    420
ccaaaatgtc atcatgctgc accccaggaa gaatgtgcag gcccatctct tttatgtgct    480
```

| | |
|---|---|
| ttgggctatt ttgattcccc gttgggtata ttccctaggt aagacccaga agacacagga | 540 |
| ggtagttgct ttgggagagt ttggacctat gggtatgagg taatagacac agtatcttct | 600 |
| cttttcatttg gtgagactgt tagctctggc cgcggactga attccacaca gctcacttgg | 660 |
| gaaaacttta ttccaaaaca tagtcacatt gaacattgtg gagaatgagg acagagaag | 720 |
| aggccctaga tttgtacatc tgggtgttat gtctataaat agaatgcttt ggtggtcaac | 780 |
| tagacttgtt catgttgaca tttagtcttg ccttttcggt ggtgatttaa aaattatgta | 840 |
| tatcttgttt ggaatatagt ggagctatgg tgtggcattt tcatctggct ttttgtttag | 900 |
| ctcagcccgt cctgttatgg gcagccttga agctcagtag ctaatgaaga ggtatcctca | 960 |
| ctccctccag agagcggtcc cctcacggct cattgagagt ttgtcagcac cttgaaatga | 1020 |
| gtttaaactt gtttatttt aaaacattct tggttatgaa tgtgcctata ttgaattact | 1080 |
| gaacaacctt atggttgtga agaattgatt tggtgctaag gtgtataaat ttcaggacca | 1140 |
| gtgtctctga agagttcatt tagcatgaag tcagcctgtg gcaggttggg tggagccagg | 1200 |
| gaacaatgga gaagctttca tgggtgg | 1227 |

<210> SEQ ID NO 44
<211> LENGTH: 1586
<212> TYPE: DNA
<213> ORGANISM: Homo sapiens
<220> FEATURE:
<221> NAME/KEY: misc_feature
<223> OTHER INFORMATION: sequence of STAR44

<400> SEQUENCE: 44

| | |
|---|---|
| cacctgcctc agcctcccaa agtgctgaga ttcaaagaaa ttttcatgga gaggggacag | 60 |
| atggagtcaa ttcttgtggg gtgaacatga gtaccacagt tagactgagg ttgggaaaga | 120 |
| ttttccagac aattggaaga gcatgtgaaa gacacagatt ttgagaaatg ttaagtctag | 180 |
| ggaactgcaa ggcttttggc acaagaaagc cactgtagac tatagaggca ggatgcctag | 240 |
| attcaaatcc caactgctac acttctaagc tttgtaattt tggcaagttt ttaccctcta | 300 |
| ttttcttatc tataaaatat agattttata tatatagata tagatatata gatagataat | 360 |
| aattgtgcat gcctaataaa gttgtcaaag attaaatgtt atatgtgaag tattttgtac | 420 |
| ggtgatagga acccaggaag ggctctatga atattatgta ttattattat tctaaagtag | 480 |
| ctggaataca atgttcaaag gagatagtgg caggagataa gtttgaattg aaagattgag | 540 |
| gccagaacat aaagtgcctc ctatattata ttttacataa ttggaacatc attgaaaaat | 600 |
| ttaagtatta tttatgtgtg tatgtgtgtt ttatataatt aattctagtt catcatttta | 660 |
| aaatatcttt ctgatgtcac tgtgaacaac agatgagaag aagtgaatcc tgagttaagg | 720 |
| agaccagctc tctgattact gccataatcc agggagggta ccataaggat ttcaactgga | 780 |
| agtgaatcca tcatgatgga gaggaaggac agggctgaaa aatacttagg aagtagtatc | 840 |
| agtaggactg gttaagagag agcagaggca ggctacaggg gttggaggtg tcaatcacag | 900 |
| agatagggaa aatgggagga gaagcaggct ttgaaaaagt ggcttgtctt gtaaaattat | 960 |
| gtgctgttaa aacagtacaa gaaattaata tattcaatcc caaaatacag ggacaattct | 1020 |
| ttttgaaaga gttacccaga tagtcttcct tgaagttttc agttaaagaa atttcttgtt | 1080 |
| aacaaataat gtagtcatag aagaaaacac ttaaaacttt attgaataaa gctaataaat | 1140 |
| catttaatat aatttatagg aaattgttac ataacacaca cattcaatac ttttgctaa | 1200 |
| agtataaatt aatggaagga gagcacgcac acagaggttg aattatgttt atgactttat | 1260 |

-continued

| | |
|---|---|
| tagtcaagaa tacaaaattg agtagctaca tcaagcagaa gcacatgctt tacaatccag | 1320 |
| cacagaatcc cttgacatcc aaactcccga aacagacatg taaatacaga tgacattgtc | 1380 |
| agaacaaaat agggtctcac ccgacctata atgttctttt cttgatataa atatgcacat | 1440 |
| gaattgcata cggtcatatg gttccaatta ccattatttc ctctgggctt agctatccat | 1500 |
| ctaaggggaa tttacaccaa cactgtactt ctacttgcaa gaatatatga aagcatagtt | 1560 |
| aacttctggc ttaggacccc aactca | 1586 |

```
<210> SEQ ID NO 45
<211> LENGTH: 1981
<212> TYPE: DNA
<213> ORGANISM: Homo sapiens
<220> FEATURE:
<221> NAME/KEY: misc_feature
<223> OTHER INFORMATION: sequence of STAR45

<400> SEQUENCE: 45
```

| | |
|---|---|
| atggatcata gggtaaataa atttataatt tcttgagaaa gcttcgtact gttttccaag | 60 |
| atggctgtac taatttccat tcctaccaac agtgtacagg gtttcttttt ctccacatcc | 120 |
| tcaccaacac ttatcttcca tcttttttta taatagccct agtaaaatgt gtgaggtgat | 180 |
| atctcattgt ggcattgatt tgcacttctc tgataattag gaatgtttat gattttttca | 240 |
| tgtacctggt tggccttttg tatgatgtag gaaatgtcta ttctgattct ttgcttattt | 300 |
| tttaataagc atagtttttt tcttattttt gagtaggttg agttgcttat atattattat | 360 |
| atgagcccct tacctgatgt atggtttaaa aatattatcc catttgtggg ttctcttaat | 420 |
| tctatcattg cttcttttcc tgtggaaaag ttttaagttt tatgcagtct catttgtgtg | 480 |
| ttttgctttt gttgcctttt ggaataatct acagaaaatc atagctcagg ccaatgtcat | 540 |
| acagtctcct tctatatttc cttgtagtag ttttacattt aaactttaat tttgatttga | 600 |
| tgcttgtata aagagcaaaa taaaagtcaa atttttattct tctgtatgtg atagtcagt | 660 |
| tttgtctaca ccatttattg aaaataattt tctttcttca ctgtgtattt ttagttattt | 720 |
| tatcaaaaaa tcaattgacc acagacacac ggatttattt acaggttcta tatcccttg | 780 |
| tactgtttta catgtctgtt tttatgccat tgctatgctg ttttaattcc tatagctttg | 840 |
| taatagagtt tggagtcagg tagtctgatg cctccagctt tgttcttttt gttcaagatt | 900 |
| gctttggttg gtccaggtct tttgtggttc catacaaatt ttagcagtaa tttttctatt | 960 |
| tctgtgaaga atgacattgg aatttgatag tggttgcatt taatctgtag attgctttgg | 1020 |
| gtagcattga cactttttaca atactaattt ttgaatccat caatgaagga tgtttctcca | 1080 |
| tttatttatg ccattttaat ttttttcatc aatgtgctat agtttttcagt atgtaaatct | 1140 |
| tttatggttt tgattaaatt tactcctgtc ttttatatat ttatatatct gttttgattc | 1200 |
| tattataaat tgaattgcct ttattttttca ggtaatagtt tgtcattagt taatagaaac | 1260 |
| aataatgata tttgtatgtt gattttgtaa ctattaactt tattgaattt cttcatcagc | 1320 |
| tataaccatt tattttggtg gaatctttaa gattttctct atcttaagat tatatttttca | 1380 |
| aaaaacagaa acaatcttac ctcttccttc cctatgtgga tttctttac gtctttgtct | 1440 |
| tgtgtaactg ttctggctag gcaattacac ataatgtttt catcatttat aattttacat | 1500 |
| cacatccatc tattgtggca cattgattgc tacttttcaa gttgtaaacc tggacattta | 1560 |
| tcactactct tcctccaata caggagtcca tggcgtggtg tgggccctac tgtgccacag | 1620 |
| tccagggcac ggctgggctg aggttctctt gtgcaagagt ccgtggctct gcggagcaag | 1680 |

-continued

| | |
|---|---|
| agttctccag tgccttagtc cagggttagg caggggtggg gctccttcag tagcttagtc | 1740 |
| cagtgcgccg ccctgcgagg gtcctcctga gcaggagtac acgatgaggc agggtcctac | 1800 |
| tgtgccttag cccaggaagc gggggggctgg gtcctctggt gccatagtcc aggctgccgg | 1860 |
| gagctgggtc ctctggtgcc atagctcagg ccggcgggag ctgggtcctc tggtgccgta | 1920 |
| gtccagggtg cagcagaaca ggagtcctgc ggagcagtag tccagggcac gctggggcgt | 1980 |
| g | 1981 |

<210> SEQ ID NO 46
<211> LENGTH: 1859
<212> TYPE: DNA
<213> ORGANISM: Homo sapiens
<220> FEATURE:
<221> NAME/KEY: misc_feature
<223> OTHER INFORMATION: sequence of STAR46

<400> SEQUENCE: 46

| | |
|---|---|
| attgttttc tcgcccttct gcattttctg caaattctgt tgaatcattg cagttactta | 60 |
| ggtttgcttc gtctccccca ttacaaacta cttactgggt ttttcaaccc tagttccctc | 120 |
| attttttatga tttatgctca tttctttgta cacttcgtct tgctccatct cccaactcat | 180 |
| ggcccctggc tttggattat tgtttttggtc ttttattttt tgtcttcttc tacctcaaca | 240 |
| cttatcttcc tctcccagtc tccggtaccc tatcaccaag gttgtcatta acctttcata | 300 |
| ttattcctca ttatccatgt attcatttgc aaataagcgt atattaacaa atcacaggt | 360 |
| ttatggagat ataattcaca taccttaaaa ttcaggcttt taaagtgtac ctttcatgtg | 420 |
| gttttttggta tattcacaaa gttatgcatt gatcaccacc atctgattcc ataacatgtt | 480 |
| caatacctca aaaagaagtc tgtactcatt agtagtcatt tcacattcac cactccctct | 540 |
| ggctctgggc agtcactgat ctttgtgtct ctatggattt gcctagtcta ggtatttta | 600 |
| tgtaaatggc atcatacaac atgtgacctt tgtttggct tttttcattt agcaaaatgt | 660 |
| tatcaaggtc tgtccctgtt gtagcatgta ttagcacttc atttcttata tgctgaatga | 720 |
| tatactttat ttgtccatca gttgttcatg ctttatttgt ccatcagttg atgaacattt | 780 |
| gcgttttgc cactttgggc tattaagaat aatgctactg tgaacaagtg tgtacaagtt | 840 |
| cctctacaaa ttttgtgtg gacatatcct ttcagttctc tcaggtgtat atctgggaat | 900 |
| tgaattgctg ggtcgtgtag tagctatgtt aaacactttg agaaactgct ataatgttct | 960 |
| ccagagctgt accattttaa attctgtgta tgaggattcc acgttctcca cttcctcacc | 1020 |
| agtgtatgga tttgggggta tacttttaa aagtgggat taggctgggc acagtggctc | 1080 |
| acacctgtaa tcccaacact tcaggaagct gaggtgggag gatcacttga gcctagtagt | 1140 |
| ttgagaccag cctgggcaac atagggagac cctgtctcta caaaaaataa tttaaaataa | 1200 |
| attagctggg cgttgtggca cacacctgta gtcccagcta catgggaggc tgaggtggaa | 1260 |
| ggattccctg agcccagaag tttgaggttg cagtgagcca tgatggcagc actatactgt | 1320 |
| agcctgggtg tcagagcaag actccgtttc agggaagaaa aaaaaagtg ggatgatatt | 1380 |
| tttgacactt ttcttcttgt tttcttaatt tcatacttct ggaaattcca ttaaattagc | 1440 |
| tggtaccact ctaactcatt gtgtttcatg gctgcatagt aatattgcat aatataaata | 1500 |
| taccattcat tcatcaaagt tagcagatat tgactgttag gtgccaggca ctgctctaag | 1560 |
| cgttaaagaa aaacacacaa aaactttgc attcttagag tttattttcc aatgagggg | 1620 |
| gtggagggag gtaagaattt aggaaataaa ttaattacat atatagcata gggtttcacc | 1680 |

```
agtgagtgca gcttgaatcg ttggcagctt tcttagtagt ataaatacag tactaaagat    1740
gaaattactc taaatggtgt tacttaaatt actggaatag gtattactat tagtcacttt    1800
gcaggtgaaa gtggaaacac catcgtaaaa tgtaaaatag gaaacagctg gttaatgtt     1859
```

<210> SEQ ID NO 47
<211> LENGTH: 1082
<212> TYPE: DNA
<213> ORGANISM: Homo sapiens
<220> FEATURE:
<221> NAME/KEY: misc_feature
<223> OTHER INFORMATION: sequence of STAR47

<400> SEQUENCE: 47

```
atcattagtc attagggaaa tgcaaatgaa aaacacaagc agccaccaat atacacctac      60
taggatgatt taaaggaaaa taagtgtgaa gaaggacgta aagaaattgt aaccctgata     120
cattgatggt agaaatggat aaagttgcag ccactgtgaa aaacagtctg cagtggctca     180
gaaggttaaa tatagaaccc ctgttggacc caggaactct actcttaggc accccaaaga     240
atagagaaca gaaatcaaac agatgtttgt atactaatgt ttgtagcatc acttttcaca     300
ggagccaaaa ggtggaaata atccaaccat cagtgaacaa atgaatgtaa taaaagcaag     360
gtggtctgca tgcaatgcta catcatccat ctgtaaaaaa cgaacatcat tttgatagat     420
gatacaacat gggtggacat tgagaacatt atgcttagtg aaataagcca gacacaaaag     480
gaatatattg tataattgta attacatgaa gtgcctagaa tagtcaaatt catacaagag     540
aaagtgggat aggaatcacc atgggctgga ataggggga aggtgctata ctgcttattg      600
tggacaaggt ttcgtaagaa atcatcaaaa ttgtgggtgt agatagtggt gttggttatg     660
caaccctgtg aatatattga atgccatgga gtgcacactt tggttaaaag gttcaaatga     720
taaatattgt gttatatata tttccccacg atagaaaaca cgcacagcca gcccacatg      780 ccagtcttgt tagctgcctt cctttacctt caagagtggg ctgaagcttg tccaatcttt     840
caaggttgct gaagactgta tgatggaagt catctgcatt gggaagaaa ttaatggaga      900 gaggagaaaa cttgagaatc cacactactc accctgcagg gccaagaact ctgtctccca     960
tgctttgctg tcctgtctca gtatttcctg tgaccacctc cttttttcaac tgaagacttt   1020 gtacctgaag gggttcccag gttttttcacc tcggcccttg tcaggactga tcctctcaac   1080
ta                                                                   1082
```

<210> SEQ ID NO 48
<211> LENGTH: 1242
<212> TYPE: DNA
<213> ORGANISM: Homo sapiens
<220> FEATURE:
<221> NAME/KEY: misc_feature
<223> OTHER INFORMATION: sequence of STAR48

<400> SEQUENCE: 48

```
atcatgtatt tgttttctga attaattctt agatacatta atgttttatg ttaccatgaa      60
tgtgatatta taatataata tttttaattg gttgctactg tttataagaa tttcattttc     120
tgtttacttt gccttcatat ctgaaaacct tgctgatttg attagtgcat ccacaaattt     180
tcttggattt tctatgggta attacaaatc tccacacaat gaggttgcag tgagccaaga     240
tcacaccact gtactccagc ctgggcgaca gagtgagaca ccatctcaca aaacacata      300 aacaaacaaa cagaaactcc acacaatgac aacgtatgtg ctttctttt tcttcctct      360 ttctataata tttctttgtc ctatcttaac tgaactggcc agaaaccccca ggacaatgat    420
```

```
aaatacgagc agtgtcaaca gacatctcat tccctttcct agcttttata aaaataacga    480
ttatgcttca acattacata tggtggtgtc gatggttttg ttatagataa gcttatcagg    540
ttaagaaatt tgtctgcgtt tcctagtttg gtataaagat tttaatataa atgaatgttg    600
tattttatca tcttattttt ttcctacatc tgctaaggta atcctgtgtt ttccccttt    660 caatctccta atgtggtgaa tgacattaaa ataccttcta ttgttaaaat attcttgcaa    720
cgctgtatag aaccaatgcc tttattctgt attgctgatg gattttgaa aaatatgtag    780 gtggacttag ttttctaagg ggaatagaat ttctaatata tttaaaatat tttgcatgta    840
tgttctgaag gacattggtg tgtcatttct ataccatctg gctactagag gagccgactg    900
aaagtcacac tgccggagga ggggagaggt gctcttccgt ttctggtgtc tgtagccatc    960
tccagtggta gctgcagtga taataatgct gcagtgccga cagttctgga aggagcaaca   1020
acagtgattt cagcagcagc agtattgcgg gatccccacg atggagcaag ggaaataatt   1080
ctggaagcaa tgacaatatc agctgtggct atagcagctg agatgtgagt tctcacggtg   1140
gcagcttcaa ggacagtagt gatggtccaa tggcgcccag acctagaaat gcacatttcc   1200
tcagcaccgg ctccagatgc tgagcttgga cagctgacgc ct                      1242

<210> SEQ ID NO 49
<211> LENGTH: 1015
<212> TYPE: DNA
<213> ORGANISM: Homo sapiens
<220> FEATURE:
<221> NAME/KEY: misc_feature
<223> OTHER INFORMATION: sequence of STAR49

<400> SEQUENCE: 49
aaaccagaaa cccaaaacaa tgggagtgac atgctaaaac cagaaaccca aaacaatggg     60
agggtcctgc taaccagaaa acccaaaaca atgggagtga agtgctaaaa ccagaaaccc    120
aaaacaatgg gagtgtcctg ctacaccaga acccaaaaac gatgggagtg acgtgataaa    180
accagacacc caaaacaatg ggagtgacgt gctaaaccag aaacccaaaa caatgggagt    240
gacgtgctaa aacctggaaa cctaaaacaa tgcgagtgag gtgctaacac cagaatccat    300
aacaatgtga gtgacgtgct aaaccagaac ccaaaacaat gggagtgacg tgctaaaaca    360
ggaacccaaa acaatgagag tgacgtgcta aaccagaaac ccaaaacaat gggaatgacg    420
tgctaaaacc ggaacccaaa acaatgggag tgatgtgcta aaccagaaac ccaaaacaat    480
gggaatgaca tgctaaaact ggaacccaaa acaatggtaa ctaagagtga tgctaaggcc    540
ctacattttg gtcacactct caactaagtg agaacttgac tgaaaggag gatttttttt    600 tctaagacag agttttggtc tgtcccccag agtggagtgc agtggcatga tctcggctca    660
ctgcaagctc tgcctcccgg gttcaggcca ttctcctgcc tcagcctcct gagtagctgg    720
gaatacaggc acccgccacc acacttggct aattttttgt attttttagta gagatggggt    780 ttcaccatat tagcaaggat ggtctcaatc tcctgacctc gtgatctgcc cacctcaggc    840
tcccaaagtg ctgggattac aggtgtgagc caccacaccc agcaaaaagg aggaatttt    900 aaagcaaaat tatgggaggc cattgttttg aactaagctc atgcaatagg tcccaacaga    960
ccaaaccaaa ccaaaccaaa atggagtcac tcatgctaaa tgtagcataa tcaaa        1015

<210> SEQ ID NO 50
<211> LENGTH: 2355
<212> TYPE: DNA
<213> ORGANISM: Homo sapiens
```

<220> FEATURE:
<221> NAME/KEY: misc_feature
<223> OTHER INFORMATION: sequence of STAR50

<400> SEQUENCE: 50

| | | | | | |
|---|---|---|---|---|---|
| caaccatcgt | tccgcaagag | cggcttgttt | attaaacatg | aaatgaggga | aaagcctagt | 60 |
| agctccattg | gattgggaag | aatggcaaag | agagacaggc | gtcattttct | agaaagcaat | 120 |
| cttcacacct | gttggtcctc | acccattgaa | tgtcctcacc | caatctccaa | cacagaaatg | 180 |
| agtgactgtg | tgtgcacatg | cgtgtgcatg | tgtgaaagta | tgagtgtgaa | tgtgtctata | 240 |
| tgggaacata | tatgtgattg | tatgtgtgta | actatgtgtg | actggcagcg | tggggagtgc | 300 |
| tggttggagt | gtggtgtgat | gtgagtatgc | atgagtggct | gtgtgtatga | ctgtggcggg | 360 |
| aggcggaagg | ggagaagcag | caggctcagg | tgtcgccaga | gaggctggga | ggaaactata | 420 |
| aacctgggca | atttcctcct | catcagcgag | cctttcttgg | gcaatagggg | cagagctcaa | 480 |
| agttcacaga | gatagtgcct | gggaggcatg | aggcaaggcg | gaagtactgc | gaggaggggc | 540 |
| agagggtctg | acacttgagg | ggttctaatg | ggaaaggaaa | gacccacact | gaattccact | 600 |
| tagccccaga | ccctgggccc | agcggtgccg | gcttccaacc | ataccaacca | tttccaagtg | 660 |
| ttgccggcag | aagttaacct | ctcttagcct | cagtttcccc | acctgtaaaa | tggcagaagt | 720 |
| aaccaagctt | accttcccgg | cagtgtgtga | ggatgaaaag | agctatgtac | gtgatgcact | 780 |
| tagaagaagg | tctagggtgt | gagtggtact | cgtctggtgg | gtgtggagaa | gacattctag | 840 |
| gcaatgagga | ctggggagag | cctggcccat | ggcttccact | cagcaaggtc | agtctcttgt | 900 |
| cctctgcact | cccagccttc | cagagaggac | cttcccaacc | agcactcccc | acgctgccag | 960 |
| tcacacatag | ttacacacat | acaatcacat | atatgttccc | atatagacac | attcacactc | 1020 |
| ataccttcac | acatgcacac | gcatgtgcac | acacagtcac | tcatttctgt | gttggagatt | 1080 |
| gggtgaggac | attcaatggg | tgaggaccaa | caggtgtgaa | gattgctttc | tagaaaatga | 1140 |
| ctcctgtctc | tctttgccat | tcttcccaat | ccgatggagc | tactaggctt | ttccctcatt | 1200 |
| tcatgtttaa | taaaccttcc | caatggcgaa | atgggctttc | tcaagaagtg | gtgagtgtcc | 1260 |
| catccctgcg | gtggggacag | gggtggcagc | ggacaagcct | gcctggaggg | aactgtcagg | 1320 |
| ctgattccca | gtccaactcc | agcttccaac | acctcatcct | ccaggcagtc | ttcattcttg | 1380 |
| gctctaattt | cgctcttgtt | ttcttttta | tttttatcga | gaactgggtg | gagagctttt | 1440 |
| ggtgtcattg | gggattgctt | tgaaacccTT | ctctgcctca | cactgggagc | tggcttgagt | 1500 |
| caactggtct | ccatggaatt | tctttttta | gtgtgtaaac | agctaagttt | taggcagctg | 1560 |
| ttgtgccgtc | cagggtggaa | agcagcctgt | tgatgtggaa | ctgcttggct | cagatttctt | 1620 |
| gggcaaacag | atgccgtgtc | tctcaactca | ccaattaaga | agcccagaaa | atgtggcttg | 1680 |
| gagaccacat | gtctggttat | gtctagtaat | tcagatggct | tcacctggga | agccctttct | 1740 |
| gaatgtcaaa | gccatgagat | aaaggacata | tatatagtag | ctagggtggt | ccacttctta | 1800 |
| ggggccatct | ccggaggtgg | tgagcactaa | gtgccaggaa | gagaggaaac | tctgttttgg | 1860 |
| agccaaagca | taaaaaaacc | ttagccacaa | accactgaac | atttgttttg | tgcaggttct | 1920 |
| gagtccaggg | agggcttctg | aggagagggg | cagctggagc | tggtaggagt | tatgtgagat | 1980 |
| ggagcaaggg | cccctttaaga | ggtgggagca | gcatgagcaa | aggcagagag | gtggtaatgt | 2040 |
| ataaggtatg | tcatgggaaa | gagtttggct | ggaacagagt | ttacagaata | gaaaaattca | 2100 |
| acactattaa | ttgagcctct | actacgtgct | cgacattgtt | ctagtcactg | agataggttt | 2160 |
| ggtatacaaa | acaaaatcca | tcctctatgg | acattttagt | gactaacaac | aatataaata | 2220 |

| | |
|---|---:|
| ataaaagtga acaaaagctc aaaacatgcc aggcactatt atttatttat ttatttattt | 2280 |
| atttatttat tttttgaaac agagtctcgc tctgttgccc aggctggagt gtagtggtgc | 2340 |
| gatctcggct cactg | 2355 |

<210> SEQ ID NO 51
<211> LENGTH: 2289
<212> TYPE: DNA
<213> ORGANISM: Homo sapiens
<220> FEATURE:
<221> NAME/KEY: misc_feature
<223> OTHER INFORMATION: sequence of STAR51

<400> SEQUENCE: 51

| | |
|---|---:|
| tcacaggtga caccaatccc ctgaccacgc tttgagaagc actgtactag attgactttc | 60 |
| taatgtcagt cttcattttc tagctctgtt acagccatgg tctccatatt atctagtaca | 120 |
| acacacatac aaatatgtgt gatacagtat gaatataata taaaaatatg tgttataata | 180 |
| taaatataat attaaaatat gtctttatac tagataataa tacttaataa cgttgagtgt | 240 |
| ttaactgctc taagcacttt acctgcagga aacagttttt tttttatttt ggtgaaatac | 300 |
| aactaacata aatttattta caattttaag cattttaagg tgtatagttt agtggagtta | 360 |
| atatattcaa aatgttgtgc agccgtcacc atcatcagtc ttcataactc ttttcatatt | 420 |
| gtaaaattaa aagtttatgc tcatttaaaa atgactccca atttcccccc tcctcaacct | 480 |
| ctggaaacta ccattctatt ttctgcctcc gtagttttgc ccactctaag tacctcacat | 540 |
| aagtggaatt tgtcttattt gcctgtttgt gaccggctga tttcatttag tataatgtcc | 600 |
| tcaagtttta ttcacgttat atagcatatg tcataatttt cttcacttt aagcttgagt | 660 |
| aatatttcat cgtatgtatc tcacattttg cttatccatt catctctcag tggacacttg | 720 |
| agttgcttct acattttagc tgttgtgaat actgctgcta tgaacatggg tgtataaata | 780 |
| tctcaagacc ttttatcag ttttttaaaa tatatactca gtagtagttt agctggatta | 840 |
| tatggtaatt ttattttaa tttttgagga actgtcctac ccttttattc aatagtagct | 900 |
| ataccaattg acaattggca ttcctaccaa cagggcataa gggttctcaa ttctccacat | 960 |
| attccctgat acttgttatt ttcaggtgtt ttttttttt tttttttttt atgggagcca | 1020 |
| tgttaatggg tgtaaggtga tatttcatta tagttttgat ttgcatttcc ctaatgatta | 1080 |
| gtgatgttaa gcatctcttc atgtgcctat tggccatttg tatatcttct ttaaaaatat | 1140 |
| atatatactc attcctttgc ccattttga attatgttta ttttttgtta ttgagtttca | 1200 |
| atacttttct atataaccta ggtattaatc ctttatcaga cttaagattt gcaaatattc | 1260 |
| tctttcattc cacaggttgc taattctctc tgttggtaat atcttttgat gctgttgtgt | 1320 |
| ccagaattga ttcattcctg tgggttcttg gtctcactga cttcaagaat aaagctgcgg | 1380 |
| accctagtgg tgagtgttac acttcttata gatggtgttt ccggagtttg ttccttcaga | 1440 |
| tgtgtccaga gtttcttcct tccaatgggt tcatggtctt gctgacttca ggaatgaagc | 1500 |
| cgcagacctt cgcagtgagg tttacagctc ttaaaggtgg cgtgtccaga gttgtttgtt | 1560 |
| cccctggtg ggttcgtggt cttgctgact tcaggaatga agccgcagac cctcgcagtg | 1620 |
| agtgttacag ctcataaagg tagtgcggac acagagtgag ctgcagcaag atttactgtg | 1680 |
| aagagcaaaa gaacaaagct tccacagcat agaaggacac cccagcgggt tcctgctgct | 1740 |
| ggctcaggtg gccagttatt attccctat ttgccctgcc cacatcctgc tgattggtcc | 1800 |
| attttacaga gtactgattg gtccatttta cagagtgctg attggtgcat ttacaatcct | 1860 |

```
ttagctagac acagagtgct gattgctgca ttcttacaga gtgctgattg gtgcatttac    1920
agtcctttag ctagatacag aacgctgatt gctgcgtttt ttacagagtg ctgattggtg    1980
catttacaat cctttagcta gacacagtgc tgattggtgg gttttttacag agtgctgatt    2040 ggtgcgtctt tacagagtgc tgattggtgc atttacaatc ctttagctag acacagagtg    2100
ctgattggtg cgtttataat cctctagcta gacagaaaag ttttccaagt ccccacctga    2160
ccgagaagcc ccactggctt cacctctcac tgttatactt tggacatttg tcccccaaa     2220 atctcatgtt gaaatgtaac ccctaatgtt ggaactgagg ccagactgga tgtggctggg    2280
ccatgggga                                                            2289
```

<210> SEQ ID NO 52
<211> LENGTH: 1184
<212> TYPE: DNA
<213> ORGANISM: Homo sapiens
<220> FEATURE:
<221> NAME/KEY: misc_feature
<223> OTHER INFORMATION: sequence of STAR52

<400> SEQUENCE: 52

```
ctcttctttg tttttttatt ttggggtgtg tgggtacgtg taagatgaga aatgtacaaa      60
cacaagtatt tcagaaactc caagtaatat tctgtctgtg agttcacggt aaataaataa     120
aaagggcaaa gtgacagaaa tacaggatta ttaaaagcaa ataatgttc tttgaaatcc     180 cccccttggt gtatttttta tcttaggatg cagcactttc agcatgccca agtattgaaa     240
gcagtgtttt tacgctacca cggtaatttt atttagaaac cccatgttca cttttagttt     300
taaaatggtc tttatgacat aaaattatca gcattcatat ttttgtgttt taatattcct     360
ttggctactt attgaaacag taaacattac gaaaattagt aaacaaatct ttgatagttg     420 cttattttg tttaattgaa tgtttatttt attaggtaaa tatacaatca aatttattta     480
aaaataatga ggaaaagaat acttttcttt cgctttgcga aagcaaagtg attttttcatt    540 cttctccgtc cgattccttc tcttccagct gccacagccg actgacaggc tcccggcggc    600
ctgaggagta gtatgcaaat tttggatgat tgacacctac agtagaagcc aatcacgtca    660
aagtaggatg ctgattggtt gacaacaata ggcgtaaacc ttgacgtttt aaaaacctga   720
cacccaatcc aggcgattca tgcaaataaa ggaagggagt cacattacca ggggccagag     780
agacttgagt acgacctcac gtgttcagtg gtggatattg cacagacgtc tgcaaggtct     840
atataaacgc tacataatgt tcaactcaat tgcttgcctt ggccttcccc aaaacttgtca   900 ctggaatata aattatccct ttttaaaaa taaaaaaata agaattatgt agtgcacata      960
tatgatggtt catgtagaaa tctaaatgga cttccaacgc atggaatttt cctatttccc    1020 cctttctttta aattaatcct cagtgaagga ggctgttttc ccctagattt caaaaggacg    1080
agatttacag agccttttcct tggagaaacc cgctctaggc acagatggtc agtaaattta    1140
gcttcttcag cgaagttcca catggcaccg ccagatggca taag                     1184
```

<210> SEQ ID NO 53
<211> LENGTH: 1431
<212> TYPE: DNA
<213> ORGANISM: Homo sapiens
<220> FEATURE:
<221> NAME/KEY: misc_feature
<223> OTHER INFORMATION: sequence of STAR53

<400> SEQUENCE: 53

```
cctgaggaa gatgacgagt aactccgtaa gagaaccttc cactcatccc ccacatccct    60
gcagacgtgc tattctgtta tgatactggt atcccatctg tcacttgctc cccaaatcat   120
tcccttctta caattttcta ctgtacagca ttgaggctga acgatgagag atttcccatg   180
ctctttctac tccctgccct gtatatatcc ggggatcctc cctacccagg atgctgtggg   240
gtcccaaacc ccaagtaagc cctgatatgc gggccacacc tttctctagc ctaggaattg   300
ataacccagg cgaggaagtc actgtggcat gaacagatgg ttcacttcga ggaaccgtgg   360
aaggcgtgtg caggtcctga gatagggcag aatcggagtg tgcagggtct gcaggtcagg   420
aggagttgag attgcgttgc cacgtggtgg gaactcactg ccacttattt ccttctctct   480
tcttgcctca gcctcaggga tacgacacat gcccatgatg agaagcagaa cgtggtgacc   540
tttcacgaac atgggcatgg ctgcggaccc ctcgtcatca ggtgcatagc aagtgaaagc   600
aagtgttcac aacagtgaaa agttgagcgt catttttctt agtgtgccaa gagttcgatg   660
ttagcgttta cgttgtattt tcttacactg tgtcattctg ttagatacta acattttcat   720
tgatgagcaa gacatactta atgcatattt tggtttgtgt atccatgcac ctaccttaga   780
aaacaagtat tgtcggttac ctctgcatgg aacagcatta ccctcctctc tccccagatg   840
tgactactga gggcagttct gagtgtttaa tttcagattt tttcctctgc atttacacac   900
acacgcacac aaaccacacc acacacacac acacacacac acacacacac   960
acacaccaag taccagtata agcatctgcc atctgctttt cccattgcca tgcgtcctgg  1020
tcaagctccc ctcactctgt ttcctggtca gcatgtactc ccctcatccg attccctgt   1080 agcagtcact gacagttaat aaaccttttgc aaacgttccc cagttgtttg ctcgtgccat  1140
tattgtgcac acagctctgt gcacgtgtgt gcatatttct ttaggaaaga ttcttagaag  1200
tggaattgct gtgtcaaagg agtcatttat tcaacaaaac actaatgagt gcgtcctcgt  1260
gctgagcgct gttctaggtg ctggagcgac gtcagggaac aaggcagaca ggagttcctg  1320 accccegttc tagaggagga tgtttccagt tgttgggttt tgtttgtttg tttcttctag  1380
agatggtggt cttgctctgt ccaggctaga gtgcagtggc atgatcatag c            1431
```

<210> SEQ ID NO 54
<211> LENGTH: 975
<212> TYPE: DNA
<213> ORGANISM: Homo sapiens
<220> FEATURE:
<221> NAME/KEY: misc_feature
<223> OTHER INFORMATION: sequence of STAR54

<400> SEQUENCE: 54

```
ccataaaagt gtttctaaac tgcagaaaaa tccccctaca gtcttacagt tcaagaattt    60
tcagcatgaa atgcctggta gattacctga cttttttgc caaaaataag gcacagcagc   120
tctctcctga ctctgacttt ctatagtcct tactgaatta tagtccttac tgaattcatt   180
cttcagtgtt gcagtctgaa ggacacccac attttctctt tgtctttgtc aattctttgt   240
gttgtaaggg caggatgttt aaaagttgaa gtcattgact tgcaaaatga gaaatttcag   300
agggcatttt gttctctaga ccatgtagct tagagcagtg ttcacactga ggttgctgct   360
aatgtttctg cagttcttac caatagtatc atttacccag caacaggata tgatagagga   420
cttcgaaaac cccagaaaat gttttgccat atatccaaag ccctttggga aatggaaagg   480
aattgcgggc tccattttt atatatggat agatagagac caagaaagac caaggcaact   540
ccatgtgctt tacattaata aagtacaaaa tgttaacatg taggaagtct aggcgaagtt   600
```

```
tatgtgagaa ttctttacac taattttgca acattttaat gcaagtctga aattatgtca      660
aaataagtaa aaattttttac aagttaagca gagaataaca atgattagtc agagaaataa      720
gtagcaaaat cttcttctca gtattgactt ggttgctttt caatctctga ggacacagca      780
gtcttcgctt ccaaatccac aagtcacatc agtgaggaga ctcagctgag actttggcta      840
atgttggggg gtccctcctg tgtctcccca ggcgcagtga gcctgcaggc cgacctcact      900
cgtggcacac aactaaatct ggggagaagc aacccgatgc cagcatgatg cagatatctc      960
agggtatgat cggcc                                                       975
```

<210> SEQ ID NO 55
<211> LENGTH: 501
<212> TYPE: DNA
<213> ORGANISM: Homo sapiens
<220> FEATURE:
<221> NAME/KEY: misc_feature
<223> OTHER INFORMATION: sequence of STAR55

<400> SEQUENCE: 55

```
cctgaactca tgatccgccc acctcagcct cctgaagtgc tgggattaca ggtgtgagcc       60
accacaccca gccgcaacac actcttgagc aaccaatgtg tcataaaaga aataaaatgg      120
aaatcagaaa gtatcttgag acagacaaaa atggaaacac aacataccaa aatttatggg      180
acacagcaaa agcagtttta ggagggaagt ttatagtgat gaatacctac ctcaaaatca      240
ttagcctgat tggatgacac tacagtgtat aaatgaattg aaaaccacat tgtgccccat      300
acatatatac aattttttatt tgttaattaa aaataaaata aaactttaaa aagaagaaa       360 gagctcaaat aaacaaccta actttatacc tcaaggaaat agaagagcca gctaagccca      420
aagttgacag aaggaaaaaa atattggcag aaagaaatga acagagact agaaagacaa       480 ttgaagagat cagcaaaact a                                                501
```

<210> SEQ ID NO 56
<211> LENGTH: 741
<212> TYPE: DNA
<213> ORGANISM: Homo sapiens
<220> FEATURE:
<221> NAME/KEY: misc_feature
<223> OTHER INFORMATION: sequence of STAR56

<400> SEQUENCE: 56

```
acacaggaaa agatcgcaat tgttcagcag agctttgaac cggggatgac ggtctccctc       60
gttgcccggc aacatggtgt agcagccagc cagttatttc tctggcgtaa gcaataccag      120
gaaggaagtc ttactgctgt cgccgccgga gaacaggttg ttcctgcctc tgaacttgct      180
gccgccatga agcagattaa agaactccag cgcctgctcg gcaagaaaac gatggaaaat      240
gaactcctca agaagccgt tgaatatgga cgggcaaaaa agtggatagc gcacgcgccc       300
ttattgcccg gggatgggga gtaagcttag tcagccgttg tctccgggtg tcgcgtgcgc      360
agttgcacgt cattctcaga cgaaccgatg actggatgga tggccgccgc agtcgtcaca      420
ctgatgatac ggatgtgctt ctccgtatac accatgttat cggagagctg ccaacgtatg      480
gttatcgtcg ggtatgggcg ctgcttcgca gacaggcaga acttgatggt atgcctgcga      540
tcaatgccaa acgtgtttac cggatcatgc gccagaatgc gctgttgctt gagcgaaaac      600
ctgctgtacc gccatcgaaa cgggcacata caggcagagt ggccgtgaaa gaaagcaatc      660
agcgatggtg ctctgacggg ttcgagttct gctgtgataa cggagagaga ctgcgtgtca      720
cgttcgcgct ggactgctgt g                                                741
```

<210> SEQ ID NO 57
<211> LENGTH: 1365
<212> TYPE: DNA
<213> ORGANISM: Homo sapiens
<220> FEATURE:
<221> NAME/KEY: misc_feature
<223> OTHER INFORMATION: sequence of STAR57

<400> SEQUENCE: 57

| | | | | | |
|---|---|---|---|---|---|
| tccttctgta | aataggcaaa | atgtatttta | gtttccacca | cacatgttct | tttctgtagg | 60 |
| gcttgtatgt | tggaaatttt | atccaattat | tcaattaaca | ctataccaac | aatctgctaa | 120 |
| ttctggagat | gtggcagtga | ataaaaaagt | tatagtttct | gattttgtgg | agcttggact | 180 |
| ttaatgatgg | acaaaacaac | acattcttaa | atatatattt | catcaaaatt | atagtgggtg | 240 |
| aattatttat | atgtgcattt | acatgtgtat | gtatacataa | atgggcggtt | actggctgca | 300 |
| ctgagaatgt | acacgtggcg | cgaacgaggc | tgggcggtca | gagaaggcct | cccaaggagg | 360 |
| tggctttgaa | gctgagtggt | gcttccacgt | gaaaaggctg | gaaagggcat | tccaagaaaa | 420 |
| ggctgaggcc | agcgggaaag | aggttccagt | gcgctctggg | aacggaaagc | gcacctgcct | 480 |
| gaaacgaaaa | tgagtgtgct | gaaataggac | gctagaaagg | gaggcagagg | ctggcaaaag | 540 |
| cgaccgagga | ggagctcaaa | ggagcgagcg | gggaaggccg | ctgtggagcc | tggaggaagc | 600 |
| acttcggaag | cgcttctgag | cgggtaaggc | cgctgggagc | atgaactgct | gagcaggtgt | 660 |
| gtccagaatt | cgtgggttct | tggtctcact | gacttcaaga | atgaagaggg | accgcggacc | 720 |
| ctcgcggtga | gtgttacagc | tcttaaggtg | gcgcgtctgg | agtttgttcc | ttctgatgtt | 780 |
| cggatgtgtt | cagagtttct | tccttctggt | gggttcgtgg | tctcgctggc | tcaggagtga | 840 |
| agctgcagac | cttcgcggtg | agtgttacag | ctcataaaag | cagggtggac | tcaaagagtg | 900 |
| agcagcagca | agatttattg | caaagaatga | agaacaaag | cttccacact | gtggaagggg | 960 |
| accccagcgg | gttgccactg | ctggctccgc | agcctgcttt | tattctctta | tctgccccca | 1020 |
| cccacatcct | gctgattggt | agagccgaat | ggtctgtttt | gacggcgctg | attggtgcgt | 1080 |
| ttacaatccc | tgcgctagat | acaaaggttc | tccacgtccc | caccagatta | gctagataga | 1140 |
| gtctccacac | aaaggttctc | caaggcccca | ccagagtagc | tagatacaga | gtgttgattg | 1200 |
| gtgcattcac | aaaccctgag | ctagacacag | ggtgatgact | ggtgtgttta | caaaccttgc | 1260 |
| ggtagataca | gagtatcaat | tggcgtattt | acaatcactg | agctaggcat | aaaggttctc | 1320 |
| caggtcccca | ccagactcag | gagcccagct | ggcttcaccc | agtgg | | 1365 |

<210> SEQ ID NO 58
<211> LENGTH: 1401
<212> TYPE: DNA
<213> ORGANISM: Homo sapiens
<220> FEATURE:
<221> NAME/KEY: misc_feature
<223> OTHER INFORMATION: sequence of STAR58

<400> SEQUENCE: 58

| | | | | | |
|---|---|---|---|---|---|
| aagtttacct | tagccctaaa | ttatttcatt | gtgattggca | ttttaggaaa | tatgtattaa | 60 |
| ggaatgtctc | ttaggagata | aggataacat | atgtctaaga | aaattatatt | gaatatattat | 120 |
| tacatgaact | aaaatgttag | aactgaaaaa | aaattattgt | aactccttcc | agcgtaggca | 180 |
| ggagtatcta | gataccaact | ttaacaactc | aactttaaca | acttcgaacc | aaccagatgg | 240 |
| ctaggagatt | cacctattta | gcatgatatc | ttttattgat | aaaaaaatat | aaaacttcca | 300 |

```
ttaaattttt aagctactac aatcctatta aattttaact taccagtgtt ctcaatgcta        360
cataatttaa aatcattgaa atcttctgat tttaactcct cagtcttgaa atctacttat        420
ttttagttac atatatatcc aatctactgc cgctagtaga agaagcttgg aatttgagaa        480
aaaaatcaga cgttttgtat attctcatat tcactaattt attttttaaa tgagtttctg        540
caatgcatca agcagtggca aaacaggaga aaaattaaaa ttggttgaaa agatatgtgt        600
gccaaacaat cccttgaaat tgatgaagt gactaatcct gagttattgt ttcaaatgtg         660
tacctgttta tacaagggta tcacctttga aatctcaaca ttaaatgaaa ttttataagc        720
aatttgttgt aacatgatta ttataaaatt ctgatataac attttttatt acctgtttag        780
agtttaaaga gagaaaagga gttaagaata attacatttt cattagcatt gtccgggtgc        840
aaaaacttct aacactatct tcaaatcttt ttctccattg ccttctgaac atacccactt        900
gggtatctca ttagcactgc aaattcaaca ttttcgattg ctaattttc tccctaaata        960 tttatttgtt ttctcagctt tagccaatgt ttcactattg accatttgct caagtatagt       1020
gacgcttcaa tgaccttcag agagctgttt cagtccttcc tggactactt gcatgcttcc       1080
aacaaaatga agcactcttg atgtcagtca ctcaaataaa tggaaatggg cccatttact       1140
aggaatgtta acagaataaa aagatagacg tgacaccagt tgcttcagtc catctccatt       1200
tacttgctta aggcctggcc atatttctca cagttgatat ggcgcagggc acatgtttaa       1260
atggctgttc ttgtaggatg gtttgactgt tggattcctc atcttccctc tccttaggaa       1320
ggaaggttac agtagtactg ttggctcctg gaatatagat tcataaagaa ctaatggagt       1380
atcatctccc actgctcttg t                                                 1401

<210> SEQ ID NO 59
<211> LENGTH: 866
<212> TYPE: DNA
<213> ORGANISM: Homo sapiens
<220> FEATURE:
<221> NAME/KEY: misc_feature
<223> OTHER INFORMATION: sequence of STAR59

<400> SEQUENCE: 59
gagatcacgc cactgcactc cagcctgggg gacagagcaa gactccatct cagaaacaaa         60
caaacacaca aagccagtca aggtgtttaa ttcgacggtg tcaggctcag gtctcttgac        120
aggatacatc cagcacccgg gggaaacgtc gatgggtggg gtggaatcta ttttgtggcc        180
tcaagggagg gtttgagagg tagtcccgca agcggtgatg gcctaaggaa gcccctccgc        240
ccaagaagcg atattcattt ctagcctgta gccacccaag agggagaatc gggctcgcca        300
cagaccccac aaccccaac ccaccccacc ccaccccctc ccacctcgtg aaatgggctc        360
tcgctccgtc aggctctagt cacaccgtgt ggttttggaa cctccagcgt gtgtgcgtgg        420
gttgcgtggt ggggtggggc cggctgtgga cagaggaggg gataaagcgg cggtgtcccg        480
cgggtgcccg ggacgtgggg cgtgggcgt ggtgggtg gccagagcct tgggaactcg         540
tcgcctgtcg ggacgtctcc cctcctggtc ccctctctga cctacgctcc acatcttcgc        600
cgttcagtgg ggaccttgtg ggtggaagtc accatccctt tggactttag ccgacgaagg        660
ccgggctccc aagagtctcc ccggaggcgg ggccttgggc aggctcacaa ggatgctgac        720
ggtgacggtt ggtgacggtg atgtacttcg gaggcctcgg gccaatgcag aggtatccat        780
ttgacctcgg tgggacaggt cagctttgcg gagtcccgtg cgtccttcca gagactcatc        840
cagcgctagc aagcatggtc ccgagg                                             866
```

```
<210> SEQ ID NO 60
<211> LENGTH: 2067
<212> TYPE: DNA
<213> ORGANISM: Homo sapiens
<220> FEATURE:
<221> NAME/KEY: misc_feature
<223> OTHER INFORMATION: sequence of STAR60
<220> FEATURE:
<221> NAME/KEY: misc_feature
<222> LOCATION: (92)..(92)
<223> OTHER INFORMATION: n can be a, c, g, or t
<220> FEATURE:
<221> NAME/KEY: misc_feature
<222> LOCATION: (293)..(293)
<223> OTHER INFORMATION: n can be a, c, g, or t
<220> FEATURE:
<221> NAME/KEY: misc_feature
<222> LOCATION: (344)..(345)
<223> OTHER INFORMATION: n can be a, c, g, or t
<220> FEATURE:
<221> NAME/KEY: misc_feature
<222> LOCATION: (411)..(411)
<223> OTHER INFORMATION: n can be a, c, g, or t
<220> FEATURE:
<221> NAME/KEY: misc_feature
<222> LOCATION: (460)..(460)
<223> OTHER INFORMATION: n can be a, c, g, or t
<220> FEATURE:
<221> NAME/KEY: misc_feature
<222> LOCATION: (465)..(465)
<223> OTHER INFORMATION: n can be a, c, g, or t
<220> FEATURE:
<221> NAME/KEY: misc_feature
<222> LOCATION: (902)..(902)
<223> OTHER INFORMATION: n can be a, c, g, or t
<220> FEATURE:
<221> NAME/KEY: misc_feature
<222> LOCATION: (906)..(906)
<223> OTHER INFORMATION: n can be a, c, g, or t
<220> FEATURE:
<221> NAME/KEY: misc_feature
<222> LOCATION: (924)..(924)
<223> OTHER INFORMATION: n can be a, c, g, or t
<220> FEATURE:
<221> NAME/KEY: misc_feature
<222> LOCATION: (1522)..(1522)
<223> OTHER INFORMATION: n can be a, c, g, or t
<220> FEATURE:
<221> NAME/KEY: misc_feature
<222> LOCATION: (1590)..(1590)
<223> OTHER INFORMATION: n can be a, c, g, or t
<220> FEATURE:
<221> NAME/KEY: misc_feature
<222> LOCATION: (1601)..(1601)
<223> OTHER INFORMATION: n can be a, c, g, or t
<220> FEATURE:
<221> NAME/KEY: misc_feature
<222> LOCATION: (1647)..(1647)
<223> OTHER INFORMATION: n can be a, c, g, or t
<220> FEATURE:
<221> NAME/KEY: misc_feature
<222> LOCATION: (1677)..(1677)
<223> OTHER INFORMATION: n can be a, c, g, or t
<220> FEATURE:
<221> NAME/KEY: misc_feature
<222> LOCATION: (1777)..(1777)
<223> OTHER INFORMATION: n can be a, c, g, or t

<400> SEQUENCE: 60
agcagtgcag aactggggaa gaagaagagt ccctacacca cttaatactc aaaagtactc      60
gcaaaaaata acaccccctca ccaggtggca tnattactct ccttcattga gaaaattagg    120
aaactggact tcgtagaagc taattgcttt atccagagcc acctgcatac aaacctgcag    180
cgccacctgc atacaaacct gtcagccgac cccaaagccc tcagtcgcac caagcctctg    240
```

```
ctgcacaccc tcgtgccttc acactggccg ttccccaagc ctggggcata ctncccagct      300
ctgagaaatg tattcatcct tcaaagccct gctcatgtgt cctnntcaac aggaaaatct      360
cccatgagat gctctgctat ccccatctct cctgcccat agcttaggca nacttctgtg       420
gtggtgagtc ctgggctgtg ctgtgatgtg ttcgcctgcn atgtntgttc ttccccacaa      480
tgatgggccc ctgaattctc tatctctagc acctgtgctc agtaaaggct tgggaaacca     540
ggctcaaagc ctggcccaga tgccaccttt tccagggtgc ttccgggggc caccaaccag     600
agtgcagcct tctcctccac caggaactct tgcagcccca cccctgagca cctgcacccc     660
attacccatc tttgtttctc cgtgtgatcg tattattaca gaattatata ctgtattctt     720
aatacagtat ataattgtat aattattctt aatacagtat ataattatac aaatacaaaa    780
tatgtgttaa tggaccgttt atgttactgg taaagcttta agtcaacagt gggacattag     840
ttaggttttt ggcgaagtca aaagttatat gtgcattttc aacttcttga ggggtcggta     900
cntctnaccc ccatgttgtt caaggtcaa ctgtctacac atatcatagc taattcacta     960
cagaaatgtt agcttgtgtc actagtatct ccccttctca taagcttaat acacatacct    1020
tgagagagct cttggccatc tctactaatg actgaagttt ttatttatta tagatgtcat    1080
aataggcata aaactacatt acatcattcg agtgccaatt ttgccacctt gaccctcttt   1140
tgcaaaacac caacgtcagt acacatatga agaggaaact gcccgagaac tgaagttcct   1200
gagaccagga gctgcaggcg ttagataaa tatggtgacg agagttacga ggatgacgag    1260
agtaaatact tcatactcag tacgtgccaa gcactgctat aagcgctctg tatgtgtgaa   1320
gtcatttaat cctcacagca tcccacggtg taattatttt cattatcccc atgagggaac   1380
agaaactcag aacggttcaa cacatatgcg agaagtcgca gccggtcagt gagagagcag   1440
gttcccgtcc aagcagtcag accccgagtg cacactctcg accctgtcc agcagactca    1500
ctcgtcataa ggcggggagt gntctgtttc agccagatgc tttatgcatc tcagagtacc   1560
caaaccatga agaatgagg cagtattcan gagcagatgg ngctgggcag taaggctggg    1620
cttcagaata gctggaaagc tcaagtnatg ggacctgcaa gaaaaatcca ttgtttngat   1680
aaatagccaa agtccctagg ctgtaagggg aaggtgtgcc aggtgcaagt ggagctctaa   1740
tgtaaaatcg cacctgagtc tcctggtctt atgagtnctg ggtgtacccc agtgaaaggt   1800
cctgctgcca ccaagtgggc catggttcag ctgtgtaagt gctgagcggc agccggaccg   1860
cttcctctaa cttcacctcc aaaggcacag tgcacctggt tcctccagca ctcagctgcg   1920
aggcccctag ccagggtccc ggccccggc ccccggcagc tgctccagct tccttcccca    1980
cagcattcag gatggtctgc gttcatgtag acctttgttt tcagtctgtg ctccgaggtc   2040
actggcagca ctagccccgg ctcctgt                                       2067
```

<210> SEQ ID NO 61
<211> LENGTH: 1470
<212> TYPE: DNA
<213> ORGANISM: Homo sapiens
<220> FEATURE:
<221> NAME/KEY: misc_feature
<223> OTHER INFORMATION: sequence of STAR61
<220> FEATURE:
<221> NAME/KEY: misc_feature
<222> LOCATION: (130)..(130)
<223> OTHER INFORMATION: n can be a, c, g, or t
<220> FEATURE:
<221> NAME/KEY: misc_feature
<222> LOCATION: (196)..(196)
<223> OTHER INFORMATION: n can be a, c, g, or t
<220> FEATURE:

<221> NAME/KEY: misc_feature
<222> LOCATION: (205)..(205)
<223> OTHER INFORMATION: n can be a, c, g, or t
<220> FEATURE:
<221> NAME/KEY: misc_feature
<222> LOCATION: (220)..(220)
<223> OTHER INFORMATION: n can be a, c, g, or t
<220> FEATURE:
<221> NAME/KEY: misc_feature
<222> LOCATION: (262)..(262)
<223> OTHER INFORMATION: n can be a, c, g, or t
<220> FEATURE:
<221> NAME/KEY: misc_feature
<222> LOCATION: (332)..(332)
<223> OTHER INFORMATION: n can be a, c, g, or t
<220> FEATURE:
<221> NAME/KEY: misc_feature
<222> LOCATION: (856)..(856)
<223> OTHER INFORMATION: n can be a, c, g, or t
<220> FEATURE:
<221> NAME/KEY: misc_feature
<222> LOCATION: (963)..(963)
<223> OTHER INFORMATION: n can be a, c, g, or t
<220> FEATURE:
<221> NAME/KEY: misc_feature
<222> LOCATION: (976)..(976)
<223> OTHER INFORMATION: n can be a, c, g, or t

<400> SEQUENCE: 61

```
cagcccccac atgcccagcc ctgtgctcag ctctgcagcg gggcatggtg ggcagagaca     60
cagaggccaa ggccctgctt cggggacggt gggcctggga tgagcatggc cttggccttc    120
gccgagagtn ctcttgtgaa ggaggggtca ggaggggctg ctgcagctgg ggaggagggc    180
gatggcactg tggcangaag tgaantagtg tgggtgcctn gcaccccagg cacggccagc    240
ctggggtatg gacccggggc cntctgttct agagcaggaa ggtatggtga ggacctcaaa    300
aggacagcca ctggagagct ccaggcagag gnacttgaga ggccctgggg ccatcctgtc    360
tcttttctgg gtctgtgtgc tctgggcctg ggcccttcct ctgctccccc gggcttggag    420
agggctggcc ttgcctcgtg caaaggacca ctctagactg gtaccaagtc tggcccatgg    480
cctcctgtgg gtgcaggcct gtgcgggtga cctgagagcc agggctggca ggtcagagtc    540
aggagaggga tggcagtgga tgccctgtgc aggatctgcc taatcatggt gaggctggag    600
gaatccaaag tgggcatgca ctctgcactc atttctttat tcatgtgtgc ccatcccaac    660
aagcagggag cctggccagg agggccccctg ggagaaggca ctgatgggct gtgttccatt    720
taggaaggat ggacggttgt gagacgggta agtcagaacg ggctgcccac ctcggccgag    780
agggccccgt ggtgggttgg caccatctgg gcctggagag ctgctcagga ggctctctag    840
ggctgggtga ccaggnctgg ggtacagtag ccatgggagc aggtgcttac ctggggctgt    900
ccctgagcag gggctgcatt gggtgctctg tgagcacaca cttctctatt cacctgagtc    960
ccnctgagtg atgagnacac ccttgttttg cagatgaatc tgagcatgga gatgttaagt   1020
ggcttgcctg agccacacag cagatggatg gtgtagctgg gacctgaggg caggcagtcc   1080
cagcccgagg acttcccaag gttgtggcaa actctgacag catgacccca gggaacaccc   1140
atctcagctc tggtcagaca ctgcggagtt gtgttgtaac ccacacagct ggagacagcc   1200
accctagccc caccccttatc ctctcccaaa ggaacctgcc ctttcccttc attttcctct   1260
tactgcattg agggaccaca cagtgtggca gaaggaacat gggttcagga cccagatgga   1320
cttgcttcac agtgcagccc tcctgtcctc ttgcagagtg cgtcttccac tgtgaagttg   1380
ggacagtcac accaactcaa tactgctggg cccgtcacac ggtgggcagg caacggatgg   1440
cagtcactgg ctgtgggtct gcagaggtgg                                     1470
```

<210> SEQ ID NO 62
<211> LENGTH: 1011
<212> TYPE: DNA
<213> ORGANISM: Homo sapiens
<220> FEATURE:
<221> NAME/KEY: misc_feature
<223> OTHER INFORMATION: sequence of STAR62

<400> SEQUENCE: 62

| | | | | | |
|---|---|---|---|---|---|
| agtgtcaaat | agatctacac | aaaacaagat | aatgtctgcc | cattttttcca | aagataatgt | 60 |
| ggtgaagtgg | gtagagagaa | atgcatccat | tctccccacc | caacctctgc | taaattgtcc | 120 |
| atgtcacagt | actgagacca | gggggcttat | tcccagcggg | cagaatgtgc | accaagcacc | 180 |
| tcttgtctca | atttgcagtc | taggccctgc | tatttgatgg | tgtgaaggct | tgcacctggc | 240 |
| atggaaggtc | cgttttgtac | ttcttgcttt | agcagttcaa | agagcaggga | gagctgcgag | 300 |
| ggcctctgca | gcttcagatg | gatgtggtca | gcttgttgga | ggcgccttct | gtggtccatt | 360 |
| atctccagcc | ccctgcggt | gttgctgttt | gcttggcttg | tctggctctc | catgccttgt | 420 |
| tggctccaaa | atgtcatcat | gctgcacccc | aggaagaatg | tgcaggccca | tctcttttat | 480 |
| gtgctttggg | ctattttgat | tccccgttgg | gtatattccc | taggtaagac | ccagaagaca | 540 |
| caggaggtag | ttgctttggg | agagtttgga | cctatgggta | tgaggtaata | gacacagtat | 600 |
| cttctctttc | atttggtgag | actgttagct | ctggccgcgg | actgaattcc | acacagctca | 660 |
| cttgggaaaa | ctttattcca | aaacatagtc | acattgaaca | ttgtggagaa | tgagggacag | 720 |
| agaagaggcc | ctagatttgt | acatctgggt | gttatgtcta | taaatagaat | gctttggtgg | 780 |
| tcaactagac | ttgttcatgt | tgacatttag | tcttgccttt | tcggtggtga | tttaaaaatt | 840 |
| atgtatatct | tgtttggaat | atagtggagc | tatggtgtgg | cattttcatc | tggcttttg | 900 |
| tttagctcag | cccgtcctgt | tatgggcagc | cttgaagctc | agtagctaat | gaagaggtat | 960 |
| cctcactccc | tccagagagc | ggtcccctca | cggctcattg | agagtttgtc | a | 1011 |

<210> SEQ ID NO 63
<211> LENGTH: 1410
<212> TYPE: DNA
<213> ORGANISM: Homo sapiens
<220> FEATURE:
<221> NAME/KEY: misc_feature
<223> OTHER INFORMATION: sequence of STAR63

<400> SEQUENCE: 63

| | | | | | |
|---|---|---|---|---|---|
| ccacagcctg | atcgtgctgt | cgatgagagg | aatctgctct | aagggtctga | gcggagggag | 60 |
| atgccgaagc | tttgagcttt | ttgtttctgg | cttaaccttg | gtggattttc | accctctggg | 120 |
| cattacctct | tgtccagggg | aggggctggg | ggagtgcctg | gagctgtagg | gacagagggc | 180 |
| tgagtggggg | ggactgcttg | ggctgaccac | ataatattct | gctgcgtatt | aatttttttt | 240 |
| tgagacagtc | tttctctgtt | gcccaggctg | gagtgtaatg | gcttgatagc | tcactgccac | 300 |
| ctccgcctcc | tgggttcaag | tgattctcct | gcttcagctt | ccggagtagc | tgggactgca | 360 |
| ggtgcccgcc | accatggctg | gctaattttt | gtatttttat | tagcaatggg | gttttgctat | 420 |
| gttgcccagg | ccggtcccga | actcctgccc | tcaagtgata | cacctgcctc | ggcctcccaa | 480 |
| agtgctggga | ttagaggctt | gagccactgc | gcctggccag | ctgcatattg | ttaattagac | 540 |
| ataaaatgca | aaataagatg | atataaacac | aaaggtgtga | aataagatgg | acacctgctg | 600 |
| agcgcgcctg | tcctgaagca | tcgcccctct | gcaaaagcag | gggtcagcat | gtgttctccg | 660 |

```
gtccttgctc ttacagagga gtgagctgcc tatgcgtctt ccagccactt cctgggctgc     720
tcagaggcct ctcacgggtg ttctgggttg ctgccacttg cagggggtgct gaggcggggc    780 tcctcccgtg cggggcatgt ccaggccgcc ctctctgaag gcttggcagg tacaggtggg     840
agtgggggtc tctgggctgc tgtggggact gggcaggctc ctggaagacc tccctgtgtt     900
tgggctgaaa gcgcagcccg aggggaggtc cccagggagg ccgctgtcgg gggtgggggc     960
ttggaggagg gaggggccga ggagccggcg acactccgtg acggcccagg aacgtcccta    1020
aacaaggcgc cgcgttctcg atggggtggg gtccgctttc ttttctcaaa agctgcagtt    1080
actccatgct cggaggactg gcgtccgcgc cctgttccaa tgctgccccg ggccctggc     1140 cttggggaat cggggccttg gactggaccc tgggggcttc gcggagccgg gcctggcggg    1200
gcgagcggag cagaggctgg gcagccccgg ggaagcgctc gccaaagccg ggcgctgctc    1260
ccagagcgcg aggtgcagaa ccagaggctg gtcccgcggc gctaacgaga gaagaggaag    1320
cgcgctgtgt agagggcgcc caccccgtgg ggcgaaccccc cttcctcaac tccatggacg    1380
gggctcatgg gttcccagcg gctcagacgc                                     1410

<210> SEQ ID NO 64
<211> LENGTH: 1414
<212> TYPE: DNA
<213> ORGANISM: Homo sapiens
<220> FEATURE:
<221> NAME/KEY: misc_feature
<223> OTHER INFORMATION: sequence of STAR64

<400> SEQUENCE: 64
tggatcagat ttgttttata ccctcccttc tactgctctg agagttgtac atcacagtct      60
actgtatctg tttcccatta ttataatttt tttgcactgt gcttgcctga agggagcctc     120
aagttcatga gtctccctac cctcctccca atgagacat ggacctttga atgctttcct     180
gggaccacca ccccacctt catgctgctg ttatccagga ttttagttca acagtgtttt     240
aaccccccaa atgagtcatt tttattgttt cgtatagtga atgtgtattt gggtttgctt     300
atatggtgac ctgtttattt gctcctcatt gtacctcatg ctctgctctt tccttctaga     360
ttcagtctct ttcctaatga ggtgtctcgc agcaattctt tacaagacag ccaagatagg     420
ccagctctca gagcacttgt tgtctgaaaa agtcttgtct tatttaattt cttttttctta    480 gagatggggt ctcattatgt tacccacact ggtctcaaac ttctggctta aagcggtcct     540
cccaccttgg cctcccaaag tgctaggatt acaggcgtga gcgacctcgt ccagcctgtc     600
tgagaaagcg tttgttttgc ccttgctctc agatgacagt tgggggatag aattctaggt     660
ggacggtttt tttccttcag ccccttttgaag agtctgtatt ttcattatct ccctgcatta    720
gatgttcttt tgcaagtaac gtgtcttttc tctctgggta ttcttaaggt tttctctttg     780
cctttggtga gctgcagtgg atttgctttt ttcaagaggt caagagaaag gaaagtgtga    840
ggtttctgtt ttttactgac aatttgtttg ttgatttgtt ttcccaccca gaggttcctt     900
gccactttgc caggctggaa ggcagacttc ttctggtgtc ctgttcacag acggggcagc    960
ctgcggaagg ccctgccaca tgcagggcct cggtcctcat tccccttgcat gtggacccgg    1020 gcgtgactcc tgttcaggct ggcacttccc agagctgagc cccagcctga ccttcctccc    1080
atactgtctt cacacccct cctttcttct gatacctgga ggttttcctt tctttcctgt     1140
cacctccact tggattttaa atcctctgtc tgtggaattg tattcggcac aggaagatgc    1200
ttgcaagggc caggctcatc agccctgtcc ctgctgctgg aagcagcaca gcagagcctc   1260
```

| | |
|---|---|
| atgctcaggc tgagatggag cagaggcctg cagacgagca cccagctcag ctggggttgg | 1320 |
| cgccgatggt ggagggtcct cgaaagctct ggggacgatg cagagctat tggcagggga | 1380 |
| gccgcagggt cttttgagcc cttaaaagat ctct | 1414 |

<210> SEQ ID NO 65
<211> LENGTH: 1310
<212> TYPE: DNA
<213> ORGANISM: Homo sapiens
<220> FEATURE:
<221> NAME/KEY: misc_feature
<223> OTHER INFORMATION: sequence of STAR65

<400> SEQUENCE: 65

| | |
|---|---|
| gtgaatgttg atggatcaaa tatctttctg tgttgtttat caaagttaaa ataaatgtgg | 60 |
| tcatttaaag gacaaaagat gaggggttgg agtctgttca agcaaagggt atattaggag | 120 |
| aaaagcagaa ttctctccct gtgaagggac agtgactcct attttccacc tcatttttac | 180 |
| taactctcct aactatctgc ttaggtagag atatatccat gtacatttat aaaccacagt | 240 |
| gaatcatttg attttggaat aaagatagta taaaatgtgt cccagtgttg atatacatca | 300 |
| tacattaaat atgtctggca gtgttctaat tttacagttg tccaaagata atgttagggc | 360 |
| atactggcta tggatgaagc tccaatgttc agattgcaaa gaaacttaga attttactaa | 420 |
| tgaaaccaaa tacatcccaa gaatttttc agaagaaaaa aagagaaact agtagcaaag | 480 |
| taaagaatca ccacaatatc atcagatttt ttttatatgt agaatattta ttcagttctt | 540 |
| ttttcaagta caccttgtct tcattcattg tactttattt tttgtgaagg tttaaattta | 600 |
| tttcttctat gtgtttagtg atatttaaaa tttttattta atcaagttta tcagaaagtt | 660 |
| ctgttagaaa atatgacgag gctttaattc cgccatctat atttttccgct attatataaa | 720 |
| gataattgtt ttctctttt aaaacaactt gaattgggat tttatatcat aattttttaa | 780 |
| tgtctttttt tattatactt taagttctgg gatacatgtg cagaacgtgc aggtgtgtta | 840 |
| catagatata cacgtgccat ggtggtttgc tgcacccact aacctgttat cgacattagg | 900 |
| tatttctcct aatgctatca cccctattt ccccaccccc cgagaggccc cagtgtgtga | 960 |
| tgttctcctc cctgtgtcca tgtgttctca ttgttcatct cccacttatg gtatctacca | 1020 |
| taaccttgaa attgtcttat gcattcactt gtttggttgt tatatagcct ccatcaggac | 1080 |
| agggatattt gctgctgctt ctttttttt tcttttgag acagtcttgc tccgtcatcc | 1140 |
| aggctggagt gcttctcggc tcaatgcaac ctccacctcc caggtttaag cgattctcca | 1200 |
| acttcagcct cccaaatggc tgggactgca ggcatgcacc actacacctg ctaattttt | 1260 |
| gtatttgtaa tagagacaat gtttcaccat gttggccagg ctggtctcga | 1310 |

<210> SEQ ID NO 66
<211> LENGTH: 1917
<212> TYPE: DNA
<213> ORGANISM: Homo sapiens
<220> FEATURE:
<221> NAME/KEY: misc_feature
<223> OTHER INFORMATION: sequence of STAR67

<400> SEQUENCE: 66

| | |
|---|---|
| aggatcctaa aatttgtga ccctagagca agtactaact atgaaagtga aatagagaat | 60 |
| gaaggaatta tttaattaag tccagcaaaa cccaaccaaa tcatctgtaa aatatatttg | 120 |
| ttttcaacat ccaggtattt tctgtgtaaa aggttgagtt gtatgctgac ttattgggaa | 180 |
| aaataattga gttttcccct tcactttgcc agtgagagga aatcagtact gtaattgtta | 240 |

```
aaggttaccc ataccacct ctactaccgt ctagcatagg taaagtaatg tacactgtga    300
agtttcctgc ttgactgtaa tgttttcagt ttcatcccat tgattcaaca gctatttatt    360
cagcacttac tacaaccatg ctggaaaccc aagagtaaat aggctgtgtt actcaacagg    420
actgaggtac agccgaactg tcaggcaagg ttgctgtcct ttggacttgc ctgctttctc    480
tctatgtagg aagaagaaat ggacataccg tccaggaaat agatatatgt tacatttcct    540
tattccataa ttaatattaa taaccctgga cagaaactac caagtttcta gacccttata    600
gtaccacctt acccttctg gatgaatcct tcacatgttg atacatttta tccaaatgaa    660
aattttggta ctgtaggtat aacagacaaa gagagaacag aaaactagag atgaagtttg    720
ggaaaaggtc aagaaagtaa ataatgcttc tagaagacac aaaaagaaaa atgaaatggt    780
aatgttggga aagttttaat acattttgcc ctaaggaaaa aaactacttg ttgaaattct    840
acttaagact ggaccttttc tctaaaaatt gtgcttgatg tgaattaaag caacacaggg    900
aaatttatgg gctccttcta agttctaccc aactcaccgc aaaactgttc ctagtaggtg    960
tggtatactc tttcagattc tttgtgtgta tgtatatgtg tgtgtgtgtg tgtgtttgta   1020
tgtgtacagt ctatatacat atgtgtacct acatgtgtgt atatataaat atatatttac   1080
ctggatgaaa tagcatatta tagaatattc ttttttcttt aaatatatat gtgcatacat   1140
atgtatatgc acatatatac ataaatgtag atatagctag gtaggcattc atgtgaaaca   1200
aagaagccta ttactttta atggttgcat gatattccat cataggagta tagtacaact   1260
tatgtaacac acatttggct tgttgtaaaa ttttggtatt aataaaatag cacatatcat   1320
gcaaagacac ccttgcatag gtctattcat tctttgattt ttaccttagg acaaaattta   1380
aaagtagaat ttctgggtca agcagtatgc tcatttaaaa tgtcattgca tatttccaaa   1440
ttgtcctcca gaaaagtagt aacagtaaca attgatggac tgcgtgtttt ctaaaacttg   1500 cattttttc cttattggtg aggtttggca ttttccatat gtttattggc atttttaattt   1560 tttttggttc atgtcttta ttcccttcct gcaaatttgt ggtgtgtctc aactttattt   1620
atactctcat tttcataatt ttctaaagga atttgacttt aaaaaaataa gacagccaat   1680
gctttggttt aatttcattg ctgcttttg aagtgactgc tgtgttttta tacttttta   1740 tattttgttg ttttagcaaa ttcttctata ttataattgt gtatgctgga acaaaaagtt   1800
atatttctta atctagataa aatatttcaa gatgttgtaa ttacagtccc ctctaaaatc   1860
atataaatag acgcatagct gtgtgatttg taattagtta tgtccattga tagatcc       1917
```

<210> SEQ ID NO 67
<211> LENGTH: 26
<212> TYPE: DNA
<213> ORGANISM: Artificial Sequence
<220> FEATURE:
<223> OTHER INFORMATION: Chemically synthesized - oligo for making
      linker containing MCSII of pd2EGFP-link

<400> SEQUENCE: 67
gtacggatat cagatctttta attaag                                        26

<210> SEQ ID NO 68
<211> LENGTH: 24
<212> TYPE: DNA
<213> ORGANISM: Artificial Sequence
<220> FEATURE:
<223> OTHER INFORMATION: Chemically synthesized - oligo for making
      linker containing MCSII of pd2EGFP-link

```
<400> SEQUENCE: 68
gtaccttaat taaagatctg atat                                      24

<210> SEQ ID NO 69
<211> LENGTH: 52
<212> TYPE: DNA
<213> ORGANISM: Artificial Sequence
<220> FEATURE:
<223> OTHER INFORMATION: Chemically synthesized - primer for
      amplification of 0.37 kb from pd2EGFP

<400> SEQUENCE: 69
gatcagatct ggcgcgccat ttaaatcgtc tcgcgcgttt cggtgatgac gg        52

<210> SEQ ID NO 70
<211> LENGTH: 41
<212> TYPE: DNA
<213> ORGANISM: Artificial Sequence
<220> FEATURE:
<223> OTHER INFORMATION: Chemically synthesized - primer for
      amplification of 0.37 kb from pd2EGFP

<400> SEQUENCE: 70
aggcggatcc gaatgtattt agaaaaataa acaaataggg g                   41

<210> SEQ ID NO 71
<211> LENGTH: 36
<212> TYPE: DNA
<213> ORGANISM: Artificial Sequence
<220> FEATURE:
<223> OTHER INFORMATION: Chemically synthesized - primer for amplifying
      zeocin resistance gene ORF

<400> SEQUENCE: 71
gatcggatcc ttcgaaatgg ccaagttgac cagtgc                         36

<210> SEQ ID NO 72
<211> LENGTH: 32
<212> TYPE: DNA
<213> ORGANISM: Artificial Sequence
<220> FEATURE:
<223> OTHER INFORMATION: Chemically synthesized - primer for amplifying
      zeocin resistance gene ORF

<400> SEQUENCE: 72
aggcgcggcc gcaattctca gtcctgctcc tc                             32

<210> SEQ ID NO 73
<211> LENGTH: 40
<212> TYPE: DNA
<213> ORGANISM: Artificial Sequence
<220> FEATURE:
<223> OTHER INFORMATION: Chemically synthesized - primer for amplifying
      d2EGFP ORF

<400> SEQUENCE: 73
gatcgaattc tcgcgaatgg tgagcaagca gatcctgaag                     40

<210> SEQ ID NO 74
<211> LENGTH: 52
<212> TYPE: DNA
<213> ORGANISM: Artificial Sequence
<220> FEATURE:
<223> OTHER INFORMATION: Chemically synthesized - primer for amplifying
      d2EGFP ORF

<400> SEQUENCE: 74
```
aggcgaattc accggtgttt aaacttacac ccactcgtgc aggctgccca gg    52

<210> SEQ ID NO 75
<211> LENGTH: 41
<212> TYPE: DNA
<213> ORGANISM: Artificial Sequence
<220> FEATURE:
<223> OTHER INFORMATION: Chemically synthesized - primer for amplifying
      d2EGFP gene

<400> SEQUENCE: 75
ttggttggtc atgaatggtg agcaagggcg aggagctgtt c    41

<210> SEQ ID NO 76
<211> LENGTH: 36
<212> TYPE: DNA
<213> ORGANISM: Artificial Sequence
<220> FEATURE:
<223> OTHER INFORMATION: Chemically synthesized - primer for amplifying
      d2EGFP gene

<400> SEQUENCE: 76
attctctaga ctacacattg atcctagcag aagcac    36

<210> SEQ ID NO 77
<211> LENGTH: 42
<212> TYPE: DNA
<213> ORGANISM: Artificial Sequence
<220> FEATURE:
<223> OTHER INFORMATION: Chemically synthesized - oligo for preparing
      linker for creating MCS in pGL3-promoter-GFP

<400> SEQUENCE: 77
cgatatcttg gagatctact agtggcgcgc cttgggctag ct    42

<210> SEQ ID NO 78
<211> LENGTH: 50
<212> TYPE: DNA
<213> ORGANISM: Artificial Sequence
<220> FEATURE:
<223> OTHER INFORMATION: Chemically synthesized - oligo for preparing
      linker for creating MCS in pGL3-promoter-GFP

<400> SEQUENCE: 78
gatcagctag cccaaggcgc gccactagta gatctccaag atatcgagct    50

<210> SEQ ID NO 79
<211> LENGTH: 40
<212> TYPE: DNA
<213> ORGANISM: Artificial Sequence
<220> FEATURE:
<223> OTHER INFORMATION: Chemically synthesized - primer for
      amplification of EF-1alfa promoter

<400> SEQUENCE: 79
gatcggcgcg ccatttaaat ccgaaaagtg ccacctgacg    40

<210> SEQ ID NO 80
<211> LENGTH: 34
<212> TYPE: DNA
<213> ORGANISM: Artificial Sequence
<220> FEATURE:
<223> OTHER INFORMATION: Chemically synthesized - primer for
      amplification of EF-1alfa promoter

<400> SEQUENCE: 80
aggcgggacc ccctcacgac acctgaaatg gaag        34

<210> SEQ ID NO 81
<211> LENGTH: 51
<212> TYPE: DNA
<213> ORGANISM: Artificial Sequence
<220> FEATURE:
<223> OTHER INFORMATION: Chemically synthesized - primer for
      amplification of SV40 promoter

<400> SEQUENCE: 81
ttggttgggg cgcgccgcag caccatggcc tgaaataacc tctgaaagag g        51

<210> SEQ ID NO 82
<211> LENGTH: 55
<212> TYPE: DNA
<213> ORGANISM: Artificial Sequence
<220> FEATURE:
<223> OTHER INFORMATION: Chemically synthesized - primer for
      amplification of SV40 promoter

<400> SEQUENCE: 82
ttggttggga gctcaagctt tttgcaaaag cctaggcctc caaaaaagcc tcctc        55

<210> SEQ ID NO 83
<211> LENGTH: 11
<212> TYPE: DNA
<213> ORGANISM: Artificial Sequence
<220> FEATURE:
<223> OTHER INFORMATION: Chemically synthesized - sequence around
      startcodon of wild-type zeocin resistance gene

<400> SEQUENCE: 83
aaaccatggc c        11

<210> SEQ ID NO 84
<211> LENGTH: 50
<212> TYPE: DNA
<213> ORGANISM: Artificial Sequence
<220> FEATURE:
<223> OTHER INFORMATION: Chemically synthesized - primer ZEOforwardMUT

<400> SEQUENCE: 84
gatctcgcga tacaggattt atgttggcca agttgaccag tgccgttccg        50

<210> SEQ ID NO 85
<211> LENGTH: 26
<212> TYPE: DNA
<213> ORGANISM: Artificial Sequence
<220> FEATURE:
<223> OTHER INFORMATION: Chemically synthesized - primer ZEO-WTreverse

<400> SEQUENCE: 85
aggcgaattc agtcctgctc ctcggc        26

<210> SEQ ID NO 86
<211> LENGTH: 45
<212> TYPE: DNA
<213> ORGANISM: Artificial Sequence
<220> FEATURE:
<223> OTHER INFORMATION: Chemically synthesized - primer ZEO-LEUreverse

<400> SEQUENCE: 86
aggccccgcc cccacggctg ctcgccgatc tcggtcaagg ccggc        45

<210> SEQ ID NO 87

```
<211> LENGTH: 45
<212> TYPE: DNA
<213> ORGANISM: Artificial Sequence
<220> FEATURE:
<223> OTHER INFORMATION: Chemically synthesized - primer ZEO-THRreverse

<400> SEQUENCE: 87
aggccccgcc cccacggctg ctcgccgatc tcggtggtgg ccggc            45

<210> SEQ ID NO 88
<211> LENGTH: 44
<212> TYPE: DNA
<213> ORGANISM: Artificial Sequence
<220> FEATURE:
<223> OTHER INFORMATION: Chemically synthesized - primer ZEO-VALreverse

<400> SEQUENCE: 88
aggccccgcc cccacggctg ctcgccgatc tcggtccacg ccgg             44

<210> SEQ ID NO 89
<211> LENGTH: 11
<212> TYPE: DNA
<213> ORGANISM: Artificial Sequence
<220> FEATURE:
<223> OTHER INFORMATION: Chemically synthesized - sequence around
      startcodon of wt d2EGFP

<400> SEQUENCE: 89
gaattcatgg g                                                 11

<210> SEQ ID NO 90
<211> LENGTH: 49
<212> TYPE: DNA
<213> ORGANISM: Artificial Sequence
<220> FEATURE:
<223> OTHER INFORMATION: Chemically synthesized - primer
      d2EGFPforwardBamHI

<400> SEQUENCE: 90
gatcggatcc tatgaggaat cgccaccat ggtgagcaag ggcgaggag         49

<210> SEQ ID NO 91
<211> LENGTH: 41
<212> TYPE: DNA
<213> ORGANISM: Artificial Sequence
<220> FEATURE:
<223> OTHER INFORMATION: Chemically synthesized - primer
      d2EGFPreverseNotI

<400> SEQUENCE: 91
aaggaaaaaa gcggccgcct acacattgat cctagcagaa g                41

<210> SEQ ID NO 92
<211> LENGTH: 57
<212> TYPE: DNA
<213> ORGANISM: Artificial Sequence
<220> FEATURE:
<223> OTHER INFORMATION: Chemically synthesized - spacer sequence

<400> SEQUENCE: 92
tcgatccaaa gactgccaaa tctagatccg agattttcag gagctaagga agctaaa  57

<210> SEQ ID NO 93
<211> LENGTH: 99
<212> TYPE: DNA
<213> ORGANISM: Artificial Sequence
<220> FEATURE:
```

```
<223> OTHER INFORMATION: Chemically synthesized - primer
      ZEOforwardBamHI-ATGmut/space

<400> SEQUENCE: 93
gatcggatcc ttggtttatg tcgatccaaa gactgccaaa tctagatccg agattttcag      60
gagctaagga agctaaagcc aagttgacca gtgaagttc                              99

<210> SEQ ID NO 94
<211> LENGTH: 38
<212> TYPE: DNA
<213> ORGANISM: Artificial Sequence
<220> FEATURE:
<223> OTHER INFORMATION: Chemically synthesized - primer
      ZEOforwardBamHI-GTG

<400> SEQUENCE: 94
gatcggatcc accgtggcca agttgaccag tgccgttc                               38

<210> SEQ ID NO 95
<211> LENGTH: 38
<212> TYPE: DNA
<213> ORGANISM: Artificial Sequence
<220> FEATURE:
<223> OTHER INFORMATION: Chemically synthesized - primer
      ZEOforwardBamHI-TTG

<400> SEQUENCE: 95
gatcggatcc accttggcca agttgaccag tgccgttc                               38

<210> SEQ ID NO 96
<211> LENGTH: 35
<212> TYPE: DNA
<213> ORGANISM: Artificial Sequence
<220> FEATURE:
<223> OTHER INFORMATION: Chemically synthesized - primer BSDBamHIforward

<400> SEQUENCE: 96
gatcggatcc accatggcca agcctttgtc tcaag                                  35

<210> SEQ ID NO 97
<211> LENGTH: 25
<212> TYPE: DNA
<213> ORGANISM: Artificial Sequence
<220> FEATURE:
<223> OTHER INFORMATION: Chemically synthesized - primer BSD150reverse

<400> SEQUENCE: 97
gtaaaatgat atacgttgac accag                                             25

<210> SEQ ID NO 98
<211> LENGTH: 25
<212> TYPE: DNA
<213> ORGANISM: Artificial Sequence
<220> FEATURE:
<223> OTHER INFORMATION: Chemically synthesized - primer BSD150forward

<400> SEQUENCE: 98
ctggtgtcaa cgtatatcat tttac                                             25

<210> SEQ ID NO 99
<211> LENGTH: 24
<212> TYPE: DNA
<213> ORGANISM: Artificial Sequence
<220> FEATURE:
<223> OTHER INFORMATION: Chemically synthesized - primer BSD250reverse
```

```
<400> SEQUENCE: 99
gccctgttct cgtttccgat cgcg                                          24

<210> SEQ ID NO 100
<211> LENGTH: 24
<212> TYPE: DNA
<213> ORGANISM: Artificial Sequence
<220> FEATURE:
<223> OTHER INFORMATION: Chemically synthesized - primer BSD250forward

<400> SEQUENCE: 100
cgcgatcgga aacgagaaca gggc                                          24

<210> SEQ ID NO 101
<211> LENGTH: 24
<212> TYPE: DNA
<213> ORGANISM: Artificial Sequence
<220> FEATURE:
<223> OTHER INFORMATION: Chemically synthesized - primer BSD350reverse

<400> SEQUENCE: 101
gccgtcggct gtccgtcact gtcc                                          24

<210> SEQ ID NO 102
<211> LENGTH: 24
<212> TYPE: DNA
<213> ORGANISM: Artificial Sequence
<220> FEATURE:
<223> OTHER INFORMATION: Chemically synthesized - primer BSD350forward

<400> SEQUENCE: 102
ggacagtgac ggacagccga cggc                                          24

<210> SEQ ID NO 103
<211> LENGTH: 38
<212> TYPE: DNA
<213> ORGANISM: Artificial Sequence
<220> FEATURE:
<223> OTHER INFORMATION: Chemically synthesized - primer BSD399reverse

<400> SEQUENCE: 103
gatcgaattc ttagccctcc cacacgtaac cagagggc                           38

<210> SEQ ID NO 104
<211> LENGTH: 103
<212> TYPE: DNA
<213> ORGANISM: Artificial Sequence
<220> FEATURE:
<223> OTHER INFORMATION: Chemically synthesized - primer
      BSDforwardBamHIAvrII-ATGmut/space

<400> SEQUENCE: 104
gatcggatcc taggttggtt tatgtcgatc caaagactgc caaatctaga tccgagattt   60
tcaggagcta aggaagctaa agccaagcct tgtctcaag aag                      103

<210> SEQ ID NO 105
<211> LENGTH: 44
<212> TYPE: DNA
<213> ORGANISM: Artificial Sequence
<220> FEATURE:
<223> OTHER INFORMATION: Chemically synthesized - primer
      BSD399reverseEcoRIAvrII

<400> SEQUENCE: 105
gatcgaattc cctaggttag ccctcccaca cgtaaccaga gggc                    44
```

<210> SEQ ID NO 106
<211> LENGTH: 42
<212> TYPE: DNA
<213> ORGANISM: Artificial Sequence
<220> FEATURE:
<223> OTHER INFORMATION: Chemically synthesized - primer
      BSDforwardBamHIAvrII-GTG

<400> SEQUENCE: 106
gatcggatcc taggaccgtg gccaagcctt tgtctcaaga ag                          42

<210> SEQ ID NO 107
<211> LENGTH: 42
<212> TYPE: DNA
<213> ORGANISM: Artificial Sequence
<220> FEATURE:
<223> OTHER INFORMATION: Chemically synthesized - primer
      BSDforwardBamHIAvrII-TTG

<400> SEQUENCE: 107
gatcggatcc taggaccttg gccaagcctt tgtctcaaga ag                          42

<210> SEQ ID NO 108
<211> LENGTH: 375
<212> TYPE: DNA
<213> ORGANISM: Artificial Sequence
<220> FEATURE:
<223> OTHER INFORMATION: Chemically synthesized - wt zeocin resistance
      gene
<220> FEATURE:
<221> NAME/KEY: CDS
<222> LOCATION: (1)..(375)

<400> SEQUENCE: 108 atg gcc aag ttg acc agt gcc gtt ccg gtg ctc acc gcg cgc gac gtc         48
Met Ala Lys Leu Thr Ser Ala Val Pro Val Leu Thr Ala Arg Asp Val
1               5                   10                  15 gcc gga gcg gtc gag ttc tgg acc gac cgg ctc ggg ttc tcc cgg gac         96
Ala Gly Ala Val Glu Phe Trp Thr Asp Arg Leu Gly Phe Ser Arg Asp
            20                  25                  30 ttc gtg gag gac gac ttc gcc ggt gtg gtc cgg gac gac gtg acc ctg        144
Phe Val Glu Asp Asp Phe Ala Gly Val Val Arg Asp Asp Val Thr Leu
        35                  40                  45 ttc atc agc gcg gtc cag gac cag gtg gtg ccg gac aac acc ctg gcc        192
Phe Ile Ser Ala Val Gln Asp Gln Val Val Pro Asp Asn Thr Leu Ala
50                  55                  60 tgg gtg tgg gtg cgc ggc ctg gac gag ctg tac gcc gag tgg tcg gag        240
Trp Val Trp Val Arg Gly Leu Asp Glu Leu Tyr Ala Glu Trp Ser Glu
65                  70                  75                  80 gtc gtg tcc acg aac ttc cgg gac gcc tcc ggg ccg gcc atg acc gag        288
Val Val Ser Thr Asn Phe Arg Asp Ala Ser Gly Pro Ala Met Thr Glu
                85                  90                  95 atc ggc gag cag ccg tgg ggg cgg gag ttc gcc ctg cgc gac ccg gcc        336
Ile Gly Glu Gln Pro Trp Gly Arg Glu Phe Ala Leu Arg Asp Pro Ala
            100                 105                 110 ggc aac tgc gtg cac ttc gtg gcc gag gag cag gac tga                    375
Gly Asn Cys Val His Phe Val Ala Glu Glu Gln Asp
        115                 120

<210> SEQ ID NO 109
<211> LENGTH: 124
<212> TYPE: PRT
<213> ORGANISM: Artificial Sequence
<220> FEATURE:

<223> OTHER INFORMATION: Chemically synthesized - wt zeocin resistance
      gene

<400> SEQUENCE: 109

Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 110
<211> LENGTH: 399
<212> TYPE: DNA
<213> ORGANISM: Artificial Sequence
<220> FEATURE:
<223> OTHER INFORMATION: Chemically synthesized - wt blasticidin
      resistance gene
<220> FEATURE:
<221> NAME/KEY: CDS
<222> LOCATION: (1)..(399)

<400> SEQUENCE: 110 atg gcc aag cct ttg tct caa gaa gaa tcc acc ctc att gaa aga gca        48
Met Ala Lys Pro Leu Ser Gln Glu Glu Ser Thr Leu Ile Glu Arg Ala
1               5                   10                  15 acg gct aca atc aac agc atc ccc atc tct gaa gac tac agc gtc gcc        96
Thr Ala Thr Ile Asn Ser Ile Pro Ile Ser Glu Asp Tyr Ser Val Ala
            20                  25                  30 agc gca gct ctc tct agc gac ggc cgc atc ttc act ggt gtc aat gta       144
Ser Ala Ala Leu Ser Ser Asp Gly Arg Ile Phe Thr Gly Val Asn Val
        35                  40                  45 tat cat ttt act ggg gga cct tgt gca gaa ctc gtg gtg ctg ggc act       192
Tyr His Phe Thr Gly Gly Pro Cys Ala Glu Leu Val Val Leu Gly Thr
    50                  55                  60 gct gct gct gcg gca gct ggc aac ctg act tgt atc gtc gcg atc gga       240
Ala Ala Ala Ala Ala Ala Gly Asn Leu Thr Cys Ile Val Ala Ile Gly
65                  70                  75                  80 aat gag aac agg ggc atc ttg agc ccc tgc gga cgg tgc cga cag gtg       288
Asn Glu Asn Arg Gly Ile Leu Ser Pro Cys Gly Arg Cys Arg Gln Val
                85                  90                  95 ctt ctc gat ctg cat cct ggg atc aaa gcc ata gtg aag gac agt gat       336
Leu Leu Asp Leu His Pro Gly Ile Lys Ala Ile Val Lys Asp Ser Asp
            100                 105                 110 gga cag ccg acg gca gtt ggg att cgt gaa ttg ctg ccc tct ggt tat       384
Gly Gln Pro Thr Ala Val Gly Ile Arg Glu Leu Leu Pro Ser Gly Tyr
        115                 120                 125 gtg tgg gag ggc taa                                                   399
Val Trp Glu Gly
        130

<210> SEQ ID NO 111
<211> LENGTH: 132
<212> TYPE: PRT
<213> ORGANISM: Artificial Sequence
<220> FEATURE:
<223> OTHER INFORMATION: Chemically synthesized - wt blasticidin resistance gene

<400> SEQUENCE: 111

```
Met Ala Lys Pro Leu Ser Gln Glu Glu Ser Thr Leu Ile Glu Arg Ala
1               5                   10                  15

Thr Ala Thr Ile Asn Ser Ile Pro Ile Ser Glu Asp Tyr Ser Val Ala
            20                  25                  30

Ser Ala Ala Leu Ser Ser Asp Gly Arg Ile Phe Thr Gly Val Asn Val
        35                  40                  45

Tyr His Phe Thr Gly Gly Pro Cys Ala Glu Leu Val Val Leu Gly Thr
    50                  55                  60

Ala Ala Ala Ala Ala Gly Asn Leu Thr Cys Ile Val Ala Ile Gly
65                  70                  75                  80

Asn Glu Asn Arg Gly Ile Leu Ser Pro Cys Gly Arg Cys Arg Gln Val
                85                  90                  95

Leu Leu Asp Leu His Pro Gly Ile Lys Ala Ile Val Lys Asp Ser Asp
            100                 105                 110

Gly Gln Pro Thr Ala Val Gly Ile Arg Glu Leu Leu Pro Ser Gly Tyr
        115                 120                 125

Val Trp Glu Gly
    130
```

<210> SEQ ID NO 112
<211> LENGTH: 600
<212> TYPE: DNA
<213> ORGANISM: Artificial Sequence
<220> FEATURE:
<223> OTHER INFORMATION: Chemically synthesized - wt puromycin resistance gene
<220> FEATURE:
<221> NAME/KEY: CDS
<222> LOCATION: (1)..(600)

<400> SEQUENCE: 112

```
atg acc gag tac aag ccc acg gtg cgc ctc gcc acc cgc gac gac gtc        48
Met Thr Glu Tyr Lys Pro Thr Val Arg Leu Ala Thr Arg Asp Asp Val
1               5                   10                  15 ccc agg gcc gta cgc acc ctc gcc gcc gcg ttc gcc gac tac ccc gcc        96
Pro Arg Ala Val Arg Thr Leu Ala Ala Ala Phe Ala Asp Tyr Pro Ala
            20                  25                  30 acg cgc cac acc gtc gat ccg gac cgc cac atc gag cgg gtc acc gag       144
Thr Arg His Thr Val Asp Pro Asp Arg His Ile Glu Arg Val Thr Glu
        35                  40                  45 ctg caa gaa ctc ttc ctc acg cgc gtc ggg ctc gac atc ggc aag gtg       192
Leu Gln Glu Leu Phe Leu Thr Arg Val Gly Leu Asp Ile Gly Lys Val
    50                  55                  60 tgg gtc gcg gac gac ggc gcc gcg gtg gcg gtc tgg acc acg ccg gag       240
Trp Val Ala Asp Asp Gly Ala Ala Val Ala Val Trp Thr Thr Pro Glu
65                  70                  75                  80 agc gtc gaa gcg ggg gcg gtg ttc gcc gag atc ggc ccg cgc atg gcc       288
Ser Val Glu Ala Gly Ala Val Phe Ala Glu Ile Gly Pro Arg Met Ala
                85                  90                  95 gag ttg agc ggt tcc cgg ctg gcc gcg cag caa cag atg gaa ggc ctc       336
Glu Leu Ser Gly Ser Arg Leu Ala Ala Gln Gln Gln Met Glu Gly Leu
            100                 105                 110
```

```
ctg gcg ccg cac cgg ccc aag gag ccc gcg tgg ttc ctg gcc acc gtc    384
Leu Ala Pro His Arg Pro Lys Glu Pro Ala Trp Phe Leu Ala Thr Val
        115                 120                 125 ggc gtc tcg ccc gac cac cag ggc aag ggt ctg ggc agc gcc gtc gtg    432
Gly Val Ser Pro Asp His Gln Gly Lys Gly Leu Gly Ser Ala Val Val
130                 135                 140 ctc ccc gga gtg gag gcg gcc gag cgc gcc ggg gtg ccc gcc ttc ctg    480
Leu Pro Gly Val Glu Ala Ala Glu Arg Ala Gly Val Pro Ala Phe Leu
145                 150                 155                 160 gag acc tcc gcg ccc cgc aac ctc ccc ttc tac gag cgg ctc ggc ttc    528
Glu Thr Ser Ala Pro Arg Asn Leu Pro Phe Tyr Glu Arg Leu Gly Phe
                165                 170                 175 acc gtc acc gcc gac gtc gag tgc ccg aag gac cgc gcg acc tgg tgc    576
Thr Val Thr Ala Asp Val Glu Cys Pro Lys Asp Arg Ala Thr Trp Cys
            180                 185                 190 atg acc cgc aag ccc ggt gcc tga                                    600
Met Thr Arg Lys Pro Gly Ala
        195
```

<210> SEQ ID NO 113
<211> LENGTH: 199
<212> TYPE: PRT
<213> ORGANISM: Artificial Sequence
<220> FEATURE:
<223> OTHER INFORMATION: Chemically synthesized - wt puromycin resistance gene

<400> SEQUENCE: 113

```
Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Cys Pro Lys Asp Arg Ala Thr Trp Cys
            180                 185                 190

Met Thr Arg Lys Pro Gly Ala
        195
```

<210> SEQ ID NO 114
<211> LENGTH: 564
<212> TYPE: DNA

```
<213> ORGANISM: Artificial Sequence
<220> FEATURE:
<223> OTHER INFORMATION: Chemically synthesized - wt DHFR gene (from
      mouse)
<220> FEATURE:
<221> NAME/KEY: CDS
<222> LOCATION: (1)..(564)

<400> SEQUENCE: 114 atg gtt cga cca ttg aac tgc atc gtc gcc gtg tcc caa aat atg ggg      48
Met Val Arg Pro Leu Asn Cys Ile Val Ala Val Ser Gln Asn Met Gly
1               5                   10                  15 att ggc aag aac gga gac cta ccc tgg cct ccg ctc agg aac gag ttc      96
Ile Gly Lys Asn Gly Asp Leu Pro Trp Pro Pro Leu Arg Asn Glu Phe
            20                  25                  30 aag tac ttc caa aga atg acc aca acc tct tca gtg gaa ggt aaa cag     144
Lys Tyr Phe Gln Arg Met Thr Thr Thr Ser Ser Val Glu Gly Lys Gln
        35                  40                  45 aat ctg gtg att atg ggt agg aaa acc tgg ttc tcc att cct gag aag     192
Asn Leu Val Ile Met Gly Arg Lys Thr Trp Phe Ser Ile Pro Glu Lys
    50                  55                  60 aat cga cct tta aag gac aga att aat ata gtt ctc agt aga gaa ctc     240
Asn Arg Pro Leu Lys Asp Arg Ile Asn Ile Val Leu Ser Arg Glu Leu
65                  70                  75                  80 aaa gaa cca cca cga gga gct cat ttt ctt gcc aaa agt ttg gat gat     288
Lys Glu Pro Pro Arg Gly Ala His Phe Leu Ala Lys Ser Leu Asp Asp
                85                  90                  95 gcc tta aga ctt att gaa caa ccg gaa ttg gca agt aaa gta gac atg     336
Ala Leu Arg Leu Ile Glu Gln Pro Glu Leu Ala Ser Lys Val Asp Met
            100                 105                 110 gtt tgg ata gtc gga ggc agt tct gtt tac cag gaa gcc atg aat caa     384
Val Trp Ile Val Gly Gly Ser Ser Val Tyr Gln Glu Ala Met Asn Gln
        115                 120                 125 cca ggc cac ctc aga ctc ttt gtg aca agg atc atg cag gaa ttt gaa     432
Pro Gly His Leu Arg Leu Phe Val Thr Arg Ile Met Gln Glu Phe Glu
    130                 135                 140 agt gac acg ttt ttc cca gaa att gat ttg ggg aaa tat aaa ctt ctc     480
Ser Asp Thr Phe Phe Pro Glu Ile Asp Leu Gly Lys Tyr Lys Leu Leu
145                 150                 155                 160 cca gaa tac cca ggc gtc ctc tct gag gtc cag gag gaa aaa ggc atc     528
Pro Glu Tyr Pro Gly Val Leu Ser Glu Val Gln Glu Glu Lys Gly Ile
                165                 170                 175 aag tat aag ttt gaa gtc tac gag aag aaa gac taa                     564
Lys Tyr Lys Phe Glu Val Tyr Glu Lys Lys Asp
            180                 185

<210> SEQ ID NO 115
<211> LENGTH: 187
<212> TYPE: PRT
<213> ORGANISM: Artificial Sequence
<220> FEATURE:
<223> OTHER INFORMATION: Chemically synthesized - wt DHFR gene (from
      mouse)

<400> SEQUENCE: 115

Met Val Arg Pro Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
```

```
                  50                  55                  60
Asn Arg Pro Leu Lys Asp Arg Ile Asn Ile Val Leu Ser Arg Glu Leu
 65                  70                  75                  80

Lys Glu Pro Pro Arg Gly Ala His Phe Leu Ala Lys Ser Leu Asp Asp
                 85                  90                  95

Ala Leu Arg Leu Ile Glu Gln Pro Glu Leu Ala Ser Lys Val Asp Met
                100                 105                 110

Val Trp Ile Val Gly Gly Ser Ser Val Tyr Gln Glu Ala Met Asn Gln
            115                 120                 125

Pro Gly His Leu Arg Leu Phe Val Thr Arg Ile Met Gln Glu Phe Glu
        130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
            180                 185

<210> SEQ ID NO 116
<211> LENGTH: 1143
<212> TYPE: DNA
<213> ORGANISM: Artificial Sequence
<220> FEATURE:
<223> OTHER INFORMATION: Chemically synthesized - wt hygromycin
      resistance gene
<220> FEATURE:
<221> NAME/KEY: CDS
<222> LOCATION: (1)..(1143)

<400> SEQUENCE: 116 atg aaa aag cct gaa ctc acc gcg acg tct gtc gag aag ttt ctg atc      48
Met Lys Lys Pro Glu Leu Thr Ala Thr Ser Val Glu Lys Phe Leu Ile
1               5                   10                  15 gaa aag ttc gac agc gtc tcc gac ctg atg cag ctc tcg gag ggc gaa      96
Glu Lys Phe Asp Ser Val Ser Asp Leu Met Gln Leu Ser Glu Gly Glu
                20                  25                  30 gaa tct cgt gct ttc agc ttc gat gta gga ggg cgt gga tat gtc ctg     144
Glu Ser Arg Ala Phe Ser Phe Asp Val Gly Gly Arg Gly Tyr Val Leu
            35                  40                  45 cgg gta aat agc tgc gcc gat ggt ttc tac aaa gat cgt tat gtt tat     192
Arg Val Asn Ser Cys Ala Asp Gly Phe Tyr Lys Asp Arg Tyr Val Tyr
        50                  55                  60 cgg cac ttt gca tcg gcc gcg ctc ccg att ccg gaa gtg ctt gac att     240
Arg His Phe Ala Ser Ala Ala Leu Pro Ile Pro Glu Val Leu Asp Ile
65                  70                  75                  80 ggg gaa ttc agc gag agc ctg acc tat tgc atc tcc cgc cgt gca cag     288
Gly Glu Phe Ser Glu Ser Leu Thr Tyr Cys Ile Ser Arg Arg Ala Gln
                85                  90                  95 ggt gtc acg ttg caa gac ctg cct gaa acc gaa ctg ccc gct gtt ctg     336
Gly Val Thr Leu Gln Asp Leu Pro Glu Thr Glu Leu Pro Ala Val Leu
            100                 105                 110 cag ccg gtc gcg gag gcc atg gat gcg atc gct gcg gcc gat ctt agc     384
Gln Pro Val Ala Glu Ala Met Asp Ala Ile Ala Ala Ala Asp Leu Ser
        115                 120                 125 cag acg agc ggg ttc ggc cca ttc gga ccg caa gga atc ggt caa tac     432
Gln Thr Ser Gly Phe Gly Pro Phe Gly Pro Gln Gly Ile Gly Gln Tyr
    130                 135                 140 act aca tgg cgt gat ttc ata tgc gcg att gct gat ccc cat gtg tat     480
Thr Thr Trp Arg Asp Phe Ile Cys Ala Ile Ala Asp Pro His Val Tyr
145                 150                 155                 160
```

```
cac tgg caa act gtg atg gac gac acc gtc agt gcg tcc gtc gcg cag    528
His Trp Gln Thr Val Met Asp Asp Thr Val Ser Ala Ser Val Ala Gln
                165                 170                 175 gct ctc gat gag ctg atg ctt tgg gcc gag gac tgc ccc gaa gtc cgg    576
Ala Leu Asp Glu Leu Met Leu Trp Ala Glu Asp Cys Pro Glu Val Arg
            180                 185                 190 cac ctc gtg cac gcg gat ttc ggc tcc aac aat gtc ctg acg gac aat    624
His Leu Val His Ala Asp Phe Gly Ser Asn Asn Val Leu Thr Asp Asn
        195                 200                 205 ggc cgc ata aca gcg gtc att gac tgg agc gag gcg atg ttc ggg gat    672
Gly Arg Ile Thr Ala Val Ile Asp Trp Ser Glu Ala Met Phe Gly Asp
    210                 215                 220 tcc caa tac gag gtc gcc aac atc ttc ttc tgg agg ccg tgg ttg gct    720
Ser Gln Tyr Glu Val Ala Asn Ile Phe Phe Trp Arg Pro Trp Leu Ala
225                 230                 235                 240 tgt atg gag cag cag acg cgc tac ttc gag cgg agg cat ccg gag ctt    768
Cys Met Glu Gln Gln Thr Arg Tyr Phe Glu Arg Arg His Pro Glu Leu
                245                 250                 255 gca gga tcg ccg cgg ctc cgg gcg tat atg ctc cgc att ggt ctt gac    816
Ala Gly Ser Pro Arg Leu Arg Ala Tyr Met Leu Arg Ile Gly Leu Asp
            260                 265                 270 caa ctc tat cag agc ttg gtt gac ggc aat ttc gat gat gca gct tgg    864
Gln Leu Tyr Gln Ser Leu Val Asp Gly Asn Phe Asp Asp Ala Ala Trp
        275                 280                 285 gcg cag ggt cga tgc gac gca atc gtc cga tcc gga gcc ggg act gtc    912
Ala Gln Gly Arg Cys Asp Ala Ile Val Arg Ser Gly Ala Gly Thr Val
    290                 295                 300 ggg cgt aca caa atc gcc cgc aga agc gcg gcc gtc tgg acc gat ggc    960
Gly Arg Thr Gln Ile Ala Arg Arg Ser Ala Ala Val Trp Thr Asp Gly
305                 310                 315                 320 tgt gta gaa gta ctc gcc gat agt gga aac cga cgc ccc agc act cgt   1008
Cys Val Glu Val Leu Ala Asp Ser Gly Asn Arg Arg Pro Ser Thr Arg
                325                 330                 335 ccg gag gca aag gaa ttc ggg aga tgg ggg agg cta act gaa aca cgg   1056
Pro Glu Ala Lys Glu Phe Gly Arg Trp Gly Arg Leu Thr Glu Thr Arg
            340                 345                 350 aag gag aca ata ccg gaa gga acc cgc gct atg acg gca ata aaa aga   1104
Lys Glu Thr Ile Pro Glu Gly Thr Arg Ala Met Thr Ala Ile Lys Arg
        355                 360                 365 cag aat aaa acg cac ggg tgt tgg gtc gtt tgt tca taa               1143
Gln Asn Lys Thr His Gly Cys Trp Val Val Cys Ser
    370                 375                 380

<210> SEQ ID NO 117
<211> LENGTH: 380
<212> TYPE: PRT
<213> ORGANISM: Artificial Sequence
<220> FEATURE:
<223> OTHER INFORMATION: Chemically synthesized - wt hygromycin
      resistance gene

<400> SEQUENCE: 117

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60
```

```
Arg His Phe Ala Ser Ala Ala Leu Pro Ile Pro Glu Val Leu Asp Ile
 65                  70                  75                  80

Gly Glu Phe Ser Glu Ser Leu Thr Tyr Cys Ile Ser Arg Arg Ala Gln
             85                   90                  95

Gly Val Thr Leu Gln Asp Leu Pro Glu Thr Glu Leu Pro Ala Val Leu
        100                 105                 110

Gln Pro Val Ala Glu Ala Met Asp Ala Ile Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Glu Ala Lys Glu Phe Gly Arg Trp Gly Arg Leu Thr Glu Thr Arg
            340                 345                 350

Lys Glu Thr Ile Pro Glu Gly Thr Arg Ala Met Thr Ala Ile Lys Arg
        355                 360                 365

Gln Asn Lys Thr His Gly Cys Trp Val Val Cys Ser
    370                 375                 380

<210> SEQ ID NO 118
<211> LENGTH: 804
<212> TYPE: DNA
<213> ORGANISM: Artificial Sequence
<220> FEATURE:
<223> OTHER INFORMATION: Chemically synthesized - wt neomycin resistance
      gene
<220> FEATURE:
<221> NAME/KEY: CDS
<222> LOCATION: (1)..(804)

<400> SEQUENCE: 118 atg gga tcg gcc att gaa caa gat gga ttg cac gca ggt tct ccg gcc    48
Met Gly Ser Ala Ile Glu Gln Asp Gly Leu His Ala Gly Ser Pro Ala
 1               5                  10                  15
```

| | | | | | | | | | | | | | | | |
|---|---|---|---|---|---|---|---|---|---|---|---|---|---|---|---|
| gct | tgg | gtg | gag | agg | cta | ttc | ggc | tat | gac | tgg | gca | caa | cag | aca | atc | 96 |
| Ala | Trp | Val | Glu | Arg | Leu | Phe | Gly | Tyr | Asp | Trp | Ala | Gln | Gln | Thr | Ile |
| | | 20 | | | | | 25 | | | | | 30 | | | | ggc tgc tct gat gcc gcc gtg ttc cgg ctg tca gcg cag ggg cgc ccg 144
Gly Cys Ser Asp Ala Ala Val Phe Arg Leu Ser Ala Gln Gly Arg Pro
            35                  40                  45 gtt ctt ttt gtc aag acc gac ctg tcc ggt gcc ctg aat gaa ctg cag 192
Val Leu Phe Val Lys Thr Asp Leu Ser Gly Ala Leu Asn Glu Leu Gln
 50                  55                  60 gac gag gca gcg cgg cta tcg tgg ctg gcc acg acg ggc gtt cct tgc 240
Asp Glu Ala Ala Arg Leu Ser Trp Leu Ala Thr Thr Gly Val Pro Cys
 65                  70                  75                  80 gca gct gtg ctc gac gtt gtc act gaa gcg gga agg gac tgg ctg cta 288
Ala Ala Val Leu Asp Val Val Thr Glu Ala Gly Arg Asp Trp Leu Leu
                 85                  90                  95 ttg ggc gaa gtg ccg ggg cag gat ctc ctg tca tct cac ctt gct cct 336
Leu Gly Glu Val Pro Gly Gln Asp Leu Leu Ser Ser His Leu Ala Pro
            100                 105                 110 gcc gag aaa gta tcc atc atg gct gat gca atg cgg cgg ctg cat acg 384
Ala Glu Lys Val Ser Ile Met Ala Asp Ala Met Arg Arg Leu His Thr
       115                 120                 125 ctt gat ccg gct acc tgc cca ttc gac cac caa gcg aaa cat cgc atc 432
Leu Asp Pro Ala Thr Cys Pro Phe Asp His Gln Ala Lys His Arg Ile
130                 135                 140 gag cga gca cgt act cgg atg gaa gcc ggt ctt gtc gat cag gat gat 480
Glu Arg Ala Arg Thr Arg Met Glu Ala Gly Leu Val Asp Gln Asp Asp
145                 150                 155                 160 ctg gac gaa gag cat cag ggg ctc gcg cca gcc gaa ctg ttc gcc agg 528
Leu Asp Glu Glu His Gln Gly Leu Ala Pro Ala Glu Leu Phe Ala Arg
                165                 170                 175 ctc aag gcg cgc atg ccc gac ggc gat gat ctc gtc gtg acc cat ggc 576
Leu Lys Ala Arg Met Pro Asp Gly Asp Asp Leu Val Val Thr His Gly
            180                 185                 190 gat gcc tgc ttg ccg aat atc atg gtg gaa aat ggc cgc ttt tct gga 624
Asp Ala Cys Leu Pro Asn Ile Met Val Glu Asn Gly Arg Phe Ser Gly
       195                 200                 205 ttc atc gac tgt ggc cgg ctg ggt gtg gcg gac cgc tat cag gac ata 672
Phe Ile Asp Cys Gly Arg Leu Gly Val Ala Asp Arg Tyr Gln Asp Ile
210                 215                 220 gcg ttg gct acc cgt gat att gct gaa gag ctt ggc ggc gaa tgg gct 720
Ala Leu Ala Thr Arg Asp Ile Ala Glu Glu Leu Gly Gly Glu Trp Ala
225                 230                 235                 240 gac cgc ttc ctc gtg ctt tac ggt atc gcc gct ccc gat tcg cag cgc 768
Asp Arg Phe Leu Val Leu Tyr Gly Ile Ala Ala Pro Asp Ser Gln Arg
                245                 250                 255 atc gcc ttc tat cgc ctt ctt gac gag ttc ttc tga 804
Ile Ala Phe Tyr Arg Leu Leu Asp Glu Phe Phe
            260                 265

<210> SEQ ID NO 119
<211> LENGTH: 267
<212> TYPE: PRT
<213> ORGANISM: Artificial Sequence
<220> FEATURE:
<223> OTHER INFORMATION: Chemically synthesized - wt neomycin resistance
      gene

<400> SEQUENCE: 119

Met Gly Ser Ala Ile Glu Gln Asp Gly Leu His Ala Gly Ser Pro Ala
1               5                   10                  15

Ala Trp Val Glu Arg Leu Phe Gly Tyr Asp Trp Ala Gln Gln Thr Ile

```
            20                  25                  30
Gly Cys Ser Asp Ala Ala Val Phe Arg Leu Ser Ala Gln Gly Arg Pro
        35                  40                  45

Val Leu Phe Val Lys Thr Asp Leu Ser Gly Ala Leu Asn Glu Leu Gln
    50                  55                  60

Asp Glu Ala Ala Arg Leu Ser Trp Leu Ala Thr Thr Gly Val Pro Cys
65                  70                  75                  80

Ala Ala Val Leu Asp Val Val Thr Glu Ala Gly Arg Asp Trp Leu Leu
                85                  90                  95

Leu Gly Glu Val Pro Gly Gln Asp Leu Leu Ser Ser His Leu Ala Pro
            100                 105                 110

Ala Glu Lys Val Ser Ile Met Ala Asp Ala Met Arg Arg Leu His Thr
        115                 120                 125

Leu Asp Pro Ala Thr Cys Pro Phe Asp His Gln Ala Lys His Arg Ile
    130                 135                 140

Glu Arg Ala Arg Thr Arg Met Glu Ala Gly Leu Val Asp Gln Asp Asp
145                 150                 155                 160

Leu Asp Glu Glu His Gln Gly Leu Ala Pro Ala Glu Leu Phe Ala Arg
                165                 170                 175

Leu Lys Ala Arg Met Pro Asp Gly Asp Asp Leu Val Val Thr His Gly
            180                 185                 190

Asp Ala Cys Leu Pro Asn Ile Met Val Glu Asn Gly Arg Phe Ser Gly
        195                 200                 205

Phe Ile Asp Cys Gly Arg Leu Gly Val Ala Asp Arg Tyr Gln Asp Ile
    210                 215                 220

Ala Leu Ala Thr Arg Asp Ile Ala Glu Glu Leu Gly Gly Glu Trp Ala
225                 230                 235                 240

Asp Arg Phe Leu Val Leu Tyr Gly Ile Ala Ala Pro Asp Ser Gln Arg
                245                 250                 255

Ile Ala Phe Tyr Arg Leu Leu Asp Glu Phe Phe
            260                 265

<210> SEQ ID NO 120
<211> LENGTH: 1121
<212> TYPE: DNA
<213> ORGANISM: Artificial Sequence
<220> FEATURE:
<223> OTHER INFORMATION: Chemically synthesized - wt glutamine synthase
      gene (human)
<220> FEATURE:
<221> NAME/KEY: CDS
<222> LOCATION: (1)..(1119)

<400> SEQUENCE: 120 atg acc acc tca gca agt tcc cac tta aat aaa ggc atc aag cag gtg      48
Met Thr Thr Ser Ala Ser Ser His Leu Asn Lys Gly Ile Lys Gln Val
1               5                   10                  15 tac atg tcc ctg cct cag ggt gag aaa gtc cag gcc atg tat atc tgg      96
Tyr Met Ser Leu Pro Gln Gly Glu Lys Val Gln Ala Met Tyr Ile Trp
            20                  25                  30 atc gat ggt act gga gaa gga ctg cgc tgc aag acc cgg acc ctg gac     144
Ile Asp Gly Thr Gly Glu Gly Leu Arg Cys Lys Thr Arg Thr Leu Asp
        35                  40                  45 agt gag ccc aag tgt gtg gaa gag ttg cct gag tgg aat ttc gat ggc     192
Ser Glu Pro Lys Cys Val Glu Glu Leu Pro Glu Trp Asn Phe Asp Gly
    50                  55                  60 tcc agt act tta cag tct gag ggt tcc aac agt gac atg tat ctc gtg     240
Ser Ser Thr Leu Gln Ser Glu Gly Ser Asn Ser Asp Met Tyr Leu Val
```

```
                65                  70                  75                  80
cct gct gcc atg ttt cgg gac ccc ttc cgt aag gac cct aac aag ctg         288
Pro Ala Ala Met Phe Arg Asp Pro Phe Arg Lys Asp Pro Asn Lys Leu
                    85                  90                  95 gtg tta tgt gaa gtt ttc aag tac aat cga agg cct gca gag acc aat         336
Val Leu Cys Glu Val Phe Lys Tyr Asn Arg Arg Pro Ala Glu Thr Asn
                100                 105                 110 ttg agg cac acc tgt aaa cgg ata atg gac atg gtg agc aac cag cac         384
Leu Arg His Thr Cys Lys Arg Ile Met Asp Met Val Ser Asn Gln His
            115                 120                 125 ccc tgg ttt ggc atg gag cag gag tat acc ctc atg ggg aca gat ggg         432
Pro Trp Phe Gly Met Glu Gln Glu Tyr Thr Leu Met Gly Thr Asp Gly
130                 135                 140 cac ccc ttt ggt tgg cct tcc aac ggc ttc cca ggg ccc cag ggt cca         480
His Pro Phe Gly Trp Pro Ser Asn Gly Phe Pro Gly Pro Gln Gly Pro
145                 150                 155                 160 tat tac tgt ggt gtg gga gca gac aga gcc tat ggc agg gac atc gtg         528
Tyr Tyr Cys Gly Val Gly Ala Asp Arg Ala Tyr Gly Arg Asp Ile Val
                165                 170                 175 gag gcc cat tac cgg gcc tgc ttg tat gct gga gtc aag att gcg ggg         576
Glu Ala His Tyr Arg Ala Cys Leu Tyr Ala Gly Val Lys Ile Ala Gly
                180                 185                 190 act aat gcc gag gtc atg cct gcc cag tgg gaa ttt cag att gga cct         624
Thr Asn Ala Glu Val Met Pro Ala Gln Trp Glu Phe Gln Ile Gly Pro
            195                 200                 205 tgt gaa gga atc agc atg gga gat cat ctc tgg gtg gcc cgt ttc atc         672
Cys Glu Gly Ile Ser Met Gly Asp His Leu Trp Val Ala Arg Phe Ile
210                 215                 220 ttg cat cgt gtg tgt gaa gac ttt gga gtg ata gca acc ttt gat cct         720
Leu His Arg Val Cys Glu Asp Phe Gly Val Ile Ala Thr Phe Asp Pro
225                 230                 235                 240 aag ccc att cct ggg aac tgg aat ggt gca ggc tgc cat acc aac ttc         768
Lys Pro Ile Pro Gly Asn Trp Asn Gly Ala Gly Cys His Thr Asn Phe
                245                 250                 255 agc acc aag gcc atg cgg gag gag aat ggt ctg aag tac atc gag gag         816
Ser Thr Lys Ala Met Arg Glu Glu Asn Gly Leu Lys Tyr Ile Glu Glu
                260                 265                 270 gcc att gag aaa cta agc aag cgg cac cag tac cac atc cgt gcc tat         864
Ala Ile Glu Lys Leu Ser Lys Arg His Gln Tyr His Ile Arg Ala Tyr
            275                 280                 285 gat ccc aag gga ggc ctg gac aat gcc cga cgt cta act gga ttc cat         912
Asp Pro Lys Gly Gly Leu Asp Asn Ala Arg Arg Leu Thr Gly Phe His
290                 295                 300 gaa acc tcc aac atc aac gac ttt tct ggt ggt gta gcc aat cgt agc         960
Glu Thr Ser Asn Ile Asn Asp Phe Ser Gly Gly Val Ala Asn Arg Ser
305                 310                 315                 320 gcc agc ata cgc att ccc cgg act gtt ggc cag gag aag aag ggt tac        1008
Ala Ser Ile Arg Ile Pro Arg Thr Val Gly Gln Glu Lys Lys Gly Tyr
                325                 330                 335 ttt gaa gat cgt cgc ccc tct gcc aac tgc gac ccc ttt tcg gtg aca        1056
Phe Glu Asp Arg Arg Pro Ser Ala Asn Cys Asp Pro Phe Ser Val Thr
                340                 345                 350 gaa gcc ctc atc cgc acg tgt ctt ctc aat gaa acc ggc gat gag ccc        1104
Glu Ala Leu Ile Arg Thr Cys Leu Leu Asn Glu Thr Gly Asp Glu Pro
            355                 360                 365 ttc cag tac aaa aat ta                                                 1121
Phe Gln Tyr Lys Asn
    370
```

```
<210> SEQ ID NO 121
<211> LENGTH: 373
<212> TYPE: PRT
<213> ORGANISM: Artificial Sequence
<220> FEATURE:
<223> OTHER INFORMATION: Chemically synthesized - wt glutamine synthase
      gene (human)

<400> SEQUENCE: 121

Met Thr Thr Ser Ala Ser Ser His Leu Asn Lys Gly Ile Lys Gln Val
1               5                   10                  15

Tyr Met Ser Leu Pro Gln Gly Glu Lys Val Gln Ala Met Tyr Ile Trp
            20                  25                  30

Ile Asp Gly Thr Gly Glu Gly Leu Arg Cys Lys Thr Arg Thr Leu Asp
        35                  40                  45

Ser Glu Pro Lys Cys Val Glu Glu Leu Pro Glu Trp Asn Phe Asp Gly
    50                  55                  60

Ser Ser Thr Leu Gln Ser Glu Gly Ser Asn Ser Asp Met Tyr Leu Val
65                  70                  75                  80

Pro Ala Ala Met Phe Arg Asp Pro Phe Arg Lys Asp Pro Asn Lys Leu
                85                  90                  95

Val Leu Cys Glu Val Phe Lys Tyr Asn Arg Arg Pro Ala Glu Thr Asn
            100                 105                 110

Leu Arg His Thr Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Arg Ala Tyr Gly Arg Asp Ile Val
                165                 170                 175

Glu Ala His Tyr Arg Ala Cys Leu Tyr Ala Gly Val Lys Ile Ala Gly
            180                 185                 190

Thr Asn Ala Glu Val Met Pro Ala Gln Trp Glu Phe Gln Ile Gly Pro
        195                 200                 205

Cys Glu Gly Ile Ser Met Gly Asp His Leu Trp Val Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Tyr Ile Glu Glu
            260                 265                 270

Ala Ile Glu Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Gly Val Ala Asn Arg Ser
305                 310                 315                 320

Ala Ser Ile Arg Ile Pro Arg Thr Val Gly Gln Glu Lys Lys Gly Tyr
            325                 330                 335

Phe Glu Asp Arg Arg Pro Ser Ala Asn Cys Asp Pro Phe Ser Val Thr
        340                 345                 350

Glu Ala Leu Ile Arg Thr Cys Leu Leu Asn Glu Thr Gly Asp Glu Pro
    355                 360                 365
```

Phe Gln Tyr Lys Asn
    370

<210> SEQ ID NO 122
<211> LENGTH: 43
<212> TYPE: DNA
<213> ORGANISM: Artificial Sequence
<220> FEATURE:
<223> OTHER INFORMATION: Chemically synthesized - primer GTGspaceBamHIF

<400> SEQUENCE: 122
gaattcggat ccaccgtggc gatccaaaga ctgccaaatc tag         43

<210> SEQ ID NO 123
<211> LENGTH: 42
<212> TYPE: DNA
<213> ORGANISM: Artificial Sequence
<220> FEATURE:
<223> OTHER INFORMATION: Chemically synthesized - primer ZEOTTTGTGBamHIF

<400> SEQUENCE: 123
gaattcggat cctttgtggc caagttgacc agtgccgttc cg          42

<210> SEQ ID NO 124
<211> LENGTH: 46
<212> TYPE: DNA
<213> ORGANISM: Artificial Sequence
<220> FEATURE:
<223> OTHER INFORMATION: Chemically synthesized - primer
      ZEOForwardGTG-Thr9

<400> SEQUENCE: 124
aattggatcc accgtggcca agttgaccag tgccgttacc gtgctc      46

<210> SEQ ID NO 125
<211> LENGTH: 46
<212> TYPE: DNA
<213> ORGANISM: Artificial Sequence
<220> FEATURE:
<223> OTHER INFORMATION: Chemically synthesized - pimer ZEOForward
      GTG-Phe9

<400> SEQUENCE: 125
aattggatcc accgtggcca agttgaccag tgccgttttc gtgctc      46

<210> SEQ ID NO 126
<211> LENGTH: 43
<212> TYPE: DNA
<213> ORGANISM: Artificial Sequence
<220> FEATURE:
<223> OTHER INFORMATION: Chemically synthesized - primer TTGspaceBamHIF

<400> SEQUENCE: 126
gaattcggat ccaccttggc gatccaaaga ctgccaaatc tag         43

<210> SEQ ID NO 127
<211> LENGTH: 46
<212> TYPE: DNA
<213> ORGANISM: Artificial Sequence
<220> FEATURE:
<223> OTHER INFORMATION: Chemically synthesized - primer
      ZEOForwardTTG-Thr9

<400> SEQUENCE: 127
aattggatcc accttggcca agttgaccag tgccgttacc gtgctc      46

<210> SEQ ID NO 128
<211> LENGTH: 46
<212> TYPE: DNA
<213> ORGANISM: Artificial Sequence
<220> FEATURE:
<223> OTHER INFORMATION: Chemically synthesized - pimer
      ZEOForwardTTG-Phe9

<400> SEQUENCE: 128
aattggatcc accttggcca agttgaccag tgccgttttc gtgctc                46

<210> SEQ ID NO 129
<211> LENGTH: 37
<212> TYPE: DNA
<213> ORGANISM: Artificial Sequence
<220> FEATURE:
<223> OTHER INFORMATION: Chemically synthesized - primer PURO BamHI F

<400> SEQUENCE: 129
gatcggatcc atggttaccg agtacaagcc cacggtg                          37

<210> SEQ ID NO 130
<211> LENGTH: 35
<212> TYPE: DNA
<213> ORGANISM: Artificial Sequence
<220> FEATURE:
<223> OTHER INFORMATION: Chemically synthesized - primer PURO300 R LEU

<400> SEQUENCE: 130
cagccgggaa ccgctcaact cggccaggcg cgggc                            35

<210> SEQ ID NO 131
<211> LENGTH: 49
<212> TYPE: DNA
<213> ORGANISM: Artificial Sequence
<220> FEATURE:
<223> OTHER INFORMATION: Chemically synthesized - primer PURO300FLEU

<400> SEQUENCE: 131
cgagttgagc ggttcccggc tggccgcgca gcaacagctg gaaggcctc             49

<210> SEQ ID NO 132
<211> LENGTH: 44
<212> TYPE: DNA
<213> ORGANISM: Artificial Sequence
<220> FEATURE:
<223> OTHER INFORMATION: Chemically synthesized - primer PURO600RLEU

<400> SEQUENCE: 132
aagcttgaat tcaggcaccg ggcttgcggg tcaggcacca ggtc                  44

<210> SEQ ID NO 133
<211> LENGTH: 42
<212> TYPE: DNA
<213> ORGANISM: Artificial Sequence
<220> FEATURE:
<223> OTHER INFORMATION: Chemically synthesized - primer PUROBamHI TTG1F

<400> SEQUENCE: 133
gaattcggat ccaccttggt taccgagtac aagcccacgg tg                    42

<210> SEQ ID NO 134
<211> LENGTH: 804
<212> TYPE: DNA
<213> ORGANISM: Artificial Sequence
<220> FEATURE:
<223> OTHER INFORMATION: Chemically synthesized - modified neomycin resistance gene lacking internal ATG sequences
<220> FEATURE:
<221> NAME/KEY: CDS
<222> LOCATION: (1)..(804)

<400> SEQUENCE: 134

| | | | | | | | | | | | | | | | | |
|---|---|---|---|---|---|---|---|---|---|---|---|---|---|---|---|---|
| atg | gga | tcg | gcc | att | gaa | caa | gac | gga | ttg | cac | gca | ggt | tct | ccg | gcc | 48 |
| Met | Gly | Ser | Ala | Ile | Glu | Gln | Asp | Gly | Leu | His | Ala | Gly | Ser | Pro | Ala | |
| 1 | | | | 5 | | | | | 10 | | | | | 15 | | |
| gct | tgg | gtg | gag | agg | cta | ttc | ggc | tac | gac | tgg | gca | caa | cag | aca | atc | 96 |
| Ala | Trp | Val | Glu | Arg | Leu | Phe | Gly | Tyr | Asp | Trp | Ala | Gln | Gln | Thr | Ile | |
| | | | 20 | | | | | 25 | | | | | 30 | | | |
| ggc | tgc | tct | gac | gcc | gcc | gtg | ttc | cgg | ctg | tca | gcg | cag | ggg | cgc | ccg | 144 |
| Gly | Cys | Ser | Asp | Ala | Ala | Val | Phe | Arg | Leu | Ser | Ala | Gln | Gly | Arg | Pro | |
| | | 35 | | | | | 40 | | | | | 45 | | | | |
| gtt | ctt | ttt | gtc | aag | acc | gac | ctg | tcc | ggt | gcc | ctg | aac | gaa | ctg | cag | 192 |
| Val | Leu | Phe | Val | Lys | Thr | Asp | Leu | Ser | Gly | Ala | Leu | Asn | Glu | Leu | Gln | |
| | 50 | | | | | 55 | | | | | 60 | | | | | |
| gac | gag | gca | gcg | cgg | cta | tcg | tgg | ctg | gcc | acg | acg | ggc | gtt | cct | tgc | 240 |
| Asp | Glu | Ala | Ala | Arg | Leu | Ser | Trp | Leu | Ala | Thr | Thr | Gly | Val | Pro | Cys | |
| 65 | | | | | 70 | | | | | 75 | | | | | 80 | |
| gca | gct | gtg | ctc | gac | gtt | gtc | act | gaa | gcg | gga | agg | gac | tgg | ctg | cta | 288 |
| Ala | Ala | Val | Leu | Asp | Val | Val | Thr | Glu | Ala | Gly | Arg | Asp | Trp | Leu | Leu | |
| | | | | 85 | | | | | 90 | | | | | 95 | | |
| ttg | ggc | gaa | gtg | ccg | ggg | cag | gat | ctc | ctg | tca | tct | cac | ctt | gct | cct | 336 |
| Leu | Gly | Glu | Val | Pro | Gly | Gln | Asp | Leu | Leu | Ser | Ser | His | Leu | Ala | Pro | |
| | | | 100 | | | | | 105 | | | | | 110 | | | |
| gcc | gag | aaa | gta | tcc | atc | ctg | gct | gac | gca | ctg | cgg | cgg | ctg | cat | acg | 384 |
| Ala | Glu | Lys | Val | Ser | Ile | Leu | Ala | Asp | Ala | Leu | Arg | Arg | Leu | His | Thr | |
| | | 115 | | | | | 120 | | | | | 125 | | | | |
| ctt | gat | ccg | gct | acc | tgc | cca | ttc | gac | cac | caa | gcg | aaa | cat | cgc | atc | 432 |
| Leu | Asp | Pro | Ala | Thr | Cys | Pro | Phe | Asp | His | Gln | Ala | Lys | His | Arg | Ile | |
| | 130 | | | | | 135 | | | | | 140 | | | | | |
| gag | cga | gca | cgt | act | cgg | ctg | gaa | gcc | ggt | ctt | gtc | gat | cag | gac | gat | 480 |
| Glu | Arg | Ala | Arg | Thr | Arg | Leu | Glu | Ala | Gly | Leu | Val | Asp | Gln | Asp | Asp | |
| 145 | | | | | 150 | | | | | 155 | | | | | 160 | |
| ctg | gac | gaa | gag | cat | cag | ggg | ctc | gcg | cca | gcc | gaa | ctg | ttc | gcc | agg | 528 |
| Leu | Asp | Glu | Glu | His | Gln | Gly | Leu | Ala | Pro | Ala | Glu | Leu | Phe | Ala | Arg | |
| | | | | 165 | | | | | 170 | | | | | 175 | | |
| ctc | aag | gcg | cgc | ctg | ccc | gac | ggc | gac | gat | ctc | gtc | gtg | acc | cac | ggc | 576 |
| Leu | Lys | Ala | Arg | Leu | Pro | Asp | Gly | Asp | Asp | Leu | Val | Val | Thr | His | Gly | |
| | | | 180 | | | | | 185 | | | | | 190 | | | |
| gac | gcc | tgc | ttg | ccg | aat | atc | ctg | gtg | gaa | aac | ggc | cgc | ttt | tct | gga | 624 |
| Asp | Ala | Cys | Leu | Pro | Asn | Ile | Leu | Val | Glu | Asn | Gly | Arg | Phe | Ser | Gly | |
| | | 195 | | | | | 200 | | | | | 205 | | | | |
| ttc | atc | gac | tgt | ggc | cgg | ctg | ggt | gtg | gcg | gac | cgc | tat | cag | gac | ata | 672 |
| Phe | Ile | Asp | Cys | Gly | Arg | Leu | Gly | Val | Ala | Asp | Arg | Tyr | Gln | Asp | Ile | |
| | 210 | | | | | 215 | | | | | 220 | | | | | |
| gcg | ttg | gct | acc | cgt | gat | att | gct | gaa | gag | ctt | ggc | ggc | gag | tgg | gct | 720 |
| Ala | Leu | Ala | Thr | Arg | Asp | Ile | Ala | Glu | Glu | Leu | Gly | Gly | Glu | Trp | Ala | |
| 225 | | | | | 230 | | | | | 235 | | | | | 240 | |
| gac | cgc | ttc | ctc | gtg | ctt | tac | ggt | atc | gcc | gct | ccc | gat | tcg | cag | cgc | 768 |
| Asp | Arg | Phe | Leu | Val | Leu | Tyr | Gly | Ile | Ala | Ala | Pro | Asp | Ser | Gln | Arg | |
| | | | | 245 | | | | | 250 | | | | | 255 | | |
| atc | gcc | ttc | tat | cgc | ctt | ctt | gac | gag | ttc | ttc | tga | | | | | 804 |
| Ile | Ala | Phe | Tyr | Arg | Leu | Leu | Asp | Glu | Phe | Phe | | | | | | |
| | | | | 260 | | | | | 265 | | | | | | | |

<210> SEQ ID NO 135
<211> LENGTH: 267
<212> TYPE: PRT

<213> ORGANISM: Artificial Sequence
<220> FEATURE:
<223> OTHER INFORMATION: Chemically synthesized - modified neomycin resistance gene lacking internal ATG sequences

<400> SEQUENCE: 135

```
Met Gly Ser Ala Ile Glu Gln Asp Gly Leu His Ala Gly Ser Pro Ala
1               5                   10                  15
Ala Trp Val Glu Arg Leu Phe Gly Tyr Asp Trp Ala Gln Gln Thr Ile
            20                  25                  30
Gly Cys Ser Asp Ala Ala Val Phe Arg Leu Ser Ala Gln Gly Arg Pro
        35                  40                  45
Val Leu Phe Val Lys Thr Asp Leu Ser Gly Ala Leu Asn Glu Leu Gln
    50                  55                  60
Asp Glu Ala Ala Arg Leu Ser Trp Leu Ala Thr Thr Gly Val Pro Cys
65                  70                  75                  80
Ala Ala Val Leu Asp Val Val Thr Glu Ala Gly Arg Asp Trp Leu Leu
                85                  90                  95
Leu Gly Glu Val Pro Gly Gln Asp Leu Leu Ser Ser His Leu Ala Pro
            100                 105                 110
Ala Glu Lys Val Ser Ile Leu Ala Asp Ala Leu Arg Arg Leu His Thr
        115                 120                 125
Leu Asp Pro Ala Thr Cys Pro Phe Asp His Gln Ala Lys His Arg Ile
    130                 135                 140
Glu Arg Ala Arg Thr Arg Leu Glu Ala Gly Leu Val Asp Gln Asp Asp
145                 150                 155                 160
Leu Asp Glu Glu His Gln Gly Leu Ala Pro Ala Glu Leu Phe Ala Arg
                165                 170                 175
Leu Lys Ala Arg Leu Pro Asp Gly Asp Asp Leu Val Val Thr His Gly
            180                 185                 190
Asp Ala Cys Leu Pro Asn Ile Leu Val Glu Asn Gly Arg Phe Ser Gly
        195                 200                 205
Phe Ile Asp Cys Gly Arg Leu Gly Val Ala Asp Arg Tyr Gln Asp Ile
    210                 215                 220
Ala Leu Ala Thr Arg Asp Ile Ala Glu Glu Leu Gly Gly Glu Trp Ala
225                 230                 235                 240
Asp Arg Phe Leu Val Leu Tyr Gly Ile Ala Ala Pro Asp Ser Gln Arg
                245                 250                 255
Ile Ala Phe Tyr Arg Leu Leu Asp Glu Phe Phe
            260                 265
```

<210> SEQ ID NO 136
<211> LENGTH: 40
<212> TYPE: DNA
<213> ORGANISM: Artificial Sequence
<220> FEATURE:
<223> OTHER INFORMATION: Chemically synthesized - primer NEO-F-HindIII

<400> SEQUENCE: 136
gatcaagctt ttggatcggc cattgaaaca agacggattg                             40

<210> SEQ ID NO 137
<211> LENGTH: 36
<212> TYPE: DNA
<213> ORGANISM: Artificial Sequence
<220> FEATURE:
<223> OTHER INFORMATION: Chemically synthesized - primer NEO EcoRI 800R

<400> SEQUENCE: 137
aagcttgaat tctcagaaga actcgtcaag aaggcg    36

<210> SEQ ID NO 138
<211> LENGTH: 564
<212> TYPE: DNA
<213> ORGANISM: Artificial Sequence
<220> FEATURE:
<223> OTHER INFORMATION: Chemically synthesized - modified dhfr gene
      lacking internal ATG sequences
<220> FEATURE:
<221> NAME/KEY: CDS
<222> LOCATION: (1)..(564)

<400> SEQUENCE: 138

```
atg gtt cga cca ttg aac tgc atc gtc gcc gtg tcc caa aat ctg ggg      48
Met Val Arg Pro Leu Asn Cys Ile Val Ala Val Ser Gln Asn Leu Gly
1               5                   10                  15 att ggc aag aac gga gac cta ccc tgg cct ccg ctc agg aac gag ttc      96
Ile Gly Lys Asn Gly Asp Leu Pro Trp Pro Pro Leu Arg Asn Glu Phe
                20                  25                  30 aag tac ttc caa aga ctg acc aca acc tct tca gtg gaa ggt aaa cag     144
Lys Tyr Phe Gln Arg Leu Thr Thr Thr Ser Ser Val Glu Gly Lys Gln
            35                  40                  45 aat ctg gtg att ctg ggt agg aaa acc tgg ttc tcc att cct gag aag     192
Asn Leu Val Ile Leu Gly Arg Lys Thr Trp Phe Ser Ile Pro Glu Lys
        50                  55                  60 aat cga cct tta aag gac aga att aat ata gtt ctc agt aga gaa ctc     240
Asn Arg Pro Leu Lys Asp Arg Ile Asn Ile Val Leu Ser Arg Glu Leu
65                  70                  75                  80 aaa gaa cca cca cga gga gct cat ttt ctt gcc aaa agt ttg gac gac     288
Lys Glu Pro Pro Arg Gly Ala His Phe Leu Ala Lys Ser Leu Asp Asp
                85                  90                  95 gcc tta aga ctt att gaa caa ccg gaa ttg gca agt aaa gta gac ctg     336
Ala Leu Arg Leu Ile Glu Gln Pro Glu Leu Ala Ser Lys Val Asp Leu
            100                 105                 110 gtt tgg ata gtc gga ggc agt tct gtt tac cag gaa gcc ctg aat caa     384
Val Trp Ile Val Gly Gly Ser Ser Val Tyr Gln Glu Ala Leu Asn Gln
        115                 120                 125 cca ggc cac ctc aga ctc ttt gtg aca agg att ctg cag gaa ttt gaa     432
Pro Gly His Leu Arg Leu Phe Val Thr Arg Ile Leu Gln Glu Phe Glu
    130                 135                 140 agt gac acg ttt ttc cca gaa att gat ttg ggg aaa tat aaa ctt ctc     480
Ser Asp Thr Phe Phe Pro Glu Ile Asp Leu Gly Lys Tyr Lys Leu Leu
145                 150                 155                 160 cca gaa tac cca ggc gtc ctc tct gag gtc cag gag gaa aaa ggc atc     528
Pro Glu Tyr Pro Gly Val Leu Ser Glu Val Gln Glu Glu Lys Gly Ile
                165                 170                 175 aag tat aag ttt gaa gtc tac gag aag aaa gac taa                     564
Lys Tyr Lys Phe Glu Val Tyr Glu Lys Lys Asp
            180                 185
```

<210> SEQ ID NO 139
<211> LENGTH: 187
<212> TYPE: PRT
<213> ORGANISM: Artificial Sequence
<220> FEATURE:
<223> OTHER INFORMATION: Chemically synthesized - modified dhfr gene
      lacking internal ATG sequences

<400> SEQUENCE: 139

Met Val Arg Pro Leu Asn Cys Ile Val Ala Val Ser Gln Asn Leu Gly
1               5                   10                  15

```
Ile Gly Lys Asn Gly Asp Leu Pro Trp Pro Leu Arg Asn Glu Phe
            20                  25                  30

Lys Tyr Phe Gln Arg Leu Thr Thr Thr Ser Ser Val Glu Gly Lys Gln
            35                  40                  45

Asn Leu Val Ile Leu Gly Arg Lys Thr Trp Phe Ser Ile Pro Glu Lys
50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Gly Leu Ala Ser Lys Val Asp Leu
            100                 105                 110

Val Trp Ile Val Gly Gly Ser Ser Val Tyr Gln Glu Ala Leu Asn Gln
            115                 120                 125

Pro Gly His Leu Arg Leu Phe Val Thr Arg Ile Leu Gln Glu Phe Glu
            130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
            165                 170                 175

Lys Tyr Lys Phe Glu Val Tyr Glu Lys Lys Asp
            180                 185

<210> SEQ ID NO 140
<211> LENGTH: 36
<212> TYPE: DNA
<213> ORGANISM: Artificial Sequence
<220> FEATURE:
<223> OTHER INFORMATION: Chemically synthesized - primer DHFR-F-HindIII

<400> SEQUENCE: 140
gatcaagctt ttgttcgacc attgaactgc atcgtc                               36

<210> SEQ ID NO 141
<211> LENGTH: 36
<212> TYPE: DNA
<213> ORGANISM: Artificial Sequence
<220> FEATURE:
<223> OTHER INFORMATION: Chemically synthesized - primer
      DHFR-EcoRI-600-R

<400> SEQUENCE: 141
aagcttgaat tcttagtctt tcttctcgta gacttc                               36

<210> SEQ ID NO 142
<211> LENGTH: 154
<212> TYPE: DNA
<213> ORGANISM: Artificial Sequence
<220> FEATURE:
<223> OTHER INFORMATION: Chemically synthesized - combined synthetic
      polyadenylation sequence and pausing signal from the human alpha2
      globin gene
<220> FEATURE:
<221> NAME/KEY: synthetic polyadenylation sequence
<222> LOCATION: (1)..(49)
<220> FEATURE:
<221> NAME/KEY: cloning site
<222> LOCATION: (50)..(62)
<220> FEATURE:
<221> NAME/KEY: pausing signal from the human alpha2 globin gene
<222> LOCATION: (63)..(154)

<400> SEQUENCE: 142
```

```
aataaaatat ctttattttc attacatctg tgtgttggtt ttttgtgtga atcgatagta        60
ctaacatacg ctctccatca aaacaaaacg aaacaaaaca aactagcaaa ataggctgtc       120
cccagtgcaa gtgcaggtgc cagaacattt ctct                                   154
```